US010300130B2

(12) United States Patent
Shenk et al.

(10) Patent No.: US 10,300,130 B2
(45) **Date of Patent: *May 28, 2019**

(54) CYTOMEGALOVIRUS VACCINES AND METHODS OF PRODUCTION

(71) Applicant: The Trustees of Princeton University, Princeton, NJ (US)

(72) Inventors: Thomas Shenk, Princeton, NJ (US); Dai Wang, Blue Bell, PA (US)

(73) Assignee: The Trustees of Princeton University, Princeton, NJ (US)

( * ) Notice: Subject to any disclaimer, the term of this patent is extended or adjusted under 35 U.S.C. 154(b) by 33 days.

This patent is subject to a terminal disclaimer.

(21) Appl. No.: 15/223,980

(22) Filed: Jul. 29, 2016

(65) Prior Publication Data

US 2017/0014504 A1 Jan. 19, 2017

Related U.S. Application Data

(63) Continuation of application No. 12/681,504, filed as application No. PCT/US2008/079494 on Jul. 22, 2010, now Pat. No. 9,439,960.

(60) Provisional application No. 60/998,426, filed on Oct. 10, 2007.

(51) Int. Cl.

*C07K 14/11* (2006.01)
*A61K 39/245* (2006.01)
*A61K 39/12* (2006.01)
*C12N 7/00* (2006.01)
*A61K 39/145* (2006.01)
*A61K 39/00* (2006.01)

(52) U.S. Cl.

CPC ............ *A61K 39/245* (2013.01); *A61K 39/12* (2013.01); *C12N 7/00* (2013.01); *A61K 2039/5252* (2013.01); *A61K 2039/5254* (2013.01); *A61K 2039/54* (2013.01); *C12N 2710/16134* (2013.01); *C12N 2710/16151* (2013.01); *C12N 2710/16164* (2013.01)

(58) Field of Classification Search

CPC ... C07K 16/085; C07K 16/088; G07K 16/088
See application file for complete search history.

(56) References Cited

U.S. PATENT DOCUMENTS 3,959,466 A 5/1976 Plotkin
4,058,598 A 11/1977 Stern et al.
6,471,965 B1 10/2002 Golubev et al.
7,407,744 B2 * 8/2008 Liu ...................... C07K 14/005 435/5
7,704,510 B2 4/2010 Shenk et al.
8,173,362 B2 5/2012 Shenk et al.
9,439,960 B2 9/2016 Shenk
2005/0064394 A1 3/2005 Liu et al.
2010/0285059 A1 11/2010 Shenk et al.

FOREIGN PATENT DOCUMENTS

WO WO 2005/012545 A2 2/2005
WO WO 2007/146024 A2 12/2007
WO WO 2009/049138 A1 4/2009

OTHER PUBLICATIONS

Čič-Šain, L., et al., "Target Deletion of Regions Rich in Immune-Evasive Genes from the Cytomegalovirus Genome as a Novel Vaccine Strategy," *J Virol.*, 81(24): 13825-13834 (2007).

Gema, G., et al., "Dendritic-cell infection by human cytomegalovirus is restricted to strains carrying functional UL131-128 genes and mediates efficient viral antigen presentation to CD8+ T cells," *J. Gene Virol.*, 86(2): 275-284 (2005).

Gonczol, E. and Plotkin, S., "Development of a cytomegalovirus vaccine: lessons from recent clinical trials," *Expert Opinion on Biological Therapy*, 1(3): 401-412 (2001).

Mousavi-Jazi, M., et al., "Growth Phenotypes of Cytomegalovirus Isolates do not Correlate with Glycoprotein B, Major Immediate Early Genotypes or Antiviral Sensitivity," *J. Medical Virology*, 62: 117-126 (2000).

Revello, M.G., et al., "In vitro selection of human cytomegalovirus variants unable to transfer virus and virus products from infected cells to polymorphonuclear leukocytes and to grow in endothelial cells," *J. Gene. Virol.*, 82: 1429-1438 (2001).

Zhong, J. and Khanna, R., "Vaccine strategies against human cytomegalovirus infection," *Expert. Rev. Anti. Infec. Ther.*, 5(3): 449-459 (2007).

Adler., B., Serivano., L., Ruzcies, L., Rupp B., Sinzget, C. & Koszinowski, U., "Role of Human Cytomegalovirus UL131A in Cell Type-Specific Vitus Entry and Release," *Journal of General Virology*, 87 2451-2460 (2006).

Bodaghi, B., Gourean, B., Zipeto, D., Laurent, L., Virelizier, J. L. & Michelson, S., "Role of IFN-γ-Induced Indoleamine 2,3 Dioxygenase of Human Cytomegalovirus in Retinal Pigment Epithelial Cells," *The Journal of Immunology*, 162: 957-964 (1999).

Borza, C. M. & Hutt-Fletcher, L. M., "Alternate Replication in B Cells and Epithelial Cells Switches Tropism of Epstein-Barr Virus," *Nature Medicine*, 8(6): 594-599 (Jun. 2002).

Compton, T., Nepornueeno, R. R. & Nowlin, D. M., "Human Cytomegalovirus Penetrates Host Cells by PH-Independent Fusion at the Cell Surface," *Virology*, 191: 387-395 (1992).

Haan, K. M. & Lougnecker, R., "Coreceptor Restriction within the HLA-DQ Locus for Epstein-Barr Virus Infection," *PNAS*, 97(16): 9252-9257 (Aug. 2000).

Haan. K. M., Kwok. W. W., Longnecker, F., & Speck, P., "Epstein-Barr Virus Entry Utilizing HLA-DP or HLA-DQ as a Coreceptor," *Journal of Virology*, 74(5), 2451-2454 (Mar. 2000).

(Continued)

*Primary Examiner* — Bao Q Li

(74) *Attorney, Agent, or Firm* — Hamilton, Brook, Smith & Reynolds, P.C.

(57) ABSTRACT

Methods of increasing diversity in cytomegalovirus vaccines through the selection of cell type in which the virus is propagated, and the use of cytomegalovirus produced by those methods in the development of vaccine compositions, are disclosed. Vaccine compositions comprising CMV isolated from epithelial cells are also disclosed.

7 Claims, 6 Drawing Sheets

Specification includes a Sequence Listing.

(56) References Cited

OTHER PUBLICATIONS

Hahn, G., Revello, M. G., Pitrone, M., Percivalle, E., Campanini, G., Sarasini A., Wagner, M., Gallina, A., Milanesi, G.., Koszinowski, U . Baldanti, F. & Gerna, G., "Human Cytomegalovirus UL131-128 Genes Are Indispensable for Virus Growth in Endothelial Cells and Virus Transfer to Leukocytes," *Journal of Virology*, 78(18): 10023-10033 (Sep. 2004).
Hutt-Fletcher, L. M. & Lake, C. M., "Two Epstein-Barr Virus Glycoprotein Complexes," *Cure Top Miembiol Immunol*, 258: 51-64 (2001 ).
Li, Q., Turk, S. M. & Hutt-Fletcher, L. M., "The Epstein-Barr Virus (EBV) BZLF2 Gene Product Associates with the gH and gL Homologs of EBV and Carries an Epitope Critical to Infection of B Cells but Not of Epithelial Cells." *Journal of Virology*, 69(7): 3987-3994 (Jul. 1995).
Li, Q., Spriggs, M. K., Kovats, S., Turk, S. M., Comeau, M. R., Nepom, B. & Hutt-Fletcher, L. M., "Epstein-Barr Virus Uses HLA Class II as a Cofactor for Infection of B Lymphocytes," *Journal of Virology*, 71(6): 4657-4662 (Jun. 1997).
Miller, N. & Hutt-Fletcher, L. M., "Epstein-Barr Virus Enters B Cells and Epithelial Cells by Different Routes," *Journal of Virology*, 66(6): 3409- 3414 (Jun. 1992).
Milne, R. S., Nicola, A. V., Whitheck, J. C. Eisenberg, R. J. & Cohen, G. H., "Glycoprotein D Receptor-Dependent Low-pH-Independent Endocytic Entry of Herpes Simplex Virus Type 1," *Journal of Virology*. 79(11): 6655-6663 (Jun. 2005).
Nemerow, G. R. & Cooper, N. R., "Early Events in the Infection of Human B Lymphocytes by Epstein-Barr Virus: The Internalization Process," Virology, 132: 186-198 (1984).
Nicola, A. V., McEvoy A. M. & Straus, S. E., "Roles for Endocytosis and Low pH in Herpes Simplex Virus Entry into HeLa and Chinese Hamster Ovary Cells," *Journal of Virology*, 77(9): 5324-5332 (May 2003).
Nicola, A. V., Hou, F. Major, E. O. & Straus, S. E., "Herpes Simplex Virus Type I Enters Human Epidermal Keratinoeytes, but Not Neurons, via a pH-Dependent Endocytic Pathway," *Journal of Virology*, 79(12): 7609-7616 (Jun. 2005).
Plachter, B., Sinzger, C. & Jahn, G.. "Cell Types Involved in Replication and Distribution of Human Cytomegalovirus," *Advances in Virus Research*, 46: 195-261. (1996).
Ryckman, B. J., Jarvis, M. A., Drummond, D. D., Nelson, J. A. & Johnson, D. C., "Human Cytomegalovirus Entry into Epithelial and Endothelial Cells Depends on Genes UL128 to UL150 and Occurs by Endocytosis and Low-pH Fusion," *Journal of Virology*, 80(2): 710-722 (Jan. 2006).
Wang, D. & Shenk, T., "Human Cytomegalovirus UL131 Open Reading Frame is Required for Epithelial Cell Tropism," *Journal of Virology*, 79(16): 10330-10338 (Aug. 2005).
Wang, D. & Shenk, T., "Human Cytomegalovinis Virion Protein Complex Required for Epithelial and Endothelial Cell Tropism," *PNAS*, 102(50): 18153-18158 (Dec. 2005).
Wang, X. & Hutt-Flotclicr, L. M., "Epstcin-Barr Virus Lacking Glycoprotein gp42 Can Bind to B Cells but is not Able to Infect," *Journal of Virology*, 72(1): 158-163 (Jan. 1998).
Wang, X., Kenyon, W. J., Li, Q., Mullbcrg, J. & Hutt-Fletcher, L. M., "Epstein-Barr Virus Uses Different Complexes of Glycoproteins gH and gL to Infect B Lymphocytes and Epithelial Cells," *Journal of Virology*, 72(7): 5552-5558 (Jul. 1998).
Wittels, M. & Spear, P. G., "Penetration of Cells of Herpes Simplex Virus does not Require a Low pH-Dependent Endocytic Pathway," *Virus Research*, 18: 271-290 (1990).
International Search Report of Int'l Application No. PCT/US2008/079494, dated Dec. 18, 2008.
GenBank Accession No. AB051431, "*Homo sapiens* mRNA for KIAA1644 protein, partial cds," Oct. 6, 2001; Retrieved from the Internet on Aug. 10, 2010: http://www.ncbi.nlm.nih.gov/sviewer/viewer.fcgi?val . . . pp. 1-3.
GenBank Accession No. AC146851, "Human Herpesvirus 5 Towne-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-60.
GenBank Accession No. AC146904, "Human Herpesvirus 5 PH-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-60.
GenBank Accession No. AC146905, "Human Herpesvirus 5 Toledo-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-59.
GenBank Accession No. AC146906, "Human Herpesvirus 5 TR-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-61.
GenBank Accession No. AC146907, "Human Herpesvirus 5 FIX-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-59.
GenBank Accession No. AC146999, "Human Herpesvirus 5 ADF169-BAC isolate, complete sequence," Dec. 10, 2003; Retrieved from the Internet on Aug. 11, 2010: http://www.ncbi.nlm.nih.gov/sviewer/viewer.fcgi?val . . . pp. 1-60.
GenBank Accession No. AF038194, "*Homo sapiens* clone 23821 mRNA sequence," Jan. 22, 1998; Retrieved from the Internet on Aug. 11, 2010: http://www.ncbi.nlm.nih.gov/sviewer/viewer.fcgi?val . . . pp. 1-2.
GenBank Accession No. AF085968, "*Homo sapiens* full length insert cDNA clone YT69G03," Aug. 29, 1998; Retrieved from the Internet on Aug. 10, 2010: http://www.ncbi.nlm.nih.gov/sviewer/viewer.fcgi?val . . . pp. 1-2.
GenBank Accession No. AF480884, "Chimpanzee cytomegalovirus, complete genome," Jan. 29, 2003; Retrieved from the Internet on Aug. 11, 2010: http://www.ncbi.nlm.nih.gov/sviewer/viewer.fcgi?val . . . pp. 1-96.
GenBank Accession No. AI369525, "1$^{st}$ strand cDNA was prepared from mRNA obtained from pooled 8-9 week (total) fetus material with a Not I-oligo(dT) primer," Jan. 11, 1999; Retrieved from the Internet on Aug. 10, 2010: http://www.ncbi.nlm.nih.gov/sviewer/viewer.fcgi?val . . . pp. 1-2.
GenBank Accession No. AI369525, GenBank gi: 4148278, Lib. Name: Soares total fetus Nb2HF8 9w, Jan. 11, 1999; Retrieved from the Internet on Aug. 10, 2010: http://www.ncbi.nlm.nih.gov/sviewer/viewer.fcgi?val . . . pp. 1-2.
GenBank Accession No. AK021804, "*Homo sapiens* cDNA FLJ11742 fis, clone HEMBA1005508," Sep. 12, 2006; Retrieved from the Internet on Aug. 10, 2010: http://www.ncbi.nlm.nih.gov/sviewer/viewer.fcgi?val . . . pp. 1-2.
GenBank Accession No. AK023391, "*Homo sapiens* cDNA FLJ13329 fis, clone OVARC1001795," Sep. 12, 2006; Retrieved from the Internet on Aug. 10, 2010: http://www.ncbi.nlm.nih.gov/sviewer/viewer.fcgi?val . . . pp. 1-2.
GenBank Accession No. AK023856, "*Homo sapiens* cDNA FLJ13794 fis, clone THYR01000092," Sep. 12, 2006; Retrieved from the Internet on Aug. 10, 2010: http://www.ncbi.nlm.nih.gov/sviewer/viewer.fcgi?val . . . pp. 1-3.
GenBank Accession No. AK055156, "*Homo sapiens* cDNA FLJ30594 fis, clone BRAWH2008903," Sep. 13, 2006; Retrieved from the Internet on Aug. 10, 2010: http://www.ncbi.nlm.nih.gov/sviewer/viewer.fcgi?val . . . pp. 1-3.
GenBank Accession No. AK055386, "*Homo sapiens* cDNA FLJ30824 fis, clone FEBRA2001698," Sep. 13, 2006; Retrieved from the Internet on Aug. 10, 2010: http://www.ncbi.nlm.nih.gov/sviewer/viewer.fcgi?val . . . pp. 1-3.
GenBank Accession No. AK056190, "*Homo sapiens* cDNA FLJ31628 fis, clone NT2R12003344, weakly similar to Presynaptic Protein SAP97," Sep. 13, 2006; Retrieved from the Internet on Aug. 10, 2010: http://www.ncbi.nlm.nih.gov/sviewer/viewer.fcgi?val . . . pp. 1-3.

(56) References Cited

OTHER PUBLICATIONS

GenBank Accession No. AK056703, "*Homo sapiens* cDNA FLJ32141 fis, clone PLACE5000067," Sep. 13, 2006; Retrieved from the Internet on Aug. 10, 2010: http://www.ncbi.nlm.nih.gov/sviewer/viewer.fcgi?val . . . pp. 1-3.

GenBank Accession No. AK074031, "*Homo sapiens* mRNA for FLJ00072 protein," Feb. 13, 2004; Retrieved from the Internet on Aug. 10, 2010: http://www.ncbi.nlm.nih.gov/sviewer/viewer.fcgi?val . . . pp. 1-3.

GenBank Accession No. AK090308, "Mus musculus adult male gall bladder cDNA, RIKEN full-length enriched library, clone:G630044J09 product:betaine-homocysteine methyltransferase 2, full insert sequence," Oct. 4, 2006; Retrieved from the Internet on Aug. 10, 2010: http://www.ncbi.nlm.nih.gov/sviewer/viewer.fcgi?val . . . pp. 1-5.

GenBank Accession No. AK090803, "*Homo sapiens* cDNA FLJ33484 fis, clone BRAMY2003117," Sep. 14, 2006; Retrieved from the Internet on Aug. 11, 2010: http://www.ncbi.nlm.nih.gov/sviewer/viewer.fcgi?val . . . pp. 1-3.

GenBank Accession No. AK094143, "*Homo sapiens* cDNA FLJ36824 fis, clone ASTRO2007221, weakly similar to Periaxin," Sep. 14, 2006; Retrieved from the Internet on Aug. 10, 2010: http://www.ncbi.nlm.nih.gov/sviewer/viewer.fcgi?val . . . pp. 1-3.

GenBank Accession No. AK094860, "*Homo sapiens* cDNA FLJ37541 fis, clone BRCAN2026340," Sep. 14, 2006; Retrieved from the Internet on Aug. 10, 2010: http://www.ncbi.nlm.nih.gov/sviewer/viewer.fcgi?val . . . pp. 1-3.

GenBank Accession No. AK123066, "*Homo sapiens* cDNA FLJ41071 fis, clone 3NB692003538," Sep. 14, 2006; Retrieved from the Internet on Aug. 10, 2010: http://www.ncbi.nlm.nih.gov/sviewer/viewer.fcgi?val . . . pp. 1-2.

GenBank Accession No. AK124132, "*Homo sapiens* cDNA FLJ42138 fis, clone TESTI2036684," Sep. 14, 2006; Retrieved from the Internet on Aug. 10, 2010: http://www.ncbi.nlm.nih.gov/sviewer/viewer.fcgi?val . . . pp. 1-2.

GenBank Accession No. AK124390, "*Homo sapiens* cDNA FLJ42399 fis, clone ASTRO2003024," Sep. 14, 2006; Retrieved from the Internet on Aug. 10, 2010: http://www.ncbi.nlm.nih.gov/sviewer/viewer.fcgi?val . . . pp. 1-3.

GenBank Accession No. AK124941, "*Homo sapiens* cDNA FLJ42951 fis, clone BRSTN2007765," Sep. 14, 2006; Retrieved from the Internet on Aug. 10, 2010: http://www.ncbi.nlm.nih.gov/sviewer/viewer.fcgi?val . . . pp. 1-3.

GenBank Accession No. AK125975, "*Homo sapiens* cDNA FLJ43987 fis, clone TESTI4019299," Sep. 14, 2006; Retrieved from the Internet on Aug. 10, 2010: http://www.ncbi.nlm.nih.gov/sviewer/viewer.fcgi?val . . . pp. 1-2.

GenBank Accession No. AL133118, "*Homo sapiens* mRNA; cDNA DKFZp586N0121 (from clone DKFZp586N0121) ," Feb. 18, 2000; Retrieved from the Internet on Aug. 10, 2010: http://www.ncbi.nlm.nih.gov/sviewer/viewer.fcgi?val . . . pp. 1-2.

GenBank Accession No. AL713743, "*Homo sapiens* mRNA; cDNA DKFZp761G0122 (from clone DKEZp761G0122)," Mar. 20, 2002; Retrieved from the Internet on Aug. 10, 2010: http://www.ncbi.nlm.nih.gov/sviewer/viewer.fcgi?val . . . pp. 1-2.

GenBank Accession No. AW444553, "The sequence contained on oligo-dT track that was present in the oligonucleotide that was used to rpime the synthesis of first strand cDNA and therefore this may represent a bonafide poly A tail," Feb. 15, 2000; Retrieved from the Internet on Aug. 10, 2010: http://www.ncbi.nlm.nih.gov/sviewer/viewer.fcgi?val . . . pp. 1-2.

GenBank Accession No. AW856073, "A mini-library was made by cloning products derived from Orestes PCR (U.S. Letters Patent application No. 196,716—Ludwign Institute for Cancer Research) profiles into the pUC 18 vector. Reverse transcription of tissue mRNA and cDNA amplification were performed under low stringency conditions," May 19, 2000; Retrieved from the Internet on Aug. 11, 2010: http://www.ncbi.nlm.nih.gov/sviewer/viewer.fcgi?val . . . pp. 1-2.

GenBank Accession No. AW856073, GenBank gi: 7951766, Lib. Name: CT0286, May 19, 2000; Retrieved from the Internet on Aug. 10, 2010: http://www.ncbi.nlm.nih.gov/sviewer/viewer.fcgi?val . . . pp. 1-2.

GenBank Accession No. AY186194, "Rhesus cytomegalovirus strain 68-1, complete genome," Jun. 4, 2003; Retrieved from the Internet on Aug. 11, 2010: http://www.ncbi.nlm.nih.gov/sviewer/viewer.fcgi?val . . . pp. 1-97.

GenBank Accession No. AY446894, "Human herpesvirus 5 strain Merlin, complete genome," Aug. 13, 2007; Retrieved from the Internet on Aug. 11, 2010: http://www.ncbi.nlm.nih.gov/sviewer/viewer.fcgi?val . . . pp. 1-95.

GenBank Accession No. BC011595, "*Homo sapiens* glycoprotein (transmembrane) nmb, mRNA (cDNA clone Image:3345861), complete cds," Sep. 16, 2003; Retrieved from the Internet on Aug. 10, 2010: http://www.ncbi.nlm.nih.gov/sviewer/viewer.fcgi?val . . . pp. 1-3.

GenBank Accession No. BC015929, "*Homo sapiens* nuclear receptor subfamily 1, group D, member 2, mRNA (cDNA clone Image:3912370), partial cds," Jan. 2, 2004; Retrieved from the Internet on Aug. 10, 2010: http://www.ncbi.nlm.nih.gov/sviewer/viewer.fcgi?val . . . pp. 1-3.

GenBank Accession No. BC018597, "*Homo sapiens*, clone Image 3869276, mRNA," Dec. 3, 2001; Retrieved from the Internet on Aug. 10, 2010: http://www.ncbi.nlm.nih.gov/sviewer/viewer.fcgi?val . . . pp. 1-2.

GenBank Accession No. BC039151, "*Homo sapiens* chromosome 20 open reading frame 119, mRNA (cDNA clone Image:4745538), with apparent retained intron," Nov. 17, 2006; Retrieved from the Internet on Aug. 10, 2010: http://www.ncbi.nlm.nih.gov/sviewer/viewer.fcgi?val . . . pp. 1-2.

GenBank Accession No. BC043212, "*Homo sapiens* cDNA clone Image:5295205, with apparent retained intron," Sep. 16, 2003; Retrieved from the Internet on Aug. 10, 2010: http://www.ncbi.nlm.nih.gov/sviewer/viewer.fcgi?val . . . pp. 1-3.

GenBank Accession No. BC048263, "*Homo sapiens* hypothetical protein LOC146909, mRNA (cDNA clone Image:4418755), partial cds," Sep. 30, 2003; Retrieved from the Internet on Aug. 10, 2010: http://www.ncbi.nlm.nih.gov/sviewer/viewer.fcgi?val . . . pp. 1-3.

GenBank Accession No. BC071797, "*Homo sapiens* cDNA clone Image: 4618441, ** Warning: chimeric clone **," Aug. 4, 2006; Retrieved from the Internet on Aug. 10, 2010:http://www.ncbi.nlm.nih.gov/sviewer/viewer.fcgi?val . . . pp. 1-2.

GenBank Accession No. BF514513, "The sequence contained an oligo-dT track that was present in the oligonucleotide that was used to prime the synthesis of first strand cDNA and therefore this may represent a bonafide poly A tail," Dec. 7, 2000; Retrieved from the Internet on Aug. 10, 2010: http://www.ncbi.nlm.nih.gov/sviewer/viewer.fcgi?val . . . pp. 1-2.

GenBank Accession No. BG001037, "A mini-library was made by cloning products derived from Orestes PCR (U.S. Letters Patent application No. 196,716-18 vector. Reverse transcription of tissue mRNA and cDNA amplification were performed under low stringency conditions," Jan. 24, 2001; Retrieved from the Internet on Aug. 11, 2010: http://www.ncbi.nlm.nih.gov/sviewer/viewer.fcgi?val . . . pp. 1-2.

GenBank Accession No. BK000394, "TPA_inf: Human herpesvirus 5 strain AD169, complete genome," Sep. 5, 2006; Retrieved from the Internet on Aug. 11, 2010: http://www.ncbi.nlm.nih.gov/sviewer/viewer.fcgi?val . . . pp. 1-92.

GenBank Accession No. BU943730, "Double-stranded cDNA was prepared from a pool of 40 cell line polyA+ RNAs," Oct. 17, 2002; Retrieved from the Internet on Aug. 10, 2010: http://www.ncbi.nlm.nih.gov/sviewer/viewer.fcgi?val . . . pp. 1-2.

GcnBank Accession No. BX104999, "1$^{st}$ strand cDNA was primed with a Pac I-oligo(dT) primer," Jan. 22, 2003; Retrieved from the Internet on Aug. 10, 2010: http://www.ncbi.nlm.nih.gov/sviewer/viewer.fcgi?val . . . pp. 1-2.

GenBank Accession No. BX360933, "1$^{st}$ strand cDNA was primed with a NotI-oligo(dT) primer. Five prime end enriched, double-strand cDNA was digested with Not I and cloned into the Not I and EcoR V sites of the pCMVSPORT 6 vector. Library was normal-

(56) References Cited

OTHER PUBLICATIONS ized," May 5, 2003; Retrieved from the Internet on Aug. 10, 2010: http://www.ncbi.nlm.nih.gov/sviewer/viewer.fcgi?val . . . pp. 1-2.
GenBank Accession No. CR594200, "full-length cDNA clone CS0DF031yH08 of Fetal brain of *Homo sapiens* (human) ," Jul. 21, 2004; Retrieved from the Internet on Aug. 11, 2010: http://www.ncbi.nlm.nih.gov/sviewer/viewer.fcgi?val . . . pp. 1-2.
GenBank Accession No. CR598364, "full-length cDNA clone CS0CAP007YJ17 of Thymus of *Homo sapiens* (human) ," Jul. 21, 2004; Retrieved from the Internet on Aug. 10, 2010: http://www.ncbi.nlm.nih.gov/sviewer/viewer.fcgi?val . . . pp. 1-2.
GenBank Accession No. CR622110, "full-length cDNA clone CS0DC025YP03 of Neuroblastoma Cot 25-normalized of *Homo sapiens* (human) ," Jul. 21, 2004; Retrieved from the Internet on Aug. 10, 2010: http://www.ncbi.nlm.nih.gov/sviewer/viewer.fcgi?val . . . pp. 1-2.
GenBank Accession No. DB318210, "NEDO human cDNA project (New Energy and Industrial Technology Developmental Organization, Japan); cDNA library construction: Helix Research Institute (HRI); 5'-end one pass sequencing: HRI, Research Association for Biotechnology (RAB) and Biotechnology Center, National Institute of Technology and Evaluation; 3'-end one pass sequencing; RAB," Dec. 10, 2005; Retrieved from the Internet on Aug. 11, 2010: http://www.ncbi.nlm.nih.gov/sviewer/viewer.fcgi?val . . . pp. 1-2.
GenBank Accession No. DB527271, "The full length cDNA libraries were prepared and sequenced using the RIKEN full length cDNA techniques in Genome Science Laboratory and Genome Exploration Research Group Genomic Sciences Center (GSC) in RIKEN. These sequences are contributed to the international ORFeome Collaboration. 3'-EST sequences are presented as anti-sense strand," Apr. 17, 2006; Retrieved from the Internet on Aug. 10, 2010: http://www.ncbi.nlm.nih.gov/sviewer/viewer.fcgi?val . . . pp. 1-2.
GenBank Accession No. DQ205516, "Natronorubrum aibiense strain 7-3 16S ribosomal RNA gene, partial sequence," Jul. 10, 2006; Retrieved from the Internet on Aug. 11, 2010: http://www.ncbi.nlm.nih.gov/sviewer/viewer.fcgi?val . . . pp. 1-2.
GenBank Accession No. HSU16307, "*Homo sapiens* glioma pathogenesis-related protein (GliPR) mRNA, complete cds," Oct. 23, 2002; Retrieved from the Internet on Aug. 10, 2010: http://www.ncbi.nlm.nih.gov/sviewer/viewer.fcgi?val . . . pp. 1-2.
GenBank Accession No. HUMYT69G03, "*Homo sapiens* full length insert cDNA clone YT69G03," Aug. 29, 1998; Retrieved from the Internet on Aug. 10, 2010: http://www.ncbi.nlm.nih.gov/sviewer/viewer.fcgi?val . . . pp. 1-2.
GenBank Accession No. L08436, "Human autonomously replicating sequence (ARS) mRNA," Nov. 8, 1993; Retrieved from the Internet on Aug. 10, 2010: http://www.ncbi.nlm.nih.gov/sviewer/viewer.fcgi?val . . . pp. 1-1.
GenBank Accession No. NM_000189, "*Homo sapiens* hexokinase 2 (HK2), mRNA," Sep. 3, 2007; Retrieved from the Internet on Aug. 10, 2010: http://www.ncbi.nlm.nih.gov/sviewer/viewer.fcgi?val . . . pp. 1-6.
GenBank Accession No. NM_000190, "*Homo sapiens* hydroxymethylbilane synthase (HMBS), transcript variant 1, mRNA," Sep. 25, 2007; Retrieved from the Internet on Aug. 11, 2010: http://www.ncbi.nlm.nih.gov/sviewer/viewer.fcgi?val . . . pp. 1-5.
GenBank Accession No. NM_000201, "*Homo sapiens* intercellular adhesion molecule 1 (CD54), human rhinovirus receptor (ICAM1), mRNA," Sep. 30, 2007; Retrieved from the Internet on Aug. 10, 2010: http://www.ncbi.nlm.nih.gov/sviewer/viewer.fcgi?val . . . pp. 1-5.
GenBank Accession No. NM_000212, "*Homo sapiens* integrin, beta 3 (platelet glycoprotein IIIA, antigen CD61) (TTGB3), mRNA," Sep. 30, 2007; Retrieved from the Internet on Aug. 10, 2010: http://www.ncbi.nlm.nih.gov/sviewer/viewer.fcgi?val . . . pp. 1-6.
GenBank Accession No. NM_000322, "*Homo sapiens* peripherin 2 (retinal degeneration, slow) (PRPH2), mRNA," Sep. 17, 2007; Retrieved from the Internet on Aug. 10, 2010: http://www.ncbi.nlm.nih.gov/sviewer/viewer.fcgi?val . . . pp. 1-4.
GenBank Accession No. NM_000362, "*Homo sapiens* TIMP metallopeptidase inhibitor 3 (Sorsby fundus dystrophy, pseudoinflammatory) (TIMP3), mRNA," Sep. 24, 2007; Retrieved from the Internet on Aug. 10, 2010: http://www.ncbi.nlm.nih.gov/sviewer/viewer.fcgi?val . . . pp. 1-8.
GenBank Accession No. NM_000364, "*Homo sapiens* troponin T type 2 (cardiac) (TNNT2), transcript variant 1, mRNA," Oct. 7, 2007; Retrieved from the Internet on Aug. 10, 2010: http://www.ncbi.nlm.nih.gov/sviewer/viewer.fcgi?val . . . pp. 1-5.
GenBank Accession No. NM_000372, "*Homo sapiens* tyrosinase (oculocutaneous albinism IA) (TYR), mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_000499, "*Homo sapiens* cytochrome P450, family 1, subfamily A, polypeptide 1 (CYP1A1), mRNA," Oct. 7, 2007; Retrieved from the Internet on Aug. 10, 2010: http://www.ncbi.nlm.nih.gov/sviewer/viewer.fcgi?val . . . pp. 1-5.
GenBank Accession No. NM_000640, "*Homo sapiens* interleukin 13 receptor, alpha 2 (IL13RA2), mRNA," Sep. 17, 2007; Retrieved from the Internet on Aug. 10, 2010: http://www.ncbi.nlm.nih.gov/sviewer/viewer.fcgi?val . . . pp. 1-4.
GenBank Accession No. NM_000641, "*Homo sapiens* interleukin 11 (IL11), mRNA," Sep. 25, 2007; Retrieved from the Internet on Aug. 10, 2010: http://www.ncbi.nlm.nih.gov/sviewer/viewer.fcgi?val . . . pp. 1-4.
GenBank Accession No. NM_000693, "*Homo sapiens* aldehyde dehydrogenase 1 family, member A3 (ALDH1A3), mRNA," Jul. 24, 2007; Retrieved from the Internet on Aug. 10, 2010: http://www.ncbi.nlm.nih.gov/sviewer/viewer.fcgi?val . . . pp. 1-4.
GenBank Accession No. NM_000782, "*Homo sapiens* cytochrome P450, family 24, subfamily A, polypeptide 1 (CYP24A1), nuclear gene encoding mitochondrial protein, mRNA," Sep. 24, 2007; Retrieved from the Internet on Aug. 10, 2010: http://www.ncbi.nlm.nih.gov/sviewer/viewer.fcgi?val . . . pp. 1-6.
GenBank Accession No. NM_000800, "*Homo sapiens* fibroblast growth factor 1 (acidic) (FGF1), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_000808, "*Homo sapiens* gamma-aminobutyric acid (Gaba), A receptor, alpha 3 (GABRA3), mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_000916, "*Homo sapiens* oxytocin receptor (OXTR), mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_000970, "*Homo sapiens* ribosomal protein L6 (RPL6), transcript variant 2, mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_001002926, "*Homo sapiens* Twist neighbor (TWISTNB), nRNA," Sep. 3, 2007; Retrieved from the Internet on Aug. 10, 2010: http://www.ncbi.nlm.nih.gov/sviewer/viewer.fcgi?val . . . pp. 1-3.
GenBank Accession No. NM_001003683, "*Homo sapiens* phosphodiesterase 1A, calmodulin-dependent (PDE1A), transcript variant 2, mRNA," Sep. 17, 2007; Retrieved from the Internet on Aug. 10, 2010: http://www.ncbi.nlm.nih.gov/sviewer/viewer.fcgi?val . . . pp. 1-5.
GenBank Accession No. NM_001003940, "*Homo sapiens* Bc12 modifying factor (BMF), transcript variant 1, mRNA," Sep. 26, 2007; Retrieved from the Internet on Aug. 10, 2010: http://www.ncbi.nlm.nih.gov/sviewer/viewer.fcgi?val . . . pp. 1-5.
GenBank Accession No. NM_001004301, "*Homo sapiens* zinc finger protein 813 (ZNF813), mRNA," Jun. 27, 2007; Retrieved from the Internet on Aug. 10, 2010: http://www.ncbi.nlm.nih.gov/sviewer/viewer.fcgi?val . . . pp. 1-3.
GenBank Accession No. NM_001009954, "*Homo sapiens* FLJ20105 protein (FLJ20105), transcript variant 2, mRNA," Jun. 3, 2007; Retrieved from the Internet on Aug. 10, 2010: http://www.ncbi.nlm.nih.gov/sviewer/viewer.fcgi?val . . . pp. 1-3.
GenBank Accession No. NM_001010911, "*Homo sapiens* chromosome 10 open reading frame 114 (C10orf114), mRNA," Jun. 3,

(56) References Cited

OTHER PUBLICATIONS

2007; Retrieved from the Internet on Aug. 10, 2010: http://www.ncbi.nlm.nih.gov/sviewer/viewer.fcgi?val . . . pp. 1-3.

GenBank Accession No. NM_001018084, "*Homo sapiens* solute carrier family 26, member 10 (SLC26A10), transcript variant 1, mRNA," Sep. 24, 2005; Retrieved from the Internet on Aug. 10, 2010: http://www.ncbi.nlm.nih.gov/sviewer/viewer.fcgi?val . . . pp. 1-3.

GenBank Accession No. NM_001033086, "*Homo sapiens* chromosome 20 open reading frame 133 (C20orf133), transcript variant 1, mRNA," Sep. 24, 2005; Retrieved from the Internet on Aug. 10, 2010: http://www.ncbi.nlm.nih.gov/sviewer/viewer.fcgi?val . . . pp. 1-3.

GenBank Accession No. NM_001034, "*Homo sapiens* ribonucleotide reductase M2 polypeptide (RRM2), mRNA," Sep. 3, 2007; Retrieved from the Internet on Aug. 10, 2010: http://www.ncbi.nlm.nih.gov/sviewer/viewer.fcgi?val . . . pp. 1-5.

GenBank Accession No. NM_001037442, "*Homo sapiens* RUN and FYVE domain containing 3 (RUFY3), transcript variant 1, mRNA," Jul. 25, 2007; Retrieved from the Internet on Aug. 10, 2010: http://www.ncbi.nlm.nih.gov/sviewer/viewer.fcgi?val . . . pp. 1-4.

GenBank Accession No. NM_001039580, "*Homo sapiens* microtubule-associated protein 9 (MAP9), mRNA," Sep. 3, 2007; Retrieved from the Internet on Aug. 10, 2010: http://www.ncbi.nlm.nih.gov/sviewer/viewer.fcgi?val . . . pp. 1-5.

GenBank Accession No. NM_001043, "*Homo sapiens* solute carrier family 6 (neurotransmitter transporter, noradrenalin), member 2 (SLC6A2), mRNA," Sep. 30, 2007; Retrieved from the Internet on Aug. 11, 2010: http://www.ncbi.nlm.nih.gov/sviewer/viewer.fcgi?val . . . pp. 1-5.

GenBank Accession No. NM_001165, "*Homo sapiens* baculoviral IAP repeat-containing 3 (BIRC3), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-6.

GenBank Accession No. NM_001511, "*Homo sapiens* chemokine (C-X-C motif) ligand 1 (melanoma growth stimulating activity, alpha) (CXCL1), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_001548, "*Homo sapiens* interferon-induced protein with tetratricopeptide repeats 1 (IFIT1), transcript variant 2, mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_001624, "*Homo sapiens* absent in melanoma 1 (AIM1), mRNA," Sep. 25, 2007; Retrieved from the Internet on Aug. 10, 2010: http://www.ncbi.nlm.nih.gov/sviewer/viewer.fcgi?val . . . pp. 1-6.

GenBank Accession No. NM_001673, "*Homo sapiens* asparagine synthetase (ASNS), transcript variant 2, mRNA," Sep. 30, 2007; Retrieved from the Internet on Aug. 10, 2010: http://www.ncbi.nlm.nih.gov/sviewer/viewer.fcgi?val . . . pp. 1-5.

GenBank Accession No. NM_001901, "*Homo sapiens* connective tissue growth factor (CTGF), mRNA," Sep. 30, 2007; Retrieved from the Internet on Aug. 10, 2010: http://www.ncbi.nlm.nih.gov/sviewer/viewer.fcgi?val . . . pp. 1-5.

GenBank Accession No. NM_001902, "*Homo sapiens* cystathionase (cystathionase gamma-lyase) (CTH), transcript variant 1, mRNA," Sep. 17, 2007; Retrieved from the Internet on Aug. 10, 2010: http://www.ncbi.nlm.nih.gov/sviewer/viewer.fcgi?val . . . pp. 1-4.

GenBank Accession No. NM_001946, "*Homo sapiens* dual specificity phosphatase 6 (DUSP6), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_002053, "*Homo sapiens* guanylate binding protein 1, interferon-inducible, 67kDa (GBP1), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_002104, "*Homo sapiens* granzyme K (granzyme 3; tryptase II) (GZMK), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_002167, "*Homo sapiens* inhibitor of DNA binding 3, dominant negative helix-loop-helix protein (ID3), mRNA," Sep. 3, 2007; Retrieved from the Internet on Aug. 10, 2010: http://www.ncbi.nlm.nih.gov/sviewer/viewer.fcgi?val . . . pp. 1-4.

GenBank Accession No. NM_002201, "*Homo sapiens* interferon stimulated exonuclease gene 20kDa (ISG20), mRNA," Sep. 3, 2007; Retrieved from the Internet on Aug. 10, 2010: http://www.ncbi.nlm.nih.gov/sviewer/viewer.fcgi?val . . . pp. 1-3.

GenBank Accession No. NM_002214, "*Homo sapiens* integrin, beta 8 (ITGB8), mRNA," Sep. 25, 2007; Retrieved from the Internet on Aug. 10, 2010: http://www.ncbi.nlm.nih.gov/sviewer/viewer.fcgi?val . . . pp. 1-7.

GenBank Accession No. NM_002234, "*Homo sapiens* potassium voltage-gated channel, shaker-related subfamily, member 5 (KCNA5), mRNA," Sep. 17, 2007; Retrieved from the Internet on Aug. 10, 2010: http://www.ncbi.nlm.nih.gov/sviewer/viewer.fcgi?val . . . pp. 1-5.

GenBank Accession No. NM_002310, "*Homo sapiens* leukemia inhibitory factor receptor alpha (LIFR), mRNA," Sep. 3, 2007; Retrieved from the Internet on Aug. 11, 2010: http://www.ncbi.nlm.nih.gov/sviewer/viewer.fcgi?val . . . pp. 1-8.

GenBank Accession No. NM_002526, "*Homo sapiens* 5'-nucleotidase, ecto (CD73) (NT5E), mRNA," Sep. 26, 2007; Retrieved from the Internet on Aug. 11, 2010: http://www.ncbi.nlm.nih.gov/sviewer/viewer.fcgi?val . . . pp. 1-5.

GenBank Accession No. NM_002609, "*Homo sapiens* platelet-derived growth factor receptor, beta polypeptide (PDGFRB), mRNA," Sep. 30, 2007; Retrieved from the Internet on Aug. 10, 2010: http://www.ncbi.nlm.nih.gov/sviewer/viewer.fcgi?val . . . pp. 1-7.

GenBank Accession No. NM_002658, "*Homo sapiens* plasminogen activator, urokinase (PLAU), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_002670, "*Homo sapiens* plastin 1 (I isoform) (PLS1), mRNA," Nov. 17, 2006; Retrieved from the Internet on Aug. 10, 2010:http://www.ncbi.nlm.nih.gov/sviewer/viewer.fcgi?val . . . pp. 1-4.

GenBank Accession No. NM_002837, "*Homo sapiens* protein tyrosine phosphatase, receptor type, B (PTPRB), transcript variant 2, mRNA," Oct. 7, 2007; Retrieved from the Internet on Aug. 10, 2010: http://www.ncbi.nlm.nih.gov/sviewer/viewer.fcgi?val . . . pp. 1-9.

GenBank Accession No. NM_002849, "*Homo sapiens* protein tyrosine phosphatase, receptor type, R (PTPRR), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-6.

GenBank Accession No. NM_002852, "*Homo sapiens* pentraxin-related gene, rapidly induced by IL-1 beta (PTX3), mRNA," Sep. 25, 2007; Retrieved from the Internet on Aug. 10, 2010: http://www.ncbi.nlm.nih.gov/sviewer/viewer.fcgi?val . . . pp. 1-4.

GenBank Accession No. NM_002930, "*Homo sapiens* RAS-like without CAAX 2 (RIT2), mRNA," Sep. 29, 2007; Retrieved from the Internet on Aug. 10, 2010: http://www.ncbi.nlm.nih.gov/sviewer/viewer.fcgi?val . . . pp. 1-3.

GenBank Accession No. NM_002982, "*Homo sapiens* chemokine (C—C motif) ligand 2 (CCL2), mRNA," Sep. 30, 2007; Retrieved from the Internet on Aug. 10, 2010: http://www.ncbi.nlm.nih.gov/sviewer/viewer.fcgi?val . . . pp. 1-4.

GenBank Accession No. NM_003414, "*Homo sapiens* zinc finger protein 267 (ZNF267), transcript variant 498723, mRNA," Sep. 3, 2007; Retrieved from the Internet on Aug. 10, 2010: http://www.ncbi.nlm.nih.gov/sviewer/viewer.fcgi?val . . . pp. 1-3.

GenBank Accession No. NM_003425, "*Homo sapiens* zinc finger protein 45 (ZNF45), mRNA," Jun. 3, 2007; Retrieved from the Internet on Aug. 10, 2010: http://www.ncbi.nlm.nih.gov/sviewer/viewer.fcgi?val . . . pp. 1-4.

(56) References Cited

OTHER PUBLICATIONS

GenBank Accession No. NM_003483, "*Homo sapiens* high mobility group AT-hook 2 (HMGA2), transcript variant 1, mRNA," Sep. 24, 2007; Retrieved from the Internet on Aug. 10, 2010: http://www.ncbi.nlm.nih.gov/sviewer/viewer.fcgi?val . . . pp. 1-5.
GenBank Accession No. NM_003558, "*Homo sapiens* phosphatidylinositol-4-phosphate 5-kinase, type I, beta (PIP5KIB), transcript variant 2, mRNA," Jun. 26, 2007; Retrieved from the Internet on Aug. 10, 2010: http://www.ncbi.nlm.nih.gov/sviewer/viewer.fcgi?val . . . pp. 1-5.
GenBank Accession No. NM_003706, "*Homo sapiens* phospholipase A2, group IVC (cytosolic, calcium-independent) (PLA2G4C), mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_003786, "*Homo sapiens* ATP-binding cassette, sub-family C (CFTR/MRP), member 3 (ABCC3), mRNA," Sep. 25, 2007; Retrieved from the Internet on Aug. 10, 2010: http://www.ncbi.nlm.nih.gov/sviewer/viewer.fcgi?val . . . pp. 1-8.
GenBank Accession No. NM_003841, "*Homo sapiens* tumor necrosis factor receptor superfamily, member 10c, decoy without an intracellular domain (TNFRSF10C), mRNA," Sep. 3, 2007; Retrieved from the Internet on Aug. 11, 2010: http://www.ncbi.nlm.nih.gov/sviewer/viewer.fcgi?val . . . pp. 1-4.
GenBank Accession No. NM_003862, "*Homo sapiens* fibroblast growth factor 18 (FGF18), mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_003897, "*Homo sapiens* immediate early response 3 (IER3), mRNA," Sep. 25, 2007; Retrieved from the Internet on Aug. 10, 2010: http://www.ncbi.nlm.nih.gov/sviewer/viewer.fcgi?val . . . pp. 1-4.
GenBank Accession No. NM_004170, "*Homo sapiens* solute carrier family 1 (neuronal/epithelial high affinity glutamate transporter, system XAG), member 1 (SLC1A1), mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_004185, "*Homo sapiens* wingless-type MMTV integration site family, member 2B (WNT2B), transcript variant VNT-2B1, mRNA," Sep. 26, 2007; Retrieved from the Internet on Aug. 10, 2010: http://www.ncbi.nlm.nih.gov/sviewer/viewer.fcgi?val . . . pp. 1-4.
GenBank Accession No. NM_004233, "*Homo sapiens* CD83 molecule (CD83), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-4.
GenBank Accession No. NM_004294, "*Homo sapiens* mitochondrial translational release factor 1 (MTRF1), nuclear gene encoding mitochondrial protein, mRNA," Jun. 26, 2007; Retrieved from the Internet on Aug. 10, 2010: http://www.ncbi.nlm.nih.gov/sviewer/viewer.fcgi?val . . . pp. 1-4.
GenBank Accession No. NM_004318, "*Homo sapiens* aspartate beta-hydroxylase (ASPH), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-6.
GenBank Accession No. NM_004334, "*Homo sapiens* bone marrow stromal cell antigen 1 (BST1), mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_004464, "*Homo sapiens* fibroblast growth factor 5 (FGFS), transcript variant 1, mRNA," Sep. 25, 2007; Retrieved from the Internet on Aug. 10, 2010: http://www.ncbi.nlm.nih.gov/sviewer/viewer.fcgi?val . . . pp. 1-5.
GenBank Accession No. NM_004466, "*Homo sapiens* glypican 5 (GPC5), mRNA," Sep. 3, 2007; Retrieved from the Internet on Aug. 10, 2010: http://www.ncbi.nlm.nih.gov/sviewer/viewer.fcgi?val . . . pp. 1-4.
GenBank Accession No. NM_004556, "*Homo sapiens* nuclear factor of kappa light polypeptide gene enhancer in B-cells inhibitor, epsilon (NFKBIE), mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_004843, "*Homo sapiens* interleukin 27 receptor, alpha (IL27RA), mRNA," Sep. 3, 2007; Retrieved from the Internet on Aug. 10, 2011: http://www.ncbi.nlm.nih.gov/sviewer/viewer.fcgi?val . . . pp. 1-5.
GenBank Accession No. NM_005031, "*Homo sapiens* FXYD domain containing ion transport regulator 1 (phospholemman) (FXYD1), transcript variant a, mRNA," Sep. 24, 2007; Retrieved from the Internet on Aug. 10, 2010: http://www.ncbi.nlm.nih.gov/sviewer/viewer.fcgi?val . . . pp. 1-4.
GenBank Accession No. NM_005039, "*Homo sapiens* proline-rich protein BstNI subfamily 1 (PRB1), transcript variant 1, mRNA," Jul. 29, 2007; Retrieved from the Internet on Aug. 10, 2010: http://www.ncbi.nlm.nih.gov/sviewer/viewer.fcgi?val . . . pp. 1-4.
GenBank Accession No. NM_005185, "*Homo sapiens* calmodulin-like 3 (CALML3), mRNA," Sep. 17, 2007; Retrieved from the Internet on Aug. 10, 2010: http://www.ncbi.nlm.nih.gov/sviewer/viewer.fcgi?val . . . pp. 1-3.
GenBank Accession No. NM_005261, "*Homo sapiens* GTP binding protein overexpressed in skeletal muscle (GEM), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-4.
GenBank Accession No. NM_005341, "*Homo sapiens* zinc finger and BTB domain containing 48 (ZBTB48), mRNA," Jun. 26, 2007; Retrieved from the Internet on Aug. 10, 2010: http://www.ncbi.nlm.nih.gov/sviewer/viewer.fcgi?val . . . pp. 1-4.
GenBank Accession No. NM_005345, "*Homo sapiens* heat shock 70kDa protein IA (HSPA1A), mRNA," Sep. 30, 2007; Retrieved from the Internet on Aug. 10, 2010: http://www.ncbi.nlm.nih.gov/sviewer/viewer.fcgi?val . . . pp. 1-4.
GenBank Accession No. NM_005347, "*Homo sapiens* heat shock 70kDa protein 5 (glucose-regulated protein, 78kDa) (HSPAS), mRNA," Sep. 3, 2007; Retrieved from the Internet on Aug. 10, 2010: http://www.ncbi.nlm.nih.gov/sviewer/viewer.fcgi?val . . . pp. 1-5.
GenBank Accession No. NM_005444, "*Homo sapiens* RCD1 required for cell differentiation) homolog (S. pombe) (RQCD1), mRNA," Sep. 25, 2007; Retrieved from the Internet on Aug. 10, 2010: http://www.ncbi.nlm.nih.gov/sviewer/viewer.fcgi?val . . . pp. 1-3.
GenBank Accession No. NM_005515, "*Homo sapiens* motor neuron and pancreas homeobox 1 (MNX1), mRNA," Sep. 30, 2007; Retrieved from the Internet on Aug. 10, 2010: http://www.ncbi.nlm.nih.gov/sviewer/viewer.fcgi?val . . . pp. 1-4.
GenBank Accession No. NM_005527, "*Homo sapiens* heat shock 70kDa protein 1-like (HSPA1L), mRNA," Sep. 3, 2007; Retrieved from the Internet on Aug. 11, 2010: 1http://www.ncbi.nlm.nih.gov/sviewer/viewer.fcgi?val . . . pp. 1-4.
GenBank Accession No. NM_005923, "*Homo sapiens* mitogen-activated protein kinase kinase kinase 5 (MAP3K5), mRNA," Sep. 3, 2007; Retrieved from the Internet on Aug. 10, 2010: http://www.ncbi.nlm.nih.gov/sviewer/viewer.fcgi?val . . . pp. 1-7.
GenBank Accession No. NM_006187, "*Homo sapiens* 2'-5'-oligoadenylate synthetase 3, 100kDa (OAS3), mRNA," Sep. 25, 2007; Retrieved from the Internet on Aug. 10, 2010: http://www.ncbi.nlm.nih.gov/sviewer/viewer.fcgi?val . . . pp. 1-6.
GenBank Accession No. NM_006393, "*Homo sapiens* nebulette (NEBL), transcript variant 1, mRNA," Sep. 17, 2007; Retrieved from the Internet on Aug. 10, 2010: http://www.ncbi.nlm.nih.gov/sviewer/viewer.fcgi?val . . . pp. 1-7.
GenBank Accession No. NM_006417, "*Homo sapiens* interferon-induced protein 44 (IFI44), mRNA," Jun. 26, 2007; Retrieved from the Internet on Aug. 10, 2010: http://www.ncbi.nlm.nih.gov/sviewer/viewer.fcgi?val . . . pp. 1-3.
GenBank Accession No. NM_006434, "*Homo sapiens* sorbin and SH3 domain containing 1 (SORBS1), transcript variant 1, mRNA," Sep. 3, 2007; Retrieved from the Internet on Aug. 10, 2010: http://www.ncbi.nlm.nih.gov/sviewer/viewer.fcgi?val . . . pp. 1-7.
GenBank Accession No. NM_006509, "*Homo sapiens* v-rel reticuloendotheliosis viral oncogene homlog B, nuclear factor of kappa light polypeptide gene enhancer in B-cells 3 (avian) (RELB),

(56) References Cited

OTHER PUBLICATIONS mRNA," Sep. 30, 2007; Retrieved from the Internet on Aug. 10, 2010: http://www.ncbi.nlm.nih.gov/sviewer/viewer.fcgi?val . . . pp. 1-5.

GenBank Accession No. NM_006516, "*Homo sapiens* solute carrier family 2 (facilitated glucose transporter), member 1 (SLC2A1), mRNA," Sep. 24, 2007; Retrieved from the Internet on Aug. 10, 2010: http://www.ncbi.nlm.nih.gov/sviewer/viewer.fcgi?val . . . pp. 1-5.

GenBank Accession No. NM_006547, "*Homo sapiens* insulin-like growth factor 2 mRNA binding protein 3 (IGF2BP3), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_006611, "*Homo sapiens* killer cell lectin-like receptor subfamily A, member 1 (KLRA1), mRNA," Jul. 29, 2007; Retrieved from the Internet on Aug. 10, 2010: http://www.ncbi.nlm.nih.gov/sviewer/viewer.fcgi?val . . . pp. 1-3.

GenBank Accession No. NM_006650, "*Homo sapiens* complexin 2 (CPLX2), transcript variant 1, mRNA," Sep. 26, 2007; Retrieved from the Internet on Aug. 10, 2010: http://www.ncbi.nlm.nih.gov/sviewer/viewer.fcgi?val . . . pp. 1-5.

GenBank Accession No. Nm 006793, "*Homo sapiens* peroxiredoxin 3 (PRDX3), nuclear gene encoding mitochondrial protein, transcript variant 1, mRNA," Sep. 17, 2007; Retrieved from the Internet on Aug. 11, 2010: http://www.ncbi.nlm.nih.gov/sviewer/viewer.fcgi?val . . . pp. 1-5.

GenBank Accession No. NM_006851, "*Homo sapiens* GLI pathogenesis-related 1 (glioma) (GLIPR1), mRNA," Sep. 25, 2007; Retrieved from the Internet on Aug. 10, 2010: http://www.ncbi.nlm.nih.gov/sviewer/viewer.fcgi?val . . . pp. 1-5.

GenBank Accession No. NM_006933, "Homo sapiens solute carrier family 5 (inositol transporters), member 3 (SLC5A3), mRNA," Sep. 3, 2007; Retrieved from the Internet on Aug. 10, 2010: http://www.ncbi.nlm.nih.gov/sviewer/viewer.fcgi?val . . . pp. 1-6.

GenBank Accession No. NM_007107, "*Homo sapiens* signal sequence receptor, gamma (translocon-associated protein gamma) (SSR3), mRNA," Jun. 3, 2007; Retrieved from the Internet on Aug. 10, 2010: http://www.ncbi.nlm.nih.gov/sviewer/viewer.fcgi?val . . . pp. 1-4.

GenBank Accession No. NM_007211, "*Homo sapiens* Ras association (RalGDS/AF-6) domain family 8 (RASSF8), mRNA," Sep. 29, 2007; Retrieved from the Internet on Aug. 10, 2010: http://www.ncbi.nlm.nih.gov/sviewer/viewer.fcgi?val . . . pp. 1-3.

GenBank Accession No. NM_007282, "*Homo sapiens* ring finger protein 13 (RNF13), transcript variant 1, mRNA," Jun. 26, 2007; Retrieved from the Internet on Aug. 10, 2010: http://www.ncbi.nlm.nih.gov/sviewer/viewer.fcgi?val . . . pp. 1-4.

GenBank Accession No. NM_007314, "*Homo sapiens* v-abl Abelson murein leukemia viral oncogene homolog 2 (arg, Abelson-related gene) (ABL2), transcript variant b, mRNA," Sep. 3, 2007; Retrieved from the Internet on Aug. 10, 2010: http://www.ncbi.nlm.nih.gov/sviewer/viewer.fcgi?val . . . pp. 1-8.

GenBank Accession No. NM_012329, "*Homo sapiens* monocyte to macrophage differentiation-associated (MMD), mRNA," Jun. 26, 2007; Retrieved from the Internet on Aug. 10, 2010: http://www.ncbi.nlm.nih.gov/sviewer/viewer.fcgi?val . . . pp. 1-3.

GenBank Accession No. NM_4012377, "*Homo sapiens* olfactory receptor, family 7, subfamily C, member 2 (OR7C2), mRNA," Jun. 3, 2007; Retrieved from the Internet on Aug. 10, 2010: http://www.ncbi.nlm.nih.gov/sviewer/viewer.fcgi?val . . . pp. 1-3.

GenBank Accession No. NM_012419, "*Homo sapiens* regulator of G-protein signaling 17 (RGS17), mRNA," Aug. 24, 2007; Retrieved from the Internet on Aug. 11, 2010: http://www.ncbi.nlm.nih.gov/sviewer/viewer.fcgi?val . . . pp. 1-3.

GenBank Accession No. NM_013261, "*Homo sapiens* peroxisome proliferator-activated receptor gamma, coactivator 1 alpha (PPARGC1A), mRNA," Oct. 7, 2007; Retrieved from the Internet on Aug. 10, 2010: http://www.ncbi.nlm.nih.gov/sviewer/viewer.fcgi?val . . . pp. 1-7.

GenBank Accession No. NM_013989, "*Homo sapiens* deiodinase, iodothyronine, type II (DI02), transcript variant 1, mRNA," Sep. 24, 2007; Retrieved from the Internet on Aug. 10, 2010:http://www.ncbi.nlm.nih.gov/sviewer/viewer.fcgi?val . . . pp. 1-6.

GenBank Accession No. NM_014314, "*Homo sapiens* DEAD (Asp-Glu-Ala-Asp) box polypeptide 58 (DDX58), mRNA," Sep. 30, 2007; Retrieved from the Internet on Aug. 10, 2010: http://www.ncbi.nlm.gov/sviewer/viewer.fcgi?val . . . pp. 1-7.

GenBank Accession No. NM_014331, "*Homo sapiens* solute carrier family 7, "cationic amino acid transporter, y+ system) member 11 (SLC7A11), mRNA, Sep. 3, 2007; Retrieved from the Internet on Aug. 10, 2010: http://www.ncbi.nlm.gov/sviewer/viewer.fcgi?val . . . pp. 1-6.

GenBank Accession No. NM_014351, "*Homo sapiens* sulfotransferase family 4A, member 1 (SULT4A1), mRNA," Sep. 3, 2007; Retrieved from the Internet on Aug. 10, 2010: http://www.ncbi.nlm.gov/sviewer/viewer.fcgi?val . . . pp. 1-4.

GenBank Accession No. NM_014632, "*Homo sapiens* microtubule associated monoxygenase, calponin and LIM domain containing 2 (MICAL2), mRNA," Sep. 25, 2007; Retrieved from the Internet on Aug. 10, 2010: http://www.ncbi.nlm.gov/sviewer/viewer.fcgi?val . . . pp. 1-6.

GenBank Accession No. NM_014729, "*Homo sapiens* thymocyte selection-associated high mobility group box (TOX), mRNA," Sep. 3, 2007; Retrieved from the Internet on Aug. 10, 2010: http://www.ncbi.nlm.gov/sviewer/viewer.fcgi?val . . . pp. 1-4.

GenBank Accession No. NM_015009, "*Homo sapiens* PDZ domain containing RING finger 3 (PDZRN3), mRNA," Sep. 3, 2007; Retrieved from the Internet on Aug. 10, 2010: http://www.ncbi.nlm.gov/sviewer/viewer.fcgi?val . . . pp. 1-4.

GenBank Accession No. NM_015074, "*Homo sapiens* kinesin family member 1B (KIF1B), transcript variant 1, mRNA," Sep. 3, 2007; Retrieved from the Internet on Aug. 10, 2010: http://www.ncbi.nlm.gov/sviewer/viewer.fcgi?val . . . pp. 1-10.

GenBank Accession No. NM_015359, "*Homo sapiens* solute carrier family 39 (zinc transporter), member 14 (SLC39A14), mRNA," Sep. 29, 2007; Retrieved from the Internet on Aug. 10, 2010: http://www.ncbi.nlm.gov/sviewer/viewer.fcgi?val . . . pp. 1-4.

GenBank Accession No. NM_016125, "*Homo sapiens* PTD016 protein (LOC51136), mRNA," Jun. 26, 2007; Retrieved from the Internet on Aug. 10, 2010: http://www.ncbi.nlm.gov/sviewer/viewer.fcgi?val . . . pp. 1-3.

GenBank Accession No. NM_016239, "*Homo sapiens* myosin XVA (MY015A), mRNA," Sep. 25, 2007; Retrieved from the Internet on Aug. 11, 2010: http://www.ncbi.nlm.gov/sviewer/viewer.fcgi?val . . . pp. 1-12.

GenBank Accession No. NM_016354, "*Homo sapiens* solute carrier organic anion transporter family, member 4A1 (SLCO4A1), mRNA," Sep. 3, 2007; Retrieved from the Internet on Aug. 10, 2010: http://www.ncbi.nlm.gov/sviewer/viewer.fcgi?val . . . pp. 1-5.

GenBank Accession No. NM_016613, "*Homo sapiens* chromosome 4 open reading frame (C4orf18), transcript variant 2, mRNA," Sep. 29, 2007; Retrieved from the Internet on Aug. 10, 2010: http://www.ncbi.nlm.gov/sviewer/viewer.fcgi?val . . . pp. 1-4.

GenBank Accession No. NM_016831, "*Homo sapiens* period homolog 3 (*Drosphila*) (PER3), mRNA," Sep. 26, 2007; Retrieved from the Internet on Aug. 10, 2010: http://www.ncbi.nlm.gov/sviewer/viewer.fcgi?val . . . pp. 1-7.

GenBank Accession No. NM_017577, "*Homo sapiens* GRAM domain containing 1C (GRAMD1C), mRNA," Sep. 29, 2007; Retrieved from the Internet on Aug. 11, 2010: http://www.ncbi.nlm.gov/sviewer/viewer.fcgi?val . . . pp. 1-4.

GenBank Accession No. NM_017600, "*Homo sapiens* golgi autoantigen, golgin subfamily A, 2-like 1 (GOLGA2L1), mRNA," Jun. 26; 2007; Retrieved from the Internet on Aug. 10, 2010: http://www.ncbi.nlm.gov/sviewer/viewer.fcgi?val . . . pp. 1-4.

GenBank Accession No. NM_017638, "Homo sapiens mediator complex subunit 18 (MED18), mRNA," Aug. 4, 2007; Retrieved from the Internet on Aug. 11, 2010: http://www.ncbi.nlm.gov/sviewer/viewer.fcgi?val . . . pp. 1-3.

(56) References Cited

OTHER PUBLICATIONS

GenBank Accession No. NM_017644, "*Homo sapiens* kelch-like 24 (*Drosophila*) (KLHL24), mRNA," Aug. 4, 2007; Retrieved from the Internet on Aug. 10, 2010: http://www.ncbi.nlm.gov/sviewer/viewer.fcgi?val . . . pp. 1-4.
GenBank Accession No. NM_018027, "*Homo sapiens* FERM domain containing 4A (FRMD4A), mRNA," Jun. 23, 2007; Retrieved from the Internet on Aug. 10, 2010: http://www.ncbi.nlm.gov/sviewer/viewer.fcgi?val . . . pp. 1-6.
GenBank Accession No. NM_018284, "*Homo sapiens* guanylate binding protein 3 (GBP3), mRNA," Sep. 25, 2007; Retrieved from the Internet on Aug. 10, 2010: http://www.ncbi.nlm.gov/sviewer/viewer.fcgi?val . . . pp. 1-4.
GenBank Accession No. NM_018371, "*Homo sapiens* chondroitin bctal,4 N-acetylgalactosaminyltransferase (ChGn), mRNA," Sep. 3, 2007; Retrieved from the Internet on Aug. 10, 2010: http://www.ncbi.nlm.gov/sviewer/viewer.fcgi?val . . . pp. 1-4.
GenBank Accession No. NM_018372, "*Homo sapiens* chromosome 1 open reading frame 103 (Clorf103), transcript variant 1, mRNA," Jun. 26, 2007; Retrieved from the Internet on Aug. 11, 2010: http://www.ncbi.nlm.gov/sviewer/viewer.fcgi?val . . . pp. 1-4.
GenBank Accession No. NM_018664, "*Homo sapiens* Jun dimerization protein p21SNFT (SNFT), mRNA," Sep. 3, 2007; Retrieved from the Internet on Aug. 11, 2010: http://www.ncbi.nlm.gov/sviewer/viewer.fcgi?val . . . pp. 1-2.
GenBank Accession No. NM_018836, "*Homo sapiens* adherens junction associated protein 1 (AJAP1), transcript variant 1, mRNA," Sep. 3, 2007; Retrieved from the Internet on Aug. 10, 2010: http://www.ncbi.nlm.gov/sviewer/viewer.fcgi?val . . . pp. 1-3.
GenBank Accession No. NM_019555, "*Homo sapiens* Rho guanine nucleotide exchange factor (GEF) 3 (ARHGEF3), mRNA," Sep. 26, 2007; Retrieved from the Internet on Aug. 10, 2010: http://www.ncbi.nlm.gov/sviewer/viewer.fcgi?val . . . pp. 1-4.
GenBank Accession No. NM_019891, "*Homo sapiens* ERO1-like beta (S. cerevisiae) (ERO1LB), mRNA," Sep. 3, 2007; Retrieved from the Internet on Aug. 10, 2010: http://www.ncbi.nlm.gov/sviewer/viewer.fcgi?val . . . pp. 1-4.
GenBank Accession No. NM_020359, "*Homo sapiens* phospholipid scramblase 2 (PLSCR2), mRNA," Nov. 17, 2006; Retrieved from the Internet on Aug. 10, 2010: http://www.ncbi.nlm.gov/sviewer/viewer.fcgi?val . . . pp. 1-3.
GenBank Accession No. NM_020436, "*Homo sapiens* sal-like 4 (*Drosophila*) (SALL4), mRNA," Sep. 25, 2007; Retrieved from the Internet on Aug. 10, 2010: http://www.ncbi.nlm.gov/sviewer/viewer.fcgi?val . . . pp. 1-5.
GenBank Accession No. NM_020683, "*Homo sapiens* adenosine A3 receptor (ADORA3), transcript variant 1, mRNA," Sep. 3, 2007; Retrieved from the Internet on Aug. 10, 2010: http://www.ncbi.nlm.gov/sviewer/viewer.fcgi?val . . . pp. 1-5.
GenBank Accession No. NM_020731, "*Homo sapiens* aryl-hydrocarbon receptor repressor (AHRR), mRNA," Sep. 30, 2007; Retrieved from the Internet on Aug. 10, 2010: http://www.ncbi.nlm.gov/sviewer/viewer.fcgi?val . . . pp. 1-6.
GenBank Accession No. NM_020799, "*Homo sapiens* STAM binding protein-like 1 (STAMBPL1), mRNA," Sep. 25, 2007; Retrieved from the Internet on Aug. 10, 2010: http://www.ncbi.nlm.gov/sviewer/viewer.fcgi?val . . . pp. 1-4.
GenBank Accession No. NM_020904, "*Homo sapiens* pleckstrin homology domain containing, family A (phosphoinositide binding specific) member 4 (PLEKHA4), mRNA," Nov. 17, 2006; Retrieved from the Internet on Aug. 10, 2010: http://www.ncbi.nlm.gov/sviewer/viewer.fcgi?val . . . pp. 1-4.
GenBank Accession No. NM_020943, "*Homo sapiens* KIAA1604 protein (KIAA1604), mRNA," Jul. 25, 2007; Retrieved from the Internet on Aug. 10, 2010: http://www.ncbi.nlm.gov/sviewer/viewer.fcgi?val . . . pp. 1-4.
GenBank Accession No. NM_020988, "*Homo sapiens* guanine nucleotide binding protein (G protein), alpha activating activity polypeptide O (GNAO1), transcript variant 1, mRNA," Sep. 25, 2007; Retrieved from the Internet on Aug. 10, 2010: http://www.ncbi.nlm.gov/sviewer/viewer.fcgi?val . . . pp. 1-4.
GenBank Accession No. NM_021101, "*Homo sapiens* claudin 1 (CLDN1), mRNA" Sep. 26, 2007; Retrieved from the Internet on Aug. 10, 2010: http://www.ncbi.nlm.gov/sviewer/viewer.fcgi?val . . . pp. 1-4.
GenBank Accession No. NM_021377, "Mus musculus VPS10 domain receptor protein SORCS 1 (Sorcs1), mRNA," Sep. 3, 2007; Retrieved from the Internet on Aug. 10, 2010: http://www.ncbi.nlm.gov/sviewer/viewer.fcgi?val . . . pp. 1-6.
GenBank Accession No. NM_021727, "*Homo sapiens* fatty acid desaturase 3 (FADS3), mRNA," Nov. 17, 2006; Retrieved from the Internet on Aug. 10, 2010: http://www.ncbi.nlm.gov/sviewer/viewer.fcgi?val . . . pp. 1-4.
GenBank Accession No. NM_021813, "*Homo sapiens* BTB and CNC homology 1, basic leucine zipper transcription factor 2 (BACH2), mRNA," Sep. 3, 2007; Retrieved from the Internet on Aug. 11, 2010: http://www.ncbi.nlm.gov/sviewer/viewer.fcgi?val . . . pp. 1-6.
GenBank Accession No. NM_021990, "*Homo sapiens* gamma-aminobutyric acid (GABA) A receptor, epsilon (GABRE), transcript variant 4, mRNA," Sep. 25, 2007; Retrieved from the Internet on Aug. 10, 2010: http://www.ncbi.nlm.gov/sviewer/viewer.fcgi?val . . . pp. 1-5.
GenBank Accession No. NM_022044, "*Homo sapiens* stromal cell-derived factor 2-like 1 (SDF2L1), mRNA," Jun. 27, 2007; Retrieved from the Internet on Aug. 10, 2010: http://www.ncbi.nlm.gov/sviewer/viewer.fcgi?val . . . pp. 1-2.
GenBank Accession No. NM_022047, "*Homo sapiens* differentially expressed in FDCP 6 homolog (mouse) (DEF6), mRNA," Sep. 3, 2007; Retrieved from the Internet on Aug. 10, 2010: http://www.ncbi.nlm.gov/sviewer/viewer.fcgi?val . . . pp. 1-4.
GenBank Accession No. NM_022097, "*Homo sapiens* calcineurin B homologous protein 2 (CHP2), mRNA." Sep. 30, 2007; Retrieved from the Internet on Aug. 11, 2010: http://www.ncbi.nlm.gov/sviewer/viewer.fcgi?val . . . pp. 1-3.
GenBank Accession No. NM_022115, "*Homo sapiens* PR domain containing 15 (PRDM15), transcript variant 1, mRNA," Jun. 25, 2007; Retrieved from the Internet on Aug. 10, 2010: http://www.ncbi.nlm.gov/sviewer/viewer.fcgi?val . . . pp. 1-6.
GenBank Accession No. NM_022160, "*Homo sapiens* DMRT-like family A1 (DMRTA1), mRNA," Jun. 3, 2007; Retrieved from the Internet on Aug. 10, 2010: http://www.ncbi.nlm.gov/sviewer/viewer.fcgi?val . . . pp. 1-3.
GenBank Accession No. NM_022842, "*Homo sapiens* CUB domain containing protein 1 (CDCP1), transcript variant 1, mRNA," Sep. 3, 2007; Retrieved from the Internet on Aug. 10, 2010: http://www.ncbi.nlm.gov/sviewer/viewer.fcgi?val . . . pp. 1-5.
GenBank Accession No. NM_023070, "*Homo sapiens* zinc finger protein 643 (ZNF643), mRNA," Jun. 3, 2007; Retrieved from the Internet on Aug. 10, 2010: http://www.ncbi.nlm.gov/sviewer/viewer.fcgi?val . . . pp. 1-3.
GenBank Accession No. NM_024050, "*Homo sapiens* chromosome 19 open reading frame 58 (C19orf58), mRNA," Jul. 1, 2007; Retrieved from the Internet on Aug. 10, 2010: http://www.ncbi.nlm.gov/sviewer/viewer.fcgi?val . . . pp. 1-2.
GenBank Accession No. NM_024050, "*Homo sapiens* chromosome 19 open reading frame 58 (C19orf58), mRNA," Jul. 1, 2007; Retrieved from the Internet on Aug. 11, 2010: http://www.ncbi.nlm.gov/sviewer/viewer.fcgi?val . . . pp. 1-2.
GenBank Accession No. NM_024525, "*Homo sapiens* tetratricopeptide repeat domain 13 (TTC13), mRNA," Jun. 3, 2007; Retrieved from the Internet on Aug. 10, 2010: http://www.ncbi.nlm.gov/sviewer/viewer.fcgi?val . . . pp. 1-4.
GenBank Accession No. NM_024861, "*Homo sapiens* chromosome 2 open reading frame 54 (C2orf54), transcript variant 2, mRNA," Jul. 1, 2007; Retrieved from the Internet on Aug. 10, 2010: http://www.ncbi.nlm.gov/sviewer/viewer.fcgi?val . . . pp. 1-3.
GenBank Accession No. NM_025169, "*Homo sapiens* zinc finger protein 167 (ZNF167), transcript variant 2, mRNA," Jun. 26, 2007; Retrieved from the Internet on Aug. 10, 2010: http://www.ncbi.nlm.gov/sviewer/viewer.fcgi?val . . . pp. 1-3.
GenBank Accession No. NM_031217, "*Homo sapiens* kinesin family member 18A (KIF18A), mRNA," Sep. 25, 2007; Retrieved

(56) References Cited

OTHER PUBLICATIONS from the Internet on Aug. 10, 2010: http://www.ncbi.nlm.gov/sviewer/viewer.fcgi?val . . . pp. 1-4.
GenBank Accession No. NM_031466, "*Homo sapiens* KIT and IKK(beta) binding protein (NIBP), mRNA," Sep. 29, 2007; Retrieved from the Internet on Aug. 10, 2010: http://www.ncbi.nlm.gov/sviewer/viewer.fcgi?val . . . pp. 1-5.
GenBank Accession No. NM_031938, "*Homo sapiens* beta-carotene dioxygenase 2 (BCD02), transcript variant 1, mRNA," Jun. 26, 2007; Retrieved from the Internet on Aug. 10, 2010: http://www.ncbi.nlm.gov/sviewer/viewer.fcgi?val . . . pp. 1-4.
GenBank Accession No. NM_032188, "*Homo sapiens* MYST histone acetyltransferase 1 (MYST1), transcript variant 1, mRNA," Sep. 30, 2007; Retrieved from the Internet on Aug. 10, 2010: http://www.ncbi.nlm.gov/sviewer/viewer.fcgi?val . . . pp. 1-4.
GenBank Accession No. NM_032228, "*Homo sapiens* male sterility domain containing 2 (MLSTD2), mRNA," Sep. 25, 2007; Retrieved from the Internet on Aug. 10, 2010: http://www.ncbi.nlm.gov/sviewer/viewer.fcgi?val . . . pp. 1-5.
GenBank Accession No. NM_032266, "*Homo sapiens* chromosome 2 open reading frame 16 (C2orf16), mRNA," Jul. 24, 2007; Retrieved from the Internet on Aug. 11, 2010: http://www.ncbi.nlm.gov/sviewer/viewer.fcgi?val . . . pp. 1-4.
GenBank Accession No. NM_032434, "*Homo sapiens* zinc finger protein 512 (ZNF512), mRNA," Jun. 22, 2007; Retrieved from the Internet on Aug. 10, 2010: http://www.ncbi.nlm.gov/sviewer/viewer.fcgi?val . . . pp. 1-4.
GenBank Accession No. NM_032523, "*Homo sapiens* oxysterol binding protein-like 6 (OSBPL6), transcript variant 1, mRNA," Nov. 17, 2006; Retrieved from the Internet on Aug. 10, 2010: http://www.ncbi.nlm.gov/sviewer/viewer.fcgi?val . . . pp. 1-5.
GenBank Accession No. NM_032778, "*Homo sapiens* MYC induced nuclear antigen (MINA), transcript variant 3, mRNA," Sep. 25, 2007; Retrieved from the Internet on Aug. 10, 2010: http://www.ncbi.nlm.gov/sviewer/viewer.fcgi?val . . . pp. 1-5.
GenBank Accession No. NM_032866, "*Homo sapiens* cingulin-like 1 (CGNL1), mRNA," Jun. 27, 2007; Retrieved from the Internet on Aug. 10, 2010: http://www.ncbi.nlm.gov/sviewer/viewer.fcgi?val . . . pp. 1-5.
GenBank Accession No. NM_033036, "*Homo sapiens* galactose-3-O-sulfotransferase 3 (GAL3ST3), mRNA," Sep. 25, 2007; Retrieved from the Internet on Aug. 10, 2010: http://www.ncbi.nlm.gov/sviewer/viewer.fcgi?val . . . pp. 1-4.
GenBank Accession No. NM_033066, "*Homo sapiens* membrane protein, palmitoylated 4 (MAGUK p55 subfamily member 4) (MPP4) mRNA," Sep. 25, 2007; Retrieved from the Internet on Aug. 10, 2010: http://www.ncbi.nlm.gov/sviewer/viewer.fcgi?val . . . pp. 1-4.
GenBank Accession No. NM_033160, "*Homo sapiens* zinc finger protein 658 (ZNF658), mRNA," Aug. 18, 2007; Retrieved from the Internet on Aug. 11, 2010: http://www.ncbi.nlm.gov/sviewer/viewer.fcgi?val . . . pp. 1-5.
GenBank Accession No. NM_033260, "*Homo sapiens* forkhead box Q1 (FOXQ1), mRNA," Sep. 25, 2007; Retrieved from the Internet on Aug. 10, 2010: http://www.ncbi.nlm.gov/sviewer/viewer.fcgi?val . . . pp. 1-3.
GenBank Accession No. NM_052875, "*Homo sapiens* vacuolar protein sorting 26 homolog B (S. pombe) (VPS26B), mRNA," Jun. 26, 2007; Retrieved from the Internet on Aug. 10, 2010: http://www.ncbi.nlm.gov/sviewer/viewer.fcgi?val . . . pp. 1-3.
GenBank Accession No. NM_052892, "*Homo sapiens* polycystic kidney disease 1-like 2 (PKD1L2), transcript variant 1, mRNA," Sep. 25, 2007; Retrieved from the Internet on Aug. 10, 2010: http://www.ncbi.nlm.gov/sviewer/viewer.fcgi?val . . . pp. 1-8.
GenBank Accession No. NM_053064, "*Homo sapiens* guanine nucleotide binding protein (G protein), gamma 2 (GNG2), mRNA," Sep. 3, 2007; Retrieved from the Internet on Aug. 10, 2010: http://www.ncbi.nlm.gov/sviewer/viewer.fcgi?val . . . pp. 1-4.
GcnBank Accession No. NM_058179, "*Homo sapiens* phosphoscrinc aminotransfcrasc 1 (PSAT1), transcript variant 1, mRNA," Sep. 25, 2007; Retrieved from the Internet on Aug. 10, 2010: http://www.ncbi.nlm.gov/sviewer/viewer.fcgi?val . . . pp. 1-3.
GenBank Accession No. NM_058188, "*Homo sapiens* chromosome 21 open reading frame 67 (C21orf67), mRNA," Dec. 13, 2006; Retrieved from the Internet on Aug. 10, 2010: http://www.ncbi.nlm.gov/sviewer/viewer.fcgi?val . . . pp. 1-2.
GenBank Accession No. NM_080927, "*Homo sapiens* discoidin, CUB and LCCL domain containing 2 (DCBLD2), mRNA," Sep. 30, 2007; Retrieved from the Internet on Aug. 11, 2010: http://www.ncbi.nlm.gov/sviewer/viewer.fcgi?val . . . pp. 1-5.
GenBank Accession No. NM_133492, "*Homo sapiens* N-acylsphingosine amidohydrolase (alkaline ceramidase) 3 (ASAH3), mRNA," Sep. 25, 2007; Retrieved from the Internet on Aug. 10, 2010: http://www.ncbi.nlm.gov/sviewer/viewer.fcgi?val . . . pp. 1-3.
GenBank Accession No. NM_138440, "*Homo sapiens* vasorin (VASN), mRNA," Sep. 3, 2007; Retrieved from the Internet on Aug. 10, 2010: http://www.ncbi.nlm.gov/sviewer/viewer.fcgi?val . . . pp. 1-3.
GenBank Accession No. NM_138467, "*Homo sapiens* tRNA-yW synthesizing protein 3 homolog (S. Cerevisiae) (TYW3), mRNA," Jul. 25, 2007; Retrieved from the Internet on Aug. 10, 2010: http://www.ncbi.nlm.gov/sviewer/viewer.fcgi?val . . . pp. 1-3.
GenBank Accession No. NM_139173, "*Homo sapiens* Na+/H+ exchanger domain containing 1 (NHEDC1), transcript variant 1, mRNA," Sep. 3, 2007; Retrieved from the Internet on Aug. 11, 2010: http://www.ncbi.nlm.gov/sviewer/viewer.fcgi?val . . . pp. 1-3.
GenBank Accession No. NM_139314, "*Homo sapiens* angiopoietin-like 4 (ANGPTL4), transcript variant 1, mRNA," Sep. 3, 2007; Retrieved from the Internet on Aug. 10, 2010: http://www.ncbi.nlm.gov/sviewer/viewer.fcgi?val . . . pp. 1-5.
GenBank Accession No. NM_144620, "*Homo sapiens* leucine rich repeat containing 39 (LRRC39), mRNA," Jun. 26, 2007; Retrieved from the Internet on Aug. 11, 2010: http://www.ncbi.nlm.gov/sviewer/viewer.fcgi?val . . . pp. 1-4.
GenBank Accession No. NM_144633, "*Homo sapiens* potassium voltage-gated channel, subfamily H (eag-related), member 8 (KCNH8), mRNA," Jan. 26, 2007; Retrieved from the Internet on Aug. 11, 2010: http://www.ncbi.nlm.gov/sviewer/viewer.fcgi?val . . . pp. 1-5.
GenBank Accession No. NM_145023, "*Homo sapiens* coiled-coil domain containing 7 (CCDC7), transcript 1, mRNA," Jul. 25, 2007; Retrieved from the Internet on Aug. 10, 2010: http://www.ncbi.nlm.gov/sviewer/viewer.fcgi?val . . . pp. 1-4.
GenBank Accession No. NM_145051, "*Homo sapiens* ring finger protein 183 (RNF183), mRNA," Jul. 24, 2007; Retrieved from the Internet on Aug. 11, 2010: http://www.ncbi.nlm.gov/sviewer/viewer.fcgi?val . . . pp. 1-3.
GenBank Accession No. NM_145306, "*Homo sapiens* chromosome 10 open reading frame 35 (C10orf35), mRNA," Jun. 26, 2007; Retrieved from the Internet on Aug. 10, 2010: http://www.ncbi.nlm.gov/sviewer/viewer.fcgi?val . . . pp. 1-3.
GenBank Accession No. NM_145867, "*Homo sapiens* leukotriene C4 synthase (LTC4S), mRNA," Sep. 25, 2007; Retrieved from the Internet on Aug. 11, 2010: http://www.ncbi.nlm.gov/sviewer/viewer.fcgi?val . . . pp. 1-4.
GenBank Accession No. NM_152377, "*Homo sapiens* chromosome 1 open reading frame 87 (Clorf87), mRNA," Nov. 17, 2006; Retrieved from the Internet on Aug. 11, 2010: http://www.ncbi.nlm.gov/sviewer/viewer.fcgi?val . . . pp. 1-3.
GenBank Accession No. NM_152408, "*Homo sapiens* chromosome 5 open reading frame 37 (C5orf37), transcript variant 2, mRNA," Jul. 5, 2007; Retrieved from the Internet on Aug. 10, 2010: http://www.ncbi.nlm.gov/sviewer/viewer.fcgi?val . . . pp. 1-3.
GenBank Accession No. NM_152525, "*Homo sapiens* amyotrophic lateral sclerosis 2 (juvenile) chromosome region, candidate 11 (ALS2CR11), mRNA," Jun. 27, 2007; Retrieved from the Internet on Aug. 10, 2010: http://www.ncbi.nlm.gov/sviewer/viewer.fcgi?val . . . pp. 1-4.
GenBank Accession No. NM_152649, "*Homo sapiens* mixed lineage kinase domain-like (MLKL), mRNA," Jun. 3, 2007; Retrieved from the Internet on Aug. 10, 2010: http://www.ncbi.nlm.gov/sviewer/viewer.fcgi?val . . . pp. 1-3.
GenBank Accession No. NM_153689, "*Homo sapiens* hypothetical protein FLJ38973 (FLJ38973), mRNA," Jun. 26, 2007; Retrieved

(56) References Cited

OTHER PUBLICATIONS from the Internet on Aug. 10, 2010: http://www.ncbi.nlm.gov/sviewer/viewer.fcgi?val . . . pp. 1-3.
GenBank Accession No. NM_172345, "*Homo sapiens* sperm associated antigen 9 (SPAG9), transcript variant 2, mRNA," Mar. 20, 2007; Retrieved from the Internet on Aug. 10, 2010: http://www.ncbi.nlm.gov/sviewer/viewer.fcgi?val . . . pp. 1-4.
GenBank Accession No. NM_173039, "*Homo sapiens* aquaporin 11 (AQP11), mRNA," Nov. 17, 2006; Retrieved from the Internet on Aug. 10, 2010: http://www.ncbi.nlm.gov/sviewer/viewer.fcgi?val . . . pp. 1-2.
GenBank Accession No. NM_173082, "*Homo sapiens* SNF2 histone linker PHD RING helicase (SHPRH), transcript variant 2, mRNA," Sep. 25, 2007; Retrieved from the Internet on Aug. 10, 2010: http://www.ncbi.nlm.gov/sviewer/viewer.fcgi?val . . . pp. 1-7.
GenBank Accession No. NM_173550, "*Homo sapiens* chromosome 9 open reading frame 93 (C9orf93), mRNA," Jun. 3, 2007; Retrieved from the Internet on Aug. 10, 2010: http://www.ncbi.nlm.gov/sviewer/viewer.fcgi?val . . . pp. 1-6.
GenBank Accession No. NM_175868, "*Homo sapiens* melanoma antigen family A, 6 (MAGEA6), transcript variant 2, mRNA," Sep. 25, 2007; Retrieved from the Internet on Aug. 10, 2010: http://www.ncbi.nlm.gov/sviewer/viewer.fcgi?val . . . pp. 1-3.
GenBank Accession No. NM_180989, "*Homo sapiens* G protein-coupled receptor 180 (GPR180), mRNA," Sep. 26, 2007; Retrieved from the Internet on Aug. 10, 2010: http://www.ncbi.nlm.gov/sviewer/viewer.fcgi?val . . . pp. 1-4.
GenBank Accession No. NM_181795, "*Homo sapiens* protein kinase (cAMP-dependent, catalytic) inhibitor beta (PKIB), transcript variant 1, mRNA," Sep. 3, 2007; Retrieved from the Internet on Aug. 10, 2010: http://www.ncbi.nlm.gov/sviewer/viewer.fcgi?val . . . pp. 1-4.
GenBank Accession No. NM_182728, "*Homo sapiens* solute carrier family 7 (cationic amino acid transporter, y+ system), member 8 (SLC7A8), transcript variant 2, mRNA," Sep. 25, 2007; Retrieved from the Internet on Aug. 10, 2010: http://www.ncbi.nlm.gov/sviewer/viewer.fcgi?val . . . pp. 1-4.
GenBank Accession No. NM_182751, "*Homo sapiens* minichromosome maintenance complex component 10 (MCM10), transcript variant 1, mRNA," Sep. 25, 2007; Retrieved from the Internet on Aug. 11, 2010: http://www.ncbi.nlm.gov/sviewer/viewer.fcgi?val . . . pp. 1-6.
GenBank Accession No. NM_182920, "*Homo sapiens* ADAM metallopeptidase with thrombospondin type 1 motif, 9 (ADAMTS9), mRNA," Sep. 3, 2007; Retrieved from the Internet on Aug. 10, 2010: http://www.ncbi.nlm.gov/sviewer/viewer.fcgi?val . . . pp. 1-8.
GenBank Accession No. NM_183040, "*Homo sapiens* dystrobrevin binding protein 1 (DTNBP1), transcript variant 2, mRNA," Sep. 30, 2007; Retrieved from the Internet on Aug. 10, 2010: http://www.ncbi.nlm.gov/sviewer/viewer.fcgi?val . . . pp. 1-5.
GenBank Accession No. NM_194303, "*Homo sapiens* chromosome 10 open reading frame 39 (C10orf39), mRNA," Nov. 17, 2006; Retrieved from the Internet on Aug. 10, 2010: http://www.ncbi.nlm.gov/sviewer/viewer.fcgi?val . . . pp. 1-3.
GenBank Accession No. NM_198353, "*Homo sapiens* potassium channel tetramerisation domain containing 8 (KCTD8), mRNA," Jun. 3, 2007; Retrieved from the Internet on Aug. 10, 2010: http://www.ncbi.nlm.gov/sviewer/viewer.fcgi?val . . . pp. 1-3.
GenBank Accession No. NM_198404, "*Homo sapiens* potassium channel tetramerisation domain containing 4 (KCTD4), mRNA," Jul. 1, 2007; Retrieved from the Internet on Aug. 10, 2010: http://www.ncbi.nlm.gov/sviewer/viewer.fcgi?val . . . pp. 1-3.
GenBank Accession No. NM_198569, "*Homo sapiens* G protein-coupled receptor 136 (GPR126), transcript variant b1, mRNA," Sep. 3, 2007; Retrieved from the Internet on Aug. 10, 2010: http://www.ncbi.nlm.gov/sviewer/viewer.fcgi?val . . . pp. 1-6.
GenBank Accession No. NM_198833, "*Homo sapiens* serpin peptidase inhibitor, Glade B (ovalbumin), member 8 (SERPINB8), transcript variant 2, mRNA," Sep. 25, 2007; Retrieved from the Internet on Aug. 10, 2010: http://www.ncbi.nlm.gov/sviewer/viewer.fcgi?val . . . pp. 1-5.
GenBank Accession No. NM_198951, "*Homo sapiens* transglutaminase 2 (C polypeptide, protein-glutamine-gamma-glutamyltransferase) (TGM2), transcript variant 2, mRNA," Sep. 25, 2007; Retrieved from the Internet on Aug. 10, 2010: http://www.ncbi.nlm.gov/sviewer/viewer.fcgi?val . . . pp. 1-5.
GenBank Accession No. NM_203434, "*Homo sapiens* immediate early response 5-like (TERSL), mRNA," Jul. 1, 2007; Retrieved from the Internet on Aug. 10, 2010: http://www.ncbi.nlm.gov/sviewer/viewer.fcgi?val . . . pp. 1-4.
GenBank Accession No. NM_205849, "*Homo sapiens* family with sequence similarity 9, member B (FAM9B), mRNA," Sep. 3, 2007; Retrieved from the Internet on Aug. 10, 2010: http://www.ncbi.nlm.gov/sviewer/viewer.fcgi?val . . . pp. 1-3.
GenBank Accession No. NR_001279, "*Homo sapiens* cystatin pseudogene (LOC164380) on chromosome 20," Jun. 27, 2007; Retrieved from the Internet on Aug. 11, 2010: http://www.ncbi.nlm.gov/sviewer/viewer.fcgi?val . . . pp. 1-2.
GenBank Accession No. NR_002186, "*Homo sapiens* hypothetical protein DKEZp58611420 (DKEZp58611420) on chromosome 7," Jun. 27, 2007; Retrieved from the Internet on Aug. 10, 2010: http://www.ncbi.nlm.gov/sviewer/viewer.fcgi?val . . . pp. 1-2.
GenBank Accession No. NR_002802, "*Homo sapiens* trophoblast-derived noncoding RNA (TncRNA) on chromosome 11," Jun. 27, 2007; Retrieved from the Internet on Aug. 10, 2010: http://www.ncbi.nlm.gov/sviewer/viewer.fcgi?val . . . pp. 1-5.
GenBank Accession No. NR_002819, "*Homo sapiens* metastasis associated lung adenocarcinoma transcript 1 (non-coding RNA) (MALAT1) on chromosome 11," Sep. 3, 2007; Retrieved from the Internet on Aug. 10, 2010: http://www.ncbi.nlm.gov/sviewer/viewer.fcgi?val . . . pp. 1-4.
GenBank Accession No. XM_210365, "Predicted: *Homo sapiens* similar to ribosomal protein L24-like (LOC284288), mRNA," Aug. 29, 2006; Retrieved from the Internet on Aug. 10, 2010: http://www.ncbi.nlm.gov/sviewer/viewer.fcgi?val . . . pp. 1-2.
Adler. S.P., et al., "A Canarypox Vector Expressing Cytomegalovirus (CMV) Glycoprotein B Primes for Antibody Responses to a Live Attenuated CMV Vaccine (Towne), " *The Journal of Infectious Diseases*, 180: 843-846 (1999).
Plotkin, S. A., et al., "Caudidate Cytomegalovims Strain for Human Vaccination," *Infection and Immunity*, 12: 521-527 (1975).
Wang, D., et al., "Human Cytomegalovirus Uses Two Distinct Pathways to Enter Retinal Pigmented Epithelial Cells", *PNAS*, 104(50): 20037-20042 (2007).
International Preliminary Report on Patentability, PCT/US2008/079494 Cytomegalovirus Vaccines and Method of Production, dated Apr. 22, 2010.
New Zealand Application No. 584459, Examination Report, dated Jan. 26, 2011.
Australia Application. No. 2008310713, Examiner's first report, dated Apr. 19, 2011.
Singapore Application No. 201002080-8, Written Opinion, dated Jul. 8, 2011.
Singapore Application No. 2010020808, Reply to Written Opinion filed Dec. 23, 2011.
Israel Patent Application No. 204850, Office Action, Free Translation from the Hebrew, State of Fe:rael, Ministry of Justice re: Notification of Defects in Patent Application No. 204.850, dated Jan. 22, 2012.
Singapore Application No. 2010020808, Final Substantive Examination Report, dated Feb. 10, 2012.
Australia Application No. 2008310713, Reply filed Apr. 19, 2012.
China Application No. 200880111084.9, First Office Action, dated Apr. 19, 2012.
New Zealand Application No. 584459, Reply filed May 7, 2012.
Israel Patent Application No. 204850, Reply filed May 29, 2012
European Application No. 08836810.5, Extended Search Report , dated Jun. 13, 2012.
China Application No. 200880111084.9, Reply to First Office Action filed Jun. 29, 2012.

(56) References Cited

OTHER PUBLICATIONS

China Application no. 200880111084.9, Second Office Action , dated Oct. 26, 2012.
European Application No. 08836810.5, Response to Search Report and Opinion filed on Jan. 4, 2013.
Israel Patent Application No. 204850, "Cytomegalovirus Vaccines and Methods of Production", Notification of Defects of Patent Application Translation from the Hebrew, State of Israel, Ministry of Justice dated Mar. 21, 2013.
Japanese Patent Application No. 2010-529076, "Cytomegalovirus Vaccines and Methods of Production", Notice of Grounds for Rejection, Translation from Japanese, dated Mar. 25, 2013.
Mexican Patent Application No. MX/a/210/003713, "Cytomegalovirus Vaccines and Methods of Production", Official Action, Translation of the Requirements Stated by the Examiner, dated May 22, 2013.
Ando, Y., et al., "Enhanced cytopathic effect of human cytomegalovirus on a retinal pigment epithelium cell line, K-1034, by serum-free medium," *Arch. Virol.*, 142(8):1645-1658 (1997).
Esclatine, A., et al., "Human Cytomegalovirus Infects Caco-2 Intestinal Epithelial Cells Basolatterally Regardless of the Differentiation State," *Journal of Virology*, 74(1):513-517 (Jan. 2000).
Guetta, E., et al., "Effect of cytomegalovirus immediate early gene products on endothelial cell gene activity," *Cardiovascular Research*, 50:538-546 (2001).
Scholz, M., et al., "Supernatants from human cytomegalovirus (HCMV)-infected retinal glial cells increase transepithelial electrical resistance in a cell culture model: evidence of HCMV immune escape in the eye?" *Med. Microbiol. Immunol.*, 193:205-208 (2004).
Sinclair, J., "Human cytomegalovirus: Latency and reactivation in the myeloid lineage," *Journal of Clinical Virology*, 41:180-185 (2008).
Smith, J.D., "Human Cytomegalovirus: Demonstration of Permissive Epithelial Cells and Nonpermissive Fibroblastic Cells in a Survey of Human Cell Lines," *Journal of Virology*, 60(2):583-588 (Nov. 1986).
Bodaghi, et al., "Entry of Human Cytomegalovirus into Retinal Pigment Epithelial and Endothelial Cells by Endocytosis," Investigative Ophthalmology & Visual Science, 40(11):2598-2607 (1999).
Dargan, et al., "Sequential Mutations Associated with Adaptation of Human Cytomegalovirus to Growth in Cell Culture," Journal of General Virology, 91(6):1535-1546 (2010).
Detrick, et al., "Cytomegalovirus Replication in Human Retinal Pigment Epithelial Cells," Investigative Ophthalmology & Visual Science, 37(5):814-825 (1996).
Gerna, et al., "Human Cytomegalovirus and Human Umbilical Vein Endothelial Cells: Restriction of Primary Isolation to Blood Samples and Susceptibilities of Clinical Isolates from Other Sources to Adaptation," Journal of Clinical Microbiology, 40(1):233-238 (2002).
Gerna, et al., "Human Cytomegalovirus Replicates Abortively in Polymorphonuclear Leukocytes After Transfer from Infected Endothelial Cells Via Transient Microfusion Events," Journal of Virology, 74(12):5629-5638 (2000).
Gerna, et al., "Rescue of Human Cytomegalovirus Strain (Ad169) Tropism for Both Leukocytes and Human Endothelial Cells," Journal of General Virology, 84(6):pp. 1431-1436 (2003).
Momma, et al., "Differential Expression of Chemokines by Human Retinal Pigment Epithelial Cells Infected with Cytomegalovirus," Investigative Ophthalmology & Visual Science, 44(5):2026-2033 (2003).
Revello, et al., "In Vitro Generation of Human Cytomegalovirus pp65 Antigenemia, Viremia, and Leukodnaemia," Journal of Clinical Investigation, 101(12):2686-2692 (1998).
Search Report, Written Opinion and Invitation to Respond to Written Opinion for Singapore Patent Application No. 2012075594, "Cytomegalovirus Vaccines and Methods of Production", dated Jan. 28, 2015.
Ryckman et al. PNAS, 2008, vol. 105, (37), pp. 14118-14123.

* cited by examiner

CYTOMEGALOVIRUS VACCINES AND METHODS OF PRODUCTION

RELATED APPLICATIONS

This application is a continuation of U.S. application Ser. No. 12/681,504, which is the U.S. National Stage of International Application No. PCT/US2008/079494, filed on Oct. 10, 2008, published in English, which claims the benefit of U.S. Provisional Application No. 60/998,426, filed on Oct. 10, 2007. The entire teachings of the above applications are incorporated herein by reference.

GOVERNMENT SUPPORT

This invention was made with government support under Grants Nos. GM071508, CA082396, CA085786 and AI054430 awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

a) File name: 45611000024SEQLIST7272016.txt; created Jul. 27, 2016, 161 KB in size.

FIELD OF THE INVENTION

The invention relates generally to the field of vaccine development. More specifically, the invention relates to methods of increasing diversity in cytomegalovirus vaccines through the selection of cell type in which the virus is propagated, and to the use of cytomegalovirus produced by those methods in the development of vaccine compositions.

BACKGROUND

Various publications, including patents, published applications, technical articles and scholarly articles are cited throughout the specification. Each of these cited publications is incorporated by reference herein, in its entirety. Full citations for publications referenced by numbers in parentheses or otherwise not cited fully within the specification are set forth at the end of the specification.

Cytomegalovirus (CMV) is a herpes virus classified as being a member of the beta subfamily of herpesviridae. According to the Centers for Disease Control and Prevention. CMV infection is found fairly ubiquitously in the human population, with an estimated 40-80% of the United States adult population infected. The virus is spread primarily through bodily fluids, and is frequently passed from pregnant mothers to the fetus or newborn. In most individuals. CMV infection is latent, although virus activation can result in high fever, chills, fatigue, headaches, nausea, and splenomegaly.

Although most human CMV infections are asymptomatic. CMV infections in immunologically immature or immunocompromised individuals, such as newborns, HIV-positive patients, allogeneic transplant patients and cancer patients, can be particularly problematic. CMV infection in such individuals can cause severe morbidity, including pneumonia, hepatitis, encephalitis, colitis, uveitis, retinitis, blindness, and neuropathy, among other deleterious conditions. In addition, CMV is a leading cause of birth defects. At present, there is no cure or preventive vaccine for CMV infection.

The entry of herpesviruses into cells is a complex process initiated by adsorption and receptor binding and followed by fusion of the virus envelope with a cell membrane. Fusion occurs at either the plasma membrane or an endosomal membrane. For instance, Epstein Barr virus (EBV) enters primary B cells via receptor-mediated endocytosis (1, 2), yet it infects epithelial cells or transformed B cells by fusion of the virion envelope with the plasma membrane (1). Herpes simplex virus fuses with the plasma membrane of some cell types, but enters others by endocytosis (3-6). Human cytomegalovirus (HCMV) infects multiple cell types in vivo, including epithelial cells, endothelial cells and fibroblasts (7). It fuses with the plasma membranes of fibroblasts (8), but enters retinal pigmented epithelial cells and umbilical vein endothelial cells via endocytosis (9, 10).

The mechanism by which herpes viruses 'choose' their route of entry remains unclear. It is generally assumed that entry pathways are mainly determined by the host cell, but there is precedent for tropic roles of virion glycoproteins (11). EBV virions contain two gH complexes, gH/gL and gH/gL/gp42 (12, 13), which have mutually exclusive functions (11). Fusion with the plasma membrane of B cells is mediated by gH/gL/gp42 (14-16), but entry into epithelial cells is triggered by gH/gL (11, 12, 17). The cell type in which EBV is produced can alter its tropism. B-cell-derived EBV virions contain less gH-gL-gp42 than epithelial-cell-derived virions. As a result. B-cell-generated virus is more infectious for an epithelial cell and epithelial cell-derived virus is B cell tropic (18).

HCMV also encodes two gH/gL complexes: gH/gL/gO and gH/gL/pUL128/pUL130/pUL131 (19, 20). The gO-containing complex is sufficient for fibroblast infection, whereas the pUL128/pUL130/pUL131-containing complex is required to infect endothelial and epithelial cells (19-21). The AD169 laboratory strain contains only the gH/gL/gO complex in its virions (19). The absence of the second gH/gL complex is responsible for the loss of epithelial and endothelial cell tropism in HCMV laboratory strains (19-22).

There is a need for variety and diversity of CMV vaccines, and for effective means to control the spread and activation of the virus, particularly in immunocompromised individuals and pregnant women. The present invention addresses that need.

SUMMARY OF THE INVENTION

One aspect of the present invention features a method of making a cytomegalovirus (CMV) vaccine. The method comprises propagating strains or isolates of CMV in cultured cells of a selected cell type, thereby producing a cell type-conditioned CMV, and producing a CMV vaccine from the cell type-conditioned CMV. In certain embodiments, the CMV strain or isolate is a human CMV (HCMV) strain or isolate. A wide variety of cell types are suitable for the method, including but not limited to epithelial cells, endothelial cells, fibroblasts, neuronal cells, smooth muscle cells, macrophages, dendritic cells and stromal cells. In a specific embodiment, the selected cell type is an epithelial cell.

The aforementioned method can further comprise producing the cell type-conditioned CMV in two or more different selected cell types and combining those CMV to produce the CMV vaccine. Alternatively or additionally, the method comprises providing two or more CMV strains or isolates, growing each of the strains or isolates in the cultured cells comprising the selected cell type or two or more different selected cell types, and combining all the CMV produced therefrom to make the CMV vaccine.

In certain embodiments, the method comprises producing a live attenuated CMV vaccine. In other embodiments, it comprises producing an inactivated or killed CMV vaccine. In still other embodiments, it comprises producing combination vaccines comprising one or more live attenuated viruses, inactivated viruses and other immunogenic components, e.g., immunogenic CMV proteins and peptides, and the like.

CMV vaccines produced by the aforementioned methods are also within the scope of the present invention.

Another aspect of the invention features a kit for practicing the methods of the invention. Such kits typically include a package in which is contained one or more CMV strains or clinical isolates, cultured cells of one or more selected cell types, and instructions for using the cultured cells and the CMV strains or isolates to produce cell type-conditioned CMV for use in a CMV vaccine.

Another aspect of the invention features a vaccine composition comprising a cytomegalovirus (CMV) population or virion components thereof, admixed with a suitable pharmaceutical carrier or adjuvant, wherein the CMV population is isolated from a cultured cells of a selected cell type. In one embodiment, the selected cell type is an epithelial cell type. In one embodiment, the vaccine composition comprises HCMV.

In various embodiments of the vaccine composition, the CMV population isolated from epithelial cell cultures is characterized by one or more features in subsequently infected host cells including but not limited to; (a) entry into the host cells by fusion with host cell plasma membranes; (b) greater virion-mediated cell-cell fusion of the host cells as compared with an equivalent CMV population isolated from cultured fibroblasts; (c) accelerated virus growth in the host cells as compared with an equivalent CMV population isolated from culture fibroblasts; (d) elicitation of a cellular response involving changes in expression greater than or equal to 2.5 fold of about two thirds fewer genes than a response elicited by an equivalent CMV population isolated from culture fibroblasts at 10 hours post-infection; or (e) elicitation of a cellular response involving a change in expression of one or more genes as shown in Table 2 and Table 4 herein, the latter being represented by GenBank Accession Nos: AK094860, NM_145023, NI\1_133492, NM_001039580, NM_001004301, NI\1_001034, Al369525, AK123066, NI\1_005345, NI\1_020731, BC071797, NI\1_003414, NI\1_000800, NI\1_138467, AK090803, AL133118, NI\1_001165. BG001037, NI\1_024861, NM_OOI043, NI\1_016239, NM_OOI018084, NI\1_001037442, NM_OI7600, NM_022097, NI\1_175868, NI\1_032266, NM_003841, NM_005039, NI\1_145051, NI\1_004294, AW856073, NI\1_024050, AF085968, NI\1_080927, NI\1_022115, AK056703, NM_000808, NI\1_012377, NI\1_006793, NM_031466, NM_005185, Niv1_139173, BX360933, NI\1_016125, NI\1_002104, NM_032188, NM_004185, NI\1_004843 or NI\1_173550.

In certain embodiments, the vaccine composition comprises a CMV population or virion components thereof isolated from a cell culture of two or more different selected cell types. For instance, the CMV population may be isolated from as an epithelial cells and cells of another cell type, such as a fibroblast cell type. In other embodiments, the CMV population comprises two or more CMV strains or clinical isolates grown in the selected cell type. Certain embodiments can comprise a plurality of CMV strains or clinical isolates grown in cell cultures of a plurality of different cell types.

In one embodiment, the vaccine composition comprises a live attenuated CMV vaccine. In another embodiment, it comprises an inactivated CMV vaccine. In still other embodiments, the vaccine composition can be a combination vaccine comprising one or more strains of live attenuated virus or components thereof, inactivated virus or components thereof, and/or other immunogenic CMV peptides or proteins.

Another aspect of the invention features a method of immunizing an individual against CMV, comprising administering to the individual a CMV vaccine composition produced by the aforementioned methods and/or comprising the aforementioned features. In one embodiment, the individual to be immunized is a human.

Other features and advantages of the invention will be understood by reference to the drawings, detailed description and examples that follow.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A: Infected cells (0.1 pfu/cell) were fixed at indicated times, and stained for IE 1 (light gray), Sp 100 (very dark gray) and DNA (dark gray). FIG. 1B: At various times after infection (0.1 pfu/cell), the percentage of IE1-expressing cells was quantified; results are shown on the graph.

FIG. 2A: epiBADrUL131. FIG. 2B: fibroBADrUL131. FIG. 2C: fibroBFXwt.

FIG. 3A: Cells were pretreated with $NH_4Cl$ or BFA for 1 h, inoculated with epiBADrUL131 or fibroBADrUL131 (1 pfu/cell) and stained for IE 1 16 h later. FIG. 3B: Cells were pretreated with 50 mM $NH_4Cl$ or 40 nM BFA for 1 h, and then inoculated with BADrUL131 (0.1 pfu/cell) or FIXwt (0.01 pfu/cell) produced in the indicated cell types and stained for IE1 16 h later.

FIG. 5A: Epithelial cell- or fibroblast-derived viruses were incubated with various concentrations of anti-pUL130, and residual infectivity was determined. FIG. 5B: Epithelial cell- or fibroblast-derived virus particles were pretreated with anti-pULI30 at a final concentration of 20 mg/ml or with PBS, and then adsorbed to ARPE-19 cells at 4° C. for 1 h. The cells were washed twice with cold PBS, and viral DNA associated with the cells was extracted to determine the relative numbers of particles attached to the cells. Alternatively, the cells were shifted to 37° C. for 2 h to allow the virus entry. Virions that did not penetrate the cells were removed by EDTA-trypsin treatment. Internalized viral DNA was subsequently quantified by real-time PCR.

FIG. 6A: Venn diagrams depict the distribution of differentially regulated genes at 6 h or 10 hpi with epiBADrULI31 or fibroBADrUL131 (3 pfu/cell) relative to mock infection. FIG. 6B: Changes in relative RNA levels assayed by real-time RT PCR. The genes tested are hydroxymethylbilane synthase (HMBS, NM_000 190). GLI pathogenesis-related 1 (glioma) (GliPR. NM_006851), pentraxin-related gene, rapidly induced by IL-1 beta (PTX3, NM_002852). 2'-5'-oligoadenylate synthetase 3 (OAS3, NM 006187), interferon-induced protein 44 (IFI44, NM_ 006417), v-rel reticuloendotheliosis viral oncogene homolog B, nuclear factor of kappa light polypeptide gene enhancer in B-cells 3 (relB, NM_006509), and ATP-binding cassette, sub-family C (CFTR/MRP), member 3 (MRP3, NM_003786).

DETAILED DESCRIPTION OF THE INVENTION

Figure 1A:
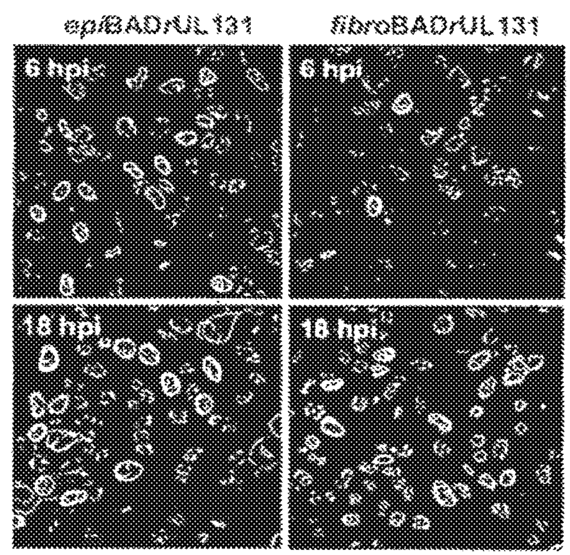
FIGS. 1A-1B. Kinetics of HCMV IE I expression in ARPE-19 cells.

Various terms relating to the methods and other aspects of the present invention are used throughout the specification and claims. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is to be understood that the terminology used herein is for the purpose of describing particular embodiments only, and is not intended to be limiting.

Definitions

As used in this specification and the appended claims, the singular forms "a", "an" and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "amplifying," "propagating," and "growing," or "amplification," "propagation," and "growth" are used interchangeably herein to refer to the general process of introducing virus into cultured cells or infecting cells with virus under conditions permitting the virus to replicate and multiply within the cells, in accordance with methods well known to virologists and medicinal biologists. In particular, these terms are used herein to refer to the step of the inventive method in which the CMV is "conditioned" by propagation on a selected cell type, as the step prior to using the conditioned CMV for the production of a vaccine.

"Biomolecules" include proteins, polypeptides, nucleic acids, lipids, polysaccharides, monosaccharides, and all fragments, analogs, homologs, conjugates, and derivatives thereof.

"Cell culture" refers generally to cells taken from a living organism and grown under controlled conditions ("in culture" or "cultured"). A "primary cell culture" is a culture of cells, tissues, or organs taken directly from an organism(s) before the first subculture. A "cell line" is a population of cells formed by one or more subcultivations of a primary cell culture.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

The terms "conditioned virus," "cell type-conditioned virus," "conditioned CMV" or "cell type-conditioned CMV" refer to CMV that has been propagated in a selected cell type prior to its use in vaccine production, in accordance with the methods described herein.

These terms are intended to be analogous to the term "conditioned medium," which describes culture medium in which a particular cell type or cell line has been grown and then removed, and which contains components or factors produced by the cells, thereby altering the functionality of the medium. For purposes of the present application. the term "conditioned virus" similarly refers to virus that has been grown in a selected cell type and then removed from those cells, wherein the virus thereafter exhibits one or more altered functional features resulting from its growth in that cell type.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, fonmliation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system. "Exogenous" refers to any material introduced from or produced outside an organism, cell, tissue or system.

The term "expression" as used herein is defined as the transcription and/or translation of a particular nucleotide sequence driven by its promoter.

As used herein, "immunization" or "vaccination" are use interchangeably herein and are intended for prophylactic or therapeutic immunization or vaccination. "Therapeutic vaccination" is meant for vaccination of a patient with CMV infection.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. Unless it is particularly specified otherwise herein, the proteins, virion complexes, antibodies and other biological molecules forming the subject matter of the present invention are isolated, or can be isolated.

The terms "patient," "subject," "individual," and the like are used interchangeably herein, and refer to any animal, or cells thereof whether in vitro or in situ, that can be infected with CMV. In certain non-limiting embodiments, the patient, subject or individual is a human.

"Parenteral" administration of an immunogenic or vaccine composition includes. e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means. i.e., the cloning of nucleic acid sequences from a recombinant library or a cell genome, using ordinary cloning and amplification technology, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A "single package" can also include virtual components. For instance, a kit may contain abbreviated physical instructions contained within the physical package, and instructions for accessing more detailed instructions from a virtual environment, such as a website for example.

The term "therapeutic" as used herein means treatment and/or prophylaxis. A therapeutic effect is obtained by avoidance, delay, suppression, remission, or eradication of a disease state associated with CMV infection.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes for instance, prevention of CMV propagation to uninfected cells of an organism. The phrase "diminishing CMV infection" is sometimes used herein to refer to a treatment method that involves reducing the level of infection in a patient infected with CMV, as determined by means familiar to the clinician.

DESCRIPTION

Cytomegalovirus (CMV) infects multiple cell types in vivo, including epithelial cells, endothelial cells and fibroblasts. As summarized above in the background material, various studies have reported that the virus fuses with the plasma membranes of fibroblasts, but enters retinal pigmented epithelial cells and umbilical vein endothelial cells via endocytosis. Due to the relative ease of propagating CMV in cultured fibroblasts as compared with epithelial or endothelial cell cultures, studies such as the above-summarized studies have been conducted using fibroblast-propagated CMV strains. Likewise, cultured fibroblasts are typically the cell type of choice in propagating CMV for clinical applications, such as the development of attenuated virus strains for vaccines.

It has now been demonstrated in accordance with the present invention that the cell type in which CMV particles are produced has a profound influence on their behavior in subsequent rounds of infection. Thus, for example, while it was heretofore reported that that CMV enters epithelial cells by endocytosis, the present inventors have demonstrated that this is the mode of entry for CMV propagated in fibroblasts, but not for CMV propagated in cultured epithelial cells. Epithelial cell-propagated CMV enters epithelial cells predominantly via fusion with the plasma membrane. This different mode of entry has a variety of physiological consequences: it influences the kinetics with which the infection proceeds and it markedly influences the cellular response to infection. For instance virus grown in epithelial cells produces a dramatically muted cellular response as compared to cells infected with virus grown in fibroblasts. Many cellular anti-viral genes expressed after infection with fibroblast-grown virus are not expressed after infection with epithelial cellgrown virus. As a consequence, CMV grown in epithelial cells is predicted to perform differently than CMV grown in fibroblasts, thus offering a new and unexpected source of diversity for the generation of CMV vaccines. Likewise, propagation of CMV in other cell types, such as endothelial cells or specialized cell types that CMV is able to infect (e.g., neurons, other cells of the central or peripheral nervous systems, smooth muscle cells, hepatocytes, stromal cells, macrophages or dendritic cells) should produce additional novel sources of diversity for the generation of CMV vaccines.

Thus, one aspect of the invention features methods of making CMV vaccines that exploit the variability associated with choosing a cell type in which to propagate the virus. Another aspect features a kit for practicing the methods described above. Another aspect of the invention features vaccine compositions for the prevention or treatment of CMV infection, and methods of immunizing an individual using such compositions. Various embodiments of these aspects of the invention are set forth below.

Methods of Producing CMV Vaccines:

The methods in accordance with an aspect of the invention comprise (1) providing a CMV strain or isolate; (2) propagating the strain or isolate in a cell culture of a selected cell type; and (3) harvesting CMV virions produced by growth in that cell type (referred to herein as "cell type-conditioned CMV") for use in producing a CMV vaccine.

The cell type selected for propagating the CMV prior to its use for vaccine development can be any cell line permissive for CMV infection that produces a yield of virus particles. The virus particles might be highly infectious in some assays or the particles might exhibit limited or no infectivity in many assays. Suitable cell types include, but are not limited to, (1) epithelial cell lines such as ARPE-19, which is exemplified herein and other retinal pigmented epithelial cell lines. e.g., epithelial cell line K-1034 (Ando, Y., et al. 1997. Arch. Virol, 142(8): 1645-1658): HCMC, derived from nonnal human colonic mucosa (Smith. J. D., 1986, J Viral. 60(2): 583-588): Caco-2 intestinal epithelial cells (Esclatine. A., et al., 2000, J. of Virol. 74(1): 513-51): SW480, HCT116, HeLa, H1299, and MCF-7 (regarding the latter five, see Wang. D. & T. Shenk, 2005, J. Viral. 79:10330) (2) endothelial cell lines such as HMEC-1, a human microvascular endothelial line, immortalized with SV-40 virus large T antigen (Guetta, E., et al., 2001, Cardiovascular Research 50:538-546); HUVEC and LMVEC (regarding the latter two, see Wang, D. & T. Shenk, 2005. J. Viral. 79:10330); (3) neuronal cells such as SK-N-SH, SK-N-AS and IMR-32 (see Wang, D. & T. Shenk, 2005. J. Viral. 79:10330) as well as primary epithelial, endothelial, smooth muscle, macrophage and dendritic cells derived from a variety of tissue/organ sources.

Any CMV or combination of CMVs amenable to development as a vaccine is suitable for use as a source of the CMV for the method, as long as they can be grown in at least one selected cell type. In one embodiment, the CMV is human CMV (HCMV), either an isolate that has been previously isolated and characterized or a new isolate of HCMV or an HCMV-like virus. In another embodiment, the CMV originates from another primate, including but not limited to chimpanzee (Davison, A. J., et al., 2003, J. Gen. Viral. 84: 17-28) and rhesus monkey (Hansen, S. G., et al., 2003, J. Viral. 77:6620-36: Rivailler, P., et al., 2006, J. Viral. 80:4179-82). The CMV can be an unmodified virus from a selected source, or it can be a chimeric virus produced by genetic modification or combination of elements from two or more different CMV strains or isolates.

Methods of making chimeric viruses are known in the art. To this end, at least six strains of human CMV have been cloned as infectious bacterial artificial chromosomes (BAC) and sequenced (Murphy, E., et al., 2003, Proc. Natl. Acad. Sci. USA 100: 14976-14981). The BAC sequences are available at GenBank Accession Nos. AC 146999 (laboratory strain AD169, from which the BADrUL131 variant described herein was made): AC 146851 (laboratory strain Towne): ACI46904 (clinical isolate PH): AC146905 (clinical-like isolate Toledo): AC146906 (clinical isolate TR); and AC146907 (clinical isolate FIX). At least two strains of human CMV have been sequenced without prior SAC cloning, and are available at GenBank Accession Nos. BK000394 (laboratory strain AD169) and AY446894 (clinical isolate Merlin). The entire genome of a chimpanzee CMV strain is available at GenBank Accession No. AF480884. The genome sequence of two rhesus CMV strains is also available (Accession Nos. AY186194 and DQ205516). Utilizing the teachings of the present application, the skilled artisan would be able to use any of the aforementioned sequences, or any other publicly available CMV sequence to prepare chimeric CMVs or to otherwise genetically modify a CMV.

It has been demonstrated in accordance with the present invention that laboratory strains of CMV that have been passaged repeatedly in fibroblasts can be successfully conditioned by propagation on the selected cell line. For instance, as described in the Example herein, BADrUL131, a BAC clone of the repeatedly passaged ADI69 HCMV strain in which the UL131 ORF has been repaired, was introduced by electroporation into cultured human foreskin fibroblasts, and the resulting virus preparation was amplified once in the epithelial cell line ARPE-19. Thus, various embodiments of the invention comprise the use of CMV (or the genomes of CMV) that has been passaged in a cell type that is different from the cell type selected for the conditioning step. For example, a CMV strain can be passaged multiple times in fibroblasts, then amplified in epithelial cells and thereafter used to produce a vaccine. It will be appreciated that the CMV can be amplified/propagated for one or more rounds in the selected cell type.

In preferred embodiments, the methods of the invention are used to produce live attenuated CMV for use as a vaccine. Methods to attenuate viruses are known in the art. Preferably, attenuated CMV exhibit a diminished capacity for infectivity, and/or pathogenicity, including latency and activation, yet remain capable of inducing an immune response that treats or protects the host against CMV infection. Examples of attenuated CMV strains include, but are not limited to, laboratory strains, such as AD169 and Towne, which replicate almost exclusively in fibroblasts. Such attenuated strains, engineered if necessary to produce the requisite surface protein or protein complexes for appropriate tropism, can be grown epithelial cells or in fibroblasts and thereafter epithelial cells as discussed above, for use in the vaccine composition of the invention.

Serial passage in cultured cells, particularly fibroblasts, can be used to attenuate CMV. Repeated passaging of virally-infected host cells is carried out in vitro until sufficient attenuation of the virus is achieved. Passaging may be conducted under specific environmental conditions, such as modulated temperature, pH, humidity, in order to select for viruses with reduced infectivity or pathogenicity. If this method of attenuation is used, the serially passaged virus is then amplified in the selected cell type for one or more passages to produce the CMV to be used in the vaccine compositions of the invention.

Mutagenesis can also be employed to attenuate a virus. For example, CMV virions can be exposed to ultraviolet or ionizing radiation or chemical mutagens, according to techniques known in the art. In addition to their use to produce chimeric viruses, recombinant techniques can also be used to produce attenuated CMV virions. For instance, site-directed mutagenesis, gene replacement, or gene knockout techniques can be used to derive virus strains with attenuated infectivity, pathogenicity or latency. An example of modifying a CMV by knockout mutagenesis is set forth in W0/2007/038316, which describes CMVs with genomes deleted in one or more latency-promoting genes, displaying an altered ability to enter or maintain a latent state.

In other embodiments, CMV isolated from the selected cell cultures are inactivated or killed and used in vaccine compositions. Methods of inactivating or killing viruses, e.g., with a chemical such as formalin, are well known in the art. It will be understood by the skilled artisan that the killed or inactivated CMV will comprise all or a substantial portion of the components of the viral particle, such that the diversity generated by the amplification in the selected cell type is maintained in the vaccine composition.

The methods of the invention can be used to create combinations of CMVs propagated in different selected cell types, thereby conferring an additional level of diversity to the vaccines that are produced. In one embodiment, a single CMV isolate or strain is used to infect two or more different cultured cell lines of different types, e.g., retinal epithelial cells and endothelial cells. The CMV produced by amplification in the respective cell types is then combined for use in a single vaccine. In another embodiment, two or more different clinical isolates or strains of CMV are used to infect a single selected cell line, and the multi-strain or multi-isolate CMV population produced by amplification in that cell type is used to produce a vaccine. In yet another embodiment, multiple isolates or strains are used to infect two or more different cultured cell lines of different types, and the CMV populations produced by amplification in the respective cell types are combined for use in the vaccine.

Another aspect of the invention features kits for producing CMV vaccine materials in accordance with the methods described above. The kits comprise in separate containers in a single package or in separate containers in a virtual package, as appropriate for the use and kit component, aliquots of cell lines of one or more selected cell types, as well as one or more CMV isolates or strains, or vectors carrying the genomes of such CMV strains, to be introduced into and amplified in the selected cultured cell lines. Such kits also typically contain instructions, or links to instructions, for how to carry out the various steps of the method. Optionally, kits can also comprise culture medium and other reagents suitable for carrying out the cell culture and virus manipulations.

Vaccine Compositions and Methods of Use:

Another aspect of the invention features an immunogenic composition (referred to interchangeably herein as a vaccine composition) comprising a cytomegalovirus (CMV) population or virion components thereof, admixed with a suitable pharmaceutical carrier or adjuvant, wherein the CMV is obtained via propagation in a selected cell type, for instance, an epithelial cell culture. As mentioned above, CMV vaccines have heretofore typically been prepared using CMV propagated in fibroblasts. However, it has been demonstrated in accordance with the present invention that propagation in epithelial cells yields virus that differs from fibroblast-propagated virus in many different ways. Virus produced in epithelial cells preferentially fuses with the plasma membrane, whereas fibroblast-derived virus mostly enters by receptor-mediated endocytosis. In addition, epithelial cell-generated virions had higher intrinsic "fusion from without" activity than fibroblast-generated particles, which influences the kinetics of infection. Furthermore, the two virus preparations trigger different cellular signaling responses, as evidenced by markedly different alterations in the transcriptional profile of infected epithelial cells.

In particular, CMV produced by propagation in epithelial cells have one or more of the following features, as compared with an equivalent strain or isolate of the virus produced by propagation in fibroblasts. First as mentioned above, they can be distinguished by their entry into the host cells by fusion with host cell plasma membranes. CMV produced on epithelial cells also display greater virion-mediated cell-cell fusion of the host cells as compared with an equivalent CMV population isolated from cultured fibroblasts, as well as accelerated virus growth in the host cells as compared with an equivalent CMV population isolated from culture fibroblasts. In addition, they elicit a subdued cellular response as compared with equivalent CMV propagated in fibroblasts. At 10 hours post-infection about two-thirds fewer genes (~50 versus ~150 genes) exhibit a 2.5 fold or more change in expression level. In addition, epithelial-grown CMV can be characterized by the particular profile of host genes whose expression is changed (increased or decreased) following infection. These gene expression profiles are detailed in the Example, and can involve a change in expression of one or more genes represented by GenBank Accession Nos: AK094860, NM_l45023, NM_l33492, NM_001039580, NM_001004301, NM_001034, Al369525, AK123066, NM_005345, NM_02073l, BC071797, NM_003414, NM_000800, NM_l38467, AK090803, AL133118, NM_001165, BG001037, NM_024861, NM_001043, NM_0l6239, NM_001018084, NM_001037442, NM_0l7600, NM_022097, NM_175868, NM_032266, NM_003841, NM_005039, NM_145051, NM_004294, AW856073, NM_024050, AF085968, NM_080927, NM 022115, AK056703, NM 000808, NM 012377, NM_006793, NM_ 031466, NM_005185, NM_l39173, BX360933, NM_0l6125, NM_002104, NM_032188, NM_004185, NM_004843 or NM_l73550.

In this aspect of the invention, as in the foregoing aspects of the invention. CMV or a combination of CMVs amenable to development as a vaccine is suitable for use as a source of the aforementioned CMV population, as long as they can be grown in at least one epithelial cell line or another selected cell type. In one embodiment the CMV is HCMV or an HCMV-like virus. In another embodiment, the CMY originates from another primate, including but not limited to chimpanzee and rhesus monkey, as described above. The CMV can be an unmodified virus from a selected source, or it can be a chimeric virus produced by genetic modification or combination of elements from two or more different CMV strains or isolates, as described above.

In preferred embodiments, the vaccine compositions comprise live attenuated CMV, which can be produced by the methods outlined above, all familiar to the skilled artisan. In other embodiments, CMV isolated from the selected cell cultures are inactivated or killed and used in vaccine compositions.

The vaccine compositions can comprise combinations of different strains or isolates of CMV, which can be propagated on a single epithelial cell cultures or on a number of different epithelial cell cultures, or on cells of another cell type, to generate additional diversity. Furthermore, live attenuated CMV can be combined with killed or inactivated CMV, or with immunogenic components of CMV to produce a combination vaccine, e.g., live attenuated CMV combined with heat killed CMV, or combined with material for a subunit vaccine, or a combination of all three types of materials. Examples of immunogenic CMV polypeptides and complexes suitable for subunit vaccines are described in WO 2007/146024 entitled "Cytomegalovirus Surface Protein Complex for Use in Vaccines and as a Drug Target."

The vaccine composition can further comprise one or more adjuvants. Adjuvants can be any substance that enhances the immune response to the antigens in the vaccine. Nonlimiting examples of adjuvants suitable for use in the present invention include Freund's adjuvant, incomplete Freund's adjuvant, saponin, surfactants such as hexadecylamine, octadecylamine, lysolecithin, demethyldioctadecyl ammonium bromide, N,N-dioctadecyl-N'—N-bis (2-hydroxyethylpropane diamine), methoxyhexa-decylglycerol, pluronic polyols, polyanions such as pyran, diethylaminoethyl (DEAE) dextran, dextran sulfate, polybrene, poly IC, polyacrylic acid, carbopol, ethylene maleic acid, aluminum hydroxide, and aluminum phosphate peptides, oil or hydrocarbon emulsions, and the like.

Vaccines can be formulated in aqueous solutions such as water or alcohol, or in physiologically compatible buffers such as Hanks' solution, Ringer's solution, or physiological saline buffer, including PBS. Vaccine fommlations can also be prepared as solid form preparations which are intended to be converted, shortly before use, to liquid form preparations suitable for administration to a subject, for example, by constitution with a suitable vehicle, such as sterile water, saline solution, or alcohol, before use.

The vaccine compositions can also be formulated using sustained release vehicles or depot preparations. Such long acting formulations may be administered by implantation (for example subcutaneously or intramuscularly) or by intramuscular injection. Thus, for example, the vaccines may be formulated with suitable polymeric or hydrophobic materials (for example as an emulsion in an acceptable oil) or ion exchange resins, or as sparingly soluble derivatives, for example, as a sparingly soluble salt. Liposomes and emulsions can be used as delivery vehicles suitable for use with hydrophobic formulations. Sustained-release vehicles may, depending on their chemical nature, release the antigens over a range of several hours to several days to several weeks to several months.

The vaccine compositions may further include one or more antioxidants. Exemplary reducing agents include mercaptopropionyl glycine. N-acetylcysteine, β-mercaptoethylamine, glutathione, ascorbic acid and its salts, sulfite, or sodium metabisulfite, or similar species. In addition, antioxidants can also include natural antioxidants such as vitamin E, C, leutein, xanthine, beta carotene and minerals such as zinc and selenium.

Vaccine compositions may further incorporate additional substances to function as stabilizing agents, preservatives, buffers, wetting agents, emulsifying agents, dispersing agents, and monosaccharides, polysaccharides, and salts for varying the osmotic balance. The vaccines can further comprise immunostimulatory molecules to enhance vaccine efficacy. Such molecules can potentiate the immune response, can induce inflammation, and can be any lymphokine or cytokine. Nonlimiting examples of cytokines include interleukin (IL)-1, IL-2, IL-3, IL-4, IL-12, IL-13, granulocyte-macrophage colony stimulating factor (GMCSF), macrophage inflammatory factor, and the like.

Vaccines can be formulated for and administered by infusion or injection (intravenously, intraarterially, intramuscularly, intracutaneously, subcutaneously, intrathecally, intraduodenally, intraperitoneally, and the like). The vaccines can also be administered intranasally, vaginally, rectally, orally, topically, buccally, transmucosally, or transdermally.

An effective antigen dosage to treat against CMV infection can be determined empirically, by means that are well established in the art. The effective dose of the vaccine may depend on any number of variables, including without limitation, the size, height, weight, age, sex, overall health of the subject, the type of formulation, the mode or manner or administration, whether the virus is active or latent, whether the patient is suffering from secondary infections, or other related conditions.

Vaccine regimens can also be based on the above-described factors. Vaccination can occur at any time during the lifetime of the subject, including development of the fetus through adulthood. Supplemental administrations, or boosters, may be required for full protection. To determine whether adequate immune protection has been achieved, seroconversion and antibody titers can be monitored in the patient following vaccination.

The following example is provided to describe the invention in more detail. It is intended to illustrate, not to limit, the invention.

EXAMPLE

Human Cytomegalovirus Uses Two Distinct Pathways to Enter Retinal Pigmented Epithelial Cells The experimental results described in this example demonstrate that HCMV produced in two different cell types enters epithelial cells via different pathways. Virions generated in epithelial cells preferentially enter via fusion at the plasma membrane, whereas virions from fibroblasts enter by pH-dependent endocytosis. The two virus preparations induced markedly different cellular responses.

Materials and Methods

Biological Reagents.

Human foreskin fibroblasts (HFFs) at passage 10 to 15 were maintained in medium with 10% newborn calf serum. Human MRC-5 embryonic lung fibroblasts and ARPE-19 retinal pigmented epithelial cells (American Type Culture Collection) at passage 24 to 34 were maintained in medium with 10% fetal bovine serum. Human renal proximal tubular epithelial cells (hRPTECs) (Cambrex) were grown in medium with 10% fetal bovine serum and used at passage 4 to 5.

BADwt is derived from a BAC clone of the ADI69 HCMV strain: BADrUL131 (19, 21) is a derivative of BADwt in which the UL131 ORF has been repaired: BFXwt is derived from a BAC clone of the VR1814 clinical HCMV isolate. Viruses were prepared by electroporation of BAC DNAs into HFFs, and the resulting virus preparation was amplified once in ARPE-19 cells or HFFs, unless otherwise specified. Cell-free virions were partially purified by centrifugation through a sorbitol cushion and resuspended in serum-free medium. Virus titers were determined by plaque assay on MRC-5 cells. Neutralization of BADrUL131 was assayed by plaque reduction assay (19), by using purified anti-pUL130 monoclonal antibody (3E3) (19).

Anti-lE1 monoclonal antibody 1B12 was described previously (21). Rabbit anti-Sp100 polyclonal antibody (Chemicon) was used to visualize the ND10s.

Electron Microscropy.

ARPE-19 cells were exposed to virus at 4° C. for 1 h, unbound virus was removed by two washes with cold PBS, growth medium (37° C.) was added for 15 min, cells were rinsed with phosphate-buffered saline (PBS), fixed and processed for electron microscopy, and examined with an FEI Tecnai-T12 microscope at 80 kv.

Assay for the Dependence of Infection on Endosome Acidification.

ARPE-19 cells were pretreated with $NH_4Cl$ or Bafilomycin A1 (BFA) (Sigma) for 1 h at 37° C., followed by infection in the continued presence of the inhibitor. 16 h later, cultures were fixed in 2% paraformaldehyde and permeabilized with 0.1% Triton X-100. IE1 was identified by immunofluorescence using monoclonal antibody IB12 (21) plus Alexa 546-conjugated secondary antibody and nuclei were stained with DAPI. Inhibition was calculated as the percentage of IE1-expressing drug-treated relative to untreated cells.

Analysis of the Fusion Activity of Virion Proteins.

To assay "fusion from without", ARPE-19 cells were grown to 90% confluence and infected. After 1 h at 37° C., the inoculum was removed and medium containing 200 μg/ml of phosphonoformic acid (PFA) was added to inhibit viral DNA synthesis. Fusion was monitored by visual inspection for syncytium formation.

A luciferase reporter assay was adapted to quantitatively analyze virion fusion activity. Reporter and effector ARPE-19 cells were prepared by electroporation (90-95% efficiency) with a plasmid carrying a luciferase gene under the control by a T7 promoter and a pcDNA3-T7 polymerase plasmid, respectively. At 24 h post transfection, the cells were mixed at a 1:1 ratio, and incubated at 37° C. for an additional 16 h. The mixed populations were then exposed to HCMV virions at 4° C. for 1 h, after which the monolayer was washed twice with cold PBS followed by addition of buffers (PBS with 10 mM 2-(N-morpholino)ethanesulfonic acid and 10 mM HEPES) with a final pH ranging of 4.5 to 8. After 3 min at 37° C., the buffers were removed, and normal growth medium was added. At 6 hpi, the cells were lysed, and luciferase activity was assayed using a luciferase reporter assay system (Promega).

Assay of Cellular Transcriptional Responses.

Confluent ARPE-19 cells were serum starved for 24 h, followed by mock infection or infection. Total RNA was extracted at 6 or 10 hpi by using Trizol (Invitrogen), and purified with an RNeasy column (Qiagen). The RNA samples were amplified and labeled (cyanine-3) with the Agilent low RNA input fluorescent linear amplification kit. To control for chip to chip variation, a reference RNA (Ciontcch) was labeled (cyanine-5) and co-hybridized with the probes prepared from mock or HCMV-infected cells. The hybridization was performed in duplicate with Aligent Human 44K oligonucleotide arrays. Arrays were scanned using an Agilent scanner at 5 micron resolution, and images were analyzed with Agilent Feature Extraction software to determine the intensities of fluorescent signals for hybridized spots and for background subtraction. Agilent GeneSpring GX software was used for normalization and quantification of relative RNA changes.

Results

Fibroblast-Derived Virions Activate Immediate-Early Gene Expression in ARPE-19 Cells with Slower Kinetics than Epithelial Cell-Derived Virions.

The AD169 HCMV strain (BADwt) replicates poorly in ARPE-19 epithelial cells due to a mutation in its ULI31 gene (10, 21). Repair of the mutation in AD169, producing BADrUL13L restores epithelial cell tropism (21) by allowing production of a gH/gL/pUL128/pUL130/pUL131 virion glycoprotein complex that is required for successful entry into these cells (19. 20).

Figure 1B:
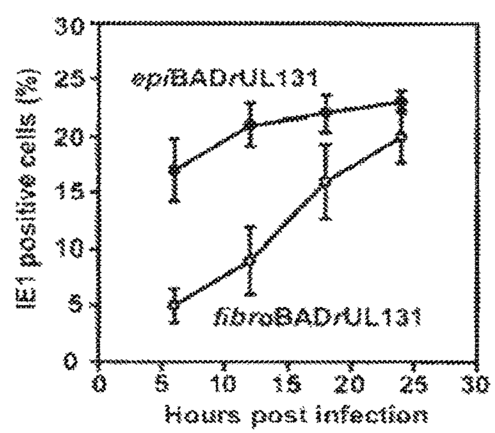

BADrUL 131 grown in ARPE-19 epithelial cells (epiBADrUL131) initiates its program of gene expression in epithelial cells more rapidly than BADrUL131 grown in HFF fibroblasts (fibroBADrUL 131) (FIG. I A). When ARPE-19 cells were infected with epiBADrUL131, ~17% of the cells expressed detectable IE1 protein at 6 h post infection (hpi). lEI expression was accompanied by disruption of ND10s in the nucleus. In contrast, infection withfibroBADrUL131 led to IE1 expression in only 2.8% of ARPE-19 cells at 6 hpi. The number of IE1-expressing cells, however, increased with time. There was no significant difference in the percentage of IE1-expressing ARPE-19 cells at 24 hpi with virus produced in the two cell types (FIG. 1B).

Virions Produced in HFFs Versus ARPE-19 Cells Enter ARPE-19 Cells Via Distinct Pathways.

An electron microscopic examination of virus entry was performed to determine if the different kinetics of IE1 accumulation for ARPE-19 cell-derived virus versus HFF-derived virus resulted from an event prior to the onset of viral gene expression. ARPE-19 cells incubated with epiBADrUL131 or fibroBADrUL131 were permitted to attach at the cell surface at 4° C., and cultures were shifted to 37° C. for 15 min to allow internalization before processing for microscopy. For each sample, 40-50 cells were examined, with at least 90% of the cells showing either intact virions or capsids. The number of virus particles in each cell varied from 2-8, with most cells showing 2-3 particles.

Figure 2A:
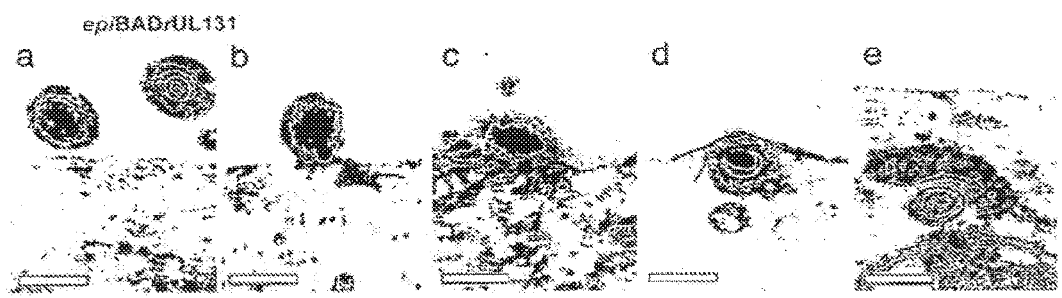
FIGS. 2A-C. Electron microscopic analysis of HCMV entry into ARPE-19 cells. epiBADrUL131 or fibroBADrUL131 particles (50 pfu/cell) were bound to cells at 4° C. and then allowed to internalize at 37° C. for 15 min. Representative images are displayed.
Figure 2B:
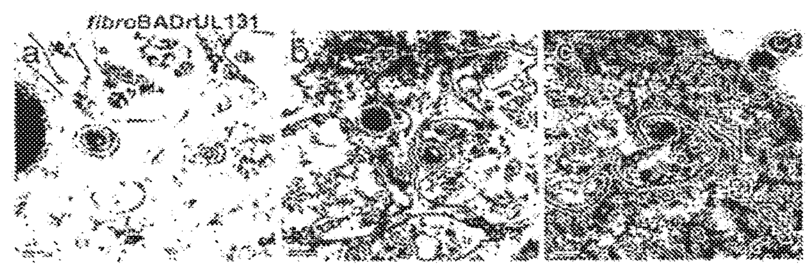

In epiBADrUL131-infected ARPE-19 cells, virions were found almost exclusively at the cell surface, with about 97% of the virions at the apical membrane. Some particles were close to the cells but the section did not reveal evidence of contact (FIG. 2A, panel a), and others were captured in the process of fusion at the plasma membrane (FIG. 2A. panels b and c). Capsids beneath the inner surface of the membrane were observed rarely; in fact, only two examples were identified (FIG. 2A, panels d and c). No enveloped virions were found inside the cells. This result indicates that epiBADrUL131 enters the ARPE-19 cells by fusion with the plasma membrane. In contrast, fibroBADrUL131-infected cells contained virions at the cell membrane (~65% of total) and inside the cell within vesicles (~35% of total) (FIG. 2B). The particles within vesicles were enveloped, indicating they entered by endocytosis.

Figure 2C:
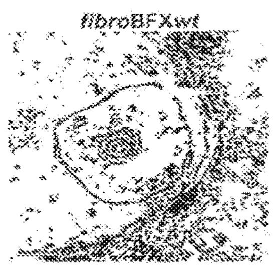

Entry of the BFXwt clinical isolate propagated in fibroblasts was also examined. This clinical isolate accumulated in vesicles within ARPE-19 cells (FIG. 2C), supporting the validity of BADrUL131 as a model for cell entry by a clinical isolate of HCMV.

Infection of ARPE-19 Cells by Fibroblast- but not Epithelial Cell-Derived Virus is pH Dependent.

Figure 3A:
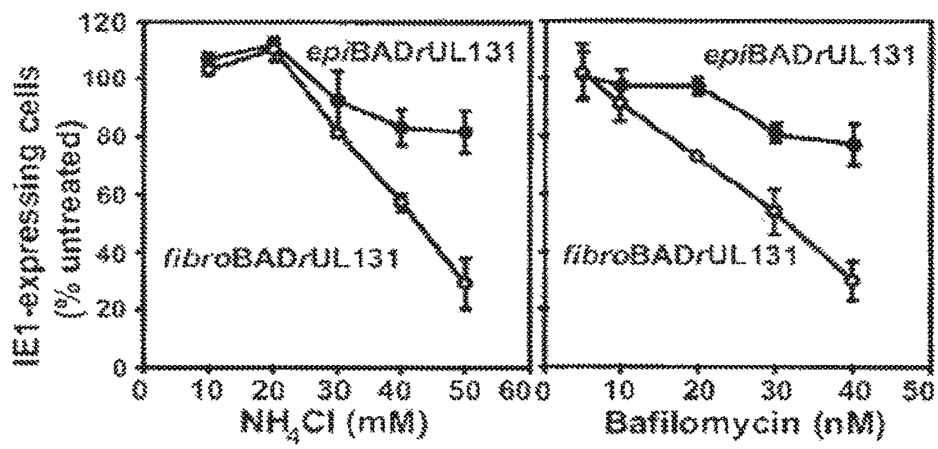
FIGS. 3A-3B. Effects of inhibitors of endosome acidification and virion source on HCMV entry into ARPE-19 cells. Experiments were performed in triplicate, and the number of positive cells in drug-treated relative to untreated cultures is reported.

Many viruses that enter cells by endocytosis (1, 4, 10) require acidification of endosomes for the virion envelope to fuse with the endosomal membrane and release the capsid into the cytoplasm. $NH_4Cl$. which buffers endosomal pH, and bafilomycin A1 (BFA), which blocks the endosomal ATPase proton pump, were tested for their effect on infection of ARPE-19 cells. After pretreatment with either agent, cells were infected and cultured in drug containing medium for a further 16 h. Successful infections were scored by assaying for IE1-positive cells. Consistent with the ultrastructural analysis described above, pretreatment with either agent had only a modest effect on epiBADrULI31 infection (FIG. 3A). In contrast, both agents inhibited IE1 expression after fibroBADrU L131 infection in a dose dependent manner, indicating that the entry of fibroblast-generated virus was dependent on endosomal acidification. The fact that the agents had little effect on entry by epiBADrUL131 shows that the inhibition of fjibroBADrUL131 did not result from toxicity.

It was next determined whether virus grown in other types of epithelial cells and fibroblasts display the same properties as ARPE 19- and HFF-derived virions. Virus stocks from hRPTEC epithelial cells and MRC-5 fibroblasts were used to infect ARPE-19 cells after treatment with $NH_4Cl$ or BFA, and they responded to the inhibitors exactly as did virus grown in ARPE-19 cells or HFFs (FIG. 38. left panel). Thus. BADrUL131 produced in two different fibroblasts was substantially more sensitive to the inhibitors than virus produced in two different epithelial cell lines.

Figure 3B:
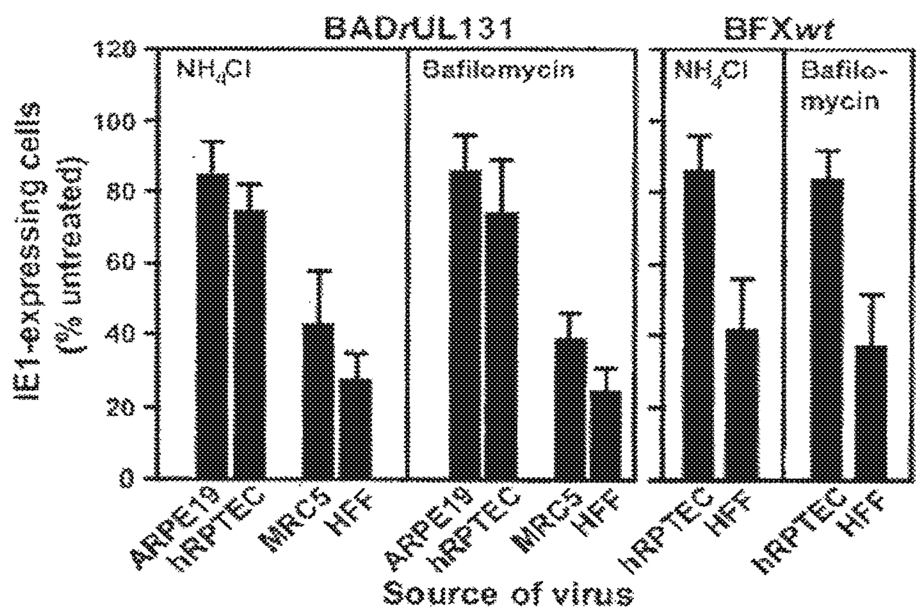

The effect of endosomal pH on entry of the BFXwt clinical isolate into ARPE-19 cells was also assayed (FIG. 3B. right panel). $NH_4Cl$ or BFA significantly reduced the number of IE1-positive ARPE-19 cells produced by infection with fibroblast-generated BFXwt, but only a slight inhibition was observed after infection with epithelial cell-derived BFXwt.

Virions Produced in Epithelial Cells have Higher Intrinsic Fusion Activity than Virions from Fibroblasts.

As is the case for other herpes viruses. HCMV clinical isolates promote cell-cell fusion that can be detected as early as 3-5 hpi. The rapid production of syncytia without de novo synthesis of virus envelope proteins indicates that it is promoted by "fusion from without", a process by which enveloped virions directly fuse target cells. Since BADrUL131 produced in epithelial cells versus fibroblasts enters epithelial cells differently, the possibility that they would exhibit different "fusion from without" activities was tested.

Figure 4A:
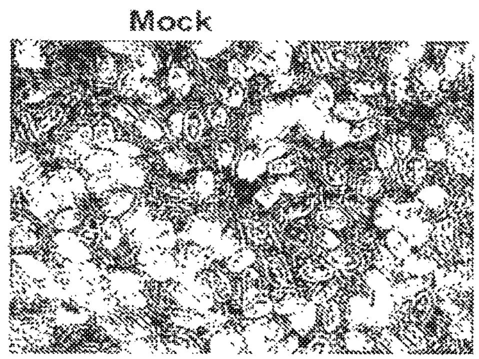
FIGS. 4A-4D. Fusion from without of ARPE-19 cells induced by epithelial cell-derived virus. Cells were inoculated with epiBADrUL131 (FIG. 4C) or fibroBADrUL131 (FIG. 4B) (20 pfu/cell) and then maintained in medium containing 200 μg/ml of PFA. Phase contrast images were taken at 16 h post infection (FIGS. 4A-4C). A mixture of reporter and effector cells were infected by epiBADrUL131 or fibroBADrUL131 (20 pfu/cell) for at 4° C. for 1 h. The culture was then shifted to 37° C. for 6 h, after which relative luciferase activity was measured (FIG. 4D).
Figure 4B:
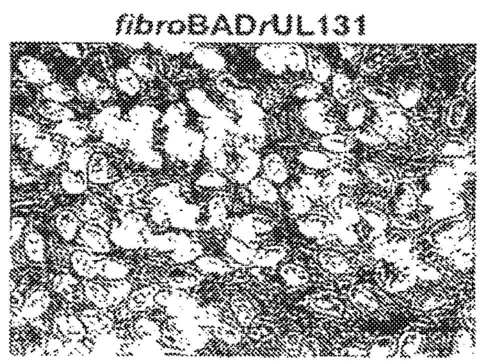
Figure 4C:
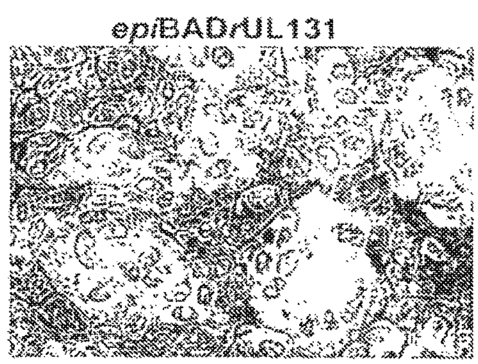
Figure 4D:
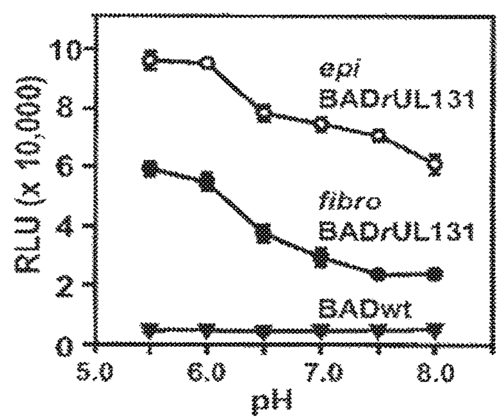

Mock-infected ARPE-19 cells exhibited no syncytia (FIG. 4A), and syncytia were rarely found after infection with fibroBADrUL131 (FIG. 48). In contrast, after exposure to epiBADrUL131, cell-cell fusion was detected as early as 6 hpi, and 20-30% of the nuclei were aggregated in syncytia by 24 hpi (FIG. 4C). Cells were treated with PFA, which blocks progression to the late phase of infection, so the fusion must have been induced by epiBADrUL131 particles and not by newly expressed virion proteins.

A luciferas reporter assay was used to quantify the fusion activity of viral particles as well as the effects of pH on fusion from without. Reporter and effector cells received a plasmid containing a luciferase gene driven by a T7 promoter or a T7 RNA polymerase expression plasmid, respectively. The two ARPE-19 derivatives were mixed, and infection dependent fusion was quantified by assaying luciferase expression. EpiBADrUL131 consistently induced higher fusion activity than fibroBADrUL131 (FIG. 40). At pH 7-8, the activity of ftbroBADrUL131 was ~3-fold lower than that of epiBADrUL131. When the cells were treated with low pH buffers after virus adsorption, both virus preparations mediated modestly enhanced fusion. BADwt did not induce fusion in this assay.

The Mode of Entry does not Alter HCMV Cell Tropism.

As discussed above, there is precedent for a herpesvirus to favor entering a specific cell type depending on the cell in which the infecting virus was produced. This phenomenon is different than the one that was observed as described above, i.e., HCMV preparations from different cell types enter epithelial cells by different mechanisms. Nevertheless, it remained possible that the different entry mechanisms would impact on the efficiency of replication and yield, resulting in a tropic effect. Therefore, experiments were conducted to determine whether the mode of entry influenced HCMV plaque production on epithelial cells as compared to fibroblasts (Table 1). Stocks of BADrUL131 were produced in ARPE-19, hRPTEC, HFF or MRC-5 cells and assayed for plaque formation on ARPE-19 or MRC-5 cells (Table 1). Although slightly more plaques were produced on ARPE-19 than MRC-5 cells neither epithelial cell-nor fibroblast-derived virus preferentially generated plaques on one cell type compared to the other.

TABLE 1

Titration of epithelial cell derived or fibroblast derived BADrUL131 in ARPE19 and MRC5 cells ($\times10^5$)

| Source of replication[a] | Target cells: ARPE-19 | Target cells: MRC5 | Ratio[b] |
|---|---|---|---|
| ARPE-19 | 8.8 | 3.4 | 2.6 |
| hRPTEC | 2.9 | 1.9 | 1.5 |
| MRC5 | 4.3 | 2.7 | 1.6 |
| HFF | 6.8 | 2.7 | 2.5 |

[a] $2 \times 10^5$ pfu of BADrUL131 originally titrated in HFFs were used to infect ARPE-19 or MRC5 cells.
[b] Ratio of ARPE-19 titer in relation to MRC5 titer.

pUL130-Specific Antibody Blocks ARPE-19 Infection by Both Epithelial- and Fibroblast-Derived Virus.

Figure 5A:
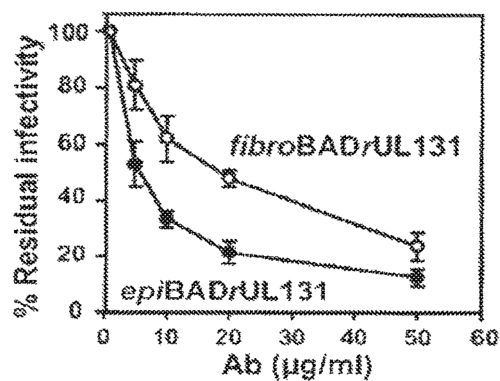
FIGS. 5A-5B. Effect of pULI30-specific neutralizing antibody on HCMV infection and entry.
Figure 5B:
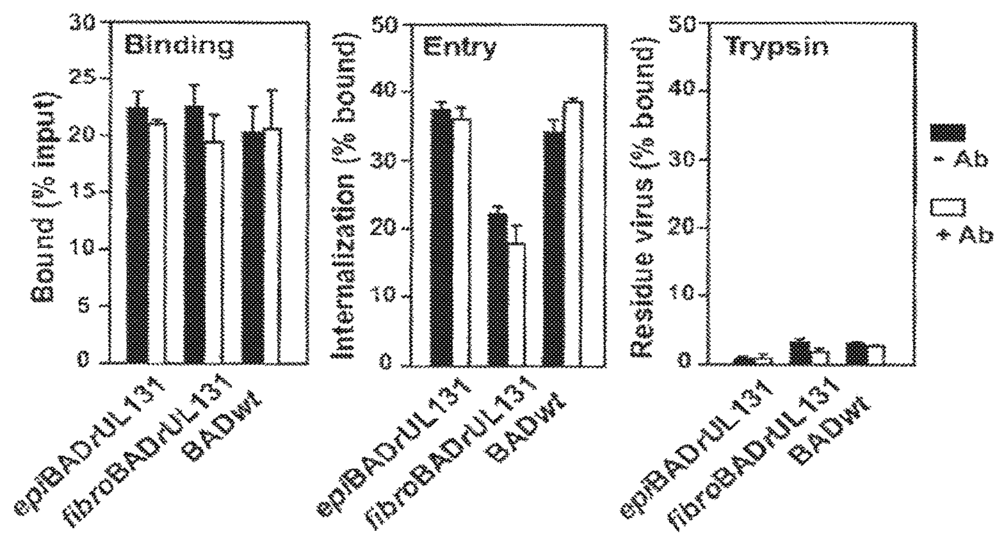

A pUL130-specific antibody, which neutralizes HCMV infection of epithelial cells (19), was able to block ARPE-19 infection by either mode of entry (FIG. 5A). It inhibited infection by both viruses in a dose dependent manner, although epiBADrUL131 was somewhat more sensitive to neutralization than fibroBADrUL131. The ability of the antibody to inhibit both modes of entry reinforces the conclusion that the pUL130-containing complex functions whether fusion occurs at the plasma membrane or the endosomal membrane.

It has been reported previously that the gH/gL/pUL128/pUL130/pUL131 complex is dispensable for HCMV to be internalized by endothelial or epithelial cells, because laboratory strains lacking this complex are efficiently endocytosed (10). However, subsequent fusion with endosomal membrane and escape into the cytoplasm requires the complex. Consistent with these earlier results, the antibody to pUL130 did not block binding or internalization of epiBADrUL131, fibroBADrUL131 or BADwt when assayed on ARPE-19 cells (FIG. 58). However, the total amount of internalized fibroblast-derived virus was lower than that of the epithelial cell-derived virus. This might reflect a reduced rate of internalization, which would be consistent with the delay in onset of IE1 expression by the fibroblast-derived virus (FIG. 1).

epiBADrUL131 and fibroBADrUL131 Induce Different Transcriptional Responses in ARPE-19 Cells.

Like many other viruses, HCMV modulates cellular signaling pathways during entry. One consequence of the altered intracellular signaling is a dramatic change in the cellular transcriptome, which results substantially from contact of virion glycoproteins with the host cell.

Figure 6A:
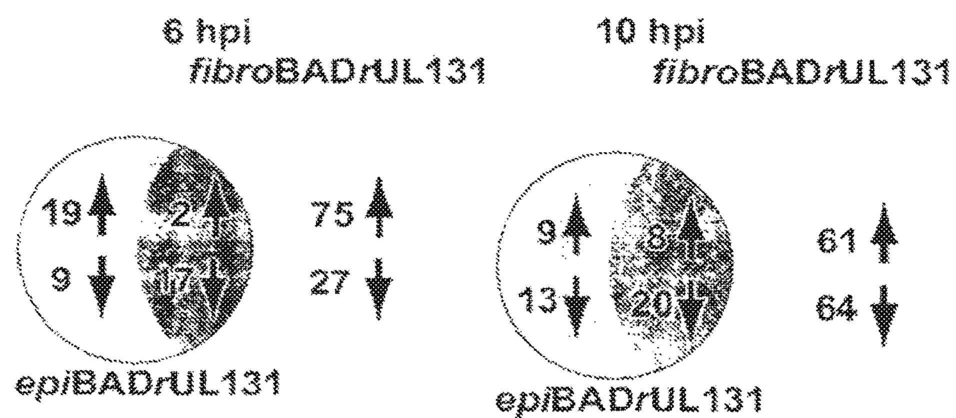
FIGS. 6A-6B. Modulation of the ARPE-19 transcriptome by HCMV produced in epithelial cells versus fibroblasts.

Accordingly, the impact of the two entry pathways on the transcriptional response of ARPE-19 cells was investigated. Cells were mock infected or infected with epiBADrUL131 or fibroBADrUL131, and total RNA was purified 6 or 10 h later. Relative RNA levels were analyzed by using microarrays, and infected-cell RNAs whose levels changed by a factor of ≥2.5 relative to mock-infected controls were identified (Tables 2-5). The distributions of RNAs with increased or decreased expression are depicted by Venn diagrams in FIG. 6A.

TABLE 2

Differentially transcribed genes from epiBADrUL131-infected ARP19 cells at 6 h after infection

| Genbank | Fold Change | Gene Name |
|---|---|---|
| NM_020904 | 7.218 | PEPP1 |
| AK124132 | 5.97 | LOC340286 |
| AK074031 | 4.89 | SLIM; FLJ34715 |
| NM_058188 | 4.658 | PRED54; MGC149386; MGC149387 |
| NM_022047 | 4.578 | IBP |
| NM_020436 | 3.172 | DRRS; HSAL4; ZNF797; MGC133050; dJ1112F19.1 |
| NM_001165 | 3.049 | AIP1; API2; MIHC; CIAP2; HAIP1; HIAP1; MALT2; RNF49 |
| NM_001039580 | 3.011 | ASAP; FLJ21159 |
| NM_000364 | 2.91 | CMH2; TnTC; cTnT; CMPD2; MGC3889 |
| NM_005031 | 2.866 | PLM; MGC44983 |
| L08436 | 2.825 | CLP; FLJ43657; MGC19733 |
| NM_145867 | 2.768 | MGC33147 |
| AL133118 | 2.731 | AL133118 |
| NM_001034 | 2.706 | R2; RR2M |
| NM_020943 | 2.674 | KIAA1604 |
| BC039151 | 2.67 | PABPC1L; FLJ42053; dJ1069P2.3 |
| NM_031217 | 2.659 | DKFZP434G2226 |
| NM_003425 | 2.61 | KOX5; ZNF13 |
| NM_000499 | 2.58 | AHH; AHRR; CP11; CYP1; P1-450; P450-C; P450DX |
| NM_182751 | 2.578 | CNA43; PRO2249; MGC126776 |
| NM_144620 | 2.572 | MGC14816; DKFZp313O1122 |
| NM_020359 | 0.4 | PLSCR2 |
| AF085968 | 0.396 | AF085968 |
| NM_053064 | 0.388 | GNG2 |
| NM_005039 | 0.38 | PM; PMF; PMS; Ps 1; Ps 2; PRB1L; PRB1M |
| NM_152525 | 0.373 | FLJ25351; FLJ40332 |
| AK125975 | 0.365 | FLJ43987 |
| NM_175868 | 0.365 | MAGE6; MAGE3B; MAGE-3b; MGC52297 |
| NM_017600 | 0.358 | DKFZp434M0331 |
| NM_006650 | 0.355 | CPX2; 921-L; CPX-2; MGC138492 |
| NM_004294 | 0.343 | RF1; MTTRF1; MGC47721 |
| NM_006434 | 0.343 | CAP; FLAF2; R85FL; SH3D5; SORB1 |
| NM_031466 | 0.339 | NIBP; T1; IBP; MGC4737; MGC4769; KIAA1882 |
| NM_000808 | 0.324 | MGC33793 |
| NM_012377 | 0.324 | OR7C3; OR19-18; CIT-HSP-87M17 |
| NM_001018084 | 0.31 | NM_001018084 |
| NM_024050 | 0.304 | DDA1; PCIA1; MGC2594 |
| NM_005185 | 0.299 | CLP |
| NM_022115 | 0.272 | PFM15; ZNF298; C21orf83 |
| NM_016125 | 0.259 | LOC51136; MGC111090 |
| NM_004843 | 0.256 | CRL1; TCCR; WSX1; IL27R; zcytor1 |
| NM_004334 | 0.242 | CD157 |
| NM_004185 | 0.233 | WNT13; XWNT2 |
| BX360933 | 0.229 | SLC25A5 |
| NM_032188 | 0.222 | MOF; hMOF; FLJ14040 |
| NM_173550 | 0.221 | FLJ39267; FLJ46740; MGC50805 |
| NM_002104 | 0.162 | TRYP2 |

Microarray targets that hybridized with labeled RNA from epiBADrUL131-infected ARPE-19 cells were compared to mock-infected cells, and probe sets whose levels varied by ≥2.5 fold are listed. The Genebank designation, fold change and gene name are listed.

TABLE 3

Differentially transcribed genes from fibroBADrUL131-infected ARP19 cells at 6 h after infection

| Genbank | Fold Change | Gene name |
|---|---|---|
| NM_183040 | 15.03 | SDY; DBND; HPS7; My031; FLJ30031; MGC20210; DKFZP564K192 |
| NM_001165 | 12.48 | AIP1; API2; MIHC; CIAP2; HAIP1; HIAP1; MALT2; RNF49 |
| NM_002852 | 11.21 | TSG-14; TNFAIP5 |
| NM_006509 | 7.008 | I-REL |
| NM_139314 | 6.679 | NL2; ARP4; FIAF; PGAR; HFARP; pp1158; ANGPTL2 |
| NM_002982 | 5.977 | HC11; MCAF; MCP1; MCP-1; SCYA2; GDCF-2 |
| NM_025169 | 5.938 | ZFP; ZNF64; ZKSCAN7; FLJ12738 |
| NM_033066 | 5.144 | DLG6; ALS2CR5 |
| NM_001946 | 4.971 | MKP3; PYST1 |
| NM_000212 | 4.92 | CD61; GP3A; GPIIIa |
| NM_001673 | 4.214 | TS11 |
| NM_004464 | 4.183 | HBGF-5; Smag-82 |
| NM_021101 | 4.072 | CLD1; SEMP1; ILVASC |
| NM_006851 | 4.07 | GLIPR; RTVP1; CRISP7 |
| AK094860 | 3.913 | AK094860 |
| NM_052875 | 3.667 | Pep8b; MGC10485 |
| NM_005347 | 3.648 | BIP; MIF2; GRP78; FLJ26106 |
| NM_022842 | 3.592 | CD318; TRASK; SIMA135 |
| U16307 | 3.36 | GLIPR; RTVP1; CRISP7 |
| NM_000800 | 3.335 | AFGF; ECGF; FGFA; ECGFA; ECGFB |
| NM_000800 | 3.306 | HBGF1; GLIO703; ECGF-beta; FGF-alpha |
| NM_198833 | 3.257 | PI8; CAP2 |
| NM_002053 | 3.21 | GBP1 |
| NM_058179 | 3.161 | PSA; EPIP; PSAT; MGC1460 |
| NM_001004301 | 3.131 | FLJ16542; FLJ34141 |
| NM_180989 | 3.117 | ITR |
| NM_000640 | 3.116 | IL-13R; IL13BP; CD213A2 |
| NM_002658 | 3.09 | ATF; UPA; URK; u-PA |
| NM_018284 | 3.076 | FLJ10961; DKFZp686E0974; DKFZp686L15228 |
| NM_000201 | 3.022 | BB2; CD54; P3.58 |
| NM_005923 | 3.007 | ASK1; MEKK5; MAPKKK5 |
| NM_018836 | 3.001 | MOT8; SHREW1; SHREW-1; RP3-426F10.1 |
| NM_004556 | 2.971 | IKBE |
| NM_022044 | 2.955 | SDF2L1 |
| NM_006611 | 2.954 | Ly49; KLRA#; LY49L; Ly-49L; MGC126520; MGC126522 |
| NM_014314 | 2.935 | RIG-I; FLJ13599; DKFZp434J1111; DKFZp686N19181 |
| NM_003897 | 2.906 | DIF2; IEX1; PRG1; DIF-2; GLY96; IEX-1; IEX-1L |
| NM_006417 | 2.899 | p44; MTAP44 |
| NM_006187 | 2.877 | p100; MGC133260 |
| NR_002186 | 2.876 | DKFZp58611420 |
| NM_033036 | 2.872 | GAL3ST2; GAL3ST-3; MGC142112; MGC142114 |
| NM_014331 | 2.86 | xCT; CCBR1 |
| NM_003786 | 2.831 | MLP2; MRP3; ABC31; MOAT-D; cMOAT2; EST90757 |
| NM_001511 | 2.829 | GRO1; GROa; MGSA; NAP-3; SCYB1; MGSA-a; MGSA alpha |
| NM_000189 | 2.827 | HKI1; HXK2; DKFZp686M1669 |
| NM_001901 | 2.821 | CCN2; NOV2; HCS24; IGFBP8; MGC102839 |
| NM_031217 | 2.811 | DKFZP434G2226 |
| NM_002849 | 2.766 | PTPRQ; EC-PTP; PCPTP1; PTP-SL; PTPBR7 |
| NM_019891 | 2.764 | ERO1LB |
| NM_002234 | 2.745 | HK2; HCK1; PCN1; HPCN1; KV1.5; MGC117058; MGC117059 |
| NM_198569 | 2.739 | DREG; VIGR; PS1TP2 |
| NM_020799 | 2.726 | AMSH-FP; AMSH-LP; ALMalpha; FLJ31524; KIAA1373; etc |
| NM_014632 | 2.726 | KIAA0750; MICAL2PV1; MICAL2PV2 |
| NM_182920 | 2.721 | FLJ42955; KIAA1312 |
| NM_003483 | 2.715 | BABL; LIPO; HMGIC; HMGI-C |
| NM_133492 | 2.706 | ACER1; MGC138327; MGC138329 |
| CR598364 | 2.633 | ENST00000370238 |
| NM_000970 | 2.62 | TXREB1; SHUJUN-2; TAXREB107 |
| NM_005444 | 2.617 | RCD1; CNOT9; RCD1+ |
| NM_194303 | 2.614 | NM_194303 |
| NM_015359 | 2.612 | ZIP14; cig19; LZT-Hs4; KIAA0062 |
| NM_016354 | 2.608 | POAT; OATP1; OATP-E; OATP4A1; OATPRP1; SLC21A12 |
| NM_015009 | 2.607 | LNX3; SEMACAP3 |
| AK124941 | 2.602 | AK124941 |
| NM_001548 | 2.602 | G10P1; IFI56; ISG56; IFI-56; IFNAI1; RNM561; GARG-16 |
| NM_145023 | 2.597 | FLJ32762; DKFZp686N0559; RP11-479G22.1 |
| NM_023070 | 2.592 | FLJ34293; RP11-656D10.1 |
| NM_001902 | 2.584 | MGC9471 |
| NM_004233 | 2.563 | BL11; HB15 |
| NM_020683 | 2.562 | A3AR; AD026; bA552M11.5; RP11-552M11.7 |
| NM_031938 | 2.56 | FLJ34464; B-DIOX-II |
| NM_152649 | 2.55 | FLJ34389 |
| BC048263 | 2.543 | LOC146909 |
| XM_210365 | 2.527 | LOC284288 |

TABLE 3-continued

| Differentially transcribed genes from fibroBADrUL131-infected ARP19 cells at 6 h after infection | | |
|---|---|---|
| Genbank | Fold Change | Gene name |
| NM_007107 | 2.515 | TRAPG; SSR gamma |
| NM_002837 | 2.513 | PTPB; HPTPB; FLJ44133; MGC59935; HPTP-BETA; |
| NM_172345 | 2.505 | NM_172345 |
| NM_002609 | 0.4 | JTK12; PDGFR; CD140B; PDGFR1; PDGF-R-beta |
| NM_198353 | 0.4 | KCTD8 |
| NM_003558 | 0.394 | MSS4; STM7 |
| NM_001010911 | 0.392 | bA418C1.3 |
| NM_017644 | 0.391 | DRE1; FLJ25796 |
| NM_052892 | 0.388 | FLJ45333; DKFZp686J19100 |
| NM_175868 | 0.387 | MAGE6; MAGE3B; MAGE-3b; MGC52297 |
| NM_007282 | 0.38 | RZF; MGC13689 |
| NM_005185 | 0.38 | CLP |
| NM_021990 | 0.378 | GABRE |
| AK055156 | 0.375 | FLJ30594; MGC120893; DKFZp761K2322 |
| AF085968 | 0.375 | AF085968 |
| NM_019555 | 0.371 | GEF3; STA3; XPLN; MGC118905; DKFZP434F2429 |
| NM_004294 | 0.368 | RF1; MTTRF1; MGC47721 |
| NM_173039 | 0.365 | AQPX1 |
| BU943730 | 0.364 | BU943730 |
| NM_017600 | 0.364 | DKFZp434M0331 |
| NM_007282 | 0.36 | RZF; MGC13689 |
| AL713743 | 0.357 | FLJ42875; MGC35434; DKFZp761G0122 |
| NM_007314 | 0.347 | ARG; ABLL |
| AK056190 | 0.345 | WHRN; CIP98; USH2D; KIAA1526; RP11-9M16.1; DKFZP434N014 |
| NM_000372 | 0.345 | OCA1A; OCAIA |
| BC015929 | 0.338 | RVR; BD73; HZF2; EAR-1r; Hs.37288 |
| NM_012377 | 0.328 | OR7C3; OR19-18; CIT-HSP-87M17 |
| NM_138440 | 0.324 | SLITL2 |
| NM_001018084 | 0.317 | NM_001018084 |
| NM_000808 | 0.311 | MGC33793 |
| NM_033260 | 0.31 | HFH1 |
| NM_022160 | 0.309 | DMO; MGC163307; MGC163309 |
| BC018597 | 0.308 | BC018597 |
| NM_198404 | 0.305 | bA321C24.3 |
| NM_024050 | 0.303 | DDA1; PCIA1; MGC2594 |
| NM_031466 | 0.299 | NIBP; T1; IBP; MGC4737; MGC4769; KIAA1882 |
| NM_016831 | 0.287 | GIG13 |
| NM_022115 | 0.251 | PFM15; ZNF298; C21orf83 |
| NM_016125 | 0.249 | LOC51136; MGC111090 |
| NM_002104 | 0.242 | TRYP2 |
| NM_013261 | 0.236 | LEM6; PGC1; PGC1A; PGC-1v; PPARGC1; PGC-1(alpha) |
| NM_002167 | 0.211 | HEIR-1 |
| NM_032188 | 0.204 | MOF; hMOF; FLJ14040 |
| BX360933 | 0.197 | SLC25A5 |
| NM_003862 | 0.194 | ZFGF5; FGF-18 |
| NM_173550 | 0.148 | FLJ39267; FLJ46740; MGC50805 |
| NM_004185 | 0.135 | WNT13; XWNT2 |

Microarray targets that hybridized with labeled RNA from fibroBADrUL131-infected ARPE-19 cells were compared to mock-infected cells, and probe sets whose levels varied by ≥2.5 fold are listed. The Genebank designation, fold change, and gene name are listed.

TABLE 4

| Differentially transcribed genes from epiBADrUL131-infected ARP19 cells at 10 h after infection | | |
|---|---|---|
| Genbank | Fold Change | Gene Name |
| AK094860 | 5.688 | AK094860 |
| NM_145023 | 4.19 | FLJ32762; DKFZp686N0559; RP11-479G22.1 |
| NM_133492 | 3.456 | ACER1; MGC138327; MGC138329 |
| NM_001039580 | 3.352 | ASAP; FLJ21159 |
| NM_001004301 | 2.982 | FLJ16542; FLJ34141 |
| NM_001034 | 2.911 | R2; RR2M |
| AI369525 | 2.764 | AI369525 |
| AK123066 | 2.753 | AK123066 |
| NM_005345 | 2.729 | HSP72; HSPA1; HSPA1B; HSP70-1 |
| NM_020731 | 2.712 | AHH; AHHR; KIAA1234 |
| BC071797 | 2.631 | BC071797 |
| NM_003414 | 2.609 | HZF2 |
| NM_000800 | 2.576 | AFGF; ECGF; FGFA; ECGFA; ECGFB; HBGF1; GLIO703; etc |
| NM_138467 | 2.571 | C1orf171; FLJ40918 |

TABLE 4-continued

| Differentially transcribed genes from epiBADrUL131-infected ARP19 cells at 10 h after infection | | |
|---|---|---|
| Genbank | Fold Change | Gene Name |
| AK090803 | 2.557 | SRrp35; FLJ14459; FLJ33484; FLJ41221; RP11-63L7.3 |
| AL133118 | 2.529 | AL133118 |
| NM_001165 | 2.508 | AIP1; API2; MIHC; CIAP2; HAIP1; HIAP1; MALT2; RNF49 |
| BG001037 | 0.392 | TXNRD1 |
| NM_024861 | 0.388 | FLJ22671; MGC150431; MGC150432 |
| NM_001043 | 0.385 | NET; NAT1; NET1; SLC6A5 |
| NM_016239 | 0.384 | DFNB3; MYO15; DKFZp686N18198 |
| NM_001018084 | 0.383 | NM_001018084 |
| NM_001037442 | 0.381 | RIPX; KIAA0871 |
| NM_017600 | 0.377 | DKFZp434M0331 |
| NM_022097 | 0.369 | LOC63928 |
| NM_175868 | 0.356 | MAGE6; MAGE3B; MAGE-3b; MGC52297 |
| NM_032266 | 0.342 | DKFZp434G118; DKFZp781D2023 |
| NM_003841 | 0.342 | LIT; DCR1; TRID; CD263; TRAILR3; MGC149501; MGC149502 |
| NM_005039 | 0.339 | PM; PMF; PMS; Ps 1; Ps 2; PRB1L; PRB1M |
| NM_145051 | 0.339 | MGC4734; FLJ31197 |
| NM_004294 | 0.336 | RF1; MTTRF1; MGC47721 |
| AW856073 | 0.335 | AW856073 |
| NM_024050 | 0.327 | DDA1; PCIA1; MGC2594 |
| AF085968 | 0.327 | AF085968 |
| NM_080927 | 0.318 | ESDN; CLCP1 |
| NM_022115 | 0.317 | PFM15; ZNF298; C21orf83 |
| AK056703 | 0.309 | LOC219731 |
| NM_000808 | 0.301 | MGC33793 |
| NM_012377 | 0.299 | OR7C3; OR19-18; CIT-HSP-87M17 |
| NM_006793 | 0.298 | AOP1; MER5; AOP-1; SP-22; PRO1748; MGC24293; MGC104387 |
| NM_031466 | 0.289 | NIBP; T1; IBP; MGC4737; MGC4769; KIAA1882 |
| NM_005185 | 0.286 | CLP |
| NM_139173 | 0.286 | MGC131641 |
| BX360933 | 0.28 | SLC25A5 |
| NM_016125 | 0.269 | LOC51136; MGC111090 |
| NM_002104 | 0.251 | TRYP2 |
| NM_032188 | 0.248 | MOF; hMOF; FLJ14040 |
| NM_004185 | 0.245 | WNT13; XWNT2 |
| NM_004843 | 0.237 | CRL1; TCCR; WSX1; IL27R; zcytor1 |
| NM_173550 | 0.208 | FLJ39267; FLJ46740; MGC50805 |

Microarray targets that hybridized with labeled RNA from epiBADrUL131-infected ARPE-19 cells were compared to mock-infected cells, and probe sets whose levels varied by ≥2.5 fold are listed. The Genebank designation, fold change and gene name are listed.

TABLE 5

| Differentially transcribed genes from fibroBADrUL131-infected ARP19 cells at 10 h after infection | | |
|---|---|---|
| Genbank | Fold Change | Gene Name |
| AK094860 | 11.26 | AK094860 |
| NM_033066 | 8.751 | DLG6; ALS2CR5 |
| NM_145023 | 6.529 | FLJ32762; DKFZp686N0559; RP11-479G22.1 |
| NM_152377 | 4.463 | FLJ44073; MGC34837 |
| NM_002310 | 4.386 | SWS; SJS2; STWS; CD118 |
| NR_001279 | 4.051 | LOC164380; MGC26611; MGC26924 |
| NM_005345 | 4.008 | HSP72; HSPA1; HSPA1B; HSP70-1 |
| NM_006417 | 3.879 | p44; MTAP44 |
| NM_017638 | 3.783 | p28b; FLJ20045 |
| NM_001165 | 3.695 | AIP1; AP12; MIHC; CIAP2; HAIP1; HIAP1; MALT2; RNF49 |
| NM_000640 | 3.659 | IL-13R; IL13BP; CD213A2 |
| NM_001673 | 3.313 | TS11 |
| NM_002526 | 3.274 | NT; eN; NT5; NTE; eNT; CD73; E5NT |
| NM_003786 | 3.244 | MLP2; MRP3; ABC31; MOAT-D; cMOAT2; EST90757 |
| NM_005527 | 3.229 | hum70t; HSP70-HOM |
| NM_018372 | 3.224 | RIF1; FLJ11269; RP11-96K19.1 |
| NM_133492 | 3.16 | ACER1; MGC138327; MGC138329 |
| NM_033160 | 3.101 | FLJ32813; MGC35232; DKFZp572C163 |
| DB318210 | 3.094 | DB318210 |
| NM_182751 | 3.093 | CNA43; PRO2249; MGC126776 |
| NM_180989 | 3.089 | ITR |
| NM_005345 | 3.048 | HSP72; HSPA1; HSPA1B; HSP70-1 |
| NM_005345 | 3.029 | HSP72; HSPA1; HSPA1B; HSP70-1 |
| NM_000212 | 2.993 | CD61; GP3A; GPIIIa |
| NM_145867 | 2.991 | MGC33147 |

TABLE 5-continued

Differentially transcribed genes from fibroBADrUL131-infected ARP19 cells at 10 h after infection

| Genbank | Fold Change | Gene Name |
|---|---|---|
| NM_021813 | 2.976 | BACH2 |
| NM_006187 | 2.943 | p100; MGC133260 |
| CR594200 | 2.942 | LOC643837 |
| NM_012419 | 2.941 | RGSZ2; RGS-17; hRGS17 |
| AF038194 | 2.923 | AF038194 |
| NM_018664 | 2.921 | SNFT; BATF3; JUNDM1 |
| NM_017577 | 2.907 | FLJ35862; FLJ40464 |
| NM_144633 | 2.887 | ELK; ELK1; elk3; Kv12.1 |
| NM_144620 | 2.86 | MGC14816; DKFZp313O1122 |
| NM_001004301 | 2.859 | FLJ16542; FLJ34141 |
| NM_002852 | 2.847 | TSG-14; TNFAIP5 |
| NM_007107 | 2.839 | TRAPG; SSR gamma |
| NM_032778 | 2.836 | MDIG; NO52; MINA53; FLJ14393; DKFZp762O1912 |
| NM_032523 | 2.828 | ORP6; FLJ36583; MGC59642 |
| NM_005515 | 2.808 | HB9; SCRA1; HOXHB9 |
| NM_002201 | 2.804 | CD25; HEM45 |
| NM_152649 | 2.799 | FLJ34389 |
| NM_033036 | 2.794 | GAL3ST2; GAL3ST-3; MGC142112; MGC142114 |
| NM_006509 | 2.791 | I-REL |
| NM_004233 | 2.789 | BL11; HB15 |
| NM_180989 | 2.772 | ITR |
| NM_020988 | 2.735 | GNAO; G-ALPHA-o; DKFZp686O0962 |
| U16307 | 2.687 | GLIPR; RTVP1; CRISP7 |
| NM_003706 | 2.672 | CPLA2-gamma; DKFZp586C0423 |
| NM_153689 | 2.662 | FLJ38973 |
| NM_000800 | 2.653 | AFGF; ECGF; FGFA; ECGFA; ECGFB; HBGF1; GLIO703; etc |
| BC043212 | 2.643 | LOC402125 |
| NM_002670 | 2.619 | I-PLASTIN |
| NM_152408 | 2.614 | FLJ35779; MGC120442; MGC120443; MGC120444 |
| NM_198951 | 2.613 | TG2; TGC |
| NM_012329 | 2.595 | MMA; PAQR11 |
| NM_001009954 | 2.589 | FLJ20105; MGC131695 |
| NM_032228 | 2.585 | FAR1; FLJ22728; FLJ33561 |
| AI369525 | 2.584 | AI369525 |
| NM_004170 | 2.583 | EAAC1; EAAT3 |
| NM_002930 | 2.571 | RIN; RIBA; ROC2 |
| AK023856 | 2.569 | LOC339803 |
| NM_024525 | 2.558 | FLJ22584 |
| NM_152649 | 2.553 | FLJ34389 |
| NM_181795 | 2.552 | PRKACN2; FLJ23817 |
| BC039151 | 2.549 | PABPC1L; FLJ42053; dJ1069P2.3 |
| NM_006547 | 2.525 | IMP3; KOC1; IMP-3; VICKZ3; DKFZp686F1078 |
| NM_000641 | 2.521 | AGIF; IL-11 |
| NM_145306 | 2.506 | C10orf35 |
| AK021804 | 0.398 | AK021804 |
| NM_007211 | 0.397 | HoJ-1; C12orf2 |
| NM_203434 | 0.397 | MGC70833; bA247A12.2 |
| NM_000362 | 0.397 | SFD; K222; K222TA2; HSMRK222 |
| AK056703 | 0.395 | LOC219731 |
| NM_003558 | 0.395 | MSS4; STM7 |
| NM_016831 | 0.394 | GIG13 |
| NM_024861 | 0.394 | FLJ22671; MGC150431; MGC150432 |
| BF514513 | 0.393 | BF514513 |
| NR_002819 | 0.392 | MALAT-1 |
| NM_002609 | 0.391 | JTK12; PDGFR; CD140B; PDGFR1; PDGF-R-beta |
| NM_018027 | 0.391 | FRMD4; FLJ10210; KIAA1294; bA295P9.4 |
| NM_001010911 | 0.39 | bA418C1.3 |
| AW444553 | 0.389 | FAM84B |
| AK056190 | 0.388 | WHRN; CIP98; USH2D; KIAA1526; RP11-9M16.1 |
| NM_175868 | 0.385 | MAGE6; MAGE3B; MAGE-3b; MGC52297 |
| AB051431 | 0.385 | KIAA1644; MGC125851; MGC125852 |
| NM_001003683 | 0.384 | HCAM1; HSPDE1A; MGC26303 |
| NM_004294 | 0.384 | RF1; MTTRF1; MGC47721 |
| NM_006516 | 0.383 | GLUT; GLUT1; MGC141895; MGC141896 |
| BX104999 | 0.382 | BX104999 |
| AL713743 | 0.381 | FLJ42875; MGC35434; DKFZp761G0122 |
| NM_000322 | 0.381 | RDS; RP7; rd2; AVMD; PRPH; AOFMD; TSPAN22 |
| NM_007314 | 0.381 | ARG; ABLL |
| NM_018371 | 0.376 | ChGn; FLJ11264; beta4GalNAcT |
| NR_002802 | 0.376 | TncRNA |
| DB527271 | 0.376 | DB527271 |
| NM_006393 | 0.374 | LNEBL; bA56H7.1; MGC119746; MGC119747 |
| NM_013989 | 0.372 | D2; 5DI1, SelY, TXDI2 |
| NM_017600 | 0.37 | DKFZp434M0331 |
| BC011595 | 0.369 | NMB; HGFIN |

TABLE 5-continued

Differentially transcribed genes from fibroBADrUL131-infected ARP19 cells at 10 h after infection

| Genbank | Fold Change | Gene Name |
|---|---|---|
| AF085968 | 0.366 | AF085968 |
| BC018597 | 0.365 | BC018597 |
| NM_014729 | 0.362 | TOX1; KIAA0808 |
| NM_001003940 | 0.362 | FLJ00065 |
| NM_000372 | 0.358 | OCA1A; OCA1A |
| NM_019555 | 0.358 | GEF3; STA3; XPLN; MGC118905; DKFZP434F2429 |
| NM_022115 | 0.357 | PFM15; ZNF298; C21orf83 |
| NM_198353 | 0.355 | KCTD8 |
| NM_032434 | 0.355 | KIAA1805; MGC111046 |
| AK055386 | 0.355 | AK055386 |
| NM_006933 | 0.352 | SMIT; SMIT2 |
| CR622110 | 0.35 | CR622110 |
| AW856073 | 0.347 | AW856073 |
| NM_015074 | 0.345 | KLP; CMT2; CMT2A; CMT2A1; HMSNI1 |
| NM_032866 | 0.342 | JACOP; FLJ14957; KIAA1749; MGC138254 |
| NM_012377 | 0.342 | OR7C3; OR19-18; CIT-HSP-87M17 |
| NM_005261 | 0.341 | KIR; MGC26294 |
| AK023391 | 0.339 | AK023391 |
| NM_002214 | 0.339 | ITGB8 |
| NM_182728 | 0.339 | LAT2; LPI-PC1 |
| NM_024050 | 0.338 | DDA1; PCIA1; MGC2594 |
| NM_005185 | 0.338 | CLP |
| NM_016613 | 0.337 | AD021; AD036; FLJ38155; DKFZp434L142 |
| NM_000782 | 0.336 | CP24; CYP24; MGC126273; MGC126274; P450-CC24 |
| NM_001624 | 0.335 | ST4 |
| NM_007282 | 0.333 | RZF; MGC13689 |
| NM_001037442 | 0.327 | RIPX; KIAA0871 |
| NM_004318 | 0.32 | BAH; HAAH; JCTN; junctin; CASQ2BP1 |
| BU943730 | 0.32 | BU943730 |
| NM_205849 | 0.319 | FLJ40182 |
| NM_000808 | 0.315 | MGC33793 |
| NM_033260 | 0.313 | HFH1 |
| NM_000916 | 0.309 | OT-R |
| NM_032188 | 0.309 | MOF; hMOF; FLJ14040 |
| BX360933 | 0.306 | SLC25A5 |
| NM_014351 | 0.304 | NST; BRSTL1; SULTX3; BR-STL-1; MGC40032; DJ388M5.3; etc |
| NM_002167 | 0.3 | HEIR-1 |
| NM_001033086 | 0.298 | dJ631M13.5; RP11-189J1.1 |
| NM_000372 | 0.292 | OCA1A; OCA1A |
| NM_001002926 | 0.289 | TWISTNB |
| AK094143 | 0.288 | C14orf78; KIAA2019 |
| NM_004466 | 0.287 | GPC5 |
| NM_031466 | 0.276 | NIBP; T1; IBP; MGC4737; MGC4769; KIAA1882 |
| NM_013261 | 0.271 | LEM6; PGC1; PGC1A; PGC-1v; PPARGC1; PGC-1(alpha) |
| NM_000693 | 0.267 | ALDH6; RALDH3; ALDH1A6 |
| NM_016125 | 0.26 | LOC51136; MGC111090 |
| AK124390 | 0.23 | AK124390 |
| NM_002104 | 0.228 | TRYP2 |
| NM_005341 | 0.209 | HKR3; pp9964 |
| NM_173082 | 0.202 | FLJ27258; FLJ37625; FLJ45012 |
| NM_173550 | 0.191 | FLJ39267; FLJ46740; MGC50805 |
| NM_004185 | 0.133 | WNT13; XWNT2 |
| NM_021727 | 0.0415 | CYB5RP; LLCDL3 |

Microarray targets that hybridized with labeled RNA from fibroBADrUL131-infected ARPE-19 cells were compared to mock-infected cells, and probe sets whose levels varied by ≥2.5 fold are listed. The Genebank designation, fold change and gene name are listed.

Figure 6B:
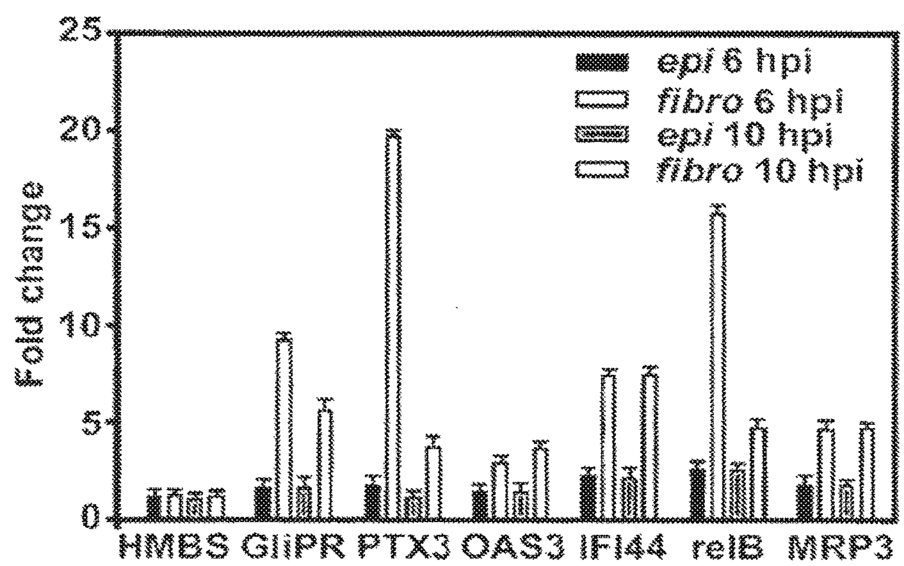

At 6 h after epiBADrULI31 infection, the levels of 47 RNAs were changed as compared to mock-infected cells, and 121 RNAs were altered in fibroBADrUL131-infected versus mock-infected cells. The set of modulated RNAs was substantially different for the two viruses; only 19 RNAs were altered after infection with either epiBADrUL131 or fibroBADrUL131. Although there might be several instances in which a gene was altered by one virus by a factor of ≥2.5-fold, while the other virus induced a more modest alteration that fell below the cut-off, inspection of the data revealed that this was not common. At 10 hpi, the number of host cell RNAs modulated by epiBADrUL131 increased only slightly (50 RNAs), whereas a more substantial increase was observed for fibroBADrUL131 (153 RNAs). At the later time, the number of RNAs modulated by both viruses increased to a limited extent (28 RNAs). The microarray results were confirmed by real time RT-PCR for one RNA that was not altered and six RNAs that were altered by infection (FIG. 6B).

To further compare the modulation of RNA levels by fibroBADrUL131 versus epiBADrUL131, the array results were filtered using a gene list comprised of four Gene Ontology groups: host-pathogen interaction (G0:0030383), cell communication (G0:0007154), viral life cycle (G0:0016032) and cell-cell signaling (G0:0007267). Nearly one third of the mRNAs (70 of 222) that were regulated greater than 2.5 fold in fibroBADrUL131-infected ARPE-19 cells were present in the combined grouping (Table 6). In marked contrast, only one of 86 RNAs induced by epiBADrUL131 was found in these four Gene Ontology groups. The two virus preparations generated substantially different transcriptional responses upon infection of epithelial cells.

TABLE 6 fibroBADrUL131-modified cellular RNA levels

| Genbank | Fold Change 6hpi | Fold Change 10hpi | Gene Name |
|---|---|---|---|
| NM_006509 | 7.008 | 2.791 | I-REL |
| NM_139314 | 6.679 | 2.067 | NL2; ARP4; FIAF; PGAR; HFARP; pp1158; ANGPTL2 |
| NM_002982 | 5.977 | nc | HC11; MCAF; MCP1; MCP-1; SCYA2; GDCF-2; etc |
| NM_000212 | 4.92 | 2.993 | CD61; GP3A; GPIIIa |
| NM_002310 | nc | 4.386 | SWS; SJS2; STWS; CD118 |
| NM_004464 | 4.183 | 2.264 | HBGF-5; Smag-82 |
| NM_021101 | 4.072 | nc | CLD1; SEMP1; ILVASC |
| NM_006851 | 4.07 | 2.364 | GLIPR; RTVP1; CRISP7 |
| NM_005347 | 3.648 | nc | BIP; MIF2; GRP78; FLJ26106 |
| U16307 | 3.36 | 2.687 | GLIPR; RTVP1; CRISP7 |
| NM_000800 | 3.335 | 2.115 | AFGF; ECGF; FGFA; ECGFA; ECGFB; HBGF1; etc |
| NM_002526 | nc | 3.274 | NT; eN; NT5; NTE; eNT; CD73; E5NT |
| NM_005527 | nc | 3.229 | hum70t; HSP70-HOM |
| NM_002053 | 3.21 | nc | GBP1 |
| NM_180989 | 3.117 | nc | ITR |
| NM_000640 | 3.116 | 3.659 | IL-13R; IL13BP; CD213A2 |
| NM_002658 | 3.09 | nc | ATF; UPA; URK; u-PA |
| NM_180989 | nc | 3.089 | ITR |
| NM_018284 | 3.076 | 2.185 | FLJ10961; DKFZp686E0974; DKFZp686L15228 |
| NM_005345 | nc | 3.048 | HSP72; HSPA1; HSPA1B; HSP70-1 |
| NM_000201 | 3.022 | nc | BB2; CD54; P3.58 |
| NM_004556 | 2.971 | nc | IKBE |
| NM_006611 | 2.954 | 2.263 | Ly49; KLRA#; LY49L; Ly-49L; MGC126520; etc |
| NM_014314 | 2.935 | 2.071 | RIG-1; FLJ13599; DKFZp434J1111; DKFZp686N19181 |
| NM_003897 | 2.906 | nc | DIF2; IEX1; PRG1; DIF-2; GLY96; IEX-1; IEX-1L |
| NM_006417 | 2.899 | 3.879 | p44; MTAP44 |
| NM_144633 | nc | 2.887 | ELK; ELK1; elk3; Kv12.1 |
| NM_006187 | 2.877 | 2.943 | p100; MGC133260 |
| NM_032778 | nc | 2.836 | MDIG; NO52; MINA53; FLJ14393; DKFZp762O1912 |
| NM_003786 | 2.831 | 3.244 | MLP2; MRP3; ABC31; MOAT-D; cMOAT2; EST90757 |
| NM_001511 | 2.829 | nc | GRO1; GROa; MGSA; NAP-3; SCYB1; MGSA-a; etc |
| NM_001901 | 2.821 | nc | CCN2; NOV2; HCS24; IGFBP8; MGC102839 |
| NM_002849 | 2.766 | nc | PTPRQ; EC-PTP; PCPTP1; PTP-SL; PTPBR7 |
| NM_002234 | 2.745 | nc | HK2; HCK1; PCN1; HPCN1; KV1.5; MGC117058; etc |
| NM_198569 | 2.739 | 2.182 | DREG; VIGR; PS1TP2 |
| NM_000970 | 2.62 | nc | TXREB1; SHUJUN-2; TAXREB107 |
| NM_198951 | nc | 2.613 | TG2; TGC |
| NM_015359 | 2.612 | nc | ZIP14; cig19; LZT-Hs4; KIAA0062 |
| NM_001548 | 2.602 | nc | G10P1; IF156; ISG56; IF1-56; IFNAI1; RNM561; etc |
| NM_012329 | nc | 2.595 | MMA; PAQR11 |
| NM_002930 | nc | 2.571 | RIN; RIBA; ROC2 |
| NM_004233 | 2.563 | 2.789 | BL11; HB15 |
| NM_020683 | 2.562 | nc | A3AR; AD026; bA552M11.5; RP11-552M11.7 |
| NM_181795 | nc | 2.552 | PRKACN2; FLJ23817 |
| NM_006547 | nc | 2.525 | IMP3; KOC1; IMP-3; VICKZ3; DKFZp686F1078 |
| NM_000641 | nc | 2.521 | AGIF; IL-11 |
| NM_172345 | 2.505 | nc | NM_172345 |
| NM_012419 | 2.359 | 2.941 | RGSZ2; RGS-17; hRGS17 |
| NM_020988 | 2.188 | 2.735 | GNAO; G-ALPHA-o; DKFZp686O0962 |
| NM_002201 | 2.028 | 2.804 | CD25; HEM45 |
| NM_004318 | 0.495 | 0.32 | BAH; HAAH; JCTN; junctin; CASQ2BP1 |
| NM_013989 | 0.492 | 0.372 | D2; 5DII; SelY; TXDI2 |
| NM_005261 | 0.468 | 0.341 | KIR; MGC26294 |
| NM_000916 | 0.434 | 0.309 | OT-R |
| NM_014351 | 0.408 | 0.304 | NST; BRSTL1; SULTX3; BR-STL-1; MGC40032; etc |
| NM_002609 | 0.4 | 0.391 | JTK12; PDGFR; CD140B; PDGFR1; PDGF-R-beta |
| NM_007211 | nc | 0.397 | HoJ-1; C12orf2 |
| NM_001003683 | nc | 0.384 | HCAM1; HSPDE1A; MGC26303 |
| NM_006516 | nc | 0.383 | GLUT; GLUT1; MGC141895; MGC141896 |
| NM_000322 | nc | 0.381 | RDS; RP7; rd2; AVMD; PRPH; AOFMD; TSPAN22 |
| NM_021990 | 0.378 | 0.49 | GABRE |
| NM_018371 | nc | 0.376 | ChGn; FLJ11264; beta4GalNAcT |
| NM_019555 | 0.371 | 0.358 | GEF3; STA3; XPLN; MGC118905; DKFZP434F2429 |
| NM_007314 | 0.347 | 0.381 | ARG; ABLL |
| NM_002214 | nc | 0.339 | ITGB8 |
| NM_182728 | nc | 0.339 | LAT2; LPI-PC1 |
| BC015929 | 0.338 | 0.453 | RVR; BD73; HZF2; EAR-1r; Hs.37288 |
| NM_016831 | 0.287 | 0.394 | GIG13 |

TABLE 6-continued

| fibroBADrUL131-modified cellular RNA levels | | | |
|---|---|---|---|
| Genbank | Fold Change 6hpi | Fold Change 10hpi | Gene Name |
| NM_013261 | 0.236 | 0.271 | LEM6; PGC1; PGC1A; PGC-1v; PPARGC1; etc |
| NM_003862 | 0.194 | nc | ZFGF5; FGF-18 |

Four GO groups were combined: host-pathogen interaction (GO:0030383), cell communication (GO:0007154), viral life cycle (GO:0016032) and cell-cell signaling (GO:0007267). The set of 9276 genes was used to filter array results from fibroBADrUL131-infected ARPE-19 cells. Genbank identifiers and gene names are shown along with the fold induction or repression at 6 and 10 hpi. Probe sets that did not change by ≥2.5 compared to mock-infected cells are designated by "nc" for no change.

Discussion

ARPE-19 epithelial cells can be infected by HCMV through two different routes: fusion at the plasma membrane or endocytosis followed by fusion at the endosomal membrane. Both modes of entry initiate a productive infection. The route of entry depends on the cell type in which the virus was propagated. HCMV from epithelial cells enters by the former route, and virus grown in fibroblasts follows the latter path. This conclusion follows from ultrastructural analysis and differential sensitivity of infection to agents that block acidification of endosomes. The observation that virus grown in epithelial cells has greater "fusion from without" activity than does virus produced in fibroblasts reinforces the view that the two virus preparations interact with ARPE-19 cells in a fundamentally different manner. Importantly, both modes of entry require pUL130 function because pUL130 antibody neutralized infection by virus produced from either source. The gH/gL/pUL128/pUL130/pUL131 complex functions at the ARPE-19 plasma membrane if the infecting virus has been produced in epithelial cells and at the endosomal membrane if the virus was grown in fibroblasts. Neutralized virus in the endosome fails to escape and presumably suffers the same fate as AD169, which lacks the pUL130-containing complex and accumulates in epithelial cell endosomes without initiating a productive infection (10).

Virus grown in fibroblasts induces 1EI protein accumulation in ARPE-19 cells after a delay relative to virus from epithelial cells, suggesting that some aspect of entry by endocytosis proceeds more slowly than entry by fusion at the plasma membrane. Many virions are evident in endosomes, but no capsids were seen in the cytoplasm after entry of fibroblast-generated virus; and capsids were found rarely in the cytoplasm of cells infected with epithelial cell-produced virus. Apparently, virions linger for a time in endosomes, but once a capsid is freed of its envelope and reaches the cytoplasm, it is rapidly disassembled.

How are HCMV virions produced in the two cell types different? It appears different "fusion from without" activities provide an indication. Not only did epiBADrUL131 induce fusion more efficiently than fibroBADrU L131, but lowered pH enhanced the activities of both virus preparations. Without intending to be bound or limited by any explanation of mechanism, it is possible that fusion of membranes requires a threshold of fusion activity. The ability of pUL130 antibody to neutralize both virus preparations indicates that both depend on the gH/gL/pUL128/pUL130/pUL131 complex for fusion, so experiments were devised to the hypothesis that the viruses contain different amounts of the complex. Several of its constituents were assayed, and it was found that a slightly higher ratio (~2-fold) of gH/gL/pUL128/pUL130/pUL131 to gH/gL/gO were present in epiBADrUL131 particles than in fibroBADrUL131 particles. The levels of gB, pp28 and pp65 were similar in the two virion preparations.

There is precedent in EBV for production of viruses with different relative amounts of a gH complex: particles produced by B cells are deficient for gH/gL/gp42 (18). However, other factors may be involved. Perhaps a constituent of the complex that was not assayed is altered. Alternatively, the ratio of the gH complex to one or more additional virion glycoprotein complexes might modify fusion activity. Finally, it may be that an unidentified cell protein, supplied to the virions when they are produced within epithelial cells or fibroblasts, might alter the complex.

Are there physiological consequences to the two modes of entry? epiBADrUL131 and fibroBADrUL131 induced markedly different cellular transcriptional responses after infection of ARPE-19 cells. Assuming that the difference is indeed due to virions or virions plus specifically associated cellular factors, the microarray experiment demonstrates a strikingly different transcriptional response to infection. Endocytosis is intimately involved in the regulation of signaling by cell surface molecules. As a consequence, a virus might modulate cell signaling, and the cellular transcriptome, differently if it enters by fusion at the plasma membrane versus endocytosis. The differences in cell signaling likely have physiological consequences that are not detected in cultured cells, such as effects on virus spread, immune vasion, or virulence.

REFERENCES

I. Miller. N. & Hutt-Fletcher, L. M. (1992) *J Viro/*66, 3409-14.
2. Nemerow. G. R. & Cooper. N. R. (I 984) *Virology* 132, 186-98.
3. Nicola. A. V., Hou. J., Major, E. 0. & Straus, S. E. (2005) *J Viro/*79, 7609-16.
4. Nicola, A. V., McEvoy, A. M. & Straus, S. E. (2003) *J Viro/*77, 5324-32.
5. Milne. R. S., Nicola, A. V., Whitbeck. I. C., Eisenberg. R. J. & Cohen. G. H. (2005) *J Viro/*79, 6655-63.
6. Wittels. M. & Spear. P. G. (1991) *Virus Res* 18, 271-90.
7. Plachtcr. B., Sinzger, C. & Jahn, G. (1996) *Adv Virus Res* 46, 195-261.
8. Compton, T., Nepomuceno. R. R. & Nowlin, D. M. (1992) *Virology* 191, 387-95.
9. Bodaghi. B., Goureau. 0., Zipeto. D., Laurent. L., Yirelizier. J. L. & Michelson. S. (1999) *J/mmuno/*162. 957-64.
I 0. Ryckman. B. J., Jarvis. M. A., Drummond, D. D., Nelson. J. A. & Johnson. D. C. (2006) *J Viro/*80, 710-22.
11. Wang. X., Kenyon. W. J., Li, Q Mullberg, J. & Hutt-Fletcher. L. M. (1998) *J Virol* 72, 5552-8.
12. Li, Q., Turk. S. M. & Hutt-Fletcher. L. M. (1995) *J Viro/*69, 3987-94.
13. Hutt-Fletcher. L. M. & Lake. C. M. (2001) *Curr Top Microbiollmmwzol* 258, 51-64.
14. Haan. K. M Kwok. W. W Longnecker. R. & Speck. P. (2000) *J Viro/*14, 2451-4.

15. Haan. K. M. & Longnecker. R. (2000) *Proc Nat! Acad Sci USA* 91, 9252-7.

16. Li. Q., Spriggs. M. K., Kovats. S., Turk, S. M., Comeau. M. R Nepom. B. & Hun-Fletcher, L. M. (1997) *J Viro/*11, 4657-62.

17. Wang. X. & Hun-Fletcher. L. M. (1998) *J Viro/*12, 158-63.

18. Borza. C. M. & Hun-Fletcher. L. M. (2002) *Nat Med* 8, 594-9.

19. Wang. D. & Shenk. T. (2005) *Proc Natl Acad Sci USA* 102, 18153-8.

20. Adler. B Scrivano. L., Ruzcics. Z., Rupp. B., Sinzger. C. & Koszinowski. U. (2006) J Gen Viro/81, 2451-2460.

21. Wang, D. & Shenk, T. (2005) *J Viro/*19, 10330-8.

22. Hahn. G., Revello. M. G., Patrone. M., Percivalle. E., Campanini. G., Sarasini. A., Wagner, M., Gallina, A., Milanesi, G., Koszinowski. U Baldanti. F. & Gerna. G. (2004) *J Viro/*18, 10023-33.

The present invention is not limited to the embodiments described and exemplified above, but is capable of variation and modification within the scope of the appended claims.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of making an immunogenic composition comprising a population of live attenuated, inactivated or killed cytomegaloviruses (CMVs), or virion components thereof, comprising:

a) passaging a single strain or isolate of CMV having a gene encoding a functional pUL131 protein in a fibroblast cell culture to thereby produce a passaged strain or isolate of CMV;

b) amplifying the passaged strain or isolate of CMV in an epithelial cell culture to thereby produce an amplified strain or isolate of CMV;

c) harvesting the amplified strain or isolate of CMV from the epithelial cell culture to thereby obtain cell-type conditioned CMV; and d) combining the cell-type conditioned CMV with a pharmaceutically acceptable adjuvant, thereby making an immunogenic composition comprising a population live attenuated, inactivated or killed CMVs, or virion components thereof.

2. The method of claim 1, wherein the passaged strain or isolate of CMV is amplified in a single epithelial cell culture.

3. The method of claim 1, wherein the passaged strain or isolate of CMV is amplified in two or more different epithelial cell cultures.

4. The method of claim 1, wherein the single strain or isolate of CMV is a human CMV strain or isolate.

5. The method of claim 1, wherein the single strain or isolate of CMV is an unmodified CMV strain or isolate, or a chimeric CMV strain or isolate.

6. The method of claim 1, wherein the immunogenic composition comprises a population live attenuated CMVs, or virion components thereof.

7. The method of claim 1, wherein the immunogenic composition comprises a population of inactivated or killed CMVs, or virion components thereof.

* * * * *

SEQUENCE LISTING

```
<160> NUMBER OF SEQ ID NOS: 50

<210> SEQ ID NO 1
<211> LENGTH: 1808
<212> TYPE: DNA
<213> ORGANISM: Homo Sapiens
<220> FEATURE:
<223> OTHER INFORMATION: AK094860

<400> SEQUENCE: 1

ttgcttcccc atgtctcaat ttgttaaatc ttattgttct atgtaatttg aattgctaca      60

tcctttctgt tgactagctc cttgctcaga ataacttttc cacacctgga actttggcgt     120

aggagttctt ttcactttta tgcatttccc gcgacattac agggtgagta cgtagcagat     180

gagtgcttgt gagcctttcc tctgggattc acacagatgg ctcactccta actttggtga     240

gtcattcagt ggccagatgt ttgcctcttt cctcctcccc actctacccc cacaattcag     300

tgtactgttc tttgaatgac atcccctctt gtttttgcct ctctttctcc tgatgcaatg     360

gccaaaatgc tggaaatggc tgccttaaat gtagggacca ttaggatctc gctcaacaca     420

gaacccaggc cacctgtaat aacacagctg gctcccagtc ctgaaaccct gcctttctgc     480

cctgaatggg gtgcagagaa ccagtccaga cacctgaaac tgccaccctt cttcatctgt     540

aggtgcaggg gccctctgta tcaggaagag agcctctctg aaatccactg tcattctggg     600

cttttcctgg accagctctc cttacctacc cccttctcta gcctgtcagt ttcactcatt     660

cattggacat ttataagcac taagtatgta ccaggcatca tgctggcctt tggtggtacc     720

aacaaataaa gagactgcta aatgcagaaa aataggcaca gagtaaagac ttgtaagtct     780

gtaaaggagt gctcagtgag aagtcacaca agctaagttt ccaaggacca tttgcagatc     840

actgctgaac attctccatc ctgcctactt tgtattagag gacttcttgc agggagaaat     900

ataatcagca ggatcctcgc tcagagacct ggcagacacc accttaaccc agtgatcaaa     960

gttaacctcc ccagtacatg tccaactact gctgccctga aaggatgcac tgagaacatt    1020

tctgtgtcat ttctaccaca gatgcgctac ttgaatctaa ttatgaagag acaagagaca    1080

aacccagatt gaggggcatt cagcaaaata attgccctgt actctttaaa aaacggcaat    1140

gttgagaaag acaaagaaag actgaggagc tattccagtt aaagtaggct agagacactg    1200

ggaaccaaat gtgatgcatg atccaggata ttcttttatt acagtgagca tcattgggac    1260

agttggtaaa atgtgaatat tgtctgaaga gtataatatt gtatcaaagt taatttcctg    1320

gtcttgagga ttgtactgtg gttatgtaag agaatgtcct tgtttttagg aaatagatgt    1380

tgaaatatct tgagataaag agcattatgt cggcgactta ttatcaaata gtacaggaaa    1440
```

```
atgagtgtgt gtgtgtgtgt gtgtgtgtgt gtgtgtggag agagagagag aagggaggga   1500

cagagggaca gagagatata aaaccaatgc acctgggtgc ggtggctcac gcctgtaatc   1560

ccagcacttt gggaggccag ggtgggcaga tcatgaggtc agaagttcga gaccagccta   1620

accaacatgg tgaaaccccg tctctacaaa aatacaaaaa tcagccaggc gtggtggcac   1680

gcgcctgtaa tcccagctac tcaggaggct gaggcaggag aattgcttga acccaggagg   1740

cggaggttgc agtgagccaa gatcacgcca ctgcactcca gcctggtgac agagcaagac   1800

tctgtctc                                                            1808


<210> SEQ ID NO 2
<211> LENGTH: 2173
<212> TYPE: DNA
<213> ORGANISM: Homo Sapiens

<400> SEQUENCE: 2

ggcgtcgggc gcctgggacg tggcttcaac ggccccatcc ggcgccggcg gcgggtgccc     60

ggcggtcttt gctgccgccc gggggcgcag aggccgggcc ttttctttca gcacaaacgt    120

cagtttgtaa aagggaggtg ctggagtctg aggagttttc aggcttccgt ctcgaaggaa    180

gtctggcagg ctcggaattg tcatcttcct caggcaaata gtttttcacc ttagagccag    240

caaggccaaa ccgcccagtc acccgacttc ccacagtctc agcaggtaca cagggcgggg    300

agcctcggga gcggctccct tagcaggacc tgagggtttc gggagagtcc tggctttgca    360

cttagttttc ccgctgcctg gctgcctccg tggcggttgt gctgcttttt atgcaggatg    420

taggatcgaa ggcaaatcat cctttcccta cgtcccctgc caacccctgc cgctctcctc    480

tattttgtac actttatcat taaaggattt gaaatgaatg gaggaataag tttttttcat    540

ctgtaatttg gaagccaagt cagtaacaaa atgaaaccag taaagcatct gttgaccacc    600

agtaacaaat cggcaaatgt tccagcatta actactaaaa aaggactaca taatttacca    660

ttatcacctg agctaaagga aaaacataat gcaaaattaa ttcatgataa aattgaacca    720

atggtcctaa gatctccacc aacaggagaa tccattttac ggtatgcttt gcccattcca    780

tcgagtaaga caaagaactt actaccagaa gatgaaatga tcggaaaaat tatcaaacat    840

ctgaagatgg ttgtttccac tttggaagaa acctatggac attgcgatca gaatggagaa    900

gaaccatttg taaagcatga acatgaagaa ttatctttat ctgttgggga tgatatgaat    960

tcattcttga catattgttc gcaatttgca gctcagctag aagaagcact taaagaagaa   1020

caaaatattt tggaatctct ttttaagtgg tttcagtggc aggtcaatca gatggaagaa   1080

ataagtaaag atcaaactct tttacaagca gagcctccaa aacctgacaa aacagtcatt   1140

ttaaatattg cagaaatagt aaggcttgta caaagatttg aagaactgaa gaatcgcctt   1200

aaacagaggt ctaaatcctc cgtgaaagtc atgttgtcta aaactatgga taaagaaaat   1260

cgaccagaag cagtgaaaag ttgtgaagct ctggcacaga aaattgaaga attcttagaa   1320

gcccactcaa ctgatgaatt taaagatgtt tctgcaacag aaccacaaac tgctcattca   1380

atgactaatc gatttaatgc catgttgaaa gtatttgaaa accaggcaaa tatgttggag   1440

agagctgtaa atgatcaagt tttgttagat gctgaataca aacagatgca gtgtgatttt   1500

cagttgttat cagaagagaa gttggtgctg gaaaatgaac tacaaaagtt gaaggacaaa   1560

gagaaaacta agcctacaaa taatcgaaca aagaaagctg tgaaaacagt gaagaaaaaa   1620

gacaaaggaa aatctgagga ttcagaaaag aagatgtctc cagaaaaaga gtttaaaata   1680
```

```
aaagaagatt tggatcaagt acagaaagta gcacgtctgg aaattgagaa caaagtcctt   1740

caggagcaat tgaaacaggc tttacaggaa gctgaaaaag ctaagcatca acttaactat   1800

ttcctaaatc aagagaagtt acttaaaagt gaggggaaaa ctgagacaac aatgcaagtg   1860

ggtaatagtc aaacaaaagt taaaggtgaa gattcaaaaa atataccatt ggagaaagaa   1920

acaagaaaat cactggtttc agattcaggt ggacaaagga caagtgataa aatccaagaa   1980

tatccacaga tcactgccca aagcggaaga ctgattgaaa agagatgcta atagagtttc   2040

tgaaatactt tggaaaagtc tcccaaacct tcagagagtg gatgggagcg aagtaaggag   2100

accccacctg agcagataca tggtattgct tacaataaag tacatttttg ctctttacaa   2160

aaaaaaaaaa aaa                                                      2173
```

<210> SEQ ID NO 3
<211> LENGTH: 795
<212> TYPE: DNA
<213> ORGANISM: Homo Sapiens

<400> SEQUENCE: 3

```
atgcctagca tcttcgccta tcagagctcc gaggtggact ggtgtgagag caacttccag     60

tactcggagc tggtggccga gttctacaac acgttctcca atatcccctt cttcatcttc    120

gggccactga tgatgctcct gatgcacccg tatgcccaga agcgctcccg ctacatttac    180

gttgtctggg tcctcttcat gatcataggc ctgttctcca tgtatttcca catgacgctc    240

agcttcctgg gccagctgct ggacgagatc gccatcctgt ggctcctggg cagtggctat    300

agcatatgga tgccccgctg ctatttcccc tccttccttg gggggaacag gtcccagttc    360

atccgcctgg tcttcatcac cactgtggtc agcacccttc tgtccttcct gcggcccacg    420

gtcaacgcct acgccctcaa cagcattgcc ctgcacattc tctacatcgt gtgccaggag    480

tacaggaaga ccagcaataa ggagcttcgg cacctgattg aggtctccgt ggttttatgg    540

gctgttgctc tgaccagctg gatcagtgac cgtctgcttt gcagcttctg gcagaggatt    600

catttcttct atctgcacag catctggcat gtgctcatca gcatcacctt cccttatggc    660

atggtcacca tggccttggt ggatgccaac tatgagatgc caggtgaaac cctcaaagtc    720

cgctactggc ctcgggacag ttggcccgtg ggctgccct acgtggaaat ccggggtgat    780

gacaaggact gctga                                                     795
```

<210> SEQ ID NO 4
<211> LENGTH: 7333
<212> TYPE: DNA
<213> ORGANISM: Homo Sapiens

<400> SEQUENCE: 4

```
acttccttcg tctgggtggt tgccccagcg acacgttggg ccgaagagcg gtgttgggta     60

cccgagagac ccggcggtgg ggaagtcact tcctcccgaa gacgctgttt cctagcaacc    120

gccctccgcc tctgttatta gcccctcctc ctcgctcggt ccaggaccgg ctctgcgggc    180

gccgccaggc ccagaccaag ctactatcag aagttgaatt ctaataatta gctattttat    240

aaaggtaacg agaaaaaata cactatgtct gatgaagttt ttagcaccac tttggcatat    300

acaaagagtc caaaagttac caaaagaact actttccagg atgagctaat aagagcaatt    360

acagctcgct cagccagaca aaggagttct gaatactcag atgactttga cagtgatgag    420

attgtttctt taggtgattt ttctgacact tcagcagatg aaaattcagt taataaaaaa    480

atgaatgact ttcatatatc agatgatgaa gaaaagaatc cttcaaaact attgtttttg    540
```

-continued

```
aaaaccaata aatcaaacgg taacataacc aaagatgagc cagtgtgtgc catcaaaaat    600
gaagaggaaa tggcacctga tgggtgtgaa gacattgttg taaaatcttt ctctgaatct    660
caaaataagg atgaggaatt tgaaaaagac aaaataaaaa tgaaacctaa acccagaatt    720
ctttcaatta aaagcacatc ttcagcagaa aacaacagcc ttgacacaga tgatcacttt    780
aaaccatcac ctcggccaag gagtatgttg aaaaagaaaa gtcacatgga ggagaaggat    840
ggactagaag ataaagaaac tgccctcagt gaagaattgg agttacattc tgcaccttct    900
tcccttccaa cgccgaatgg catacaatta gaagctgaga aaaaagcatt ctctgaaaac    960
cttgatcctg aggattcatg cttaacaagt ctagcatcat catcacttaa acaaattctt   1020
ggagattctt tttcaccagg atctgaggga aacgcatctg gaaaagatcc aaatgaagaa   1080
atcactgaaa accataattc cttgaaatca gatgaaaata aagagaattc attttcagca   1140
gaccatgtga ctactgcagt tgagaaatcc aaggaaagtc aagtgactgc tgatgacctt   1200
gaagaagaaa aggcaaaagc ggaactgatt atggatgatg acagaacagt tgatccacta   1260
ctatctaaat ctcagagtat cttaatatct accagtgcaa cagcatcttc aaagaaaaca   1320
attgaagata gaaatataaa gaataaaaag tcaacaaata atagagcatc cagtgcatct   1380
gccagattaa tgacctctga gtttttgaag aaatctagtt ctaaaaggag aactccatcg   1440
acaactacct cttctcacta tttagggact ttaaaagtct tggaccaaaa accttcacag   1500
aaacagagca tagaacctga tagagcagat aacataaggg cagctgttta tcaggagtgg   1560
ttagaaaaga aaaatgtgta tttacatgaa atgcacagaa taaaaagaat tgaaagtgaa   1620
aacttaagga tccaaaatga acagaaaaaa gctgctaaaa gagaagaagc attagcatca   1680
tttgaggcct ggaaggctat gaaagaaaag gaagcaaaga aaatagctgc caaaaagagg   1740
cttgaagaaa aaaacaagaa gaaaactgaa gaagaaaatg ctgcaagaaa aggagaagca   1800
ctacaagctt ttgaaaaatg gaaagagaaa aagatggaat atcttaaaga gaaaaataga   1860
aaggagagag aatatgaaag agcaaagaaa cagaaagagg aggaaactgt tgccgagaaa   1920
aagaaagata atttaactgc tgttgagaaa tggaatgaaa aaaaggaagc tttttttcaag   1980
caaaaggaaa aagaaaaaat aaatgagaaa agaaaggaag aactgaaaag agctgagaaa   2040
aaagataaag ataaacaagc tattaatgaa tatgaaaaat ggctggaaaa taaggaaaaa   2100
caagaaagaa ttgaacgaaa acagaagaaa cgtcattcct ttcttgaaag tgaggcactt   2160
cctccgtgga gccctccaag cagaactgtg ttcgcaaaag tgttttgata attctagttc   2220
ttacattatt tggttattta tcggtttgcc aatattagcc atagatttaa aaccattcaa   2280
ttatttatag ttagaggaat atattttaat taaatgccag acactcctgc tgacaatgaa   2340
agaaatactt tggaatgtaa tcagtgaaag cattttttttg aactgtagat aaactgcctc   2400
aaacaaagac ctaataatca gattgttttt accattaaga tacataagat tttatcatgt   2460
cctgataatt cttatggtgg agtgattcat gatctttttc attaagctct gtatgttatt   2520
taagtatatt taattccagt aataaaaagg aaatcatcta ggtaccataa tgatagaaat   2580
tattcctttt gtggatgatt gtgaatctag attcaggttt ttaaatgaag ggtcgctggg   2640
aagtgcgcat atattattcc ttctgaaact gatgtttagc tcaaagcagt tgcatttgta   2700
ctgtgctagt tagaattttc atcagttgag gcagtagctc agtagaactc taatcatcaa   2760
ggctttttat ttaagaattt tgccttatgt tttaatatga gtgtacttta tctgttccag   2820
gcttatgtga taatcatagg tactttataa tgagtccacc tctgaaattt ttctttctga   2880
```

-continued

```
attctatctc actttattat ttcagtgata ccaaaagaca tcaatgtcac agtagtgata   2940
tacttatgta ttagttatgg aaattccaca ggagttcaag gtcattatca ctataattat   3000
tttcctgact aaagccataa aggtgattta ggcaattatt gtcatcttag ctagtcctgt   3060
tttatagctt atattcagca gacagctgta tgggaaggta aatatgttga caatgtccac   3120
aaagccttta tttatttatt tatttgatct ctgcatgtcc tcgtagtaac tggtctcata   3180
cttgacctgg tcatctggtt taagacagac caagtgtatg ctcacggagc tgaaatgcat   3240
tagtcagttg tgcaatgagg agatgatgga tgagaatata tagttcctat ttattgagca   3300
tctaatatat aatctctact ggacctttac aaatgtattt aacatcttta caacaacttt   3360
tcagggtagg tgttaccggc ttcatcttac atataaaaat actggcgctc agataaacca   3420
agtaacttac cgtccatctg gagtgtgcct gagttgagat caaacgggat tcagtacgtc   3480
tgactgaatc tgcctccttc tgaaatctct atgctctttt tcacacttct ctgtagcctc   3540
agagactgcc aagttctgtc aagacctctg cataatatca acgttacaaa cacgttttaa   3600
cttttagagc ctaaaatcat gtattgttat ccaaagatga tctttctcta cagaaatagc   3660
tgcttgttct tagagatggt ggaggtcatt aaatctataa agtgagataa aaatccataa   3720
gatttcatga gttactcagg catcttataa ctactatcag aatatcagaa aactcagcaa   3780
gttatgtgac aaaggctttg agatgatcac tccagacgtt ccacatactg agcatcagcc   3840
ttcttgctgc agtgcatgtg caagataaga tgtcataggc agctttgtaa gattgtatca   3900
gtgctataga caattaagag aaatttcata gataaaacta gaaccctttc tatatggcca   3960
gaactgtaat actttatgaa attgatctga ttatcagcaa tatgtagtat cagcatggaa   4020
tttaggacct ctcttactca ttcctgtgtc cccatagta ccaaaaacag tgcctgccaa   4080
aatagattaa aagtgtttat tgtattagct gtttagagct gaaaagatat ttacaaattc   4140
cagggaagta aaaggaaaaa aactgaaaaa ggtacagcta cttttgggga tgtgagatca   4200
tggatgtgta tcttatagat ttcacattat ttatttactt tccattattt tcttctacat   4260
tatcatattt agtggctaac cattattact tcttaggttg ttgtgagaac cgagttaatt   4320
aatgtaaact atttgacaca taataaggac ttaaatgttc attgttgtca ttattgattt   4380
attaccatga gccctacatt tccccattca tgagtgtgcg aacattaaca tagatagggt   4440
tgataatggt tatttgacat tacacatttt taggaagaag aaatttctgt cttgctggcc   4500
agtccaggct gtaacactca aaaaaacaaa acaaaacaaa acaaaacaaa aaaacagaaa   4560
gatgccttgt attagggcct tcctaaaaag aaagctaagt aagtattaat ttcttaggat   4620
tgcttctgag gtaggatgag gtgtttgcat agacccaaca agtcattcac ttcaaatttt   4680
ttttgtctta ctatgataaa taacatatta tttcctgttt acagcaacct gcactgaaat   4740
taactagttg aataaaatca cctcttctag cacaaataaa gctgagttcg gggaggtggg   4800
tgaaaataca gtactgttgt ttacttccta agatccaagg gagagaatca agcttggtaa   4860
tattctcttg aatatacatt tacctattta aaaggtatga ttttcccata tttccttagg   4920
aagtatgtca tgtcaatata gatatttact cattaggttt acattaattt gtattataag   4980
ggaatgttta attcaaatta aggacattaa aagtatatag actttcatat aaaagttccg   5040
gttttataaa ttgcgttgat cacttaaaga atgcagagat ctcaaagtaa agaaaacaaa   5100
ttttatgaat attttaaaac attacttaaa acaagtttcc ttagaaagca catttgtgga   5160
taaatttaaa tattaatact aaataataaa gtagtataca gaatttaaat ttcataataa   5220
tgaagaaagt ggtaatgcta tttaacttaa aagatgcaat atggcatttt agatcaagag   5280
```

gttaaagttt tcttaatgaa agaaagtaac gatttatggg ataaaaatat tccagtggtt 5340
tgtatttgct tcatacttca aaagtgttag tccatttatt gtttaaagtt atattgaaac 5400
tgatattttc actgctgcca aagcagtacc tgacagtaga taggtatcca cagtcttatg 5460
ttccttagag ttatagaact atgcctctga aaggggtttt aatactttaa taaacctggc 5520
ctaaactgtt ttatttctaa gttgaagaaa ctgattgtca agtactttga cttgtccaat 5580
ctcatacaac taactatggt acatctagag ttagatctca gtatcagggg tcccagttgt 5640
attctgctca ccattccaca atttcgatat tgataaaact ttcacactaa cttttgaact 5700
gtggttatta ttaatttagt tgattcatgt cctcttattt atctccttac tcctccactg 5760
ctgccttcat aactgtccac cagatcaaag ctatttgggt acctacactt taaagtgagg 5820
ggaaataatg aagtttctta aatcctgtgt catggactaa gatacaataa agaaaaggaa 5880
tttcacaaag taggggaaat tacgtgttag ttataatcat tcccaagaat aaactagtaa 5940
aagaaactta gatttcccta atttaatctt gactccgatt ttgatagtgc tatataaaaa 6000
ggtatttaaa cccatatgct tccttttaca taaaagaaag atatcaactt tcctagtttg 6060
catttacact ggctaatagg ataataaaat gctgtgtaaa tgttaaactg gaagtttctc 6120
tgagttattt ttactttaaa atttcatgtg attatgccat tttgaatatg tatattacat 6180
gtaattgtat aatgttaact cgggtaggca aaattcttgg tattaaattt aggatgtttt 6240
aaaaattatt aagaagatat taatgtctgc tttttgatag catatatttt catgtaatgt 6300
ttagtgtatt aaaatcaacc attcaagatt tattttattg ggtgacacta ttgactgtgt 6360
tccaaaatgc ccatagtgtt aggaaatgtg gtgtgagttt tatttgtggg ctaaggataa 6420
aataatcata tgctaatata ccttttatta taaatgacta aaaatttgga tataaaactg 6480
atgttttact acacaaatta cagagagaga taatataatt atataattat taaataatta 6540
gaaaatgcaa ataagcaaaa gtcacccatg ttcccagttc tcatctcctg aagatagtta 6600
taactaacat attattttgt actcttcctg ttaattagtt tctagtgtac tttctcctgt 6660
agctgaaatt aagctgagaa aaaaggaaga gatagttcct ccctcctctt tctctctccc 6720
actctgtctc tctcctgtgc tatctgtgtg tatatacaaa tatgtatgca tatatatata 6780
atgatgtaca taatatatat aaaatacaaa tactaatgtg catattttca aacatacaca 6840
tattttttat tatttgaaat aagaatgagt cagactacat atttggtagc cagatttttt 6900
tcactcagtg atatatcatg aacatatttc catgctaata taattttcta ataattttag 6960
atgctgtaac tacaatttca ttgttaatgg gcaatttgtt gctttacaaa tggtaaatta 7020
tatgataaat aatatgatca ttattcttgt agccaatatc attattagaa atgatggacc 7080
gcattaaagc tataaaatta aataagaatt tataaatgta aggagttatt cagacatctt 7140
gtatctagta ttacaatatc agaaaactca gcaggttata tgacatatac actttgagat 7200
agtcactcag aggttttcac atacaggatt aaccttgctg cagtgcgtgt gcaagattaa 7260
aaaagatgtc acgggtcact ttgtaatgtc atatcgttgc tgttgataaa taaaggaaat 7320
gttataaata aaa 7333

<210> SEQ ID NO 5
<211> LENGTH: 4188
<212> TYPE: DNA
<213> ORGANISM: Homo Sapiens

<400> SEQUENCE: 5

-continued

```
agattcgcga aaacccggaa gcggatcgcg tggagtgacg gtcccacggc agcgcgattg     60
acttctaaag actcttggta tgtgaggaag aaacctggaa gaggaagagg aaagcaaagg    120
agtcagggat ggctcttcct cagggtctat tgacattcag ggatgtggcc atagaattct    180
ctcaggagga gtggaaatgc ctggaccctg ctcagaggac tctatacagg gacgtgatgc    240
tggagaatta taggaacctg gtctccctgg atatctcttc caaatgcatg atgaaggagt    300
tctcatcaac agcacaaggc aatagagaag tgatccacac agggacattg caaagacatg    360
aaagtcatca cactggagac tttcgctttc aggaaattga taaagatatt cataacttag    420
agtttcagtg gcaagaagat gaaagaaata gccatgaagc acccatgaca gaaatcaaaa    480
agttgactgg tagtgcagac cgatatgatc aaaggcatgc tggaaacaag cctattaaag    540
atcagcttgg atcaagcttt cattcgcatc tgcctgaact ccacatgttt cagacccaag    600
ggaaaattgg taatcaagtg gagaagtcta tcaacgatgc ttcctcaatt tcaacatccc    660
aaagaatttc ttgtaggccc aaaacccata tttctaataa ctatgggaat aatttccgga    720
attcttcgtt actcacacaa aaacaggagg tacacatgag agaaaagtct ttccaatgta    780
atgagagtgg caaagccttt aattatagct cactcttaag gaaacatcaa ataatccatt    840
taggagagaa acaatataaa tgtgatgtat gtggcaaggt ctttaatcgg aagcgaaacc    900
tagtgtgcca tcgtagatgt cacactgggg agaaacctta caggtgtaat gagtgtggca    960
agactttcag tcagacgtat tcccttacat gccatcgtag acttcatact ggagagaaac   1020
cttacaaatg tgaagaatgt gacaaagctt tcagtttcaa atcaaacctt aaaagacata   1080
ggagaattca tgctggagaa aaaccataca agtgtaatga atgtggcaag acctttagtc   1140
agacgtcatc ccttacatgc catcgtagac ttcatactgg agagaaacct ttcaagtgta   1200
atgagtgtgg caagaccttt agtcggaagt catcccttac atgccatcat agacttcata   1260
cgggagagaa accttataag tgtaatgaat gtggcaagac cttcagtcag gagttaaccc   1320
ttaaatgcca tcgtagactt cataccggag agaagcctta caagtgtaat gaatgtggca   1380
aggtttttaa taaaaaggca aaccttgcac gtcatcatag acttcatagt ggagagaaac   1440
cctacaagtg tactgagtgt gtcaagacgt tcagtcgaaa ttcagccctt gtaattcata   1500
aggctattca tattggagag aaacgttaca agtgtaatga gtgtggcaag acgttcagtc   1560
gaatttcagc cctcgtaatt catacggcaa ttcatactgg agagaaacct tacaagtgta   1620
atgaatgtgg caagggtttt aatcggaaaa cacaccttgc atgtcatcat agacttcata   1680
ctggagagaa accttacaag tgtaatgaat gtggcaaggt ttttaatcga aaaacacacc   1740
ttgcacatca tcatagactt catactggag ataaacctta caagtgtaat gaatgtggca   1800
aggtttttaa tcaaaaagca caccttgcac gtcaccatag acttcatact ggagagaaac   1860
cttacaagtg taatgaatgt ggcaaggttt ttaatcaaaa agcaaacctt gcacgtcatc   1920
atagacttca tactggagag aaaccttaca agtttaatga gtgtggcaaa gcttttaatt   1980
gaaaagcaaa gcttgcacat catcatacaa ttcatactgg aaagaaacaa gtgcaatgag   2040
tgtggcaaga ccttctgtca caattcagtc cttgtaattc ataagaattc atactggaga   2100
gaaacaagtg taatgaacgt tgcaaaattt ttaatcaaca agcacacctt ccacgtcatc   2160
atagacttca tagtggagag aaaccttaga aatgtgaagc atgtgacaaa gtttacagtg   2220
gcaaatcgag cctcaaaaga caggagaatt catactggag agaaagctta caaaggtgaa   2280
gaatatcaca gagttttcag tcacaagtca aaccttgaaa gacataaaat aaatcatact   2340
gcagagaaac cataaaattg taagagttcg tgacaaggct ttcgggcatg actcacacct   2400
```

```
ggcacaacat cctagaattt atactggaga gaaaccttac aagtgtaatg agtctggcaa   2460

agccttaatg agcagtcaac acttactcac catcaggcaa tccatggtga aggaaacttg   2520

actaatgtaa tgattgtcac caagtcttca gtaacgctac aaccattgca aatcattgga   2580

gaacccataa ggaagagaga tcatacaagt gtaataatcg gcaaattttt cagacatcgt   2640

ccataccttg cagttcattg gcgaactcat actggagaca aaccttataa atgtcatgat   2700

tgaggcaagg tcttcagtca agcttcatcc tatgcaaaac ataggagaat tcatacagga   2760

gagaaacctc acgtgtgatg attgtggcaa agcctttact tcacgttcac acctccttag   2820

acatcagaga atgcacactg gacggaaatc ttacaaatgt catcagtgtg gcaaggtttt   2880

cagtctgact tcactccttg cagaatatca gaaaattcat tttgagataa ttgttccaaa   2940

tgcaatgagt agagcaaacc atcaagcagt aattgacatt aaagtgttta tgttaagagg   3000

attgggccag gtacagtgtc tcacacctgt aatcccagca ctttgggagg ccaaggcggg   3060

tagatcactt gaggtcagga gtttcagatc agtctggcca acaaacatga gccacttttc   3120

ccagtttgct ttttgttctt taacaaaaac tgatagggat ttttatgggt accgtgttga   3180

atctaaatca cattgggtta tataatcatt taacaatatt aatttttcca atccatcaat   3240

atgggttata tgtctgtata tgtttttaat catattgatg tatatttgta gatttcaagg   3300

tacaaacttc tcaccttttt acttttattt ctatttcttt aagttctcta gcaaatggaa   3360

gtgtttttaa attttctttt aaaattgttt attgttacaa acttctcatc tttttgcttt   3420

tattcctaag tatttcttac tttaagttct ctagcaaatg gaagtgtttt taaattttct   3480

tttaaaattg tttattgtta atgtatggaa attcagctaa tttttggtgc tgatattgta   3540

ctgtgcagat acactgaatc tgtttattac ttccagtagt attttggttg agtctttgtg   3600

attttctaca cagaagatca tgtcatctac aaacacatat aattttactt ctttctttct   3660

gatttggatg ggtttgattt cttttgctat ttcattgctc tggctaggac agccagtatt   3720

tattgaatag aaggggtgag agcattcttc catcatgtga gatcctacag gaaaatcatt   3780

ccatgttccc tgcttcgtta tctactcgtt ggtcatttca tggatggcct ttctattgtt   3840

gaggtaaatt tccttttctg tctattttgt tcagaatttc tatgatgagt ggattttgaa   3900

ttttgtgaaa tactttttct ccatctattg agatgatgtg gttttcatct ttcattctgt   3960

tcaagtggca tatcacattg atttgcttga ctatgttgaa ccatccttgc atcccagaaa   4020

taagtggcac ttgagtatct acagtccttt ttacatcctc ttgaatacag ctttttagta   4080

caaggggtct tcaagaagtt catggaaaaa tacatatttt gcatattatg agaaaattgt   4140

gtatgaattt cccagttttt gcaccaaaat aaactggtac gaatctgt               4188
```

<210> SEQ ID NO 6
<211> LENGTH: 2500
<212> TYPE: DNA
<213> ORGANISM: Homo Sapiens

<400> SEQUENCE: 6

```
cccaggcgca gccaatggga agggtcggag gcatggcaca gccaatggga agggccgggg     60

caccaaagcc aatgggaagg gccgggagcg cgcggcgcgg gagatttaaa ggctgctgga    120

gtgaggggtc gcccgtgcac cctgtcccag ccgtcctgtc ctggctgctc gctctgcttc    180

gctgcgcctc cactatgctc tccctccgtg tcccgctcgc gcccatcacg gacccgcagc    240

agctgcagct ctcgccgctg aaggggctca gcttggtcga caaggagaac acgccgccgg    300
```

-continued

```
ccctgagcgg gacccgcgtc ctggccagca agaccgcgag gaggatcttc caggagccca    360
cggagccgaa aactaaagca gctgcccccg gcgtggagga tgagccgctg ctgagagaaa    420
acccccgccg ctttgtcatc ttccccatcg agtaccatga tatctggcag atgtataaga    480
aggcagaggc ttccttttgg accgccgagg aggttgacct ctccaaggac attcagcact    540
gggaatccct gaaacccgag gagagatatt ttatatccca tgttctggct ttctttgcag    600
caagcgatgg catagtaaat gaaaacttgg tggagcgatt tagccaagaa gttcagatta    660
cagaagcccg ctgtttctat ggcttccaaa ttgccatgga aaacatacat tctgaaatgt    720
atagtcttct tattgacact tacataaaag atcccaaaga aagggaattt ctcttcaatg    780
ccattgaaac gatgccttgt gtcaagaaga aggcagactg ggccttgcgc tggattgggg    840
acaaagaggc tacctatggt gaacgtgttg tagcctttgc tgcagtggaa ggcatttttct   900
tttccggttc ttttgcgtcg atattctggc tcaagaaacg aggactgatg cctggcctca    960
cattttctaa tgaacttatt agcagagatg agggtttaca ctgtgatttt gcttgcctga   1020
tgttcaaaca cctggtacac aaaccatcgg aggagagagt aagagaaata attatcaatg   1080
ctgttcggat agaacaggag ttcctcactg aggccttgcc tgtgaagctc attgggatga   1140
attgcactct aatgaagcaa tacattgagt ttgtggcaga cagacttatg ctggaactgg   1200
gttttagcaa ggttttcaga gtagagaacc catttgactt tatggagaat atttcactgg   1260
aaggaaagac taacttcttt gagaagagag taggcgagta tcagaggatg ggagtgatgt   1320
caagtccaac agagaattct tttaccttgg atgctgactt ctaaatgaac tgaagatgtg   1380
cccttacttg gctgattttt tttttccatc tcataagaaa aatcagctga agtgttacca   1440
actagccaca ccatgaattg tccgtaatgt tcattaacag catctttaaa actgtgtagc   1500
tacctcacaa ccagtcctgt ctgtttatag tgctggtagt atcacctttt gccagaaggc   1560
ctggctggct gtgacttacc atagcagtga caatggcagt cttggcttta aagtgagggg   1620
tgacccttta gtgagcttag cacagcggga ttaaacagtc ctttaaccag cacagccagt   1680
taaaagatgc agcctcactg cttcaacgca gattttaatg tttacttaaa tataaacctg   1740
gcactttaca aacaaataaa cattgttttg tactcacggc ggcgataata gcttgattta   1800
tttggtttct acaccaaata cattctcctg accactaatg ggagccaatt cacaattcac   1860
taagtgacta aagtaagtta aacttgtgta gactaagcat gtaattttta agttttattt   1920
taatgaatta aaatatttgt taaccaactt taaagtcagt cctgtgtata cctagatatt   1980
agtcagttgg tgccagatag aagacaggtt gtgtttttat cctgtggctt gtgtagtgtc   2040
ctgggattct ctgccccctc tgagtagagt gttgtgggat aaaggaatct ctcagggcaa   2100
ggagcttctt aagttaaatc actagaaatt taggggtgat ctgggccttc atatgtgtga   2160
gaagccgttt cattttattt ctcactgtat tttcctcaac gtctggttga tgagaaaaaa   2220
ttcttgaaga gttttcatat gtgggagcta aggtagtatt gtaaaatttc aagtcatcct   2280
taaacaaaat gatccaccta agatcttgcc cctgttaagt ggtgaaatca actagaggtg   2340
gttcctacaa gttgttcatt ctagttttgt ttggtgtaag taggttgtgt gagttaattc   2400
atttatattt actatgtctg ttaaatcaga aattttttat tatctatgtt cttctagatt   2460
ttacctgtag ttcataaaaa aaaaaaaaaa aaaaaaaaaa                          2500
```

<210> SEQ ID NO 7
<211> LENGTH: 279
<212> TYPE: DNA
<213> ORGANISM: Homo Sapiens

<400> SEQUENCE: 7

```
tttttttaaa tttaaatgct tttattaaca atcttcttac attacaagga taatatgaca      60

aaaagaaagt ttctgcgtac atattatgat aaaccaacat agctctattt gtatccagtg     120

ttctaggtcc cgtcacacag gtactataaa gcgtagtctg caaaataata acatcaagag     180

gttttttta aagaaagtat taacatatta atatgtatgt gataatagac tcctaggtat     240

ttccccccat ccccacttat ttttcctttg tgattgaca                            279
```

<210> SEQ ID NO 8
<211> LENGTH: 1166
<212> TYPE: DNA
<213> ORGANISM: Homo Sapiens

<400> SEQUENCE: 8

```
atgcgcataa cctcaggata taaataatgc tgaagcagag ttacgttttt tttgttgttg      60

ttttttttgt ttttgttttt ttaggtttcc gtgtgtttct attgagctgc tcagtgcccg     120

gcttagaaga ccaggaaaag gagtcacagg tcgtatgctg gaggcttgag ccgcggcacc     180

gtggcgcggc tcgcctcgct gcggttggtg gtggcggtgg acattgcagc gcggctggag     240

gggtgagata ttcctgcaca tcctctggtg accccagaat gagggggact cgctggtgaa     300

ttgcctcggg cttcacgtcc agtacaggct gggtccccgt ggtcgccaag cctcctgcct     360

gctcaatgat gtaggccacg ggattgcatt catacaggag ccggagctgt ggaggaacag     420

aggcaggaca aattcaccaa gagcctagca acatgaagag agatgccagg aagaagagag     480

aagccaggaa acagaagcca accgcacaat ccccacatca gagcaggaga agatgggggc     540

ctgctggcag agctggggct tggctgtggt cactctgagc ctgctctttg gtgttttcat     600

gagtggtggg aagaataggg accatatgga gcccacacag gaagctctag cagtaacaca     660

gcaagcagga agacaattct aaggaagcag cccatagtct tctttctttt cctgtgcatc     720

ttccactgtc agtgaggctc ctcatttatg gtgaacccaa ctgtgtgtat ctcccaagtt     780

ctcacccccca gattaatgtt ttcaggaaga taggccatca acagtgagag gaagaagtta     840

cattgtcgta tgagggatgc attttaacca ttaatttgtg gtacaggctg ggcgcagtgg     900

cttacgcatg taatcccagc actttgggag gccgaggcgg gtggatcacg aggtcaggag     960

attgagacca tcctggctaa catggtgaaa ccccgtcttt gctaaatata caaaaaattg    1020

gccaggcgtg gtggtgggca cctgtagtcc cagctactcg ggggctgag gcaggagaat    1080

ggtgtgaacc cgggaggcag agcttgcagt gagccgagat cgcgccactg cactccagcc    1140

tggatgacag agcaagactc catctc                                         1166
```

<210> SEQ ID NO 9
<211> LENGTH: 2383
<212> TYPE: DNA
<213> ORGANISM: Homo Sapiens

<400> SEQUENCE: 9

```
gctgctgcga cagtccacta cctttttcga gagtgactcc cgttgtccca aggcttccca      60

gagcgaacct gtgcggctgc aggcaccggc gcgtcgagtt tccggcgtcc ggaaggaccg     120

agctcttctc gcggatccag tgttccgttt ccagccccca atctcagagc cgagccgaca     180

gagagcaggg aaccggcatg gccaaagccg cggcgatcgg catcgacctg ggcaccacct     240

actcctgcgt gggggtgttc caacacggca aggtggagat catcgccaac gaccagggca     300
```

-continued

```
accgcaccac ccccagctac gtggccttca cggacaccga gcggctcatc ggggatgcgg    360
ccaagaacca ggtggcgctg aacccgcaga acaccgtgtt tgacgcgaag cggctgatcg    420
gccgcaagtt cggcgacccg gtggtgcagt cggacatgaa gcactggcct ttccaggtga    480
tcaacgacgg agacaagccc aaggtgcagg tgagctacaa gggggacacc aaggcattct    540
accccgagga gatctcgtcc atggtgctga ccaagatgaa ggagatcgcc gaggcgtacc    600
tgggctaccc ggtgaccaac gcggtgatca ccgtgccggc ctacttcaac gactcgcagc    660
gccaggccac caaggatgcg ggtgtgatcg cggggctcaa cgtgctgcgg atcatcaacg    720
agcccacggc cgccgccatc gcctacggcc tggacagaac gggcaagggg gagcgcaacg    780
tgctcatctt tgacctgggc gggggcacct tcgacgtgtc catcctgacg atcgacgacg    840
gcatcttcga ggtgaaggcc acggccgggg acacccacct gggtggggag gactttgaca    900
acaggctggt gaaccacttc gtggaggagt tcaagagaaa acacaagaag gacatcagcc    960
agaacaagcg agccgtgagg cggctgcgca ccgcctgcga gagggccaag aggaccctgt   1020
cgtccagcac ccaggccagc ctggagatcg actccctgtt tgagggcatc gacttctaca   1080
cgtccatcac cagggcgagg ttcgaggagc tgtgctccga cctgttccga agcaccctgg   1140
agcccgtgga gaaggctctg cgcgacgcca agctggacaa ggcccagatt cacgacctgg   1200
tcctggtcgg ggctccacc cgcatcccca aggtgcagaa gctgctgcag gacttcttca   1260
acgggcgcga cctgaacaag agcatcaacc ccgacgaggc tgtggcctac ggggcggcgg   1320
tgcaggcggc catcctgatg gggacaagt ccgagaacgt gcaggacctg ctgctgctgg   1380
acgtggctcc cctgtcgctg ggctggaga cggccggagg cgtgatgact gccctgatca   1440
agcgcaactc caccatcccc accaagcaga cgcagatctt caccacctac tccgacaacc   1500
aacccggggt gctgatccag gtgtacgagg gcgagagggc catgacgaaa gacaacaatc   1560
tgttggggcg cttcgagctg agcggcatcc ctccggcccc caggggcgtg ccccagatcg   1620
aggtgacctt cgacatcgat gccaacggca tcctgaacgt cacggccacg gacaagagca   1680
ccggcaaggc caacaagatc accatcacca acgacaaggg ccgcctgagc aaggaggaga   1740
tcgagcgcat ggtgcaggag gcggagaagt acaaagcgga ggacgaggtg cagcgcgaga   1800
gggtgtcagc caagaacgcc ctggagtcct acgccttcaa catgaagagc gccgtggagg   1860
atgaggggct caagggcaag atcagcgagg ccgacaagaa gaaggtgctg gacaagtgtc   1920
aagaggtcat ctcgtggctg gacgccaaca ccttggccga gaaggacgag tttgagcaca   1980
agaggaagga gctggagcag gtgtgtaacc ccatcatcag cggactgtac cagggtgccg   2040
gtggtcccgg gcctgggggc ttcggggctc agggtcccaa gggagggtct gggtcaggcc   2100
ccaccattga ggaggtagat taggggcctt tccaagattg ctgtttttgt tttggagctt   2160
caagactttg catttcctag tatttctgtt tgtcagttct caatttcctg tgtttgcaat   2220
gttgaaattt tttggtgaag tactgaactt gcttttttc cggtttctac atgcagagat   2280
gaatttatac tgccatctta cgactatttc ttctttttaa tacacttaac tcaggccatt   2340
ttttaagttg gttacttcaa agtaaataaa ctttaaaatt caa                     2383
```

<210> SEQ ID NO 10
<211> LENGTH: 5661
<212> TYPE: DNA
<213> ORGANISM: Homo Sapiens

<400> SEQUENCE: 10

```
ggcacgtgga ctccctttaa tccagtgact gtcaggtcga tcatatgccg aggacgatga      60
```

```
tcccgccggg ggagtgcacg tacgcgggcc ggaagcggag gaggcccctg cagaaacaga    120
ggcccgccgt gggggcagag aagtccaacc cctccaagcg acaccgggac cgcctcaacg    180
ccgagttgga ccacctggcc agcctgctgc cgttcccgcc tgacatcatc tccaagctgg    240
acaagctttc tgtcctgcgc ctcagtgtca gttacctccg ggtgaagagc ttcttccaag    300
tcgtgcagga gcagagctca cggcagcctg cggccggcgc ccccctcgccc ggagacagct   360
gtcctcttgc agggtctgcc gtgctggagg gaaggctgct gttggagtct cttaatggct    420
ttgctctggt cgtgagtgca gaagggacga tattttatgc atcagcaacg atcgtggact    480
atctgggctt ccatcagacg gatgtaatgc accagaacat ttatgactac atccacgtgg    540
acgaccgcca ggacttctgc cggcagctcc actgggccat ggaccctccc caggtggtgt    600
ttgggcagcc cccgcccttg gagacaggag atgatgctat cctggggagg ctgctcaggg    660
cccaggagtg gggcacaggc acgcccaccg agtactcggc cttcctgacc cgctgcttca    720
tctgccgtgt gcgctgcctg ctggacagca cctcgggctt cctggcccgg gggtcacagg    780
cttggcagct gcggctctgc tgtcccgagc cactcatgac gatgcagttt caaggaaaac    840
taaaattcct gtttggacag aagaagaagg cgccgtcagg agccatgctc ccgccgcggc    900
tgtcgctgtt ctgcattgcg gcacccgttc tcctcccctc cgcagcggag atgaaaatga    960
ggagcgcgct cctgagggca aaacccagag cagacaccgc agccaccgcg gatgcaaaag   1020
taaaagccac caccagtctg tgcgaatcgg aactgcatgg aaaacccaat tactcagcag   1080
gaaggagcag cagagagagc ggcgttttgg tgctcaggga acagactgac gctggccgat   1140
gggcacaggt tcccgccagg gccccatgcc tgtgcctccg ggtggccct gaccttgtcc    1200
ttgaccccaa ggggggctca ggggacaggg aggaggagca gcacaggatg ctgagcaggg   1260
cctctggagt gacagggcgg agggagactc caggacccac aaagcccctg ccctggacag   1320
cgggaaagca cagtgaggat ggtgccaggc cgaggctgca gcccagcaag aatgacccgc   1380
cctccctgcg ccccatgccc cgcggctcct gcctgccctg cccgtgtgtc cagggcactt   1440
tcaggaactc gcccatctct cacccgccga gcccgtcccc cagtgcctac tccagccgga   1500
ccagcagacc catgcgggat gtcggtgagg accaggtgca ccctcccctc tgccactttc   1560
cccagaggag cctgcagcac cagctccctc agcctggagc tcagcgtttt gccacgaggg   1620
gctatcccat ggaggacatg aagctgcaag gtgtaccgat gcctccgggg gacctgtgtg   1680
gtccgacgct gctgctagat gtgtccatca agatggagaa ggactctggg tgtgagggtg   1740
ctgcagacgg ctgtgtgccc agccaggtgt ggctgggggc cagtgacagg agccacccag   1800
ccaccttccc taccaggatg cacctgaaaa cagagccaga ctctcggcaa caggtgtaca   1860
tctcgcacct ggggcacggc gtgcgggggg ctcagcccca tgggagggcc actgctgggc   1920
gcagcaggga gctgacccct ttccaccctg cacactgtgc ctgcctggag cccacagacg   1980
gccttcccca gtcggagcct ccccaccagc tctgtgcacg gggccgaggt gaacagtcct   2040
gcacctgcag agctgctgag gccgcccctg tggtcaagcg ggagcccttg gactcacccc   2100
agtgggctac tcacagccag ggaatggtgc ccgggatgtt gcccaaaagt gccttggcca   2160
cgctggtccc gccccaagct tcggggtgca cattcctgcc atagcgcagt gaccaccatc   2220
caagctcaga tctgtgtgtc tacgctcaga tgcgtcggtg gctgggctgc cctgctcctg   2280
gtcaggccgg agcccgtcct aagacacacg ctttgcagag ctgtgcatgc gcagtctgct   2340
agtgtgtgtg tgcagcatac gcaggagcct atcctgaatt ttgtaaaata tcccaacagt   2400
```

```
tcttaaatga aaactggcct taagtctatt caagcatgac agcatttctc tttgaggaat   2460
taaaatcttt aggaaagtga tcatggctgg acagcttcat gccccagagg cagcgagcac   2520
ccgtcccatg gctgccaagt ccacagtcgg ggatgaagca gtcgggtgat gctcccaagt   2580
ccgcagtcgg ggatgaagcg gtcgggtgat gctcccaagt ccgcagtcgg ggatgaagcg   2640
gtcgggtgac acacctagct cagccctccc aggccacctg cagctcccag cctgtgctgt   2700
gcaggcaggg tcagcccatc gccacagtgc actgtagagg ccagcacacg gcaaattaga   2760
aatacaacac gcggagaaag gggtccgtga gcccactcat agaggaatct agaacgttcc   2820
aggcagcaga ggctggcagc gtgggtccca cactgcccca caccgtgcgg caggtgctcc   2880
atggcgccat gacagagtct gaggccagac ctggactgga attgacagca taacccctgt   2940
tccttctgga catctcccga gttctcagtg ggtctctgcg gacggttctt cctaatctgc   3000
ctcttggtac atcacgtaat acagagttca cagactccgg gtttggaagt acagagaaac   3060
acacaacgta gagagaagac acaggaaact gcgctgcctg tgggggtttc tctctggctg   3120
gctgtacagt tcactcaaat gagggttccc attgccatcc taggagaata attagggaca   3180
agacagacaa gtattaatag cattaaaaca gttgtaaagg cgatattttc tgagagtagg   3240
aaatttggat acaaaagcat aagtcagaaa gtgaaggtca ccaatccacc aacccgagaa   3300
cctacagctg atggtgcatt tcaggcttct tccacggtct ggcctggaac cccacccggc   3360
tggtgcaggc atcagatcag ggtgtagaag tcaccccaag caagaggaag ccaggcagtg   3420
aggccctggg gtgtggctgc agctgggccc acctgtgcgg gggtgggaag gccccatcct   3480
cagggagagg gcatcggcgc cctgacgtca gctccactgg gagtggcagg agctgtggga   3540
gcccatgggt gagggaccca ccaccccgct gcactgtgca ttgtgcctcc cgtgtggacg   3600
ccctctctgt tgttggcccg cgggtgaggg acccaccacc cctagggacc caccaccccg   3660
ccgcactgtg cattctgcct cctgtgtgga cgccctctct gttgtcagtg gctttgaggt   3720
gtcagtgctt acttagatgc tggtttaatg ctggacccat ttgttaaacg caccttcact   3780
ttgtcaaaac ccaggtttgg ttggcaggac tgggtcttct gcccaatgcc aggtgcctgc   3840
gcctctcagt ggcctggttc ttggacagtt tgcccccatg tggcagggat agggataagg   3900
atctcctctc agtactggaa gagaacagcc aaccatctga gcccagagtc acagatccat   3960
cgtggccccc tatgaccccc aagccctacc gagggggcac tcactctctg cttagccagg   4020
gggcgtcttt caaaaggtga cctccatgct gtgctgtcgt gggtgtgaga cgtgctcatg   4080
gccttccact gccatctctc ccttatctga tgcctaaagt cacgatgggg acagagctac   4140
ccaggggcca gccatggggt gaccagccac ctgagggtca gtcacctgtg gagagcaggc   4200
acctgtgaag accaggcacc tgaggactgg cgcctacttc ccactttggc cctacactgg   4260
cacagagccc ctctttattc atttctcatg ctgagcatgg cacacttctg gcctctgggc   4320
atttatggat ttaagaccag gatggtattt cagaagcttc ccacttcctt cctattctaa   4380
ccgagtgccc agctcctttg ctgatcatgg aaagaccctt aataattagg cctgcaggcc   4440
aggcgcagtg gctcatgcct ataatcccag cactttagga ggtcaaggta ggaggatcgc   4500
ttaagcccag gagttcaaga ccagcctggg caacacagga agaatgtgtc tctacaaaaa   4560
ataattaaaa atcagatctg ctgtatccct gaaaaagtct caatcaacat gcatgttcca   4620
ctcttggagt tccctgttct gagggccagc cacgtcctgt gtcctggagc ttagccctca   4680
gcagctccct tcagcctggg cgccgcctgg gtcccaaacg tggcagctgc tcttccagtc   4740
tcggggccga ggagggcagg gagctcagtg actgagagtc ttgtgtatca catgtcttga   4800
```

gtgtcctgga gccaacggct gtcactggga aaaacaccag gccccaaaga tcgaatcaga 4860
gacgtggctg cgtgtttgcg attgtagcca ggcccttcag tgtcatcaaa ggagcactgg 4920
ggcctcctta agcacagacg gcagcccctg cccaggaggc ttcttcacca cgtcctgccc 4980
tgcagcctcc cagaccttta gatgcgcccc tgcccaaggc cctcctggtg acaggtgcca 5040
gattgagtgg tgggttgctg ccaggcaggc cacgctgtgt tgacgctgca ctcagcacgt 5100
gggtgttggc tctgccggtt ttgtggtgtg gggaccctac aggaggctgc ggccctgaga 5160
gcctgggatc agcgaggtgt ccgacatccc ttcctcaacg gcaacaaaaa ctccccaagt 5220
cagcactttg gttattttat agccacaacc ctcttggaaa acagtgggga agactatgga 5280
acatagaaag tgtggatgta tcacttctct ctaaaatgtc attgttagca ctaattacag 5340
gttcatgttt ttctgtgtat gtagcttttc cctatatagc tgaaaaagta ttaaagtcaa 5400
atataaggtg ggaatgggat ggaagggagg agatcaatac aacttatatt tttgcagttt 5460
ctactggaag aaaaaagttt tcaataccta gaccaacttg ttgaattttt aaaacttatg 5520
cactataaat gcaactttct ctactgcttt ctcagtgcct ttaggaagct ttcaaatttt 5580
tttgtactgt ggtttgtatt aaatttgcaa tattgatgta aaatacatga catgctagta 5640
catgtttaac aaaaatttaa a 5661

<210> SEQ ID NO 11
<211> LENGTH: 1415
<212> TYPE: DNA
<213> ORGANISM: Homo Sapiens

<400> SEQUENCE: 11
agtactatgt tgaagaagag tggtgagagt gggctcctcg tcttgttcca gttctcaaag 60
ggaatgcttt caccatttcc ccattcagta ttatgttggc tgtgggtttg tatagatggc 120
ttttattaca ttaagggatc atggcacaag ttgcagtttc caccctgccc atggaagatg 180
agaagtccat ggaagatgag gagtccattg aagatgagga gtctgttgaa gatgattccg 240
tggagagcag gatggtggtg acattgctca tatcagctct cgagtccacg atgttggaat 300
tcctgatgaa tctgcagtca gcattttgca tgaactgtgt gtggattcat tgcctacatt 360
ggatgatgaa gacttgagtg ttgctactaa gtgtgtcccc gagaaagtgt cagagccttt 420
acgtggacct tctcatgaaa aaggaaacag aatagtcaat ggaaaaggaa aagggcctcc 480
tgcaaaacat ccttccttga agcctagcac tgaagtggaa gatcctgctg tgaaaggagc 540
agtacaaaga aagaatgtac agacattgag agcagaacaa accttaccag tggctttaga 600
ggaagagcaa gaaaggtgtg aaagaagtga aaagaagcaa tcacaggtca aagaaggaaa 660
taatacaaac aaaagtgaaa aaatacaact atcagaaaat gtatgtcata gtacatcttc 720
tgctgctgct gacagattaa ccaaagaaag aaagattggg aaaacatatc ctcagcaatt 780
tcccaagaaa ctgaaggaag agcatgatag atgcatctta agacaagaaa gtgaagaaaa 840
aacaaatgtt aatatgctgt acaaaaaaat agagaagaat tagaaaggaa agagaaacaa 900
tataagaaag aagttgaagc aaaacaactt gaaccaacta ttgaatcact agagatgaaa 960
ccgaagacta caagaaatac tccaaatcag ataaatcaat ctttggattt tcataatcag 1020
gaagaaatga aagatctgat ggatgaaaat tgcattttga agacagatat tgctatactc 1080
cgacaggaaa tatgcacaat gaaaaatgac aacctggaaa aagaaaataa atatcttaag 1140
gacgctaaaa ttgttaaaaa aacaaatgtt gcccttgaaa agtatataaa actcaatgag 1200

```
gaattgataa caaaaacagc attccggtat caacaagagc ttaatgatct caaagctgag   1260

aatacaaggc tcaattccga actgttgaag gaagaagaaa gcaacaaaag actggaagct   1320

gaaattgaat catcagtcta gactgactgc tgctataagt aagcacagtg aaagtgtgaa   1380

aacagaaaaa aaaaaaaaaa aaaaaaaaaa aaaaa                              1415
```

<210> SEQ ID NO 12
<211> LENGTH: 3205
<212> TYPE: DNA
<213> ORGANISM: Homo Sapiens

<400> SEQUENCE: 12

```
agcgggagtc tttcgttctg ggaggcccag gcggcttcgc gttctgagaa taaacagaac     60

ctctgttgct ctgcgacttg caggcactgg gagattcgta gctaagacgc cagggcatcc    120

cggaagctgg gaaatgggac tgttgacatt cagggatgtg gccgtagaat tctctttgga    180

ggagtgggaa cacctggaac cagctcagaa gaatttgtat cagaatgtga tgttagaaaa    240

ctacagaaac ctggtctctc tgggtcttgt tgtctctaag ccggacctga tcaccttttt    300

ggaacaaagg aaagagcctt ggaatgtgaa gagtgaggag acagtagcca tccagccaga    360

tgtgttttcg cattataaca aggacctgtt gacagagcac tgcacagaag cttcattcca    420

aaaagtgata tcgaggagac atgggagctg tgatcttgag aatttacatt taagaaaaag    480

gtggaaaagg gaggagtgtg aagggcacaa tggatgttat gatgaaaaga cttttaaata    540

tgatcaattt gatgaatcct ctgttgaaag tttgtttcac cagcaaatac tttcttcttg    600

tgccaaaagc tataactttg atcaatatag gaaggtcttt actcattcat cattgcttaa    660

tcaacaagag gaaatagata tttggggaaa acatcacata tatgataaaa cttcagtgtt    720

atttaggcag gtctctactc taaatagtta ccgaaatgtt tttattggag agaaaaatta    780

tcattgcaat aattctgaaa aaaccttgaa ccaaagctca agccctaaaa atcatcagga    840

aaattatttt ctagaaaaac aatacaaatg taaagaattt gaggaagtct ttcttcagag    900

tatgcatggg caagagaaac aagaacagtc ttacaaatgt aataaatgtg tagaagtttg    960

tacccagtca ttaaaacata ttcaacatca gaccatccat atcagagaaa actcatatag   1020

ctataacaaa tatgataaag atcttagtca gtcatcaaat cttagaaagc agataatcca   1080

taatgaagag aaaccataca aatgtgaaaa atgtggggat agcttaaacc atagtttgca   1140

ccttactcaa catcagatca ttcctaccga agagaaaccc tataaatgga aagaatgtgg   1200

caaggtcttt aaccttaact gtagtttata ccttactaaa cagcagcaaa ttgatactgg   1260

agaaaacctt tacaaatgta aagcatgtag caaatctttt actcgttcct ccaatcttat   1320

tgtgcatcag agaattcaca ctggagagaa accatacaaa tgtaaagaat gtggcaaagc   1380

ctttcgctgt agttcatacc ttactaaaca taagcgaatt catactggag agaaacctta   1440

taaatgtaaa gaatgtggaa aagcttttaa ccgtagttca tgccttactc aacatcagac   1500

aactcataca ggagaaaaac tttacaaatg taaagtatgt agcaaatctt atgctcgttc   1560

ttcaaatctt attatgcatc agagagttca tactggagag aagccttata aatgtaaaga   1620

atgtggcaaa gtctttagcc gtagttcttg ccttactcaa catcggaaaa ttcatactgg   1680

agaaaatctt tacaaatgca aagtatgtgc taaacctttt acttgtttct caaatcttat   1740

tgtgcatgag agaattcata ctggagagaa accctataaa tgtaaagaat gtggcaaagc   1800

ctttccttat agttcacacc ttattcgaca tcatcgaatt catactggag aaaaaccata   1860

caaatgtaaa gcatgtagca aatcttttag tgactcctca ggtcttactg tgcatcggcg   1920
```

```
aactcatact ggagagaaac cctatacatg taaagaatgt ggcaaagcct ttagttatag   1980
ttcagatgtt attcagcatc ggagaattca tactggccag agaccctaca aatgtgaaga   2040
atgtggcaaa gccttcaact ataggtcata cctcactaca catcagagaa gtcatactgg   2100
agagagaccc tacaaatgtg aagaatgtgg caaagccttc aactctaggt catacctcac   2160
tacacatcgg agaagacata ctggagagag accctacaaa tgtgatgaat gtggtaaagc   2220
cttcagctat aggtcatacc tcactacaca tcggagaagt catagtggag agagacccta   2280
caaatgtgaa gaatgtggca aagcctttaa ctctaggtca tacctcattg cacatcagag   2340
aagtcatact agagaaaaac tttaaaaatg taaaacatgg agcagatttt ttacttgtta   2400
cccatgtctt attgtgcatc agataattta tatgggagtg aaaccctaca aatgttaaga   2460
atgtggcata acctttaact attttcaagc cttacacaat agcagagaat ataaactgaa   2520
aaaatccata caaatattaa aaatgtggca aattatttta aactgtgctc aacccttact   2580
caagataatc catactagag aaacactata gatgtaaaaa tgtgaaaagt tttattcaaa   2640
atatcaaact tatgagtcac ctaggggttc atagaaaaag gaagtttgca gatgcaataa   2700
atgtgaggaa gtatttaata aaaaatgaag tctaaatgtg tcagagaatt tatgtgagaa   2760
aggactaaag cacagacact ttcagccttt atactaaata agagtatttt ttgtacagaa   2820
taatctaaag gcaaaataat tagataattt atttgcttat atgttttaaa gtagcaagaa   2880
cattgatgtt ttgacaggta tatttcatag atacttcatt tgtatttaca gtatttgagg   2940
tttttggaaa gcaaatatta tttatataat tcagctttca aatctgttgc tgcttttcct   3000
taatccgtgg tgttcatgtg aaaatatgtg ttctgttttt ttttctgcat cagaacaatg   3060
tgaggtcatt ctacgttaat atcattaata tcagcatttt tcatggaagt ttaatgccaa   3120
atgtaaaaca catgaaaatt tttaaaaata tgctctttgt gtttgaataa agtagtaatg   3180
cacgtaaaca aaaaaaaaaa aaaaa                                         3205
```

<210> SEQ ID NO 13
<211> LENGTH: 2357
<212> TYPE: DNA
<213> ORGANISM: Homo Sapiens

<400> SEQUENCE: 13

```
gagccgggct actctgagaa gaagacacca agtggattct gcttcccctg ggacagcact     60
gagcgagtgt ggagagaggt acagccctcg gcctacaagc tctttagtct tgaaagcgcc    120
acaagcagca gctgctgagc catggctgaa ggggaaatca ccaccttcac agccctgacc    180
gagaagttta atctgcctcc agggaattac aagaagccca aactcctcta ctgtagcaac    240
gggggccact tcctgaggat ccttccggat ggcacagtgg atgggacaag ggacaggagc    300
gaccagcaca ttcagctgca gctcagtgcg gaaagcgtgg gggaggtgta tataaagagt    360
accgagactg gccagtactt ggccatggac accgacgggc ttttatacgg ctcacagaca    420
ccaaatgagg aatgtttgtt cctggaaagg ctggaggaga accattacaa cacctatata    480
tccaagaagc atgcagagaa gaattggttt gttggcctca agaagaatgg gagctgcaaa    540
cgcggtcctc ggactcacta tggccagaaa gcaatcttgt ttctcccccct gccagtctct    600
tctgattaaa gagatctgtt ctgggtgttg accactccag agaagtttcg aggggtcctc    660
acctggttga cccaaaaatg ttcccttgac cattggctgc gctaaccccc agcccacaga    720
gcctgaattt gtaagcaact tgcttctaaa tgcccagttc acttctttgc agagcctttt    780
```

```
acccctgcac agtttagaac agagggacca aattgcttct aggagtcaac tggctggcca    840
gtctgggtct gggtttggat ctccaattgc ctcttgcagg ctgagtccct ccatgcaaaa    900
gtggggctaa atgaagtgtg ttaaggggtc ggctaagtgg gacattagta actgcacact    960
atttccctct actgagtaaa ccctatctgt gattccccca aacatctggc atggctccct   1020
tttgtccttc ctgtgccctg caaatattag caaagaagct tcatgccagg ttaggaaggc   1080
agcattccat gaccagaaac agggacaaag aaatcccccc ttcagaacag aggcatttaa   1140
aatggaaaag agagattgga ttttggtggg taacttagaa ggatggcatc tccatgtaga   1200
ataaatgaag aaagggaggc ccagccgcag gaaggcagaa taaatccttg ggagtcatta   1260
ccacgccttg accttcccaa ggttactcag cagcagagag ccctgggtga cttcaggtgg   1320
agagcactag aagtggtttc ctgataacaa gcaaggatat cagagctggg aaattcatgt   1380
ggatctgggg actgagtgtg ggagtgcaga gaaagaaagg gaaactggct gaggggatac   1440
cataaaaaga ggatgatttc agaaggagaa ggaaaaagaa agtaatgcca cacattgtgc   1500
ttggcccctg gtaagcagag gctttggggt cctagcccag tgcttctcca acactgaagt   1560
gcttgcagat catctgggga cctggtttga atggagattc tgattcagtg ggttgggggc   1620
agagtttctg cagttccatc aggtcccccc caggtgcagg tgctgacaat actgctgcct   1680
tacccgccat acattaagga gcagggtcct ggtcctaaag agttattcaa atgaaggtgg   1740
ttcgacgccc cgaacctcac ctgacctcaa ctaaccctta aaaatgcaca cctcatgagt   1800
ctacctgagc attcaggcag cactgacaat agttatgcct gtactaagga gcatgatttt   1860
aagaggcttt ggccaatgcc tataaaatgc ccatttcgaa gatatacaaa aacatacttc   1920
aaaaatgtta aacccttacc aacagctttt cccaggagac catttgtatt accattactt   1980
gtataaatac acttcctgct taaacttgac ccaggtggct agcaaattag aaacaccatt   2040
catctctaac atatgatact gatgccatgt aaaggccttt aataagtcat tgaaatttac   2100
tgtgagactg tatgttttaa ttgcatttaa aaatatatag cttgaaagca gttaaactga   2160
ttagtattca ggcactgaga atgatagtaa taggatacaa tgtataagct actcacttat   2220
ctgatactta tttacctata aaatgagatt tttgttttcc actgtgctat tacaaatttt   2280
cttttgaaag taggaactct taagcaatgg taattgtgaa taaaaattga tgagagtgtt   2340
aaaaaaaaaa aaaaaaa                                                  2357
```

<210> SEQ ID NO 14
<211> LENGTH: 2380
<212> TYPE: DNA
<213> ORGANISM: Homo Sapiens

<400> SEQUENCE: 14

```
tcggccaccg ctcgcttcaa tatggctgcc cccagggaga gacgaggcta ccatgaagga     60
gccgagcgca gaccctgagt ccgtcaccca tggatcgcag cgcggagttc aggaaatgga    120
aggcgcaatg tttgagcaaa gcggacctca gccggaaggg cagtgttgac gaggatgtgg    180
tagagcttgt gcagtttctg aacatgcgag atcagttttt caccaccagc tcctgcgctg    240
gccgcatcct actccttgac cggggtataa atggttttga ggttcagaaa caaaactgtt    300
gctggctact ggttacacac aaactttgtg taaaagatga tgtgattgta gctctgaaga    360
aagcaaatgg tgatgccact ttgaaatttg aaccatttgt tcttcatgtg cagtgtcgac    420
aattgcagga tgcacagatt ctgcattcca tggcaataga ttctggtttc aggaactctg    480
gcataacggt gggaaagaga ggaaaaacta tgttggctgt ccggagtaca catggcttag    540
```

```
aagttccatt aagccataag ggaaaactga tggtgacaga ggaatatatt gacttcctgt    600

taaatgtggc aaatcaaaaa atggaggaaa acaagaaaag aattgagagg ttttacaact    660

gcctacagca tgctttggaa agggaaacga tgactaactt acatcccaag atcaaagaga    720

aaaataactc atcatatatt cataagaaaa aaagaaaccc agaaaaaaca cgtgcccagt    780

gtattactaa agaaagtgat gaagaacttg aaaatgatga tgatgatgat ctaggaatca    840

atgttaccat cttccctgaa gattactaag ctttggttct gatgtgtctt ggccgtaatg    900

tttctagtag gttttataaa gctgctcttc ataagagtat tttagtttgt tgagtgtatc    960

agccattcat aagccagtaa tgacaagtgc agagcttcaa actataactt tgttgcccag   1020

aggatgtgca gttgtcatct aagctctcag cagtacccgg cttatcctac gacttcacct   1080

gaaatgctat agttatccct actttttac cagtttctcc cagaagcacc tgcttaataa   1140

atcaaagatg tttgaatggt gtcttattct gaaataacct gacctaagac aggtatttag   1200

attattttgg atacattttg aaaagggata gcataaatat tttaagtaaa aagaccttta   1260

ttttaaataa tagtggatat tttaatgctg gaaattagca ttatagttga tatgccagaa   1320

attatatctt tggttgtgat ttaaacttat gctataaact aaattaatga tgtaaataca   1380

tagttttaaa cattctttta gggacatgta acttttaagt atcacttcaa taatacgtat   1440

tattatagga acaaagattt gggaataatt gattacaggt gaggaagtac tggaattcca   1500

gttcaaggag ataccatttc atttaggact aaaaggacaa gatacaagtt cacatgatgg   1560

gaaaaatcag aaaacctctc gcagacaaag ggtatataat ggatatgagg catcaaaaag   1620

catggtatag tcagtgatgg ggaatagtcc agaaaggctg aaacacagca tgtgatgcga   1680

gtcaaggtag ttgatgccca actgtgaagg gccgttctaa tctagcatgg aggtagacag   1740

tgtttcctta atatggctgc atatcagaat tacctaggtc aggacgaggc atggagatgc   1800

tactttaata ggccctgccg cagatcttcc aaaccagaat cttaatcctg gagtctagga   1860

atctttattt ttcacacaac tcatccaagt ggttctgata aaatcagtcc agcactttta   1920

gaacccactg ataacagact tattcctgga gacagcattt gaggaggaat tgaagatttt   1980

tctaatgaaa agaaaaaggg tcacatgaac agatgttgca gtgtacctgt gccagggatt   2040

tcatgtgtac actttatagg agaataagca agagcttagg taagttatag tccttaccat   2100

tgggtctaag gcagtttcca ggaaagcatg gcaactcgtt cagctatgta agttgaactc   2160

tgtaccactt gggagggaac attcccctag atgacaatgt cagtggcact cgaagttgtg   2220

cagtgcacat tcttatctac caacatatac agcagtcctt ctgggaagga aatttgggca   2280

ggaaagggaa ctcacagtgt cggaatgcct ggagcatttc ttctagtctg gtggacagaa   2340

tatgaaagta tctgcctggc agtgcagtaa atgaaaagag                         2380
```

```
<210> SEQ ID NO 15
<211> LENGTH: 2122
<212> TYPE: DNA
<213> ORGANISM: Homo Sapiens

<400> SEQUENCE: 15

tctgatgttc caaaaagtag aatatatata gagatcaaac attcaaaaga tacattctct     60

cctaagctca aaggttatat ttttattggg tagaacagta taggtaagtt gacatgaaat    120

tgcatcctgc accatgacca cattagtaat atcagaactt ttgagaaata ctggattttg    180

aatggtttga gactaattct ttaaaaatta ggctgagcaa cactcacaat ccaaaaatat    240
```

```
tcatattaag acttacacat ttgaagaatg gtacattttg tataaaatca tatttgatac    300
cattatttcc acatacctac ttttcatctg ttgcttaatt ttttcttttt agagttcttg    360
ctcaacttta tatggaacaa gtcttattat ttttgaaaga gtgtttagta ccttgtatta    420
agaaacttgg ccaagcgtgg tggttcactc ctgtaatccc agcactttgg gaggtcgagg    480
cgggcagatt gcttgaggcc aggagattga gaccagcctg ggcaacatgg tgaaatcctg    540
tctctaaaat ttaaaaaaaa gaagaagaag aaactcgaga ccacatcttc aaaaaacaac    600
tttgcagtat ttgaatttta cattatactg cccttcattt ctgacagcca aataacttta    660
ttgatattta ttgcttttgt agttgttata actaataatt tctttgaaaa tgtgttgtag    720
tttatgtttt tcaaagggtt ttggtagtgt ttgtgataga atggttttgc atatgattat    780
tataggggat atatttatag agctctactt gtatactttg tgacttacat tatgaaaact    840
tcaaagttct caatccatac agttagtatt tgtatccaga gtgtttaaga aaaaaatctg    900
tcttatattt ttagtatata ggagccagtg ttgcttctat ttgttttgaa tacaaattcc    960
agttttcttt gcatattaga tcccacatgt aagaaacaac cttaaacaat aatttgtatg   1020
ctggtaatat ttggacaagt gccataaatt aatgtatatt gtactttctg aatagatttt   1080
ctctaatcat agcaaaattt atttcaaaac tacaactctt tgaattattc cgctataata   1140
aaatttagtt ataaaattat gtggcactac tgaaaatcta aaggataatc tgaagaatga   1200
gtaagacaga tattgataga aatttttagt attttcagaa tgtttgggtt catacacata   1260
agtgaaatca ttttaaaaac taggggctgg gcacagtggc tcacaccagt aatcctagca   1320
ctttgggagg ccaaggcagg aggattgctt gagcccagga gtttgagacc agcctgggca   1380
acatagcaag accccttat ctataaaaat aataataact aggtaccatt gtgaaaaata    1440
ataactaggg attgattata gtatctttac tctgtattca caaatctctg tattcctgaa   1500
catatttaat cctttgattt acctctgact aggtttgtca ttgtaatccc tgggctgctt   1560
aggaggatac catttggttt gatgaaaaag ctggaatgat aatagctcaa actcttttga   1620
gcatttagta catgcttggc actgttctat atgtcttaag ttattcactc ttgtatttaa   1680
ccatcaacac tcttatgagg taaatatccc gcaattactt ttgcgccaac ctagtaccac   1740
tacagacaag gaaacagatg cagagaggct aagttacaag ggcacacagc cataaacttt   1800
ggatctgtgg agtgactggg cttcagagtc ctcttcctga ctgctgttcc tatgtctttt   1860
gcaaagagaa gtctttgaca ggtatatgct ttattaaaat catgtttaga aagaaatgag   1920
agaatagaat tagaaaaagg aatgactgta ggcttcgatg aaaatgactt ttgtgactag   1980
gtgaaaattg tttggctggg tatcctggaa aattgtcttc tgggaatatc tatattccag   2040
ggttcacttt tgtcatagaa ttgtttcttg gcccatttaa gagagatact ttgtttatta   2100
ataaatcaaa cgttttaatt tt                                             2122
```

<210> SEQ ID NO 16
<211> LENGTH: 2253
<212> TYPE: DNA
<213> ORGANISM: Homo Sapiens

<400> SEQUENCE: 16

```
attcattaag ataataggat catgattttt cattaactca tttgattgat attatctcca     60
tgcatttttt atttctttta gaaatgtaat tatttgctct agcaatcatt gctaacctct    120
agtttgtaga aaatcaacac tttataaata cataattatg atattatttt tcattgtatc    180
actgttctaa aaataccata tgattatagc tgccactcca tcaggagcaa attcttctgt    240
```

taaaagctaa ctgatcaacc ttgaccactt ttttgacatg tgagatcaaa gtgtcaagtt 300
ggctgaggtt ttttggaaag ctttagaact aataagctgc tggtggcagc tttgtaacgt 360
atgattatct aagctgattt tgatgctaaa ttatcttagt gatctaaggg gcagtttagt 420
gaagatggaa tcttgtattt aaaatagcct tttaaaattt gttttgtggt gatgattttg 480
acaacttcca tctttaggag ttatataatc accttgattt tagtttcctg atgtttggac 540
tatttataat caaggacacc aagcaagcat aagcatatct atatttctga ctggtgtctc 600
tttgagaagg atgggaagta gaaaaaaaaa aaagaaagaa aggaaaggaa gagaggagag 660
aagaaggcag ggatctccac tatgtatgtt ttcactttag aactgttgag cccatgctta 720
attttaatct agaagtcttt aaatggtgag acagtgactg gagcatgcca atcagagagc 780
atttgtcttc agaaaaaaaa aaaatctgag tttgagacta gcctggccaa catgttgaaa 840
ccccatatct actaaaaata caaaaattag cctggtgtgg tggcgcacgc ctgtagtccc 900
agctactctg gagcctgagg aacgtgaatc gcttgaaccc agaagacaga ggttgcagtg 960
agctgagatg gcactattgc actccagcct gggtgacaca gcaagactct gtctcaaaaa 1020
aaaaaaaaaa aaaaaaggaa aaaaaagaaa gaaagaaagt cccagcacac ctagataatt 1080
taccgagctc ttcagcaaaa accatgttac atacagcata ttccaaagaa atgaactctt 1140
ctgcaattta aattataagt aatatgttat tttggatcct agagaaacca ttttctctac 1200
atttcatgag catggttaga aaagagttta caagaattag gaagagggaa caattttaat 1260
ggtcagaaaa gaataaaatt tattctagtt caagaagtgc acacaaagaa tatgcattaa 1320
tctaacaact atgagattaa atctttcaaa aaggtcaaag gaggattgag aagtttacag 1380
agatgtccac ggcattttat atcaatctca aaggtaaggt ctgcattttt ataaaccaac 1440
ttaaacttct gttgagatag gatattttgt tttcaagcca gaattaccat taatcaaata 1500
tgttttaatt atctgattta gatgatctac tttttatgcc tggcttactg taagtttttt 1560
attctgatac acagttcaaa catcattgca acaaagaagt gcctgtattt agatcaaagg 1620
caagactttc tatgtgtttg ttttgcataa taatatgaat ataatttaag tctatcaata 1680
gtcaaaacat aaacaaaagc taattaactg gcactgttgt cacctgagac taagtggatg 1740
ttgttggctg acatacaggc tcagccagca gagaaagaat tctgaattcc ccttgctgaa 1800
ctgaactatt ctgttacata tggttgacaa atctgtgtgt tatttctttt ctacctacca 1860
tatttaaatt tatgagtatc aaccgaggac atagtcaaac cttcgatgat gaacattcct 1920 gatttttgc ctgattattc tctgttgagc tctacttgtg gtcattcaag attttatgat 1980
gttgaaagga aaagtgaata tgacctttaa aaattgtatt ttgggtgatg atagtctcac 2040
cactataaaa ctgtcaatta ttgcctaatg ttaaagatat ccatcattgt gattaattaa 2100
acctataatg agtattctta atggagaatt cttaatggat ggattatccc ctgatctttt 2160
ctttaaaatt tctctgcaca cacaggactt ctcattttcc aataaatggg tgtactctgc 2220
cccaatttct agggaaaaaa aaaaaaaaaa agg 2253

<210> SEQ ID NO 17
<211> LENGTH: 5243
<212> TYPE: DNA
<213> ORGANISM: Homo Sapiens

<400> SEQUENCE: 17
agcgtgagac tcgcgccctc cggcacggaa aaggccaggc gacaggtgtc gcttgaaaag 60

```
actgggcttg tccttgctgg tgcatgcgtc gtcggcctct gggcagcagg tttacaaagg    120
aggaaaacga cttcttctag attttttttt cagtttcttc tataaatcaa aacatctcaa    180
aatggagacc taaaatcctt aaagggactt agtctaatct cgggaggtag ttttgtgcat    240
gggtaaacaa attaagtatt aactggtgtt ttactatcca aagaatgcta attttataaa    300
catgatcgag ttatataagg tataccataa tgagtttgat tttgaatttg atttgtggaa    360
ataaaggaaa agtgattcta gctggggcat attgttaaag catttttttc agagttggcc    420
aggcagtctc ctactggcac attctcccat tatgtagaat agaaatagta cctgtgtttg    480
ggaaagattt taaaatgagt gacagttatt tggaacaaag agctaataat caatccactg    540
caaattaaag aaacatgcag atgaaagttt tgacacatta aaatacttct acagtgacaa    600
agaaaaatca agaacaaagc tttttgatat gtgcaacaaa tttagaggaa gtaaaaagat    660
aaatgtgatg attggtcaag aaattatcca gttatttaca aggccactga tattttaaac    720
gtccaaaagt ttgtttaaat gggctgttac cgctgagaat gatgaggatg agaatgatgg    780
ttgaaggtta cattttagga aatgaagaaa cttagaaaat taatataaag acagtgatga    840
atacaaagaa gatttttata acaatgtgta aaatttttgg ccagggaaag gaatattgaa    900
gttagataca attacttacc tttgagggaa ataattgttg gtaatgagat gtgatgtttc    960
tcctgccacc tggaaacaaa gcattgaagt ctgcagttga aaagcccaac gtctgtgaga   1020
tccaggaaac catgcttgca aaccactggt aaaaaaaaaa aaaaaaaaaa aaaaaagcca   1080
cagtgacttg cttattggtc attgctagta ttatcgactc agaacctctt tactaatggc   1140
tagtaaatca taattgagaa attctgaatt ttgacaaggt ctctgctgtt gaaatggtaa   1200
atttattatt ttttttgtca tgataaattc tggttcaagg tatgctatcc atgaaataat   1260
ttctgaccaa aactaaattg atgcaatttg attatccatc ttagcctaca gatggcatct   1320
ggtaactttt gactgtttta aaaaataaat ccactatcag agtagatttg atgttggctt   1380
cagaaacatt tagaaaaaca aaagttcaaa aatgttttca ggaggtgata agttgaataa   1440
ctctacaatg ttagttcttt gagggggaca aaaaatttaa aatctttgaa aggtcttatt   1500
ttacagccat atctaaatta tcttaagaaa atttttaaca aagggaatga aatatatatc   1560
atgattctgt ttttccaaaa gtaacctgaa tatagcaatg aagttcagtt ttgttattgg   1620
tagtttgggc agagtctctt tttgcagcac ctgttgtcta ccataattac agaggacatt   1680
tccatgttct agccaagtat actattagaa taaaaaaact taacattgag ttgcttcaac   1740
agcatgaaac tgagtccaaa agaccaaatg aacaaacaca ttaatctctg attatttatt   1800
ttaaatagaa tatttaattg tgtaagatct aatagtatca ttatacttaa gcaatcatat   1860
tcctgatgat ctatgggaaa taactattat ttaattaata ttgaaaccag gttttaagat   1920
gtgttagcca gtcctgttac tagtaaatct ctttatttgg agagaaattt tagattgttt   1980
tgttctcctt attagaagga ttgtagaaag aaaaaaatga ctaattggag aaaaattggg   2040
gatatatcat atttcactga attcaaaatg tcttcagttg taaatcttac cattatttta   2100
cgtacctcta agaaataaaa gtgcttctaa ttaaaatatg atgtcattaa ttatgaaata   2160
cttcttgata acagaagttt taaaatagcc atcttagaat cagtgaaata tggtaatgta   2220
ttattttcct cctttgagtt aggtcttgtg cttttttttc ctggccacta aatttcacaa   2280
tttccaaaaa gcaaaataaa catattctga atatttttgc tgtgaaacac ttgacagcag   2340
agctttccac catgaaaaga agcttcatga gtcacacatt acatctttgg gttgattgaa   2400
tgccactgaa acattctagt agcctggaga agttgaccta cctgtggaga tgcctgccat   2460
```

```
taaatggcat cctgatggct taatacacat cactcttctg tgaagggttt taattttcaa   2520
cacagcttac tctgtagcat catgtttaca ttgtatgtat aaagattata caaaggtgca   2580
attgtgtatt tcttccttaa aatgtatcag tataggattt agaatctcca tgttgaaact   2640
ctaaatgcat agaaataaaa ataataaaaa atttttcatt ttggcttttc agcctagtat   2700
taaaactgat aaaagcaaag ccatgcacaa aactacctcc ctagagaaag gctagtccct   2760
tttcttcccc attcatttca ttatgaacat agtagaaaac agcatattct tatcaaattt   2820
gatgaaaagc gccaacacgt ttgaactgaa atacgacttg tcatgtgaac tgtaccgaat   2880
gtctacgtat tccacttttc ctgctggggt tcctgtctca gaaaggagtc ttgctcgtgc   2940
tggtttctat tacactggtg tgaatgacaa ggtcaaatgc ttctgttgtg gcctgatgct   3000
ggataactgg aaaagaggag acagtcctac tgaaaagcat aaaaagttgt atcctagctg   3060
cagattcgtt cagagtctaa attccgttaa caacttggaa gctacctctc agcctacttt   3120
tccttcttca gtaacaaatt ccacacactc attacttccg ggtacagaaa acagtggata   3180
tttccgtggc tcttattcaa actctccatc aaatcctgta aactccagag caaatcaaga   3240
tttttctgcc ttgatgagaa gttcctacca ctgtgcaatg aataacgaaa atgccagatt   3300
acttactttt cagacatggc cattgacttt tctgtcgcca acagatctgg caaaagcagg   3360
cttttactac ataggacctg gagacagagt ggcttgcttt gcctgtggtg gaaaattgag   3420
caattgggaa ccgaaggata atgctatgtc agaacacctg agacattttc ccaaatgccc   3480
atttatagaa aatcagcttc aagacacttc aagatacaca gtttctaatc tgagcatgca   3540
gacacatgca gcccgcttta aaacattctt taactggccc tctagtgttc tagttaatcc   3600
tgagcagctt gcaagtgcgg gtttttatta tgtgggtaac agtgatgatg tcaaatgctt   3660
ttgctgtgat ggtggactca ggtgttggga atctggagat gatccatggg ttcaacatgc   3720
caagtggttt ccaaggtgtg agtacttgat aagaattaaa ggacaggagt tcatccgtca   3780
agttcaagcc agttaccctc atctacttga acagctgcta tccacatcag acagcccagg   3840
agatgaaaat gcagagtcat caattatcca ttttgaacct ggagaagacc attcagaaga   3900
tgcaatcatg atgaatactc ctgtgattaa tgctgccgtg gaaatgggct ttagtagaag   3960
cctggtaaaa cagacagttc agagaaaaat cctagcaact ggagagaatt atagactagt   4020
caatgatctt gtgttagact tactcaatgc agaagatgaa ataagggaag aggagagaga   4080
aagagcaact gaggaaaaag aatcaaatga tttattatta atccggaaga atagaatggc   4140
actttttcaa catttgactt gtgtaattcc aatcctggat agtctactaa ctgccggaat   4200
tattaatgaa caagaacatg atgttattaa acagaagaca cagacgtctt tacaagcaag   4260
agaactgatt gatacgattt tagtaaaagg aaatattgca gccactgtat tcagaaactc   4320
tctgcaagaa gctgaagctg tgttatatga gcatttattt gtgcaacagg acataaaata   4380
tattcccaca gaagatgttt cagatctacc agtggaagaa caattgcgga gactacaaga   4440
agaaagaaca tgtaaagtgt gtatggacaa agaagtgtcc atagtgttta ttccttgtgg   4500
tcatctagta gtatgcaaag attgtgctcc ttctttaaga aagtgtccta tttgtaggag   4560
tacaatcaag ggtacagttc gtacatttct ttcatgaaga agaaccaaaa catcgtctaa   4620
actttagaat taatttatta aatgtattat aactttaact tttatcctaa tttggtttcc   4680
ttaaaatttt tatttattta caactcaaaa aacattgttt tgtgtaacat atttatatat   4740
gtatctaaac catatgaaca tatatttttt agaaactaag agaatgatag gcttttgttc   4800
```

ttatgaacga aaaagaggta gcactacaaa cacaatattc aatcaaaatt tcagcattat 4860
tgaaattgta agtgaagtaa aacttaagat atttgagtta acctttaaga attttaaata 4920
ttttggcatt gtactaatac cgggaacatg aagccaggtg tggtggtatg tgcctgtagt 4980
cccaggctga ggcaagagaa ttacttgagc ccaggagttt gaatccatcc tgggcagcat 5040
actgagaccc tgcctttaaa aacaaacaga acaaaaacaa aacaccaggg acacatttct 5100
ctgtcttttt tgatcagtgt cctatacatc gaaggtgtgc atatatgttg aatgacattt 5160
tagggacatg gtgtttttat aaagaattct gtgagaaaaa atttaataaa gcaacaaaaa 5220
ttactcttaa aaaaaaaaaa aaa 5243

<210> SEQ ID NO 18
<211> LENGTH: 425
<212> TYPE: DNA
<213> ORGANISM: Homo Sapiens

<400> SEQUENCE: 18
gctctgagga tcccccgtat agcaccggga aatctggcta gagttgatcg cagatgtact 60
tgttttggga atatatgaga gaagaaactg ctgagcaggt cagtaaagaa cagtccattt 120
cagctgcagg acagttctct ttcccgggac aagcctacat agcctccaag ggagccaaac 180
tatcccttcc atgcaacaag acaccttgca tggatactct agccatgact tgcttttgga 240
caaaaatcaa ctgctaacgt tttcatctc taatatcatt aacaccatgg agaaaaaaga 300
aaaaaattca accctagaaa acttgacaac gagaataaga aaatccacaa ggaaaggtca 360
tgctaaaact gatttgacag ttgttccatc accgcctacc acggtgctat aacggggtac 420
cgagc 425

<210> SEQ ID NO 19
<211> LENGTH: 1958
<212> TYPE: DNA
<213> ORGANISM: Homo Sapiens

<400> SEQUENCE: 19
actggtgctg caagtcgctg agctgacagt tgtgccgagg actgtcacca ttgggcaggc 60
atggtggcca gctcctcact tggctgaggt ccagggatgg acacaggttc gctgaacgcg 120
gccagcctga gggaggagca gctccacctg tccttgctgg tgtccagcgg ctggagaaca 180
atcagcttcc acgtggtgcc cgtggtgaga aggaagcttg ggcgcctgc cctggagggg 240 gtgcagcaga tgcccggatt ccctgagggc agcttgagaa ggatcctcag ccaaggggtg 300
gacctggtgc cggccagcgc ccagctctgg aggacctcca ctgactacct gctcacgagg 360
ctgctggggg agctgggctc cctgcagggt catcgcctgg acagcctctc catcctcgac 420
cgggtcaacc acgagagctg gcgtgacagt ggccagactg acggcctgac ctttggccac 480
ctgaagatgg tgctgctgtg ggcctctgtg ctcttcctgg cgcccgagga ctgggcagaa 540
ctgcagggcg ccgtgtaccg cctgctggtg gtgctgctct gttgcctggc cacgcggaag 600
ctgccccact tcctccaccc gcagcgcaac ctgctgcagg gcagcggcct ggaccttggt 660
gccatctacc agcgcgtgga gggcttcgcc agccagcccg aggcggccct gcgcatccac 720
gccacccacc tgggccgcag ccccccgccg cgcatcggct ccgggctcaa ggcgctcctg 780
cagctgccag ccagtgaccc cacttactgg gccactgcct acttcgacgt cctgctggac 840
aagttccagg tcttcaacat ccaggataag gaccggatct ctgccatgca gagcatcttc 900
cagaagacca ggactctggg aggcgaggag agctgagctg ggccacctgg tctcagccac 960

```
ctgttcttgg ctccccaaca gactctgcac tgcaccatgg gaggctcctg ggatgtttgg   1020

aagaagaaac gggcttctcc ttgagggggt agtggaggga ttttgtcccc agcagtggcc   1080

tctgagagtc tttcagtgcc tggtggggca gggcaggcct cttggagcac ctcctccctg   1140

ggtcagggcc tggatgcagg tgccaagctc tccatgtggt gcatgttgac ccagccacgt   1200

ggtgttgtca agcaaacagc atcggcagga gacctggagc tgaggacttg gccctgcctg   1260

cactgtatgc cattccttgg tgacgaaatg ctgtatattt ggttttgaaa aaatgaatgt   1320

gctgggtata cacagcagaa agggtactgt ccactttttg tatatcagtg tggaaaatat   1380

ttcccctaga agtagaaaag gctcatgtgc tgatggataa ttttgagtct tctccattct   1440

ctgtgaatga ccccccttccc caggcatccc cacctcctac ctcgttctta gagcaaacta   1500

aagccaactg agggtgcaca cacagccatg agcccacctg cccaggacta ctcccatctg   1560

cttcttcccg tccccgtgga agtggcccct gatatggatt gtatctgtat ccccacccaa   1620

atctcaggta gaattggatc tgtgtcccca cccaagtctc aggtagactt gtaatcccca   1680

gtgttggagg aggggcccag tgggaggtga ttggatcatg ggggtggatt tctcccttac   1740

tgttctcatg atagtgagtg agttctcatg agatctggtt ttttgagtgt gtggcccctc   1800

cccctctcct tttgctctct tcctctttct ccggccatgt aagatatgcc tccttctcct   1860

tcaccttcca ccatgattgt cagtttcctg aggcctccca gccatgcttc ctgtatagcc   1920

tgcgggactg tgagtcaatt aaacctcttt attcatta                           1958
```

<210> SEQ ID NO 20
<211> LENGTH: 3347
<212> TYPE: DNA
<213> ORGANISM: Homo Sapiens

<400> SEQUENCE: 20

```
agcctcggcg tgcccccagg accggtaaag ttcctctcgc cagccgcatc catgcttctg     60

gcgcggatga acccgcaggt gcagcccgag aacaacgggg cggacacggg tccagagcag    120

ccccttcggg cgcgcaaaac tgcggagctg ctggtggtga aggagcgcaa cggcgtccag    180

tgcctgctgg cgccccgcga cggcgacgcg cagccccggg agacctgggg caagaagatc    240

gacttcctgc tgtccgtagt cggcttcgca gtggacctgg ccaacgtgtg gcgcttcccc    300

tacctctgct acaagaacgg cggcggtgcc ttcttgatcc cgtacacact gttccttatc    360

atcgcgggga tgcccctgtt ctacatggag ctggctctgg gacagtacaa ccgggagggg    420

gctgccaccg tttggaaaat ctgcccattc ttcaaaggcg ttggctatgc tgtcatcctg    480

atcgccctgt acgttggctt ctactacaac gtcatcatcg cctggtcact ctactacctc    540

ttctcctcct tcaccctcaa cctgccctgg accgactgtg gccacacctg gaacagcccc    600

aactgtaccg accccaagct cctcaatggc tccgtgcttg gcaaccacac caagtactcc    660

aagtacaagt tcacgccggc agccgagttt tatgagcgtg gtgtcctgca ccttcacgag    720

agcagcggga ttcatgacat cggcctgccc cagtggcagc tcttgctctg tctgatggtc    780

gtcgtcatcg tcttgtattt tagcctctgg aaaggggtga agacatcagg aaaggtggtg    840

tggatcacag ccacgctgcc ttacttcgtg ctgttcgtgc tcctggtcca tggcgtcacg    900

ctgcccggag cctccaatgg catcaatgcc tacctgcaca tcgacttcta ccgcttgaaa    960

gaggccacgg tatggattga tgccgcaact cagatatttt tttccttggg ggctggattt   1020

ggagtattga ttgcatttgc cagttacaac aaatttgaca acaactgtta cagggatgcc   1080
```

```
ctgctgacca gcagcatcaa ctgtatcacc agcttcgtct ctgggttcgc catcttctcc   1140
atccttggtt acatggccca tgaacacaag gtcaacattg aggatgtggc cacagaagga   1200
gctggcctag tgttcatcct gtatccagag gccatttcta ccctgtctgg atctacattc   1260
tgggctgttg tgtttttcgt catgctcctg gcgctgggcc ttgacagctc aatgggaggc   1320
atggaggctg tcatcacggg cctggcagat gacttccagg tcctgaagcg acaccggaaa   1380
ctcttcacat ttggcgtcac cttcagcact ttccttctcg ccctgttctg cataaccaag   1440
ggtggaattt acgtcttgac cctcctggac acctttgctg cgggcacctc catccttttt   1500
gctgtcctca tggaagccat cggagtttcc tggttttatg gagtggacag gttcagcaac   1560
gacatccagc agatgatggg gttcaggccg ggtctatact ggagactgtg ctggaagttc   1620
gtcagtcctg ccttcctcct gttcgtggtt gtggtcagca tcatcaactt caagccactc   1680
acctacgacg actacatctt cccgccctgg gccaactggg tggggtgggg catcgccctg   1740
tcctccatgg tcctggtgcc catctacgtc atctataagt tcctcagcac gcagggctct   1800
ctttgggaga gactggccta tggcatcacg ccagagaacg agcaccacct ggtggctcag   1860
agggacatca gacagttcca gttgcaacac tggctggcca tctgagcctg cctggaggag   1920
aaggaggaac ccccatgcca atgtccaggt cacaggcatc cgctgcgctc ccacctcgga   1980
caccatcttg ggattcctcc cctggaagtt gtcctttctg atcctctctt cttttcccat   2040
ttacaaatga tttcgtgact gtagtttttg ttcaccttct gtgcatctgg cctgggggct   2100
gttagctcag aggagaggag caaacaggaa aatgacttct gttctgtccc cgctgttttg   2160
ggggaagtct ctcccacttt gggatcctgc tgaagctagg ttcatgaggt cggaaatccc   2220
caccacattt gcctagactt tgggcacagg agttcttagt ccaccaaatc agagagagga   2280
tgggcttttg atcagatacc cctcccaaaa aaaaaaaaaa ctaaaactaa agcaaaaatc   2340
aaacaaaatc tggctgagtt tagtggggtg gttggggaag gtacatagac cctcctcttg   2400
cccaccctag acagccctct catgtctgaa cctcagcctg ggagttagat ttatttgtct   2460
ctaaaatgaa gtcagtggat agatgctttg agggattttg agtagaaaca ttcatagtta   2520
attttcactc tggccaatct gagtttgatg tgtgtgttct ggaacattcc tccagctttt   2580
ggtggtcaga tggcccagag atatggggga caggaggaag agggtaaatg aaccacagtg   2640
agcaggttct aggaggtacc tgcatcagac aagctggtgg aggccacgtg gcaagccaca   2700
tctactgagg cctcatgctg ctcttgctct gtaagacacg gagcccagaa acccatctgc   2760
acttcctgag acctgcctgg ggaaacgggg gcagggacca agtgaggcct catgtgtgtc   2820
ttcaccgtgc tgtcctcaca aggccaggtg ggtgcccaaa gggagcctga caggctgttg   2880
tgttaattta ttgttcttgc acacctgcac agcctccctc tggggatccc acctggagtg   2940
gaccaggggt cttgagaaat ggagagttgg ctgcaaaaac tctcatgcac tagatgtggc   3000
accttggagg gcagggtgag acaagcagcc cagaaatact ctctcaagtg gaggggagaa   3060
ttttgagagt ggatggaaca gtttggtggt ttcagagaat ttctaggttt ctacttggat   3120
ctacttctga tacaaacttg cacttggtgc cctctggtgg tgtttagttt tagttccgta   3180
agagaaatga ttcctagttt gctaaattgg tggcatcttt gggaggggtt tctgtttatg   3240
gttagagtct cttacaccct tgttggaggg attcttattc tgactgtggg agctcctgtt   3300
gcgggatctt gggaaaaaat aaagaagccg ctgcattcgc acgtcaa                 3347
```

<210> SEQ ID NO 21
<211> LENGTH: 11876

<212> TYPE: DNA
<213> ORGANISM: Homo Sapiens

<400> SEQUENCE: 21

```
gggctgggcc tcccttcccc ataacactga gctgctctgc tgggccaacc gtgctcctgg      60
gccagccaga ggaccccat gaggcggcat gcaggcgggg agcaggccac agaacgcagg     120
gtgaaaccca aggcgctcta gaggagatga attatggatc cgccctcccg gaatcctggc    180
tcggccctcc ccacgccacc cagggccagt cgggtctgct cacagcccga ggaggccgcg    240
tgtccagccg cgggcaagag acagagcagg tccctgtgtc tccaagtccc tgagcccgtg    300
acaccggccc caggccctgt agagagcagg cagccaccat ggcgaaggag gaagatgagg    360
agaagaaagc caagaaaggg aagaagggga agaaggcacc ggagccggag aagcccaaac    420
ggagcctgaa ggggacgtcg cggctgttca tgggcttccg cgaccgtaca cccaagatct    480
ccaagaaggg ccagttccgc agcgcctcgg ccttcttctg ggcctccac accggccccc     540
agaagaccaa gcgcaagagg aaggcccgca ccgtgctcaa gtccacgtca aagctcatga    600
cgcagatgcg catgggcaag aagaagcggg cgatgaaggg caagaagccg tccttcatgg    660
tgatccgctt cccaggccgc cgtggctacg gccgcctgcg gccgcgcgcc cggtcactca    720
gcaaagcgtc cacggccatc aactggctca caaaaaagtt cctcctcaag aaggccgagg    780
agtcgggcag cgaacaggcc acagtggacg cctggctgca gcgctcgagc tcccgcatgg    840
gctcccgcaa actccccttc ccgtcgggtg ccgagatcct gcggcctggg ggccggctcc    900
ggaggttccc ccgcagccgc agcatctacg cgtcaggcga gcccctgggc ttcctgccct    960
tcgaggacga ggccccattc catcactcgg gctcccgcaa gtcgctgtac gggcttgagg   1020
gcttccagga cctgggcgag tattatgact atcaccgcga cggcgacgac tactacgacc   1080
ggcagtcact ccaccgctac gaggagcagg aaccctacct ggcgggcctc ggcccctaca   1140
gcccggcctg gccaccctac ggcgaccact actacgggta cccgcccgag gatccctacg   1200
actactacca ccccgactat tacggtggcc cctttgatcc ggggtacacc tacggctacg   1260
gctacgacga ttacgaaccc ccatatgcgc ccccgtcggg gtactcgtct ccttacagct   1320
accacgatgg gtacgagggc gaggcgcacc cttatggcta ctacctggat ccctatgcgc   1380
cgtacgacgc gccataccca ccctatgacc tcccatacca cactccctac gatgtaccct   1440
actttgatcc ctacggagtc cactacaccg tcccctatgc cgaaggcgtc tatggcggtg   1500
gggacgaggc catctacccc cccgaggtgc cctattttta cccggaggag tcggcttcgg   1560
cctttgtgta cccctgggta ccaccgccca tcccgtcgcc ccacaacccg tatgcccacg   1620
ccatggatga catcgccgag ctggaggaac cagaggacgc gggcgtagag cgtcagggga   1680
cctccttccg cctgcccagc gccgccttct tcgagcagca aggcatggat aagcccgcca   1740
ggtccaagct gtccctcatc cgcaagttcc gcctcttccc gcgaccccag gtgaagctgt   1800
ttgggaagga gaagctggag gtgcccctgc caccctctct ggacattcct ctccccttgg   1860
gggatgcgga cgaagaagag gacgaggagg agctgccccc ggtttccgct gtgccctacg   1920
gccacccttt ctggggcttc ctcacgccgc gccagcgcaa cctccagcgc gcgctgtcgg   1980
ccttcggcgc ccaccggggc ctgggcttcg gccctgagtt tggccgcccc gtgcctcgcc   2040
ctgccacctc gcttgcgcgg ttcctcaaga agacgctgtc ggagaagaag cccatcgcgc   2100
ggctcagggg cagccagaag gcccgggcgg gcggccctgc tgtcagggag gcggcctaca   2160
aacgcttcgg ctacaagctg gctggcatgg accccgagaa gcccggcacg cccatcgtgc   2220
```

-continued

```
tgaggagggc ccagccacgc gctcgcagca gcaacgacgc gcgccgcccg cccgcgccac   2280
agcccgcgcc caggaccctc tcccactgga gcgcgctcct gtctccgccc gtgcccccgc   2340
ggcccccaag ctccgggccc ccgcccgcgc cgccgctctc cccggcgctc tcgggcctgc   2400
cccggccggc ctcgccctac ggctccctcc gccgccaccc gccgccctgg gccgccccag   2460
cgcacgtgcc accggcgccg caggccagct ggtgggcctt cgtggagccc cctgccgtga   2520
gcccggaggt gccccccgac ctactagcct tcccagggcc ccgaccctcg ttcaggggct   2580
cccgccggag aggggcggct ttcggcttcc ccggggcctc tccacgggcg tcgcggaggc   2640
gagcttggtc accgctggcc tcgccccagc cctcgctgag gagctcgccg ggcctcggct   2700
actgctcacc cttggcgccc ccgtcgcctc agctgtcctt gcgcacgggc cccttccagc   2760
cgcccttcct gcccccggcc cgccggcccc gctcgctgca ggagtcccca gccccacgcc   2820
gagccgctgg gcgcctgggc ccacccggct cgccgctgcc gggctcaccc aggccgccct   2880
cgccgcccct ggggctctgc cacagcccgc ggcgcagctc cctgaatctg ccctcgcgcc   2940
tcccgcacac gtggcggcgc ctcagcgagc cacccactcg ggctgtgaag ccgcaagtgc   3000
gcctgccctt ccaccgaccg cccagggccg gggcctggcg ggcgcccctg gaacaccggg   3060
agagcccgcg agaacccgag gactcagaga cgccctggac tgtgccccca ctggccccca   3120
gctgggacgt ggacatgcct cccacccaac gcccaccctc cccctggcca ggaggtgcag   3180
gcagccgccg aggcttttcc aggccacccc ctgtgccgga aaaccccttt ctccagctcc   3240
tgggccctgt gccatccccc accctccagc ctgaggatcc agctgctgat atgaccaggg   3300
tcttcctggg cagacaccat gagccggggc ctggacagct caccaaatca gctggcccaa   3360
cccctgagaa gcctgaagaa gaggccaccc tgggggaccc ccagctgcca gcagagacca   3420
agcctccaac cccagcacct cccaaggatg tcactccccc caaggatatc actcccccca   3480
aggatgtcct cccagagcaa aagacattaa ggcccagcct ctcataccca ctggctgcgt   3540
gtgaccagac cagggccaca tggccaccat ggcaccgctg gggaacactg ccccaagccg   3600
cagccccctt ggcgcccatc agggccccag agcccctgcc caaggggggt gaacggcgcc   3660
aggcagcccc tgggcgtttt gctgtggtca tgcctcgtgt gcagaagctg agctctttcc   3720
agcgagttgg gcctgcaacc ctgaagcctc aagtccagcc cattcaggac cccaagccaa   3780
gagcctgtag tcttcgctgg tcctgcctct ggcttcgggc agatgcctat ggaccctggc   3840
cacgagtaca cacccatccc cagtcctgcc acctgggccc tggagctgcc tgcctgtccc   3900
ttaggggctc ctgggaggag gtcggcccgc caagctggcg gaacaagatg cactccatcc   3960
gcaacctgcc atccatgcgg ttccgtgagc agcacgggga ggatggtgtg gaggacatga   4020
cacagctgga agacctccag gaaaccactg tgctgtccaa cctcaagatt agatttgaac   4080
ggaacctcat ctacacatac attgggagca tcctggtgtc ggtgaaccca taccaaatgt   4140
ttggaatcta tgggccggag caggtgcagc agtacaacgg acgggccctg ggagagaatc   4200
ccccgcacct ctttgctgtt gcaaatctcg ccttcgccaa aatgctcgat gccaaacaga   4260
accagtgcat aatcattagt ggagagagcg gctctggcaa aactgaggcc accaagctga   4320
ttctgcgcta cctggccgcc atgaaccaga aacgggaggt catgcagcag ataaagatcc   4380
tggaggcaac acccctcttg gagtccttcg gtaatgccaa aaccgtcagg aacgacaact   4440
ccagccgctt tgggaagttt gtggaaatct ttctggaagg gggcgtgatc tctggtgcca   4500
taacctccca gtacctgctt gagaaatcca ggatcgtgtt tcaggccaaa aacgagagga   4560
attaccacat cttctacgag ttgctggccg ggttgcctgc ccagctcagg caggccttta   4620
```

```
gcctgcaaga ggctgagacc tactactatc tgaaccaggg tgggaactgt gagatagcag   4680
gaaagagcga tgcagatgac tttcgccggc tcctggctgc catggaggtg ttgggcttca   4740
gcagtgagga ccaggacagc atcttccgca tcctggcctc catcctgcac ctgggcaacg   4800
tctactttga gaagtatgag acggatgcac aggaggtggc ctcagtggtg agtgcccgag   4860
agatccaggc cgtggcagag ctgctgcaga tctcccctga gggcctgcag aaggccatca   4920
ccttcaaagt gaccgagaca atgcgagaga agatcttcac gcccctaact gtggagagcg   4980
ctgtggatgc cagggacgcc atcgccaagg tcttgtatgc actgctgttc agctggctca   5040
tcaccagggt caacgcgctg gtgtccccaa ggcaggacac actgtccatc gccatcctgg   5100
acatctatgg tttcgaggac ctgagcttca acagctttga gcagctgtgt attaactacg   5160
caaacgagaa ccttcagtac cttttcaaca agatcgtctt ccaggaggag caggaggagt   5220
acatccgtga gcagatagac tggcaggaga tcacctttgc tgacaaccag ccctgcatca   5280
acctcatctc actgaagcct tatggcatcc tgcggatcct tgacgaccag tgttgctttc   5340
cccaggctac agaccacacc ttcctacaga agtgccacta ccatcatggc gccaacccgc   5400
tctattccaa acccaagatg ccgctgcctg agttcaccat caagcactat gcaggcaagg   5460
tcacctacca ggtgcacaag ttcctggaca agaaccacga ccaagtgcgc caggatgtgc   5520
tggacctgtt cgtacggagc cggacacggg tggtggcaca cctcttctcc agccatgccc   5580
cacaggctgc ccctcagcgc ctgggcaaga gcagctccgt cactcggctc tacaaggcgc   5640
acactgtggc cgccaagttc cagcagtcac tcctggatct ggtggaaaag atggagaggt   5700
gcaacccctt gttcatgcgt tgcctgaagc ccaaccacaa gaaggagcca ggtctctttg   5760
agccagatgt ggtaatggca caattacgct attcaggggt gctggagacc gtgaggatcc   5820
gcaaggaggg atttccagtg cgcctgcctt tccaggggtt catcgacagg tactgctgtc   5880
tagtggccct caagcatgac ctgccggcta atggggacat gtgtgtgtca gtgctgagtc   5940
gcctgtgcaa agtcatgcca aacatgtacc gtgttggggt cagcaagctg ttccttaagg   6000
aacacctata ccagctgctg gagagtatgc gagagcatgt cctgaatctg gcagccctca   6060
ctctgcagcg ctgcctccgt ggcttcttca ttaagcggcg attccgctct ctgcgccaca   6120
agatcatcct gctgcaaagc cgggcccgtg gctaccttgc caggcaacgc tatcagcaga   6180
tgaggaggag tctggtgaag ttccggtccc tggtacacgc atacgtgagc cgccgacgct   6240
atctcaagct gagggcagag tggaggtgcc aggtggaggg ggcgctgctg tgggagcagg   6300
aggagctgag caagcgggag gtagtcgctg tggggcacct ggaggtaccg gctgagctgg   6360
ctgggctctt gcaagcagtg gcaggcctcg ggctggccca ggtgcctcag gtggcccctg   6420
tgaggactcc tcgactccag gctgagcccc gtgtcacact gcccctggac atcaacaact   6480
atcctatggc caagtttgtc cagtgccact tcaaggaacc tgcctttggg atgctgacag   6540
tgcccctgag gacacccctc acgcagctgc cagccgagca ccatgcagaa gccgtgagca   6600
tcttcaagct gatcctgcgc ttcatgggcg acccccacct gcatggtgcc cgggagaaca   6660
tcttcgggaa ctacatcgtg cagaaggggc tggcggtgcc tgagctgcgg gatgagatcc   6720
tggcacagct ggccaatcag gtgtggcaca atcacaatgc ccacaatgct gagcggggct   6780
ggctgctgct ggccgcctgc ctcagtggct ttgcaccttc cccgtgcttc aacaagtacc   6840
ttctcaagtt tgtgtctgat tatgggcgga atggcttcca ggctgtgtgt cagcaccgcc   6900
tcatgcaggc catgggccgg gcccaacagc agggctcggg ggctgcccgc accttacccc   6960
```

```
cgacccagct cgagtggaca gcgacctatg agaaggccag catggcgctg gacgtgggct   7020
gcttcaatgg tgaccagttc tcctgcccgg tgcactcctg gagtacgggg gaagaggtgg   7080
ctggagacat tctgaggcac agggggctgg cagatggctg gcgcggctgg accgtggcca   7140
tgaagaatgg tgtccagtgg gcagagctgg ctggccacga ctacgtgtta gacctggtgt   7200
cggacctgga gctgctcagg gacttccctc gacagaagtc ctacttcatt gtgggcacag   7260
aggggcctgc agccagcagg ggaggcccca aagtggtgtt tgggaacagc tgggactcgg   7320
atgaggacat gtccactaga ccccagcccc aggagcacat gcccaaagta cttgactctg   7380
atgggtacag cagccacaat caggacggta caaatgggga gactgaggcc caaagaggga   7440
cagcaaccca ccaagagtca gacagtcttg gagagcctgc tgtgccccac aaggggctgg   7500
actgctacct ggatagcctc tttgaccctg tgctgtccta cggggatgcg gacctggaga   7560
agccaacagc cattgcctac cgcatgaaag gggaggccca gcccggtgga ggcagcagta   7620
gtggtactga agacaccccc aggagacccc cagagccaaa gccaatccca ggcctggatg   7680
cctccacatt ggctctgcag caagccttca tccacaaaca ggccgtgctg ctggcccggg   7740
agatgaccct gcaggccacg gcactccagc agcagcccct gagtgctgcc ctgagatcct   7800
tgcccgcaga gaaaccccca gcaccagagg cacagccgac gtctgtaggc accggtcccc   7860
ctgccaaacc cgtgctcctg cgtgccactc caaagccctt ggccccagcc cctctggcca   7920
aggctccaag gctccccatc aagcctgtgg ctgcccctgt tctagctcag gatcaggctt   7980
ctccagaaac cacttcaccc tccccagagc tggtccggta ctctacgctc aactctgagc   8040
acttcccaca gcccacacag cagatcaaga atattgtcag gcagtaccag cagccgttcc   8100
ggggaggccg gcctgaggcc ctcaggaagg atggcgggaa agtgttcatg aagcggccag   8160
accctcatga ggaggccctg atgatcctga aagggcagat gacccacctg gcagctgcac   8220
ctggcaccca ggtgtccaga gaggccgtgg ccctggtgaa gccggtgacc agtgcaccaa   8280
ggccatccat ggcacccact tcagctctgc cctcgcgatc gctggagccc cctgaggaac   8340
tcacgcagac gcggctgcac cgcctcatca atcccaactt ctacggctat caggacgccc   8400
cctggaagat cttcctgcgc aaagaggtgt tttaccccaa ggacagctac agccatcctg   8460
tgcagcttga cctcctgttc cggcagatcc tgcacgacac gctctccgag gcctgccttc   8520
gcatctctga ggatgagagg ctcaggatga aggccttgtt tgcccagaac cagctggaca   8580
cacagaagcc tctggtaacg gaaagcgtga agcgggccgt ggtcagcact gcacgagaca   8640
cctgggaggt ctacttctcc cgcatcttcc ccgccacggg cagcgtgggc actggtgtgc   8700
agctcctagc tgtgtcccac gtgggcatca aactcctgag gatggtcaag ggtggccagg   8760
aggccggcgg gcagctgcgg gtcctgcgtg catacagctt tgcagatatc ctgtttgtga   8820
ccatgccctc ccagaacatg ctggagttca acctggccag tgagaaggtc atcctcttct   8880
cagcccgagc gcaccaggtc aagaccctgg tagatgactt catcttggag ctgaagaagg   8940
actctgacta cgtggtcgct gtgaggaact tcctgcctga ggaccctgcg ctgctggctt   9000
tccacaaggg tgacatcata cacctgcagc ccctagagcc acctcgagtg ggctacagtg   9060
ctggctgcgt ggttcgcagg aaggtggtgt acctggagga gctgcgacgt agaggccccg   9120
actttggctg gaggttcggg accatccacg ggcgcgtggg ccgcttccct tcggagctgg   9180
tgcagcccgc tgctgccccc gacttcctgc agctgccaac ggagccaggc cgcggccgag   9240
cagccgccgt ggccgctgct gtggcctctg cagccgctgc acaggaggtg ggccgcagga   9300
gagagggtcc cccagtcagg gcccgctctg ctgaccatgg ggaggacgcc ctggcgctcc   9360
```

```
caccctacac aatgctcgag tttgcccaga agtatttccg agaccctcag aggagacccc   9420
aggatggcct caggctgaaa tccaaggagc ctcgggagtc cagaaccttg gaggacatgc   9480
tttgcttcac caagactccc ctccaggaat ccctcatcga actcagcgac agcagcctca   9540
gcaagatggc caccgacatg ttcctagctg taatgaggtt catgggggat gccccactga   9600
agggccagag tgacctggac gtgctttgta acctcctgaa gctgtgcggg gaccatgagg   9660
tcatgcggga tgaatgttac tgccaagttg tgaagcagat cacagacaat accagctcca   9720
agcaggacag ctgccagcga ggctggaggc tgctgtatat cgtgaccgcc taccacagct   9780
gctctgaggt cctccaccca cacctcactc gcttcctcca agacgtgagc cggaccccag   9840
gcctgccctt tcaggggatc gccaaggcct gcgagcagaa cctgcagaaa accttgcgct   9900
tcggaggtcg tctggagctc cccagcagca tagagcttcg ggccatgttg gcaggccgca   9960
gttccaagag gcaactcttt cttcttcctg gaggccttga acgccatctc aaaatcaaaa  10020
catgcactgt ggccctggac gtggtggaag agatatgtgc tgagatggct ctgacacgcc  10080
ctgaggcctt caatgaatat gttatcttcg ttgtcaccaa ccgtggccag catgtgtgcc  10140
cactcagtcg ccgtgcttac atcctggatg tggcctcaga gatggagcag gtggacggcg  10200
gctacatgct ctggttccgg cgtgtgctct gggatcagcc actcaagttc gagaatgagc  10260
tatatgtgac catgcactac aaccaggtcc tgcctgacta cctgaaggga ctcttcagca  10320
gtgtgccggc cagccggccc agcgagcagc tgctgcagca ggtgtccaag ctggcttcac  10380
tgcagcatcg cgccaaggac cacttctacc tgccgagcgt gcgggaagtc caggagtaca  10440
tcccagccca gctctaccgt acaacggcag gctcgacctg gctcaacctg gtcagccagc  10500
accggcagca gacacaggcg ctcagccccc accaggcccg tgcccagttt ctgggcctcc  10560
tcagcgcctt acctatgttc ggctcctcct tcttcttcat ccagagctgc agcaacattg  10620
ctgtgccagc cccttgcatc cttgccatca accacaatgg cctcaacttt ctcagcacag  10680
agactcatga attgatggtg aagttccccc tgaaggagat ccagtcgacg cggacccagc  10740
ggcccacggc caactccagc taccccctatg tggagattgc gctgggggac gtggcggccc  10800
agcgcacctt gcagctgcag ctggagcagg gactggaact gtgtcgtgtg gtggccgtgc  10860
acgtggagaa cctgctcagt gcccatgaga agcggctcac attgcccccc agcgagatca  10920
ccctgctctg acccagcccc cagccctcca gtaccttctg ccagaagact cactgtgtgg  10980
cctcagagaa atcactgaac ctctcaggat caatgacccc tgtaaggggc cagagccttg  11040
gaggacacta agaggaggca ggaggagcaa ctcaaatccc caagaacaca agaagaccca  11100
tcctgaactg ggatggaatg gcagcatgca aacttggatc agatagcagg aggaactttc  11160
aaaagtctgg cccactgtgc agtggagcag aaggcaggac catgaggcct cctgccatgt  11220
acccattgca gaccctgccc ctaactcctg cctatgacac agaagcccca caccagttgc  11280
ccagatgaac tggcctctgc ctttggttta ctcagggtct gatgttggaa tctgctccaa  11340
ctccacaccc tagcccttac atgtcctcct aaggggcccc tccttgtgct gccagtcagc  11400
ctggatttct ggtctttggt tatttctgtg caaacaaaag gtgtgcctgg cagccatttc  11460
tccatggagt tgctaagtgg ccggaaaaca agcctgaggg aggaggcagg agttggagtt  11520
accttaggcc cctgattcac tgcctatgaa cagaccatcc cccactcctt gggtatcccc  11580
aaccccagac ccccatcact tgatgggcca cacaagtttg agagtggtac aagggagaag  11640
tttgggaaaa gccttcttgg aaaatgggac attagcattg agttttgaaa gatgagtagg  11700
```

```
agtttgctaa gaatagatgg aagacagcag gataaacatt ccagagaaaa tcatgtttat  11760

tccctgctgt atcttccaga acctaggagg atgcctaaca gagagtaagc acttaaaaaa  11820

tatttgtcat atgaatgaaa aaataaacga gtgaatgttg ataaaaaaaa aaaaaa      11876


<210> SEQ ID NO 22
<211> LENGTH: 2258
<212> TYPE: DNA
<213> ORGANISM: Homo Sapiens

<400> SEQUENCE: 22

cacaagctct agagggcttc cgggaggagg cttagggagc tgggaatccg ggagcagatg     60

gtgggttcct accgtcgagg gtgggagaga gggatctgag gccaagtttg aggtaaggac    120

tgtggagctc catcagatcc ccatccccac ctcccctcat ctgcgcaatc ctgcgagaag    180

ccttagacag gttctggctc agagaaccgg agagaggcac aacgcctggc ccccaggact    240

tggccacagc gtccctgacc ttgtctgctc catgacctct cactgaggcc cattaacccc    300

tcagttccct gatgaggctt gatttagcat ccttgatgtc agctcctaag agtctgggaa    360

gtgcatttaa gtcctggagg ttggacaagg ccccctcccc acagcacacc tttccatcca    420

cttctatccc aggcatggct tttgctctcc tggcctccgt gcccccggtg tttggactct    480

acacttcttt cttccccgtc ctcatctaca gcttgctagg tactgggaga cacctgtcca    540

caggaacttt cgccatactc agcctcatga caggctcggc cgtcgagcgg ctggtgccgg    600

aacccctcgt ggggaatctg agcggaatcg agaaggagca gctggacgct caacgggttg    660

gggtagccgc ggccgtggcc ttcgggagcg gggcgttgat gctggggatg ttcgtgctgc    720

agctcggcgt cttgtccacc tttttgtccg agcctgtggt caaggcgctg accagcgggg    780

ccgcgctgca cgtgctcttg tcccagctgc cgagcctctt ggggttgtcc ctcccgcgcc    840

agatcggctg cttctctctc ttcaagacgc tggcctcctt gctgactgcg ctgcctcgga    900

gcagtccggc cgaactgacc atctccgcgc tcagcctggc gctgctcgtg ccggtcaagg    960

aattgaacgt gagattccga gaccggctac ccacgccgat cccgggggaa gtcgtcttgg   1020

tgcttctggc ctccgtgctc tgcttcacct cttctgtgga cacaagatac caagtccaga   1080

tagtggggct gttgcctgga ggatttcccc aacccctcct ccccaacctg gctgagctgc   1140

ccaggattct ggctgactcg ctgcccattg cactggttag ttttgcggtg tctgcctccc   1200

tggcctccat ccatgcagac aagtatagct acactattga ctccaaccag gagttcctgg   1260

cacatggtgc ctccaacctc atctcctccc tcttctcttg ctttcccaac tcggctacgc   1320

tggccaccac caatctactg gtggatgctg gtgggaaaac acagctggca ggcctcttct   1380

cctgcacagt ggtcctgtcg gtgctgctgt ggctggggcc cttcttttac tatctgccca   1440

aggctgtcct ggcttgcatc aacatctcca gcatgcgcca ggtgttctgc cagatgcagg   1500

aacttccaca actatggcac atcagccgag tggactttgc tgtgtggatg gtcacctggg   1560

tggcagtagt gaccctgagt gtggatttgg gcctggctgt gggtgtggtc ttctccatga   1620

tgactgtggt ctgccgcacc cggagctcct ccaggtcccg gggctctgca tcctgagcta   1680

tccaacacca ctgtactttg ggacccgtgg gcagtttcgc tgcaacctgg agtggcacct   1740

ggggctcgga gaaggagaaa aggagacttc aaagccagat ggcccaatgg ttgcagttgc   1800

tgagcctgtc agggtggtgg tcctagactt cagtggtgtc acctttgcag atgctgctgg   1860

ggccagagaa gtggtgcagc tggccagccg atgtcgagat gctaggatcc gcctcctcct   1920

ggctcagtgt aatgccttgg tgcaggggac actgacccgg gtaggactcc tggacagggt   1980
```

```
gactccagat cagctgtttg tgagtgtgca ggatgcagct gcttatgccc tggggagcct   2040

gttaaggggc agtagcacca ggagcgggag ccaggaggca ctgggctgcg gcaagtgagg   2100

caggggagct cactgaccca aagatttgca ccgtgtgggt ctgacctcat catgtggagt   2160

gcagagggcc ctgatgacat gtgtgtgatg aggaccatga cccttgaacc cccttaccta   2220

acgtaactaa taaaatgaag ctgagagctt tggaatcc                           2258


<210> SEQ ID NO 23
<211> LENGTH: 2991
<212> TYPE: DNA
<213> ORGANISM: Homo Sapiens

<400> SEQUENCE: 23

ctgcttactg cgcacggcca atcctatgag aactcagcat cccagctcat ctgagcagat     60

cctggaagtg atttctgcag ctcaggattt tttttttaag ctacattgaa aatataggtt    120

tattttttgt tcaggttttt cttttatatt ttttttctgc acaaaggagg aggatttttc    180

acttactcat atcgaggcca gatttttaaa gccagctaag gcagcatcag ctgtgcggga    240

tttaaagcct atagctcagc tgaaaaaaaa ggtgggggc agggaaggga agataaaagg    300

agaggaagct gggagaagac aagcatcatc ttattttgct atgtggtagg aactgtctat    360

aagatagtgt agaattgttt atcttgagca gtttgttctt aacctataag gtatttttcc    420

ttttttttt ttttaaacct cccccaccct tttcctgaaa gctttgtttc agagctttgt    480

attgggtttt tttggtgagg aggttgtatt tatttttttg gtgtgtgtgt gtgagtgtgt    540

gtgtgtctgt gtgtgtgttg tggtcccagc tgagtcatca tgtctgctct gacgcctccg    600

accgatatgc caacccccac cactgacaag atcacacagg ctgccatgga gaccatctac    660

ctttgcaaat tccgagtgtc catggatgga gaatggctct gcctgcgaga gctggatgac    720

atctcactta cacctgaccc agagcctacc catgaagatc ctaattatct catggctaat    780

gaacgcatga acctcatgaa catggccaag ctgagtatca agggcttgat tgaatcagct    840

ctgaacctgg ggaggactct tgactctgac tatgcacctc tccagcaatt ctttgtggtg    900

atggagcact gtctgaaaca tggcttgaaa gctaaaaaaa cttttctcgg acaaaataaa    960

tccttctggg ggcctctaga actggtagaa aagcttgttc cagaagccgc agagataaca   1020

gcaagtgtta aagatcttcc aggacttaag acaccagtag gtagaggaag agcctggctt   1080

cgtttggcat taatgcaaaa gaaactttca gaatatatga aagctttgat caataagaaa   1140

gaacttctca gtgaattcta cgaacccaat gccctcatga tggaagaaga aggagccata   1200

attgctggtc tgttggtggg tctgaatgtc attgatgcca atttctgtat gaaaggagaa   1260

gacttggact ctcaggttgg agttatagat ttttcaatgt atctcaagga cgggaacagc   1320

agtaaaggta ctgaaggaga cggtcagatt actgcaattc tggaccagaa gaactatgta   1380

gaagaactga acagacattt gaatgctact gtaaacaacc ttcaggcaaa agtagatgca   1440

ttagaaaaat ccaacactaa actgacagag gagcttgcag ttgcaaacaa caggatcatt   1500

accttacaag aagaaatgga acgagttaaa gaggaaagtt cctacatact ggaatccaat   1560

cggaagggtc ccaagcaaga cagaactgca gaagggcaag cactaagtga agcaagaaag   1620

catttaaaag aagagacaca attacgattg gatgttgaga aagaactgga gatgcagatc   1680

agcatgaggc aggagatgga attggctatg aagatgctgg agaaggatgt ctgtgagaag   1740

caggatgccc tggtatctct tcggcagcag ctggatgacc tcagagctct caagcatgaa   1800
```

```
cttgccttta agctgcagag ttcagactta ggagtaaaac agaaaagtga actaaacagt   1860

cgcttggaag agaagactaa tcagatggct gctaccatta aacaacttga acaaagattg   1920

cgccaggctg agcgaagccg ccaatctgct gagttggaca accggctctt caaacaggac   1980

tttggagaca agatcaacag tctgcagctg gaagtcgagg agctcaccag gcagcggaac   2040

cagcttgagt tagaactaaa acaggaaaaa gaaagaagat tacaaaacga caggagcatc   2100

ccaggaaggg gttcccagaa gtcagaatcc aagatggatg ggaagcacaa aatgcaagag   2160

gaaaatgtta aactaaaaaa gcccctggaa gaaagccaca ggctgcaacc ccaccctatg   2220

gatgaacagg atcagctgct gctctctgaa aagccacagt tgtgtcagct atgccaggaa   2280

gacggcagcc taacaaagaa tgtgtgtaag aactgcagcg gaaccttctg tgatgcctgt   2340

tcaacaaatg aactgcctct tccttcaagt atcaagcttg agcgagtttg caatccctgt   2400

cacaagcatc tgatgaagca atattctacc agcccatcat aagactggag gccaagacct   2460

ggaccaaaac gtttatgcag gctcctctgt acctgtgttt tagctgtcag gatctcatag   2520

agcccagttc ttagagtcaa ctaaagagtt gataggaatt tactaggtcc agggagaaaa   2580

ggcagtggtt ggggttactg gaaattttgc tcattttctc taatgactgt atgaataaaa   2640

gtgaacttac ttgagccttt ctcttctaaa tctaaacaac ctgatattga aggtttgctt   2700

tatagcatat ctttggaaag gcaactcatt tttatgatta gtgatactgg ggtggattta   2760

ataggagaga gaatccaggc agataagaat aaaaaggaaa atgatcatct ccttctatag   2820

catttgcaga ttcaaggggg agaggtagat gctgagatca aaatgacagt tgttacttat   2880

ttttccaggt gctgttagta taaacattgt ttcctcttca cccctgctaa ctacctcttt   2940

aaagtatttc taccaaactg tgaacccaat ctcagggaaa agaaattaaa a            2991
```

<210> SEQ ID NO 24
<211> LENGTH: 2279
<212> TYPE: DNA
<213> ORGANISM: Homo Sapiens

<400> SEQUENCE: 24

```
gcattctagt gcgaccttgt ttacacctcc cctggctcag tcacacagct gtgtggtagg     60

ctactagaag tgtttagtag ttgtcactgg gatcatgctg atgtggcccc atccccgcct    120

ctccctgccc tgtgatatcg gaggaaacct gacagagcaa attggccatg gccaagaaaa    180

aggaaaagaa agagtgccac caaaagcagg gagccctaag ggagcagtta caggtcctct    240

ttggattcca gcacgacgca tcaaaccata ccatgacgtg actaggaccc aacctagaaa    300

tgaaggaact gaccctacag gactcacaac cctggataat gcagtgtcct cggacggcaa    360

caagctctgg acattacctg ggggatgctg aaggcggcaa ctgaggaggc tgaatgaatc    420

ctgctccaga cacagacacc attcactcca gataatttgt tgcttgctat gctctctgtt    480

gtacattgca actcgcatag ggatgcaaag ccggaataag agcaatgacc accatgcctg    540

acagacctgt tgctgcgcac acctgtactc tccaatgaac aagactgaat gcaaaaaaaa    600

cagaaaatgg ggagatttag gggatcagtc agtgtggttg gaaaattgta agatgaagtt    660

acaggatata gacacaaacc ttcttggaag gccagaaggt ttgcatagct tcagtaaagg    720

atttggctga aatccttttt acctctaatc ccctttacct tgagttgata gcaatagagc    780

aaataacatg ggaatgtggg ggagtttatc tgaatagctt gtttactcat gtggtcctaa    840

gaccaacctt tgattatccg caggtgcatg attgctctct acctgggggc agggggagtt    900

aattacccac aggtggagct gaagagccag gaggctcaga gtctgcagca gcagcaggac    960
```

```
cagtacctgg gtcatctgca gcagtatgtg gccacctatc agcagcaggt ggtcacctat   1020
cagcagctga cctctgagga ggaggagctg cacaaccagt tactgctgca gacccagctc   1080
gtggaccggc tgcagcagca gaaagctcaa agcaaagctg tggccaagat gggctgccaa   1140
gagttgcggg agacccagga gcacctggaa gctatcagcc agcagaacca gcagcctcag   1200
gcccagttga gcctcatggc tctccctggg gaaggagatg gacagtgagg aggaggagga   1260
ggtgcctcag cccatgccaa gcatcccgga ggatctagag agccagaagg ccatggtggc   1320
atttttcaac tcagctgtag ctagtgccga ggaggagcag gcacggctat gtgggcagct   1380
gaaggagtgc actgccagcg cctggctcat ctgttggcct cggcccagaa ggaacctgag   1440
gcagcagccc cagccccaag aactggggt gatcccatgt gtggggagac ccaccaggcc   1500
ctgcaggggg ccatggagaa gctgtgggag agtacatcgc actgtaccag agccagaggg   1560
cagtgcggaa ggaggaggag tgcatcagca ggctggccca ggacaaggga gaggtgaagg   1620
tgaagctgct ggagctggcg tggcttgtgg acgactgcaa caagtggcat agcagattcc   1680
tggcagctgc ccagaaccct gctgatgagc ccactccagg ggcccccgcc ccccagtagc   1740
ttggggctac tgacaagcca gggtagtgag tagagtcctc aggcacagtg ggcacgcagg   1800
agcaggggag ggctcccaca gcaccctgcc tccctctctc caaagatctt tgtgaggtga   1860
gccttgccag cagtggggag tctgcacaag gagaggcggg gaagcattct ccctgtgaca   1920
accccactga gcagcagatc atgcaactgc ttcatgagat gcagaacctc caggagcacc   1980
caggcttggg cagcagccct tgcattcctt ttttgtacca gactgatgag aacaatgagg   2040
tgaagatcac catcatctaa aagccggcca ctgtcagcaa aacctgggga agtggggctg   2100
gaggctctgc ccctaccatg tccctaccac cccttcccag tcaacccttt accctcacag   2160
tagcaagcat aagacccctg tctaatgtgg ggagacaggt ggagatgagg tgaagatcac   2220
cataatctaa aaggccacta aataaaaaaa taaaaaattt taaaaaaaaa aaaaaaaaa    2279
```

```
<210> SEQ ID NO 25
<211> LENGTH: 2391
<212> TYPE: DNA
<213> ORGANISM: Homo Sapiens

<400> SEQUENCE: 25

caggtctccc aggcttcctc agcgtcgacg ccggggagcg ccctggggtt gggagcgccc     60
ggggcccgcg aaggaggagg tggctcaggt gtcagggcgc accgtgggaa ccggccccgg    120
gggaggcgtg gaaacgcggg gcctgggact cgaccagcct ctcccgtgcg gatcgcaaaa    180
tctcggagct gaaacagccc gttgttcgca gcctccctct gacccgccac cctgcacatt    240
gttttccatt cgcccgggtc gcgggtggga ggagaggcac gccggggttc tggagcttgg    300
ccgcgcgcca ggcttgtggc cttcgtcccc ctggggccac tggggcggcc acgcctctcc    360
ggcgggagga gagaacgcgt gggtccgggt ggctgctccg gcccttccgc ctccagctcg    420
gccatggggt cgcgcagctc ccacgccgcg gtcattcccg acggggacag tattcggcga    480
gagaccggct tctcccaagc cagcctgctc cgcctgcacc accggttccg ggcactggac    540
aggaataaga agggctacct gagccgcatg gatctccagc agataggggc gctcgccgtg    600
aaccccctgg gagaccgaat tatagaaagc ttcttccccg atgggagcca gcgagtggat    660
ttcccaggct ttgtcagggt cttggctcat tttcgccctg tagaagatga ggacacagaa    720
acccaagacc ccaagaaacc tgaacctctc aacagcagaa ggaacaaact tcactatgca    780
```

```
tttcagctct atgacctgga tcgcgatggg aagatctcca ggcatgagat gctgcaggtt    840

ctccgtctga tggttggggt acaggtgaca gaagagcagc tggagaacat cgctgaccgc    900

acggtgcagg aggctgatga agatggggat ggggctgtgt ccttcgtgga gttcaccaag    960

tccttagaga agatggacgt tgagcaaaaa atgagcatcc ggatcctgaa gtgactccgt   1020

ttgtgccttg ggcttgctcc tgcaaccagt atctccttgg aattcatcca aagcccccat   1080

ggacgcatgg acgcagggcg acaataaact gtattttcgt ttctaactct atttagggcc   1140

aagagaagaa agctggaagg atgtgtacta aagtctagct cagcagtccc caaccttttt   1200

ggcatcaggg acagtttttc cacggatggg tgacagggga tggttttggg atgattcaag   1260

tgcattacat ttattgtgca ctttatttct attatgatta cattgtaata tataatgaaa   1320

taattataca actcaccata atgtagaatc agcaggagcc ctgagcttgt tttcctgcaa   1380

ttagacggtc ccatatggga gtgatgggag acagtgacag atcatcaggc attagattct   1440

cataaggagt gcacaatcta gatcctttgg tgtgcagttc acagtaggat ttgggctcct   1500

atgataatct aatgccactg ctgatctgac aggaggcaga gctcaggcgg taatgcaagc   1560

aatggggagt ggctgtaaat atagatgaag cttcagctcg cctgccgctc accttgtgct   1620

gtgcagcccg gttcctaaca gaccacagac cccacaccag gtctatctca tttggtctca   1680

gagctgtgaa tcagccagca atattttagt tgcaaatcac tgaaaaccca actcaaagtg   1740

acttaagtca gaaagaaatt ttatgaattc aggtaattaa aaagtccaga agtatctgcc   1800

tttaggcaca gctggatcca agggcacaaa tgatgtcatc aggctccagt tattctccat   1860

ctcccagctc agctttttct gtctgtaagc ctgattttca ggaaggctct ttcctagtga   1920

tggagatgac caccatcagc tccaggcttc tatcctgcta acccagtaac ccagtgggaa   1980

gagatttact tattccaata attccaagtg gagagtgtca ttgacccgtt tggggtctca   2040

tctctacttc taggggaatg aaacactttg agtggccagg cctgtgtcat gtgctaattc   2100

ctagagccag ggaaataagg tctgaggatt caggatgggg tgaaaggtgg ttgcttaaag   2160

gaaaatgaaa tacaattagc agaataaggg gaaacgagtg gtctgctctg ctcgggcaaa   2220

acaagagatg cccattactg tgagggaccc ttgaagtctg gactcttaaa tgggtttttg   2280

ctgatttcct gggtgcatgc taggatgatg gggcttgatg cagtagggaa gagacgatgt   2340

aaaaataata aacaatatat accttcaaaa aaaaaaaaaa aaaaaaaaaa a            2391
```

<210> SEQ ID NO 26
<211> LENGTH: 1787
<212> TYPE: DNA
<213> ORGANISM: Homo Sapiens

<400> SEQUENCE: 26

```
agcaacgagc gacggcctga cgtcggcgga gggaagccgg cccaggctcg gtgaggaggc     60

aagtcctgca gcctcagcat gcgctggccg gatgtaccct gaggtgccct ctcacttcct    120

ccttcaggtt ctgaggggac aggctgacct ggaggaccag aggcccccgg aggagcactg    180

aaggagaaga tctgccagtg ggtctccatt gcccagctcc tgcccacact cccgcctgtt    240

gccctgacca gagtcatcat gcctcttgag cagaggagtc agcactgcaa gcctgaagaa    300

ggccttgagg cccgaggaga ggccctgggc ctggtgggtg cgcaggctcc tgctactgag    360

gagcaggagg ctgcctcctc ctcttctact ctagttgaag tcaccctggg ggaggtgcct    420

gctgccgagt caccagatcc tccccagagt cctcagggag cctccagcct ccccactacc    480

atgaactacc ctctctggag ccaatcctat gaggactcca gcaaccaaga agaggagggg    540
```

```
ccaagcacct tccctgacct ggagtctgag ttccaagcag cactcagtag gaaggtggcc    600
aagttggttc attttctgct cctcaagtat cgagccaggg agccggtcac aaaggcagaa    660
atgctgggga gtgtcgtcgg aaattggcag tacttctttc ctgtgatctt cagcaaagct    720
tccgattcct tgcagctggt ctttggcatc gagctgatgg aagtggaccc catcggccac    780
gtgtacatct ttgccacctg cctgggcctc tcctacgatg gcctgctggg tgacaatcag    840
atcatgccca agacaggctt cctgataatc atcctggcca taatcgcaaa agagggcgac    900
tgtgcccctg aggagaaaat ctgggaggag ctgagtgtgt tagaggtgtt tgaggggagg    960
gaagacagta tcttcgggga tcccaagaag ctgctcaccc aatatttcgt gcaggaaaac   1020
tacctggagt accggcaggt ccccggcagt gatcctgcat gctatgagtt cctgtggggt   1080
ccaagggccc tcattgaaac cagctatgtg aaagtcctgc accatatggt aaagatcagt   1140
ggaggacctc gcatttccta cccactcctg catgagtggg ctttgagaga gggggaagag   1200
tgagtctgag cacgagttgc agccagggcc agtgggaggg ggtttgggcc agtgcacctt   1260
ccggggcccc atcccttagt ttccactgcc tcctgtgacg tgaggcccat tcttcactct   1320
ttgaagcgag cagtcagcat tcttagtagt gggtttctgt tctgttggat gactttgaga   1380
ttattctttg tttcctgttg gagttgttca aatgttcctt ttaacggatg gttgaatgag   1440
cgtcagcatc caggtttatg aatgacagta gtcacacata gtgctgttta tatagtttag   1500
gagtaagagt cttgtttttt attcagattg ggaaatccat tccattttgt gaattgtgac   1560
ataataatag cagtggtaaa agtatttgct taaaattgtg agcgaattag caataacata   1620
catgagataa ctcaagaaat caaaagatag ttgattcttg ccttgtacct caatctattc   1680
tgtaaaatta aacaaatatg caaaccagga tttccttgac ttctttgaga atgcaagcga   1740
aattaaatct gaataaataa ttaaaaaaaa aaaaaaaaaa aaaaaaa                 1787
```

<210> SEQ ID NO 27
<211> LENGTH: 6218
<212> TYPE: DNA
<213> ORGANISM: Homo Sapiens

<400> SEQUENCE: 27

```
gttaaatctg tggcctttgc atcgaagcca tgctttcaag atgtaaaacc tatggagctg     60
acaccagggg cccaacagca aggtataaat tatcaagagt tgacttcagg atggcaagat    120
gtgaaatcaa tgatgttggt accagagcca actaggaagt tcccatcagg accactgttg    180
actagtgtca gattttcaaa tttgtctcca gaatcacagc aacaggatgt gaaatctttg    240
gagtttactg tagagccaaa gttgcaaagc gtaaaacatg tgaaattatc ttcagtgtct    300
ctgcagcaaa ctataaaatc tgtggaatta gcaccagggt cactgcctca aagagtgaaa    360
tatggggagc aaactccaag aacaaattat caaatcatgg aatcctctga actaatccct    420
agaccagggc atcagtttgc aaaatatgca gagatgatcc cacagccaaa gtatcaaatc    480
cctaaatctg caaatttgat ttcaatacca atttatcacg ccacagaatc ttcagaaatg    540
gcacaaggat tggcatataa aggcatagat actgtagaga aatctgtggg gttgacccca    600
aagctaacag gtagagctaa ggaatcctta gggatgctgc tgcagccaga tcttcaggta    660
ccaaaatttg ttgatctgac tccaatggta agggatcaag gctcaaaatt cttaggatta    720
actccagaga aaagctacca aatcctagaa actatggaat tgctctctca gtcacggccc    780
cgagttaagg atgtggggga gttatatatg aagccactgc agcaaactgt ggaatatgaa    840
```

```
gggattactc cggaactcaa gcattacttt acagaagcta tggggttgac cgctgaggca    900
aggatacaag caaatgaatt ctttggaatg accccaaagc caacaagtca agccactgga    960
tttgcagaga gatccccaag gctctgtcct caaaacttag aatgtgtgga ggtgatctct   1020
gagaaaagac tgcaagggga agaatctgtg gtattgattc caaagtcatt acatcacgtc   1080
ccagattctg cttcagggat gacacctggg ttaggacatc gagttcctga atctgtggag   1140
ttgacttcta agtcaggagt gcaggtagag aaaactttgc aattaacccc caaaccacag   1200
catcatgtgg gatctccagg gataatatca gggttaggac atcaagtccc agaatctgta   1260
aatctgacct gtaagcaatg gctacaaatg gaggaatctt tagaggtgcc cctgaagcaa   1320
acaagtcaag ttataggaca tgaagaatct gtagagctca cctctgaggc acggcagcac   1380
agggaggtat caatggggct aacaaagtca aagaatcaaa gtatgaaatc tccagggaca   1440
accccaggac cactgggtcg aattgtagaa tttatgagga ttagtccaga gccactagat   1500
caagtcacag aatctgcaag gacacagctt caagttgctc aatctgaaga ggtaatcctc   1560
atagatgtcc caaaagttgt tcaatctgtg aaagtgaccc ctggaccacc atttcaaatt   1620
gtaaagtctg tgacgatacc aaggccaacc cctcaaatgg tagaatatat tgagttgact   1680
ccaaaactgc aatatgtgag accttcagag caccacacag ggccatgttt gcaagatgtg   1740
aaatctacaa aattaatcac aaagccaaaa caccagattt tggaaacagt ggagttgaca   1800
gggtttcaaa ttgtaaaaac tatgttaatc ccagggccat cccttcaaat cgtaaaatct   1860
gaggagttag caccaggacc aattcctcag gttgtagaac caataggagt agccctagaa   1920
tcaggaattg aagcaataaa ttgtgtggat ttacttccaa ggccacatct tcaagaactg   1980
atagtacctg cagaattaac tccaagtcca tgtactcaag tgaagtctgc agaattaacc   2040
tcaccgcaaa catctccatt tgaggaacat acaatattga ctcataaaca agggcttcag   2100
gctgtgaaat ctacagtgat aaaaacagag cctcctaaag ttatggaaac tgaggatttg   2160
aatctaggac acgtgtgtca gaatagggac tgtcagaagt taacatcaga agagttacaa   2220
gtagggactg acttctctag gttcctacaa agctcttcaa ccacactcat ttcaagctct   2280
gtcagaacag catctgaatt aggaggactt tgggattctg ggatacagga agtatccaga   2340
gctttggata taaaaaaccc tgggacagat attttgcagc ctgaagagac ctatatagac   2400
cctactatga tacaatcttt aacttttcct ttggcccttc ataatcaaag ctccgataag   2460
acagctaaca ttgtggaaaa cccatgtcct gagattctag gagtggatgt aatatctaaa   2520
gagacaacta agaggaagca aatggaggag ctagagaact cacttcagag acatctacca   2580
caaagctgga gatcacgatc taggacattc caggcagaat caggggttca gaaaggtctc   2640
atcaagtctt tcccgggcag acaacacaat gtctgggaga gtcatgcctg gaggcagcga   2700
ctaccaagaa aatatctctc cactatgcta atgctgggga atattttagg gaccactatg   2760
gaaaggaagc tttgttctca aacatcttta gcagaaagag ccactgcaga tacctgtcaa   2820
tctattcaga atttatttgg gattccagct gaactgatgg aaccttccca gagcctgcca   2880
gagaagggtc cagttactat ttctcagcct tctgtggtca aaaactatat tcagagacat   2940
actttttatc atggtcataa gaaaagaatg gccttaagga tatggacacg tggctccaca   3000
tcttccataa tacagcaata ctctgggact agagtgagaa taaagaagac aaactcaacg   3060
ttcaatggta tatcccaaga agtcattcaa catatgcctg tctcatgtgc agggggccag   3120
cttcctgtcc tggtaaagtc agagtcttcc ctcagcatat tttacgatag agaagatctt   3180
gttccaatgg aagaaagtga ggactcacag agtgattccc agacaaggat ttctgagtcc   3240
```

```
caacactccc tcaagccaaa ttatctttcc caggccaaga ctgacttctc agaacagttc   3300
cagttgctag aagatctgca gctaaaaata gcagcaaaac tcttaaggag tcaaataccc   3360
cccgatgtgc ctccacctct agcttcaggt ctagtcctaa aataccctat ctgcctacag   3420
tgtggccgat gttcaggact taattgccat cataaattac agaccacttc ggggccttat   3480
cttcttatct atccacagct ccaccttgta cgcactcctg aaggccatgg tgaggttcgg   3540
ttgcatcttg gctttaggct gagaattggg aaaagatccc aaatctcaaa gtatcgtgaa   3600
agagatagac ccgtcatacg gagaagccct atatcaccat cacaaaggaa agctaaaatc   3660
tatactcaag cttccaagag tcctacttcc acaatagatt tgcagtctgg gccttcccag   3720
tcccctgctc ctgtacaagt ctacatcagg cgaggacaac gcagcaggcc tgacttagta   3780
gaaaagacaa aaactagagc acctgggcac tatgaattca ctcaagttca caacctacca   3840
gagagtgact ctgaaagcac tcagaatgaa aaacgggcta aagtgagaac caaaaagacc   3900
tctgattcaa aatatccaat gaagagaatc accaagcgac ttagaaaaca cagaaagttc   3960
tacacaaaca gtagaaccac aatagagagt ccttctaggg aattagcagc ccatttaaga   4020
aggaagagga ttggagcaac tcagacaagt actgcctctt taaaaagaca acctaagaaa   4080
ccttcccaac ccaagttcat gcaactgctt tttcagagcc taaagcgggc attccaaaca   4140
gcacacagag ttatagcttc tgttgggcgg aagcctgtgg acgggacaag gccagacaat   4200
ttgtgggcaa gcaaaaacta ttatccaaaa caaaatgcca gggactattg cttaccaagc   4260
agtatcaaaa gagacaagag gtcagctgac aagctaacgc cagcaggctc aaccattaag   4320
caggaggaca tattgtgggg aggaacggtc cagtgcagat cagctcaaca gccaagaaga   4380
gcttactctt tccaacccag acctcttcga ctgcccaagc ccacagattc ccaaagtggt   4440
attgctttcc aaactgcctc agtggggcag cctctgagaa ctgttcaaaa ggacagtagt   4500
agcagatcaa agaaaaactt ctatagaaat gaaacctcca gccaggagtc taagaacttg   4560
tccacaccag gaaccagagt tcaggcccga ggaagaatcc tacctggttc ccctgtgaag   4620
agaacctggc accgacatct taaagacaaa ctcacacaca aggagcataa ccaccccagc   4680
ttctataggg agagaacccc acgcggtcct tctgagagaa cccgtcataa cccctcttgg   4740
agaaaccatc gcagtccctc tgagagaagc caacgcagtt ccttggagag aagacatcac   4800
agtccctctc agaggagcca ctgcagtccc tctaggaaaa accattccag tccttctgag   4860
agaagctggc gcagtccgtc tcagagaaat cactgcagtc cccccgagag gagctgtcac   4920
agtctctctg aaaggggcct tcacagtccc tctcagagga gccatcgcgg tccctctcag   4980
agaagacatc acagtccctc agagagaagc catcgcagtc cctcagagag aagccatcgc   5040
agttcctctg agagaagaca tcgcagtccc tcccagagga gccatcgcgg tccctcagag   5100
agaagccatt gcagtccctc tgagagaaga catcgcagtc cctctcagag gagccatcgt   5160
ggtccctctg agagaagaca tcacagtccc tctaagagaa gccatcgcag tcccgctcgg   5220
aggagccatc gcagtccctc agagagaagc catcacagtc cctctgagag aagccatcac   5280
agtccctctg agagaagaca tcacagtccc tctgagagaa gccattgcag tccctctgag   5340
agaagccatt gcagtccctc tgagagaaga catcgcagtc cctctgagag aagacatcac   5400
agtccctcag agaaaagcca tcacagtccc tctgagagaa gccatcacag tccctctgag   5460
agaagacgtc acagtccctt ggagaggagc cgtcacagtc tcttggagag gagccatcgc   5520
agtccctctg agaggagatc tcacaggtcc tttgagagga gccatcgtag gatttctgag   5580
```

```
agaagtcaca gtccctcaga gaagagccac ctcagtccct tggaaagaag ccgttgcagt   5640

ccctctgaga ggagaggaca cagttcctct gggaaaacct gtcacagtcc ctctgagaga   5700

agccatcgca gtccctccgg gatgaggcaa gggaggacct ctgagaggag ccatcgcagt   5760

tcctgtgaga gaacccgtca cagtccctct gagatgaggc cagggaggcc ctctgggagg   5820

aaccattgca gtccctctga gaggagccga cgcagtcccc ttaaggaggg actcaagtac   5880

agtttccctg gagagaggcc cagccatagt ttgtctagag atttcaagaa tcaaacaact   5940

ctcctcggga ccacacataa aaatcccaaa gcagggcaag tgtggaggcc tgaagctact   6000

cgatgaggcg aggtccgccc ctattattca ttgtcctaag tcttcatcgt gctgcccttt   6060

ccaggcttct ttcctgctca gccactgcct ccaattcctg cgcccccagc gtggaaaggc   6120

ttccatttct ctctaccggg ggggaggcgg gtgagaatgg gtctgtaatt tctctaagat   6180

gaataaaggg gcagtaaatg aaaaaaaaaa aaaaaaaa                           6218
```

```
<210> SEQ ID NO 28
<211> LENGTH: 1404
<212> TYPE: DNA
<213> ORGANISM: Homo Sapiens

<400> SEQUENCE: 28

ggcagtgcag ctgtgggaac ctctccacgc gcacgaactc agccaacgat ttctgataga     60

tttttgggag tttgaccaga gatgcaaggg gtgaaggagc gcttcctacc gttagggaac    120

tctggggaca gagcgccccg gccgcctgat ggccgaggca gggtgcgacc caggacccag    180

gacggcgtcg ggaaccatac catggcccgg atccccaaga ccctaaagtt cgtcgtcgtc    240

atcgtcgcgg tcctgctgcc agtcctagct tactctgcca ccactgcccg gcaggaggaa    300

gttccccagc agacagtggc cccacagcaa cagaggcaca gcttcaaggg ggaggagtgt    360

ccagcaggat ctcatagatc agaacatact ggagcctgta acccgtgcac agagggtgtg    420

gattacacca acgcttccaa caatgaacct tcttgcttcc catgtacagt ttgtaaatca    480

gatcaaaaac ataaaagttc ctgcaccatg accagagaca cagtgtgtca gtgtaaagaa    540

ggcaccttcc ggaatgaaaa ctccccagag atgtgccgga agtgtagcag gtgccctagt    600

ggggaagtcc aagtcagtaa ttgtacgtcc tgggatgata tccagtgtgt tgaagaattt    660

ggtgccaatg ccactgtgga aaccccagct gctgaagaga caatgaacac cagcccgggg    720

actcctgccc cagctgctga agagacaatg aacaccagcc cagggactcc tgccccagct    780

gctgaagaga caatgaccac cagcccgggg actcctgccc cagctgctga agagacaatg    840

accaccagcc cggggactcc tgccccagct gctgaagaga caatgaccac cagcccgggg    900

actcctgcct cttctcatta cctctcatgc accatcgtag ggatcatagt tctaattgtg    960

cttctgattg tgtttgtttg aaagacttca ctgtggaaga aattccttcc ttacctgaaa   1020

ggttcaggta ggcgctggct gagggcgggg ggcgctggac actctctgcc ctgcctccct   1080

ctgctgtgtt cccacagaca gaaacgcctg cccctgcccc aagtcctggt gtctccagcc   1140

tggctctatc ttcctccttg tgatcgtccc atccccacat cccgtgcacc ccccaggacc   1200

ctggtctcat cagtccctct cctggagctg gggtccaca catctcccag ccaagtccaa   1260

gagggcaggg ccagttcctc ccatcttcag gcccagccag gcagggggca gtcggctcct   1320

caactgggtg acaagggtga ggatgagaag tggtcacggg atttattcag ccttggtcag   1380

agcagaaaaa aaaaaaaaaa aaaa                                          1404
```

<210> SEQ ID NO 29
<211> LENGTH: 1173
<212> TYPE: DNA
<213> ORGANISM: Homo Sapiens

<400> SEQUENCE: 29

```
gcacagagtt gggagtgact ccagagcctc ctgcaagatg ctgttgattc tgctgtcagt     60

ggccttgctg gccctgagct cagctcagaa cttaaatgaa gatgtcagcc aggaagaatc    120

tccctcccta atagcaggaa atccacaagg accatcccca caaggaggca acaagcccca    180

aggcccccca cctcctccag gaaagccaca aggaccaccc ccacaaggag gcaacaaacc    240

tcaaggtccc ccacctccag gaaagccaca aggaccaccc ccacaagggg acaagtcccg    300

aagtccccga tctcctccag gaaaaccaca aggaccaccc ccacaaggag gtaaccagcc    360

ccaaggtccc ccacctcctc caggaaagcc acaaggacca cccccacaag gaggcaacag    420

acctcaaggt cccccacctc caggaaagcc acaaggacca cccccacaag gagacaagtc    480

ccgaagtccc cgatctcctc caggaaagcc acaaggacca cccccacaag gaggtaacca    540

accccaaggt cccccacctc ctccaggaaa gccacaagga ccacccccac aaggaggcaa    600

gaaacctcag ggtcccccac ctccaggaaa gccacaagga ccacccccac aaggagacaa    660

gtcccgaagt tcccaatctc ctccaggaaa gccacaagga ccacccccac aaggaggcaa    720

ccagccccaa ggtcccccac ctcctccagg aaagccacaa ggaccacccc cacaaggagg    780

caacaaacct caaggtcccc cacctccagg aaagccacaa ggaccacccg cacaaggagg    840

cagcaagtcc caaagtgccc gatctcctcc aggaaagcca caaggaccac cccaacaaga    900

aggcaacaat cctcaaggtc ccccacctcc agcaggaggc aatccccagc agcctcaggc    960

acctcctgct ggacagcccc agggaccacc acgccctcct caagggggca gaccttccag   1020

acctccccag tgacagcctc cccagtcatc taggattcaa tgacaggaag tgaataagaa   1080

gatgagagtg attcaaatga ttcaaattcc atgacattgg aaaaaggtca tcatagctct   1140

aacttcaata taccaataaa ataatcagct tgc                                 1173
```

<210> SEQ ID NO 30
<211> LENGTH: 1404
<212> TYPE: DNA
<213> ORGANISM: Homo Sapiens

<400> SEQUENCE: 30

```
ggcagtgcag ctgtgggaac ctctccacgc gcacgaactc agccaacgat ttctgataga     60

tttttgggag tttgaccaga gatgcaaggg gtgaaggagc gcttcctacc gttagggaac    120

tctggggaca gagcgccccg gccgcctgat ggccgaggca gggtgcgacc caggacccag    180

gacggcgtcg ggaaccatac catggcccgg atccccaaga ccctaaagtt cgtcgtcgtc    240

atcgtcgcgg tcctgctgcc agtcctagct tactctgcca ccactgcccg gcaggaggaa    300

gttccccagc agacagtggc cccacagcaa cagaggcaca gcttcaaggg ggaggagtgt    360

ccagcaggat ctcatagatc agaacatact ggagcctgta acccgtgcac agagggtgtg    420

gattacacca acgcttccaa caatgaacct tcttgcttcc catgtacagt ttgtaaatca    480

gatcaaaaac ataaaagttc ctgcaccatg accagagaca cagtgtgtca gtgtaaagaa    540

ggcaccttcc ggaatgaaaa ctccccagag atgtgccgga agtgtagcag gtgccctagt    600

ggggaagtcc aagtcagtaa ttgtacgtcc tgggatgata tccagtgtgt tgaagaattt    660

ggtgccaatg ccactgtgga aaccccagct gctgaagaga caatgaacac cagcccgggg    720
```

```
actcctgccc cagctgctga agagacaatg aacaccagcc cagggactcc tgccccagct    780
gctgaagaga caatgaccac cagcccgggg actcctgccc cagctgctga agagacaatg    840
accaccagcc cggggactcc tgccccagct gctgaagaga caatgaccac cagcccgggg    900
actcctgcct cttctcatta cctctcatgc accatcgtag ggatcatagt tctaattgtg    960
cttctgattg tgtttgtttg aaagacttca ctgtggaaga aattccttcc ttacctgaaa   1020
ggttcaggta ggcgctggct gagggcgggg ggcgctggac actctctgcc ctgcctccct   1080
ctgctgtgtt cccacagaca gaaacgcctg cccctgcccc aagtcctggt gtctccagcc   1140
tggctctatc ttcctccttg tgatcgtccc atccccacat cccgtgcacc ccccaggacc   1200
ctggtctcat cagtccctct cctggagctg gggtccacac catctcccag ccaagtccaa   1260
gagggcaggg ccagttcctc ccatcttcag gcccagccag gcaggggca gtcggctcct    1320
caactgggtg acaagggtga ggatgagaag tggtcacggg atttattcag ccttggtcag   1380
agcagaaaaa aaaaaaaaaa aaaa                                           1404
```

<210> SEQ ID NO 31
<211> LENGTH: 2174
<212> TYPE: DNA
<213> ORGANISM: Homo Sapiens

<400> SEQUENCE: 31

```
cgtgatctcg ggtttgtcgg gctgaaatgt ggcgggtctc ggaaggttcc gacctcagta     60
aagagagcta acgtgtattc ttctttttct tagatgctga gatgaatcgt cacctgtgtg    120
tttggctttt tagacatcca tctcttaatg gttacctcca gtgtcacatc cagctccatt    180
ctcatcaatt tagacagata catcttgata caaggctgca agtttttaga caaaacagga    240
attgcattct tcatctgtta agtaagaatt ggtccaggag atattgccat caagacacca    300
agatgctctg gaagcataaa gcactacaga aatatatgga gaacctgagt aaggagtacc    360
aaacacttga gcaatgtctg cagcatatcc ctgtgaatga ggaaaaccga aggtccttga    420
acagaaggca tgctgagttg gcacctcttg cagccattta ccaagaaatt caggagactg    480
aacaagcaat tgaagaatta gaatcaatgt gtaaaagcct aaataaacaa gatgaaaagc    540
agttacaaga acttgcactg gaagaaaggc aaaccattga tcaaaaaatc aacatgttgt    600
acaatgagct tttccagagc cttgtgccaa aggagaaata tgacaaaaat gatgttattt    660
tagaggtgac agctggaagg actactggag gtgacatctg ccaacaattt acccgagaaa    720
tatttgacat gtaccagaat tattcgtgct ataaacactg gcaatttgaa cttctgaatt    780
atacaccagc agattatggt ggactacatc atgcagccgc ccgaatttcc ggtgacggtg    840
tctataagca tttgaagtat gagggtggga ttcaccgagt tcagcgcatc cccgaggtgg    900
gcctgtcctc aaggatgcag cgcattcaca caggaacgat gtcggttatt gtccttcctc    960
agccagatga ggtggatgtg aaattggacc ccaaggattt gcgaatagat acatttcgag   1020
ccaaaggagc aggagggcag catgttaata aaactgatag tgccgtcaga cttgtccaca   1080
tccccacagg gctagtagta gaatgccaac aagaaagatc acagataaaa aataaagaaa   1140
tagcctttcg tgtgttgaga gctagactct accagcagat tattgagaaa gacaagcgtc   1200
agcaacaaag tgctagaaaa ctgcaggtgg gaacaagagc ccagtcagag cgaattcgga   1260
catataattt cacccaggat agagtcagtg accacaggat agcatatgaa gttcgtgata   1320
ttaaggaatt tttatgtggt gggaagggcc tggatcagct aattcagaga ctgcttcaat   1380
cagcagatga agaagccatt gctgaacttt tggatgaaca ccttaaatca gcaaaataaa   1440
```

```
tactaactta ttattattta tgattatata aatgaaatgg acctatatca agaggcagac   1500
tgaagcttgg aaatcattat gaatatttgt aaattacagc tttaagaaca cattacacat   1560
aaatatatgt tttgtaatta atcgaagtca catttcctga cctaagaatt tattttaggt   1620
ttcctgtaaa gtacaatcca actcatcaag tagaaaataa gcatgcatca ttgaaaagag   1680
aaagtattga gaattgattg tgtcatttag gacaagtcac ttgttctctt tatatgcctt   1740
ttttccccag ccatctatga attaatttaa atatattttt aatctactac ttcaggaaaa   1800
tatggtaaaa tttagtaaaa tatgaatttt agacttcctt ataaaccttt tatttaaata   1860
caaagtacct tggcctatag tggatgctta tgcctgtaat cccagtgctt tgaagggcca   1920
aagggggaag atctcttgag gtaagaattt gagaccagcc tgggcaaaat agaccccatg   1980
tctacaaaaa aactcaaaac ataaagaaaa accataatac tgttaatcat gttaaagtta   2040
agacttagac tgcaactttt aaataaaaat tatgaagaat atgagtcatt caataacaat   2100
gagcatctgg gtacagacag taaagccctt tgattgctgt atgaattcca cactatataa   2160
acaataagct gata                                                      2174

<210> SEQ ID NO 32
<211> LENGTH: 349
<212> TYPE: DNA
<213> ORGANISM: Homo Sapiens

<400> SEQUENCE: 32

atggcaggcc aagcgaacat atcttgagaa cagtgctata ttaaggaaag ctctgcaaga     60
aatcaaaata agattctact agaaaacctg ctaaggagtg cccgggggta ggtggggaag    120
tatggaaagg caagaaccga agtctagcta ggcagtgtca ggagacacct ggaagagtgg    180
tattcagcta gaggaaattg ccacaaaatt agatggaaat tttcagtgtt gagggatcta    240
aaaaagacca atgtgattca gtccagtgca tagatgcaga actcatactg caaatgtcca    300
aattgtcctt cctgtctttt cttgtcaaac ttggccttgc catatgcaa                349

<210> SEQ ID NO 33
<211> LENGTH: 1086
<212> TYPE: DNA
<213> ORGANISM: Homo Sapiens

<400> SEQUENCE: 33

agtacgcggg ggggctgtgc cgtggctgga agttactgtg aggcggcggc taagaaggcg     60
gctctggtgg cggcggtgga ggctgaggcg gcggccgagg cggcgacgga ggaaacagaa    120
gatggcagat tttttgaaag gactgcctgt ctacaacaaa agcaatttta gtcgatttca    180
cgcggactcc gtgtgcaaag cctcgaaccg acggccctca gtctacctgc ctacccgcga    240
gtacccgtct gaacagatca tcgtgacaga aaagacaaac atcctcctgc gctacctgca    300
tcagcaatgg gacaaaaaga acgctgccaa gaagagagac caggagcaag tggagctgga    360
aggcgagagc tccgcacctc cccgcaaggt ggcgcggacc gacagcccag acatgcacga    420
ggacacttaa gactctcaac tccacaggcg cctcctgcca ggtctgctcc tcggtcgccc    480
acccgcctgc ccgccatgtg taagcacccc gcccgcccgc ctccctgccg gcccatccac    540
accctgcgtc cacaccactt ccaacctcat aggagccgat gtatttattt tccttgagtt    600
tttatttatg ctgtaacctg tatcaagcgt tggttaaagg ggacatcaga cccagtagtg    660
tgatgttggt agatgctttt taaaaaaaac aacattgtcc ccccgacccc cgccttccat    720
```

```
cgggccagtt ccccgattcc tgcccccagt tctccagaga accagagtgt gtctgtgaga    780

gtctctagcg gggctttac tgtggccggg tgacaggggc gggcccgggg tggcctgacc    840

taccaggaca gccgagtggc cttctccccc ccaacaccgg tccaggccat tgagactcgg    900

tcttgtccca cgcttcgccc ggaactttcc catgcccaga cctcactcag cgtgcacgca    960

cgttggggag aagtcggccc ttgggatctt tctcttgagt cattttattt ttatcatgga   1020

ctagtgcgtg ctccgtgtcc acccccaata aaagggtctt tcctaaaaaa aaaaaaaaaa   1080

aaaaaa                                                              1086
```

```
<210> SEQ ID NO 34
<211> LENGTH: 398
<212> TYPE: DNA
<213> ORGANISM: Homo Sapiens

<400> SEQUENCE: 34

ccaatattta tttaatggtg gatcttgacg tggcactata atctggctcc cagtccatga     60

aactgaagtc cagaagcagt ttttcctaac ctgggacctg ccaaaaaaca cactatatgt    120

gcccctgtag gcatgctggc tgactttatt cccactgtga atcttgaagc agtcctaaaa    180

cccagctcca gtcccaaaac ctacctccag tccctgtcaa ctaaagtctg ggagcagtcc    240

tgcccaccca ggaatctgga gggagaaatg ccatgaagcc agaaacaaac ctgaagactt    300

tggtctcagc tgtgtatcct gaagcagccc tatgaatcag ttccacaccc ccattccccc    360

actccagata aagcttcagt tatatctcaa aaaaaaaa                            398
```

```
<210> SEQ ID NO 35
<211> LENGTH: 6093
<212> TYPE: DNA
<213> ORGANISM: Homo Sapiens

<400> SEQUENCE: 35

gcctgccagc tagccggagc cgcgggtgag cgcggcgagc ggcgaccctg gtgaggagcg     60

cggcgcggga ggcacgttcc ttagctccgc cgcggccgtc ctccgcggct cgaggactcc    120

gcttccttcc ctcccctccc ctgcgctccg gcctggggtc tcggcgcggg gagcggaggg    180

aagggacgaa ggaggagtag gtgaaagcgg ggtgaggggc ggaagggtcc cggcgcgggg    240

tgaggcgagg gctgcctctt gttctcccgc cgctgccgcc gtctcctggt cgggtgccgc    300

ggccagaggc gcgcggggct gccgaggcac ccgcactatg caggcagact gccggccgcc    360

gcgatggcga gccgggcggt ggtgagagcc aggcgctgcc cgcagtgtcc ccaagtccgg    420

gccgcggccg ccgcccccgc ctgggccgcg ctccccctct cccgctccct ccctccctgc    480

tccaactcct cctccttctc catgcctctg ttcctcctgc tcttacttgt cctgctcctg    540

ctgctcgagg acgctggagc ccagcaaggt gatggatgtg gacacactgt actaggccct    600

gagagtggaa cccttacatc cataaactac ccacagacct atcccaacag cactgtttgt    660

gaatgggaga tccgtgtaaa gatgggagag agagttcgca tcaaatttgg tgactttgac    720

attgaagatt ctgattcttg tcactttaat tacttgagaa tttataatgg aattggagtc    780

agcagaactg aaataggcaa atactgtggt ctggggttgc aaatgaacca ttcaattgaa    840

tcaaaaggca atgaaatcac attgctgttc atgagtggaa tccatgtttc tggacgcgga    900

tttttggcct catactctgt tatagataaa caagatctaa ttacttgttt ggacactgca    960

tccaattttt tggaacctga gttcagtaag tactgcccag ctggttgtct gcttcctttt   1020

gctgagatat ctggaacaat tcctcatgga tatagagatt cctcgccatt gtgcatggct   1080
```

```
ggtgtgcatg caggagtagt gtcaaacacg ttgggcggcc aaatcagtgt tgtaattagt   1140
aaaggtatcc cctattatga aagttctttg gctaacaacg tcacatctgt ggtgggacac   1200
ttatctacaa gtctttttac atttaagaca agtggatgtt atggaacact ggggatggag   1260
tctggtgtga tcgcggatcc tcaaataaca gcatcatctg tgctggagtg gactgaccac   1320
acagggcaag agaacagttg gaaacccaaa aaagccaggc tgaaaaaacc tggaccgcct   1380
tgggctgctt ttgccactga tgaataccag tggttacaaa tagatttgaa taaggaaaag   1440
aaaataacag gcattataac cactggatcc accatggtgg agcacaatta ctatgtgtct   1500
gcctacagaa tcctgtacag tgatgatggg cagaaatgga ctgtgtacag agagcctggt   1560
gtggagcaag ataagatatt tcaaggaaac aaagattatc accaggatgt gcgtaataac   1620
tttttgccac caattattgc acgttttatt agagtgaatc ctacccaatg gcagcagaaa   1680
attgccatga aaatggagct gctcggatgt cagtttattc ctaaaggtcg tcctccaaaa   1740
cttactcaac ctccacctcc tcggaacagc aatgacctca aaaacactac agcccctcca   1800
aaaatagcca aaggtcgtgc cccaaaattt acgcaaccac tacaacctcg cagtagcaat   1860
gaatttcctg cacagacaga acaaacaact gccagtcctg atatcagaaa tactaccgta   1920
actccaaatg taaccaaaga tgtagcgctg gctgcagttc ttgtccctgt gctggtcatg   1980
gtcctcacta ctctcattct catattagtg tgtgcttggc actggagaaa cagaaagaaa   2040
aaaactgaag gcacctatga cttaccttac tgggaccggg caggttggtg gaaaggaatg   2100
aagcagtttc ttcctgcaaa agcagtggac catgaggaaa ccccagttcg ctatagcagc   2160
agcgaagtta atcacctgag tccaagagaa gtcaccacag tgctgcaggc tgactctgca   2220
gagtatgctc agccactggt aggaggaatt gttggtacac ttcatcaaag atctaccttt   2280
aaaccagaag aaggaaaaga agcaggctat gcagacctag atccttacaa ctcaccaggg   2340
caggaagttt atcatgccta tgctgaacca ctcccaatta cggggcctga gtatgcaacc   2400
ccaatcatca tggacatgtc agggcacccc acaacttcag ttggtcagcc ctccacatcc   2460
actttcaagg ctacggggaa ccaacctccc ccactagtgg gaacttacaa tacacttctc   2520
tccaggactg acagctgctc ctcagcccag gcccagtatg ataccccgaa agctgggaag   2580
ccaggtctac ctgccccaga cgaattggtg taccaggtgc cacagagcac acaagaagta   2640
tcaggagcag gaagggatgg ggaatgtgat gtttttaaag aaatcctttg aagatgatgc   2700
tgctttttac aaagcatcgt tttaaagcac atggcctttt ttttttaatt attagtggta   2760
gtaatatata gaatgtatta cataactgtc actgaagtgg ttggggaaaa tgtggtgact   2820
gaggtacagg aaactactaa tcttgccatc ttgctttaag gtgttatggt ggcacagtta   2880
ctgctcgcct gttaaatttc aaatgtcctg tttgatacta ctgtagaaca ctatttttaa   2940
tacagaaaaa gctccctata atgcacttca gagaaattaa aaatcacaga gtatttatta   3000
ccaatgctgc aggtacatta atgaactcga gatggctctg taagcctgac tggcaataac   3060
gcacggtact gttcttgaaa tacctaatgg cttgaaattc tagtctgttt gtgaaagatg   3120
ggtactatca tgatttcctc ttctattcct atattctttt ctggattttt tttaataatt   3180
agtgatataa gcattgtttt tattgcagcc atatccactt atccatctta agatctgtag   3240
ctgggatttt ctgacttgta atgagcaggg ggattgcttt ttcactttgt gacactcttt   3300
agagctttaa tgcttcacag tatatggcct ggtctcatcc ttgcgtgttc cacttgaggc   3360
cctttggtgt cttgccccat tcttgtgttt ataaaatgtt tgagtatttc tgatgagtga   3420
```

```
tgcttgcctt agtctcatga attcagatcc cttcatgtcc tttaagtatg ctcctcaatg   3480

tgtaaacagg aacaacttta tgatttgaaa gctttaaagg agattcttct cccaccccca   3540

actttatttg caatgggatt tttcctagga gagttatgaa aagttgaagg cttctaaggg   3600

aatactgtaa acatgaccca cttatattta tcacagtgaa aggcaaaatt attcactcag   3660

aagtaatata aattacctct ttaaaaagta accagaattt gtcctttttg gttttataca   3720

ttcacaaaca tatacatttt tcttgagtct caaggtattt tatattttta gtcagaaaaa   3780

ataattttc atttcagttt tccataaact gttacacaaa atataaacct aacgtgtatt   3840

tttcaggact gcgtgatcgt gcactttgtg tggtaagagg tttgagtagt cctatatgtc   3900

acctagggaa cagacattat agcttactag caaatgaata ttcatgcctt gtttttgata   3960

cctcctggca gcttccatgt caccacttgt tcatacctgc ccagagctag ttttagacat   4020

ggcaaaatag aaatcatctg taatttatta gctaacaatg taaaaccatc ttttaaagcc   4080

ttcagactgt caagacgaca tgagcagctc accatatgat aaaaatacat aaatttgaca   4140

ttccctcttc cataaacctt tgtttgtaga tttaatgttg aacagtactt ttccataaag   4200

ttctagtcac ttctgttggc ctgagccacc agattatgat gttgccagaa ttcactcaat   4260

ttgaataaag atgaacagta tttgttttct tgtttccatg aattatatca gtattctaaa   4320

acatcgcttc agaaagagaa ctgtttattt ctgcaggctt cctgtccttt tgtggtatgg   4380

tttttggcc ttattttcac tggcttttcc ttctccaaac tttgaggcgt gatttcattc   4440

attgaagaat caatacatat tttgtttcaa aatgtttgaa acaaaagaca tagatggtag   4500

acttttatta aaacatatat ggatgtggaa agcacatata ttaatgcagt catccctttt   4560

caggtgggaa gagagcaaac cagttgattt tttaattcat ccttagtaca cagagaatat   4620

acttttcctc aagtaatata cctgtttgaa gctttaagag agatgttttt ggtaactatt   4680

tcattttccc aaagaagttt gctattcttg tgttaattgt gtatacctga ttgtttttc   4740

ctggaggttt ttgttgttgt tgtttagttt tgggtttttt ttttttaag aggggcaagt   4800

gttttctgaa atgatgcata ttttaagact cgattcatat tgccactgtg ctatccttga   4860

actaccaata atttttataa aatatctagt ttttactact tttatataaa ctttactttc   4920

cagatgaaga gctgagcctg attcaaatgg tttttctgct ttatacttct ttttagttca   4980

ttggttttta tagtagaggt tttctatttt tttttttttt ttttttacta catttatatg   5040

tctgatacat atacggcttt ggagacaatc aagtaacaac tgaaaatgtg aaagtaacca   5100

tatctgacaa aattcccttg aatttttatc ctttgcttgc aacatttaag actcaaagtc   5160

actggtatat tggattaagt tttttcctgt taatgcaatt atagaaatac atcggagaca   5220

caacaaatgt ggccattaca ggtttcataa aattacactg acttggctgt tacttgatct   5280

taggaaacag cacagtttaa gatattgtga attctgactt atactttatt aaatgctgta   5340

aatctaaata gatcctgttg gatgtgatgg gtctagtcca gtttatttaa gttcatgttt   5400

cactgtttgc actttgcatt gaacaatggg tttattcgct gatgtaaacg gttcgagtga   5460

agaattaatg cagtaagtat gacaacacat acacacttgc ctctccccat ctccagaaga   5520

ggggagcaga gtccgagctt atctaaatat gaatgtggcc acaaagctgt ggaaggtgac   5580

aaagcttaaa cacctttgcc ctggctctgc attgtcacct agagagcaag aggtctatag   5640

aaacatcatg tcacatgaaa cgattctctg ctttttggtt ctgaacttga agtccctaaa   5700

ctgcaaaatc taagagttgg gtggttatta aaatgctttt aaagtcaact gtggcaccaa   5760

ttctaatgta atccaacttg tgactgtttt tttttgtttt gttttgtttt tgtgtgtgtg   5820
```

```
tgtgtggcac tgggaaaagt ggaaacaaac atgtattgaa atacatattg gaaataaaaa   5880

tggtttgagc gtcagtgata ttctcccaga atgtacttat cttacctcgg catgtactgt   5940

agtcactcag tatttgtata tgttgctaga atttagattg taaaatagtg aaattttaat   6000

gtgttcattt gtttttaatg tatatatgtc ttgctcagat tatttggttt aaataaaaca   6060

accttgaggt ttgtagcttt tccttatact ata                                6093


<210> SEQ ID NO 36
<211> LENGTH: 4710
<212> TYPE: DNA
<213> ORGANISM: Homo Sapiens

<400> SEQUENCE: 36

cgctgccccg tccacgccgc ccgcgccccg cagtcccacc cgcaggaccc ccggccgcgc     60

cagggtctcg cctgcgcccc ccgcgcccgc ccgcggacta caagtcccgc catgccccgc    120

cgccgccccc cggcttccgg tgctgcgcag tttccggagc ggatcgcaac ccggagtccg    180

gatccgatcc cgctctgcac attccaaagg cagccgcgcg ccgcccccggt ccagccgcca    240

tgccgactgt tctttgttac attcgccggc tgcgggcacc gttggcgatc ggagtcaaaa    300

cccggctgga tttcccggag ccgctccggg atcgccctgc gcgccgcccg cccgccgggg    360

tcttcgccgc cccggcccgc ggccccgcgg cccccgccgc cgggcggcgt cgtcgccgag    420

gccccagggg atgtcgttat cccccgccct cgggtacagc ccatgcgggt cgcacggggg    480

ggtccctgga cccccaaccc cgcgtttaga gaagctgagt cctggtccca gattgggaac    540

cagagggtca gtgagcagct cttggaaaca tctctaggga atgaggtgtc cgacactgag    600

ccactgagcc ctgcgagtgc aggcctgcga cgcaatcctg ccctacctcc tggacccttt    660

gcacaaaact tttcctgggg gaaccaggaa aatctgcccc cagccctggg gaagattgcg    720

aacggaggag gaactggggc aggcaaggcc gaatgcggct atgaaactga gtcacacttg    780

ctagagccgc acgagatacc tttgaacgtg aatacacaca agttcagtga ctgtgagttt    840

ccatatgagt tttgcacggt ctgcttttca cccttcaagc tgctggggat gagcggggtg    900

gagggcgtgt ggaatcagca ttcaagaagt gccagcatgc acactttcct aaaccactca    960

gcaacgggca tcagagaagc aggttgcagg aaggacatgc cggtgtcaga gatggctgaa   1020

gatgggagcg aagagatcat gttcatctgg tgtgaagact gcagccagta ccacgactcc   1080

gaatgtcccg agctgggccc agtggtcatg gtcaaagact cctttgtgtt aagcagggca   1140

aggtcttggc ctgccagcgg acacgtgcac acccaggcgg ggcaggggat gcggggttat   1200

gaggacaggg acagggctga cccacagcag cttccagaag cagtccctgc aggcctggtg   1260

aggcggctca gtgggcagca gctgccctgc cgttccaccc tcacctgggg gaggctgtgc   1320

cacctggtgg cccagggcag gtcatccctt cctcccaact tggagatcag acgactggaa   1380

gatggagccg agggggtgtt cgccatcact cagctcgtca agcggacaca gttcggtccc   1440

tttgagtcca ggagggtcgc caaatgggaa aaggagtctg catttcccct gaaggtgttc   1500

cagaaggacg ggcaccccgt gtgcttcgac acctccaacg aggatgactg caactggatg   1560

atgctggtgc ggccagcggc ggaggccgag caccagaacc tgacggccta ccagcacggc   1620

agcgacgtgt acttcaccac ctccagagac atccccccgg gtaccgagct gcgcgtgtgg   1680

tatgcggcct tctatgccaa gaagatggac aagcccatgc tgaagcaggc cggctctggc   1740

gtccacgctg caggcacccc agaaaacagc gcccccgtgg agtcggagcc cagccagtgg   1800
```

-continued

```
gcgtgtaaag tgtgttctgc caccttcctg gagctgcagc tcctcaatga acatctgttg   1860
ggccacttag aacaagccaa aagccttcct ccaggcagcc aaagcgaggc agcagctccc   1920
gagaaggagc aggacacacc ccgggggga cccccctgcag tgcccgagag cgagaatgtt   1980
gccaccaaag aacagaagaa aaagcctcga aggggggagaa aacccaaagt gtccaaagct   2040
gagcagcctc tagtcatcgt ggaagacaag gaacccacag agcaagtggc agagatcatt   2100
accgaggtcc ctccggatga gcctgtgagt gcaacgccag atgagcggat catggagctg   2160
gttctgggga agctggccac caccaccact gacaccagct cggttccaaa gttcacccat   2220
catcagaata acaccatcac gctcaagagg agcttaattc tctcaagcag acacggcatc   2280
cggcgcaagc tcatcaaaca gctcggggag cacaagcggg tttaccagtg caatatctgc   2340
agcaagatct tccagaacag cagcaacctg agcaggcacg tgcgctcgca tggtgacaag   2400
ctgtttaagt gcgaagagtg tgcaaaattg ttcagccgca aagagagcct aaagcagcac   2460
gtttcctaca agcacagcag gaacgaggtg gacggcgagt acaggtaccg ctgcggcact   2520
tgtgagaaga ccttccgcat cgagagcgcg ctggagttcc acaactgcag gacagatgac   2580
aagacgttcc aatgtgagat gtgtttcaga ttcttctcca ccaacagcaa cctctccaag   2640
cacaagaaga agcacggcga caagaagttt gcctgtgagg tctgcagcaa gatgttctac   2700
cgcaaggacg tcatgctgga ccaccagcgc cggcacctgg aaggagtgcg gcgagtgaag   2760
cgagaggacc tggaggccgg tggggagaac ctggtccgtt acaagaagga gccttccggg   2820
tgcccggtgt gtggcaaggt gttctcctgc cggagcaata tgaacaagca cctgctcacc   2880
cacggcgaca agaagtacac ctgcgagatc tgcgggcgca agttcttccg cgtggatgtg   2940
ctcagggacc acatccatgt ccacttcaag gacatcgcgt tgatggatga ccaccagagg   3000
gaagagttta tcggcaagat cgggatctcc tcggaagaaa acgatgacaa ttctgacgag   3060
agcgcagact cggagcctca caagtacagc tgcaagcggt gccagctcac cttcggccgg   3120
gggaaggagt acctgaagca catcatggag gtgcacaagg agaagggcta tggctgcagc   3180
atctgcaacc ggcgctttgc actgaaggcc acctaccacg cccacatggt catccaccgt   3240
gaaaacctgc cggaccccaa cgtgcagaag tacatccacc cctgcgagat ctgcgggcgg   3300
atcttcaaca gcatcgggaa cctggagcgc cacaagctca tccacacagg tgtgaagagc   3360
cacgcctgcg agcagtgtgg gaagtccttt gccaggaagg acatgctgaa ggagcacatg   3420
cgtgtgcacg acaatgtccg cgagtacctg tgtgccgagt gtgggaaagg catgaagacc   3480
aagcacgcgc tgcgccacca catgaagctg cacaagggca tcaaggagta cgagtgcaag   3540
gagtgccacc gcaggttcgc gcagaaggtc aacatgctca agcactgcaa gcggcacacg   3600
gggattaaag atttcatgtg tgaattgtgt gggaagacat tcagcgagag gaacaccatg   3660
gagacccaca agctcatcca cacagtgggc aagcagtgga cgtgctccgt gtgcgacaag   3720
aagtacgtga ccgagtacat gctgcagaag cacgttcagc tcacacacga caaggtggag   3780
gcgcagagct gccagctgtg cgggaccaag gtgtccacca gggcctccat gagccgacac   3840
atgcggcgca agcaccccga ggtgctcgcg gtgaggatcg atgacctgga ccacctcccg   3900
gagaccacca ccatcgacgc ctcctccatt ggcatcgtcc agcctgagct gactctggag   3960
caggaggatt tggccgaagg gaagcacggg aaagctgcca agcgaagtca caagagaaag   4020
cagaagccag aagaggaggc gggtgctccg gtgcccgagg acgccacctt cagcgaatac   4080
tcagagaaag agacggagtt cacaggcagt gtaggcgacg agaccaattc cgcagtacag   4140
agcattcagc aggtagtggt gaccctgggt gacccaaatg tgaccacacc atcgagctca   4200
```

```
gtcggcttaa ccaacatcac cgtgaccccc atcaccactg cggccgcgac tcagtttacc   4260

aatctccagc cggtggccgt ggggcacctt accacccctg aacgccagtt acagctggac   4320

aactcaatcc tgaccgtgac ctttgatacc gtcagcggct ctgccatgtt gcacaaccgc   4380

caaaatgacg tccagatcca cccccagccg gaagcctcga acccacagtc tgtggcccat   4440

ttcatcaacc tgacgaccct ggtcaactcc atcacgcccc tggggagcca gcttagtgac   4500

cagcacccgc tcacgtggcg ggcagtgccc cagactgacg tcttgccacc ctcgcagccg   4560

caggcacccc cacagcaggc ggcccagccc caggtgcagg cggagcagca gcagcagcag   4620

atgtacagct actgagctgc gttccgggag actcggggca agaactgcag agggatgttt   4680

gggatttgtt tagatgtgtt tgctggatac                                     4710
```

<210> SEQ ID NO 37
<211> LENGTH: 3140
<212> TYPE: DNA
<213> ORGANISM: Homo Sapiens

<400> SEQUENCE: 37

```
agtcgcatgc aggacagcac cgcgtgcggc agctgctctg gtggcctcct gcttacccgg     60

ccctccactt taccgttagc acggagtgcg gcaccctgct tgggcctttc ggctctgcct    120

cccctgcccg tcacggcggg tcacgacatc ggccaggacg cagcagaagg gacaagacac    180

gcaaagaaga tggcgcaccc acctcggcac cgaaggccag tgcgacctcc cgggagcagg    240

cgggccagca tgggccttcc cggaggagac agctaagccg agacctggga ctgcagagga    300

gaaacaagga ggaggcaggc ggggcccggt gccctcctcg tctgccgtgc cgggtggaca    360

gtctgctcgc ctgtctgcgt gacgaaaccg aggcacagag acgcgctatg ccagcggcgg    420

gtatagcaag ggctccctcc gcgccacgtg ttgccatcca ccacacagga atgaccgtct    480

ccgtgtcata gatgggaaac caggacgtgt aggcatcagg gtttctccat tttggccaga    540

ctggtctgga acttctgagt tcaagcggtc ctcccgtctc agccttccaa agtgctggga    600

tgacaggtgt gagcagctgc gccctgcagg tgcaggccct ggaagacaag ggaggagcct    660

gtgagccacc ggcccacgtg aaagtaaatg catgaagttc cctctcgctg aactgaaaag    720

agcctcaacc tggacctgac accaacttcg ccggtgctgc ctggctggtt gctctagcgc    780

cctgaaggag aggaatgcag tcatatttca ctgtgatttt cagtgtcatt tccacgaaga    840

ctaatgatgt tgagcttttt tttctccata atacaggaaa gagacccaaa cccatgaaga    900

atgagataca tgtacagttt tgattataaa accaaagaat aatggcttca caagatgacg    960

gctgggctcc tgggctgcct tcagtgtctt taaacagaga tagagtcttg ctatgttgtc   1020

caggctgaca ctgaactctt gggctccaac gatcctcctg ccccggcctc ctgagtacct   1080

gggattatag gcacaagtca ccatgcccag ccggaataat ctgaaggaaa gacgggtata   1140

ttcaagatga ctttgctgct ggaaatatga cagaataatg tggtatcttc ttctgcactt   1200

ccaagctctt tcacactcag gctcttcctg gcttttctgc ctcagccacc ataaactgtg   1260

gttgcttctc cagctctgtt acagttcaga cttgagggga ggtgacaaga gctaacatgt   1320

taccatgggg agcctggctg acatctccga aactgaagac tctatggaag cctcatgcta   1380

ttgcaatgtg tacatcaaaa gtaaagtacc ccaggttaaa actatgagga agttgccatc   1440

tttacttcca ggagcaaaga cactgaaact gtcccctgca agccccttaa tttcatacag   1500

tcctctgact gccccccaac cctggctact tttttttgaa ataaggtctc actctgtcat   1560
```

```
ccaggctgga gtgcagtggc aaaatcacaa taccctgcag ccttgacctc atgggctcaa   1620
gcagtcctcc cacctcagcc tcctgggtag ctgggactac aggcttgcac taccacaccc   1680
agcttatttt ttgtagagac agagtttcgt catgttgccc aggctggtct caggagtcac   1740
tcctgagctc aagtgatccg cctgccttgg cctcccacag tgctgggatt acaggagtga   1800
gccaccatgt ctggtcctct gaccctttta gcaggaaatc cagcccagcc cctgaacggc   1860
atgttagaca gttcaacaaa gccttctaga agaccaaaga agactcatag gaataagcct   1920
cttgctgatt aatggaaaca tgaccatttg tggagaaagt gcaatctgca ttgaacacct   1980
ttaggggaac ctgtcattta agacttcaag cattaccatg aaaacttcct ctgaaacacc   2040
ttacagacat ctctgtaaaa cagatttaaa gagaaacaca tttctgctta atcggtacac   2100
atcaaatggc gatttaagag caaggctagg aaaccagaag atgatatgca tatacataaa   2160
gttgccacta ttccaaatag taaaataaag acaaagtcaa tggtcctagg agagctggtg   2220
ggttgtggag ccaggagaga aaggcagctc ccttcacctt ccctgtacat tccaggaggc   2280
cctagaatga cctagatggt gttacgcaca aagccctcct tctcccatcc cgccatcatc   2340
tcaggagcaa atggccacac tcgggtatac ggagcagctc aagcaaccag gtcttcctgc   2400
cattcccctg aaagggctgg ttttgccaaa cgccagagcc acattgtgtt aatcagcgcc   2460
catccctaga cacaggggct tgcagccttg tcacacaaat gagccatgga gatgtttccg   2520
actcctcccc tccctgccac tcacaagcag ccagctgccg agccctgcag actcttcctt   2580
tacgacgtcg gttgtatcca cttcccttct ggtcccacac ccaagttcag gaccatttta   2640
gcacgtgcct acattattgc cacagccatt gtcttcatct gttttgtgct gctgtacaag   2700
gaacaaactt atttggcttg tggtttggga ggttgggaaa tccaagatcc agggccacat   2760
ctgctgaagg ccttcctgct gtaccgtaac ataacgggag gcatcactgg tgagagagag   2820
agagcacaag aaagggccaa actcgctttt atagtgaacc cactcctgca ataacaacgt   2880
tcaaatgcta accacctctt cccgtccctg cccctcaaca tggccatgct ggggattaag   2940
tgtccaacac atgagctttg ggatacatgt tccaactaca gccgccacct gctgtcctcc   3000
ttgccttctc cctcttctct acacttctgc cggattctct agttggatta atcttgaaac   3060
atcacttaat tgttaccact ctcccaaaag cagtcaattt taacccattc ccaacaggct   3120
tgagaataaa agtttcagcc                                               3140
```

<210> SEQ ID NO 38
<211> LENGTH: 2785
<212> TYPE: DNA
<213> ORGANISM: Homo Sapiens

<400> SEQUENCE: 38

```
gagagagaga gagagagaga gagagagaga gagcgagaga gcgtgagcgc gcgcaagcta     60
gcgagcaaac cagagagaca gaccgagaga gggaccagga gagagaccca gagagagaag    120
aagaagccag aagccgagct ctgtcagggc tcaacctcca acttgtttca gttcattcat    180
ccttctctcc tttccgctca gactgtagag ctcggtctct ccaagtttgt gcctaagaag    240
atgataatca cacaaacaag tcactgttac atgaccagcc ttgggattct tttcctgatt    300
aatattctcc ctggaaccac tggtcaaggg gaatcaagac gacaagaacc cggggacttt    360
gtgaagcagg acattggcgg gctgtctcct aagcatgccc cagatattcc tgatgacagc    420
actgacaaca tcactatctt caccagaatc ttggatcgtc ttctggacgg ctatgacaac    480
cggctgcgac ctgggcttgg agatgcagtg actgaagtga agactgacat ctacgtgacc    540
```

```
agttttggcc ctgtgtcaga cactgacatg gagtacacta ttgatgtatt ttttcggcag    600
acatggcatg atgaaagact gaaatttgat ggccccatga agatccttcc actgaacaat    660
ctcctggcta gtaagatctg gacaccggac accttcttcc acaatggcaa gaaatcagtg    720
gctcataaca tgaccacgcc caacaagctg ctcagattgg tggacaacgg aaccctcctc    780
tatacaatga ggttaacaat tcatgctgag tgtcccatgc atttggaaga ttttcccatg    840
gatgtgcatg cctgcccact gaagtttgga agctatgcct atacaacagc tgaagtggtt    900
tattcttgga ctctcggaaa gaacaaatcc gtggaagtgg cacaggatgg ttctcgcttg    960
aaccagtatg accttttggg ccatgttgtt gggacagaga taatccggtc tagtacagga   1020
gaatatgtcg tcatgacaac ccacttccat ctcaagcgaa aaattggcta ctttgtgatc   1080
cagacctact tgccatgtat catgactgtc attctgtcac aagtgtcgtt ctggctcaac   1140
agagagtctg ttcctgcccg tacagtcttt ggtgtcacca ctgtgcttac catgaccacc   1200
ttgagtatca gtgccagaaa ttccttacct aaagtggcat atgcgacggc catggactgg   1260
ttcatagccg tctgttatgc ctttgtattt tctgcactga ttgaatttgc cactgtcaac   1320
tatttcacca agcggagttg ggcttgggaa ggcaagaagg tgccagaggc cctggagatg   1380
aagaagaaaa caccagcagc cccagcaaag aaaaccagca ctaccttcaa catcgtgggg   1440
accacctatc ccatcaacct ggccaaggac actgaatttt ccaccatctc caagggcgct   1500
gctcccagtg cctcctcaac cccaacaatc attgcttcac ccaaggccac ctacgtgcag   1560
gacagcccga ctgagaccaa gacctacaac agtgtcagca aggttgacaa aatttcccgc   1620
atcatctttc ctgtgctctt tgccatattc aatctggtct attgggccac atatgtcaac   1680
cgggagtcag ctatcaaggg catgatccgc aaacagtaga tagtggtggc agtgcagcaa   1740
ccagagcact gtataccccg tgaagcatcc aggcacccaa accccggggc tccccttcgc   1800
gtatttcagg attctccttt ttacccctct accaagctgt gaccctcaat tcatatttat   1860
gaatctctac gcaaaaaata actacagaaa aattacttgt ccctccaata ttgcccagta   1920
taaccccatc aaagccaaac actgccattt gtccagttgc tcatcttagt ctgccaatct   1980
cccctagctg agggcactgc atgtatttta ttgcactctg cccgctgcaa aaagaacaag   2040
agattctact ctccatagtg gaagccttgg ctgtttgaga ggcccagaac aaggagaatt   2100
gttgactccc atctagatca gatgactcta acttactagg cagccaggtt aggctaggcc   2160
atgtgatcct gcgtgccacc tcccctgcct tcagcaaggc ctactaggca taagtactga   2220
tagcaaaggt gggagccagt tctacacccc caacccattt attggtttgg aaattagtgg   2280
ggacaattgg tactaaccac cgtctaccat gtatggccaa aataaataga actagctctg   2340
ccagcctggc accaagatgg ctggtgccct gccatgtcca gcccctcggg aaaatagtcc   2400
cctccttggt acatctctcc tccagaaaat cttcttcccc cactgccttt ggcacccttg   2460
tagccaactg agcactactt aatttggact cattaccacc tgtaaacttt tcaggaaaaa   2520
atgatcaagc attttttatt tatatcgaaa agttgcaaat agaaacaaag tgatctagat   2580
ttaaaaaaaa catttttta aaatatggga gagatacaaa agtcacctcc ctgccaaggc    2640
aactagccta tactggattg ggtaagaggt ttggagtgga tggtagttga ggattgaagt   2700
ctggctcaaa agagaaggct actggcagat gaaagtcaaa ttcttccttc catacactcc   2760
acattccaca ccctggccca ggcac                                        2785
```

<210> SEQ ID NO 39

<211> LENGTH: 960
<212> TYPE: DNA
<213> ORGANISM: Homo Sapiens

<400> SEQUENCE: 39

```
atggaaagag gaaaccaaac agaagttgga aactttctcc tcctgggatt cgcagaggac     60
tctgacatgc agcttctcct ccatgggctg ttcctctcca tgtacctggt taccatcatc    120
ggaaacctgc tcatcatcct gaccatcagt tcagactccc acctccacac ccccatgtac    180
ttcttcctct ccaacctgtc ctttgctgac atctgtttca catccacgac tgtcccaaag    240
atgctggtga atatccaaac acaaagcaaa atgatcactt ttgcaggctg cctcactcag    300
atattttttt tcattgcatt tggatgcctg gacaatttgc tcctgaccat gacggcctat    360
gaccgcttcg tggccatctg ttacccccctg cactacacgg tcatcatgaa cccccggctc    420
tgtggactgc tggttctggg gtcctggtgc atcagtgtca tgggttcctt gcttgagacc    480
ttgaccattt tgaggctgtc cttctgcaca aatatggaaa ttccgcactt tttttgtgat    540
ccttccgaag tcctgaagct ggcctgttct gacaccttca tcaataacat cgtgatgtat    600
tttgtgacca ttgtcctggg tgtttttcct ctctgtggaa tcctattctc ttattctcag    660
atttctcct ccgtcctaag agtatctgcc agaggccagc acaaagcctt ttccacctgt    720
ggttcccacc tctcagtggt cagcttgttc tatggcactg gccttggggt ctatctcagt    780
tctgcagtta caccaccttc taggacaagt ctggcagcct cggtgatgta caccatggtc    840
acccccatgc tgaacccctt catctacagc ctgaggaaca aggacatgaa ggggtcactg    900
gggagactcc tcctcagggc aacgtctctc aaagagggga ccattgctaa gctctcatga    960
```

<210> SEQ ID NO 40
<211> LENGTH: 1591
<212> TYPE: DNA
<213> ORGANISM: Homo Sapiens

<400> SEQUENCE: 40

```
ccctgcgtct ctgcccgccc cgtggcgccc gagtgcactg aagatggcgg ctgctgtagg     60
acggttgctc cgagcgtcgg ttgcccgaca tgtgagtgcc attccttggg gcatttctgc    120
cactgcagcc ctcaggcctg ctgcatgtgg aagaacgagc ttgacaaatt tattgtgttc    180
tggttccagt caagcaaaat tattcagcac cagttcctca tgccatgcac ctgctgtcac    240
ccagcatgca ccctatttta agggtacagc cgttgtcaat ggagagttca aagacctaag    300
ccttgatgac tttaagggga aatatttggt gcttttcttc tatcctttgg atttcacctt    360
tgtgtgtcct acagaaattg ttgcttttag tgacaaagct aacgaatttc acgacgtgaa    420
ctgtgaagtt gtcgcagtct cagtggattc ccactttagc catcttgcct ggataaatac    480
accaaggaag aatggtggtt tgggccacat gaacatcgca ctcttgtcag acttaactaa    540
gcagatttcc cgagactacg gtgtgctgtt agaaggttct ggtcttgcac taagaggtct    600
cttcataatt gaccccaatg gagtcatcaa gcatttgagc gtcaacgatc tcccagtggg    660
ccgaagcgtg gaagaaaccc tccgcttggt gaaggcgttc cagtatgtag aaacacatgg    720
agaagtctgc ccagcgaact ggacaccgga ttctcctacg atcaagccaa gtccagctgc    780
ttccaaagag tactttcaga aggtaaatca gtagatcacc catgtgtatc tgcaccttct    840
caactgagag aagaaccaca gttgaaacct gcttttatca ttttcaagat ggttatttgt    900
agaaggcaag gaaccaatta tgcttgtatt cataagtatt actctaaatg ttttgttttt    960
gtaattctgg ctaagacctt ttaaacatgg ttagttgcta gtacaaggaa tcctttattg   1020
```

```
gtaacatctt ggtggctggc tagctagttt ctacagaaca taatttgcct ctatagaagg   1080
ctattcttag atcatgtctc aatggaaaca ctcttctttc ttagccttac ttgaatcttg   1140
cctataataa agtagagcaa cacacattga aagcttctga tcaacggtcc tgaaattttc   1200
atcttgaatg tctttgtatt aaactgaatt ttcttttaag ctaacaaaga tcataatttt   1260
caatgattag ccgtgtaact cctgcaatga atgtttatgt gattgaagca aatgtgaatc   1320
gtattatttt aaaaagtggc agagtgactt aactgatcat gcatgatccc tcatccctga   1380
aattgagttt atgtagtcat tttacttatt ttattcatta gctaactttg tctatgtata   1440
tttctagata ttgattagtg taatcgatta taaaggatat ttatcaaatc cagggattgc   1500
attttgaaat tataattatt ttctttgctg aagtattcat tgtaaaacat acaaaataaa   1560
catattttaa aacatttgca ttttaccacc a                                  1591
```

```
<210> SEQ ID NO 41
<211> LENGTH: 4472
<212> TYPE: DNA
<213> ORGANISM: Homo Sapiens

<400> SEQUENCE: 41

aaagtcggga gtgccatggt gccagctggg gatcaagacc gcgcgccaca caggggggaag     60
ccggcccagg ctggggctcg cacctcacgt gcctcccggg ccctgcgatc ctggaggcgc    120
tcccaggccg cgcgcgccac ggtcacccac ccacgtgggg ggcacgaccg tgggagtcac    180
ggggggtacc gtgagggtca caggggggtgc cgcagggatc cacagtgggc ttccgcgggg   240
cctccacccc tgagcttcac agaggaagtg aaatttgagc tgcgcgccct gaaggactgg    300
gacttcaaaa tgagcgtccc tgactacatg cagtgtgctg aggaccacca gacgctgctc    360
gtggtggtcc agcctgtggg catcgtctcc gaggagaact tcttcaggat ctataagagg    420
atttgctctg tgagtcagat cagcgtgcgg gactcccagc gagtcctcta catccgctac    480
aggcaccact acccacccga gaacaacgag tggggtgact tccagaccca ccgcaaagtc    540
gtgggcctca tcaccatcac agactgcttc tcggccaagg actggccaca gacctttgag    600
aagttccacg tgcagaagga gatctacggc tccacactgt atgactcccg gctctttgtc    660
ttcgggctgc agggggagat cgtggagcag ccgcgcaccg acgtggcttt ctaccccaac    720
tacgaggact gccagacggt ggagaagaga atcgaggact tcatcgagtc actgttcatc    780
gtgctggagt ccaagcgtct ggacagagcc acagacaagt ctggggataa gatccccctt    840
ctctgtgtcc cgtttgagaa aaaggacttt gtaggactgg acacagacag cagacattac    900
aagaagcggt gccaaggccg catgcggaag cacgtggggg acctgtgcct gcaggcaggg    960
atgctgcagg actccctggt gcattaccac atgtcggtgg agctgctgcg ttctgtgaat   1020
gactttctgt ggcttggagc tgccctggaa ggattgtgtt cagcttctgt catctatcac   1080
tatcctggtg gaactggtgg gaagagtgga gctcggaggt tccagggcag caccccttcct   1140
gctgaagcag ccaatagaca ccggccaggg gcacaggaag ttctcattga tccaggtgcc   1200
ctcaccacca atggcatcaa ccctgacacc agtactgaga tcggacgtgc taagaactgc   1260
cttagccctg aagacataat tgacaagtat aaagaggcga tttcctatta cagcaagtat   1320
aagaatgcgg gagtgattga gttggaagcg tgcatcaagg ctgtacgtgt ccttgcaatt   1380
cagaaacgga gcatggaagc atcagaattt cttcagaatg cagtttacat taaccttcga   1440
cagctttctg aggaagagaa aattcagcgc tacagcatcc tctccgagct ctatgagctg   1500
```

```
atcggcttcc atcgcaagtc tgcgttcttc aagcgcgtgg ccgccatgca gtgcgtggcc   1560
ccaagcatcg cggagcctgg gtggagggcc tgctacaaac tcctcctgga aacgctgccc   1620
ggctacagtc tgtcgctgga tcccaaagat ttcagcagag gcacgcacag aggctgggct   1680
gcggtccaga tgcgtttgct ccatgaattg gtctacgcct cccgaaggat ggggaaccct   1740
gccctctctg tcagacacct gtccttcctt ctacagacca tgctggactt cttgtcggat   1800
caggaaaaga aagatgtggc ccaaagccta gagaactata cgtccaagtg tcctgggacc   1860
atggagccca tcgccctccc tggcggcctc accctgccac cggtgccctt caccaagctt   1920
cccgtcgtca ggcatgtgaa actattgaac cttcctgcta gcctccggcc acacaaaatg   1980
aaaagcttgc tgggtcagaa cgtgtcaacc aaaagtcctt tcatctattc accaattatc   2040
gcacacaacc gtggagaaga gcggaacaag aaaatagatt tccagtgggt tcaaggagat   2100
gtgtgtgaag ttcagctgat ggtatataac ccaatgccgt ttgaacttcg agttgaaaac   2160
atggggctgc tcaccagcgg agtggagttc gagtctctcc ctgcggcgct ttctcttccg   2220
gctgaatctg gtctgtaccc agtgacgctc gtcggggtcc cgcagacgac tggaacgatt   2280
actgtgaacg gttaccatac cacggtcttc ggtgtgttca gtgactgttt gctggataac   2340
ctgccgggaa taaaaaccag tggctccaca gtggaagtca ttcccgcgtt gccaagactg   2400
cagatcagca cctctctgcc cagatctgca cattcattgc aaccttcttc tggtgatgaa   2460
atatctacta atgtatctgt ccagctttac aatggagaaa gtcagcaact aatcattaaa   2520
ttggaaaata ttggaatgga accattggag aaactggagg tcacctcgaa agttctcacc   2580
actaaagaaa aattgtatgg cgacttcttg agctggaagc tagaggaaac ccttgcccag   2640
ttccctttgc agcctgggaa ggtggccacg ttcacaatca acatcaaagt gaagctggat   2700
ttctcctgcc aggagaatct cctgcaggat ctcagtgatg atggaatcag tgtgagtggc   2760
tttcccctgt ccagtccttt tcggcaggtc gttcggcccc gagtggaggg caaacctgtg   2820
aacccacccg agagcaacaa agcaggcgac tacagccacg tgaagaccct ggaagctgtc   2880
ctgaatttca aatactctgg aggcccgggc cacactgaag gatattacag gaatctctcc   2940
ctggggctgc atgtagaagt cgagccgtct gtatttttca cccgagtcag caccctccca   3000
gcaaccagta cccggcagtg tcacctgctc ctggatgtct tcaactccac cgagcatgag   3060
ctgaccgtca gcaccaggag cagcgaggca ctcatcctgc acgccggcga gtgccagcga   3120
atggctattc aagtggacaa gttcaacttt gagagtttcc cggagtcccc tggggagaag   3180
gggcaatttg caaaccccaa gcagctggag gaagagcggc gggaagcccg aggcctggag   3240
atccacagca agctgggcat ctgctggaga atcccctccc tgaagcgcag tggcgaggcg   3300
agtgtggaag gactcctgaa ccagctcgtc ctggagcacc tgcagctggc gcctctgcag   3360
tgggatgtgc tggtggacgg acagccatgt gaccgcgagg ctgtggcggc ctgccaggtg   3420
ggcgaccccg tgcgcctgga ggtgcggctg accaaccgga gcccgcgcag cgtagggccc   3480
ttcgccctca ctgtggtccc cttccaggac caccagaacg gcgtgcacaa ctacgacctg   3540
cacgacaccg tctccttcgt gggctccagc accttctacc tcgacgcggt gcagccgtcc   3600
ggccagtcgg cctgcctcgg ggccctcctc ttcctctaca cgggagactt cttcctccac   3660
atccggttcc acgaggacag caccagcaag gagctgccac cctcttggtt ctgcctgccc   3720
agtgtgcacg tgtgtgccct ggaggcgcag gcctgagccc gcctacttcc gtccctcttt   3780
ctgcagggcc agaggtgacc ctgcctggcc tcccacaccc cctgcaatga gcaaggcctt   3840
cactgcagcc ccatctcctc ctcctccccc agacccctcc cagccctctc ctcctgttcc   3900
```

```
tcctgtagca tctttgctgg gctacgcaga agccccggac atggcagccc caccccatgc   3960

cacgcccctt cctacactgt tccctggacc atacacaggc tgaagcagag gaaatcccaa   4020

agcgggtgcc catccagccc aggtcccagg atccctgcac ccatttctgt gacctggggc   4080

cccagccgtg ctgtgctgct catcccagca gagggacctc cctcgtccag cgacttccct   4140

ttggccatag aaagaaatgg tgagcatgag actgggcaca gcctgagggc gtgggcagct   4200

tcccaccctc cctgggcctt ggaatccccc aaggctggtt ttcttcctgg agacccccat   4260

gggcaacttg gcaggagaga tggtgccgta ggaggtcgtg gatggttgat gccaagagag   4320

gccctccacc cgtggtgggc aaatgtccag gcctgggctg gcagcccagg gctgtttctg   4380

ggtgctccct ggccccaggg tggcgtctgg ttaccatggc tgtgtgtgtc catgtctgca   4440

agcagttctt caataaatgg cctgcctccc cc                                 4472
```

<210> SEQ ID NO 42
<211> LENGTH: 1302
<212> TYPE: DNA
<213> ORGANISM: Homo Sapiens

<400> SEQUENCE: 42

```
gagacagccc gccggccgcc cggatctcca cctgccaccc cagagctggg acagcagccg     60

ggctgcggca ctgggaggga gaccccacag tggcctcttc tgccacccac gcccccaccc    120

ctggcatggc cgaccagctg actgaggagc aggtcacaga attcaaggag gccttctccc    180

tgtttgacaa ggatggggac ggctgcatca ccacccgcga gctgggcacg gtcatgcggt    240

ccctgggcca gaaccccacg gaggccgagc tgcgggacat gatgagtgag atcgaccggg    300

acggcaacgg caccgtggac ttccccgagt tcctgggcat gatggccagg aagatgaagg    360

acacggacaa cgaggaggag atccgcgagg ccttccgcgt gttcgacaag gacggcaacg    420

gcttcgtcag cgccgccgag ctgcgacacg tcatgacccg gctgggggag aagctgagtg    480

acgaggaggt ggacgagatg atccgggccg cggacacgga cggagacgga caggtgaact    540

acgaggagtt tgtccgtgtg ctggtgtcca agtgaggccg gcgcccacca tgctcctggg    600

cgcccacgcg gcccacaggg caagaacccg gggcctcccg cctcctcccc catccccctg    660

cctcccctgg gcactgtggc ttcctcctgc gcctggttga ttcagcccac ctctctgcat    720

cccgcttccc gcgtctcttc tctgcactcc tgccgacctt cccacctgct catctgaatg    780

acacggaacg ctcccactgc aggcaaaccg tgacgccctc cccactcggg agaagcagag    840

ctgaccttag gaccgagcac cagggcaggt tgcgctgact ctgcggccct ccaggacgga    900

caccgggtga ccccttaggg cacccaggca agatccctaa gaggcaccca atgcccaggc    960

caggggggct gcagccctca gcccccgcca ggattcccgc aggctcctgg actggaagct   1020

ccctccgcgg tcggattctg gagggtggga ggcatcttgg cctgcagtaa gcggtgctga   1080

cggggactct ggccacagag gtcaggcctc ctgaaaacag cactgccttc cgcgctgccc   1140

cagcttgccc cattccttgt ccgccaaccc accgtgattc atcttctgaa gctgggagtg   1200

aaactgggtc agctgtaacc tgttcctatt catctggaag gagggaggct tggatgagca   1260

ggggatgaga gctgcaggga aataaatgag atattcgtcc tt                      1302
```

<210> SEQ ID NO 43
<211> LENGTH: 1859
<212> TYPE: DNA
<213> ORGANISM: Homo Sapiens

<400> SEQUENCE: 43

```
ggaagtctat ccgggctttc gcgtcaccac cctgcccacc tgggtggcgc gtggcttacg     60
caacggtcac tgggctcctg ggccgctccc gggccagcga gggctgcgaa agaagttgta    120
gcatgcatac cacagaatca aaaaatgaac atttggagga tgaaaacttc caaacatcta    180
caactcctca gagtctcatt gatcctaata atactgcaca tgaagaaact aaaactgtct    240
tatcagatac agaagaaata aaaccacaga caaaaaagga gacatacatt tcttgtcctc    300
taagaggagt attgaatgta attattacaa atggagttat actgtttgtg atatggtgta    360
tgacctggtc aatcttaggc tctgaagctc tccctggtgg aaatttattt gggttgttca    420
ttatttttta tagtgccatt attgggggaa aaattttaca actcattaga atacctttag    480
tgcctccact tccacctctt cttgggatgt tactggctgg ttttacgatt aggaatgttc    540
cattcatcaa tgaacatgtc catgttccta acacatggtc ttcaatttta agaagcattg    600
cccttaccat tattctaata agagctgggc ttggactcga tccacaggct ttgaggcatt    660
tgaaggtcgt ttgtttcaga ttggctgtag gtccatgcct tatggaggca agtgcagctg    720
ctgttttttc acacttcatt atgaaatttc cctggcaatg ggcatttcta ttaggttttg    780
ttctaggtgc tgtctctcct gctgttgttg tcccttacat gatggtgctg caagaaaatg    840
gatatggtgt tgaggaaggc attccaacct tattaatggc tgctagcagt atggatgaca    900
ttctggctat cactggattc aatacatgct tgagcatagt cttttcctca ggtggtatac    960
ttaataacgc catagcctct ataaggaacg tatgtattag tctgctggca ggaattgttt   1020
tgggattttt tgttcgatat tttccaagtg aagaccagaa aaaacttaca ttgaagagag   1080
gattccttgt tttgactatg tgtgtttctg ccgtcttagg cagccaacgt attggtttac   1140
atggatctgg aggattatgc acactagtgt tgagtttcat tgcagggaca aaatggtccc   1200
aagaaaagat gaaagtccaa aagattatta cgactgtatg ggatattttt caaccacttc   1260
tttttggttt agttggagca gaagtatctg tttcatcgct tgaatcaaat attgttggca   1320
tatctgttgc cactctaagt ttggcattat gtgttcgaat tttaaccaca tatctattga   1380
tgtgctttgc tggttttagt tttaaggaga aaatatttat tgctttagca tggatgccca   1440
aagctacagt acaggctgtg ttaggtcctc tggctctaga aacagcaaga gtctccgcac   1500
cccacttgga accatatgcg aaggatgtga tgacagtagc atttttagcc atcttgatca   1560
cagctccaaa tggagctcta cttatgggca ttctggggcc taaaatgctt acacgccatt   1620
atgatccaag caaaataaaa ctgcagttgt caacattaga acatcattaa aaagtttacc   1680
tgtcatcatc tgcctgcttc ttttaatgaa ttatttcaca tgacagaaga attttaaagt   1740
agaaatatgt ggggactgta cagagaatcc aggatttagt aaacatgtga tttcagtaca   1800
gggcttttct tggacttttt actccaaagt taatttaata aaaataatat taaatggaa    1859
```

<210> SEQ ID NO 44
<211> LENGTH: 1035
<212> TYPE: DNA
<213> ORGANISM: Homo Sapiens
<220> FEATURE:
<221> NAME/KEY: misc_feature
<222> LOCATION: 30, 32, 86
<223> OTHER INFORMATION: n = A,T,C or G

<400> SEQUENCE: 44

```
ycactccccc aaatcyccwa tttatcaggn gntcactgaa ataaaaaata caattgagct     60
cccatcatca gtkckagtcr atgggnaatg cgcctttaag agaaaactgg tcagatgaat    120
```

```
attattgctt cccattttca accagtaaat agttgccact gagaaactga cagccaggag    180
tctgtcaaga atgctcaaga tatgttatat aatacaacat gcctgttcac agggggaaaa    240
atcctaggaa ataacttatg tgtacttctt gatttcatca tacaagacaa gcacaaaagc    300
accacccatg cctctgagaa cattggacca tgcacccttg aaaaaagctt tgcctccttc    360
atcacgagcm atcttccgcc agcagtcaag cgtgcctgtg tacatgatgt cagttccttt    420
gcgccctgac tgcatcatca tgcggcggcg aacggtgtca aatggatagg aagtcaaccc    480
ggcaacagca gtgacagtct gtgcgatcat ccagctgatg acgatgtgag tgttcttggg    540
atccggaagc attccctttg cagtgtcata gataccgaag taggcggctc ggtagatgat    600
aataccctgc acagacacgt taaagccttg gtacaggccc ttaatcccat cagatttgta    660
gatcttaacc aggcagtcac cgaggcctcg gaattccctt tcagctccag ctttacccac    720
atcagctgct agacgggtac gggcaaaatc aagagggtac acaaaacaca gggatgtggc    780
ccctgcggca ccacccgatg ccagattccc tgcaaagtag cgccaaaact gggttctctt    840
gtccacacca cccaggaaga tctgcttgta tttatctttg aaggcgaagt taagagcctg    900
ggtggggaag tatctgatga cattggccag gttaccgcgc cagaaggaca gaactccctg    960
ctccttggga atacggacca cgcagtctat aatgcctttg tattgcttat ctgcagtgat   1020
ctgcttgcck gcatg                                                    1035
```

```
<210> SEQ ID NO 45
<211> LENGTH: 2031
<212> TYPE: DNA
<213> ORGANISM: Homo Sapiens

<400> SEQUENCE: 45

gagcgcgcgc gccgccgccg ttgccgccgg gctgagagaa gagcttgcgg ggtttgcggt     60
tgatggcccc gactgaaggg ctggaggcgg tgtatgccgc tgttcttgct gtcgctcccg    120
acacctccgt ccgcttctgg tcatgagagg agacagaggc ctgaagcaaa gacatctggg    180
tcagagaaaa agtatttaag ggccatgcaa gccaatcgta gccaactgca cagtcctcca    240
ggaactggaa gcagtgagga tgcctcaacc cctcagtgtg tccacacaag attgacagga    300
gagggttctt gccctcattc tggagatgtt catatccaga taaactccat acctaaagaa    360
tgtgcagaaa atgcaagctc cagaaatata aggtcaggtg tccatagctg tgcccatgga    420
tgtgtacaca gtcgcttacg ggtcactccc cacagtgaag caaggctgac tgatgatact    480
gccgcagaat ctggagatca tggtagtagc tccttctcag aattccgcta tctcttcaag    540
tggctgcaaa aaagtcttcc atatattttg attctgagcg tcaaacttgt tatgcagcat    600
ataacaggaa tttctcttgg aattgggctg ctaacaactt ttatgtatgc aaacaaaagc    660
attgtaaatc aggtttttct aagagaaagg tcctcaaaga ttcagtgtgc ttggttactg    720
gtattcttag caggatcttc tgttctttta tattacacct ttcattctca gtcactttat    780
tacagcttaa ttttttaaa tcctactttg gaccatttga gcttctggga agtattttgg    840
attgttggaa ttacagactt cattctgaaa ttctttttca tgggcttaaa atgccttatt    900
ttattggtgc cttctttcat catgcctttt aaatctaagg gttactggta tatgctttta    960
gaagaattgt gtcaatacta ccgaactttt gttcccatac cagtttggtt tcgctacctt   1020
ataagctatg gggagtttgg taacgtaact agatggagtc ttgggatact gctggcttta   1080
ctctacctca tattaaaact tttggaattt tttgggcatc tgagaacttt cagacaggtt   1140
```

```
ttacgaatat tttttacaca accaagttat ggagtggctg ccagcaagag acagtgttca   1200

gatgtggatg atatttgttc aatatgtcaa gctgaatttc agaagccaat tcttctcatt   1260

tgtcagcata tattttgtga agagtgcatg accttatggt ttaacagaga gaaaacatgt   1320

ccactctgca gaactgtgat ttcagaccat ataaacaaat ggaaggatgg agccacttca   1380

tcacaccttc aaatatatta agttgtataa actatcaagg ccacaaaata ctaatgtcat   1440

ttggtcataa tgactactga taaggcatca gaatggattt tcagggctac cagaaaaatg   1500

tttccagatg gttttagaat gtaggactta tgatccaatt caccaaaaga ttaaatgaaa   1560

ccaccctgtg ttttaaaata tatataatgt tcaacctaat gtatatgcaa catttattct   1620

attctaatta tttgacaggt aactgcagtg ttaaattgta aatgtgtttt ctttatgtta   1680

ccaaaacagc aatttgaaat tagaactagt ggttttagag aactcaggta ttctttcctg   1740

acattgtttt cagaataaag aatatttttc ataatatttt aagatacata ctatctaaaa   1800

gtagaatttt gttcagcatt gacttttata attcccatcc taaaaattct taatattttc   1860

ataaaatttg tatttttaaa tgaaaattct aaatgttgta ttttatcagt aacatttttct  1920

aagtgaagat taatttactg aggatgatac attatagtat tgtattattc tctgtagtaa   1980

gattagtaat aagtgaaaat aaatgattta aattcaaaaa aaaaaaaaaa a            2031
```

<210> SEQ ID NO 46
<211> LENGTH: 1074
<212> TYPE: DNA
<213> ORGANISM: Homo Sapiens

<400> SEQUENCE: 46

```
gatcaacaca tttcatctgg gcttcttaaa tctaaatctt taaaatgact aagttttctt     60

ccttttctct gtttttccta atagttgggg cttatatgac tcatgtgtgt ttcaatatgg    120

aaattattgg agggaaagaa gtgtcacctc attccaggcc atttatggcc tccatccagt    180

atggcggaca tcacgtttgt ggaggtgttc tgattgatcc acagtgggtg ctgacagcag    240

cccactgcca atatcggttt accaaaggcc agtctcccac tgtggtttta ggcgcacact    300

ctctctcaaa gaatgaggcc tccaaacaaa cactggagat caaaaaattt ataccattct    360

caagagttac atcagatcct caatcaaatg atatcatgct ggttaagctt caaacagccg    420

caaaactcaa taaacatgtc aagatgctcc acataagatc caaaacctct cttagatctg    480

gaaccaaatg caaggttact ggctggggag ccaccgatcc agattcatta agaccttctg    540

acaccctgcg agaagtcact gttactgtcc taagtcgaaa actttgcaac agccaaagtt    600

actacaacgg cgaccctttt atcaccaaag acatggtctg tgcaggagat gccaaaggcc    660

agaaggattc ctgtaagggt gactcagggg gccccttgat ctgtaaaggt gtcttccacg    720

ctatagtctc tggaggtcat gaatgtggtg ttgccacaaa gcctggaatc tacaccctgt    780

taaccaagaa ataccagact tggatcaaaa gcaaccttgt cccgcctcat acaaattaag    840

ttacaaataa ttttattgga tgcacttgct tcttttttcc taatatgctc gcaggttaga    900

gttgggtgta agtaaagcag agcacatatg gggtccattt ttgcacttgt aagtcatttt    960

attaaggaat caagttcttt ttcacttgta tcactgatgt atttctacca tgctggtttt   1020

attctaaata aaatttagaa gactcaaaaa aaaaaaaaaa aaaaaaaaaa aaaa         1074
```

<210> SEQ ID NO 47
<211> LENGTH: 1518
<212> TYPE: DNA
<213> ORGANISM: Homo Sapiens

<400> SEQUENCE: 47

```
cacttccctt cccgcgatgg cggcacaggg agctgctgcg gcggttgcgg cggggacttc     60
aggggtcgcg ggggagggcg agcccgggcc cggggagaat gcggccgctg aggggaccgc    120
cccatccccg ggccgcgtct ctccgccgac cccggcgcgc ggcgagccgg aagtcacggt    180
ggagatcgga gaaacgtacc tgtgccggcg accggatagc acctggcatt ctgctgaagt    240
gatccagtct cgagtgaacg accaggaggg ccgagaggaa ttctatgtac actacgtggg    300
ctttaaccgg cggctggacg agtgggtaga caagaaccgg ctggcgctga ccaagacagt    360
gaaggatgct gtacagaaga actcagagaa gtacctgagc gagctcgcag agcagcctga    420
gcgcaagatc actcgcaacc aaaagcgcaa gcatgatgag atcaaccatg tgcagaagac    480
ttatgcagag atggacccca ccacagcagc cttggagaag gagcatgagg cgatcaccaa    540
ggtgaagtat gtggacaaga tccacatcgg gaactacgaa attgatgcct ggtatttctc    600
accattcccc gaagactatg ggaaacagcc caagctctgg ctctgcgagt actgcctcaa    660
gtacatgaaa tatgagaaga gctaccgctt ccacttgggt cagtgccagt ggcggcagcc    720
ccccgggaaa gagatctacc gcaagagcaa catctccgtg cacgaagttg atggcaaaga    780
ccataagatt tactgtcaga acctgtgtct gctggccaag cttttcctgg accataagac    840
actgtacttt gacgtggagc cgttcgtctt ttacatcctg actgaggtgg accggcaggg    900
ggcccacatt gttggctact tctccaagga gaaggagtcc ccggatggaa acaatgtggc    960
ctgcatcctg accttgcccc cctaccaacg ccgcggctac gggaagttcc tcatcgcttt   1020
cagttatgag ctctccaagc tggagagcac agtcggctcc ccggagaagc cgctgtctga   1080
cctgggcaag ctcagctacc gcagctactg gtcctgggtg ctgctggaga acctgcggga   1140
cttccggggc acactgtcca tcaaggacct cagccagatg accagtatca cccaaaatga   1200
catcatcagt accctgcaat ccctcaatat ggtcaagtac tggaagggcc agcacgtgat   1260
ctgtgtcaca cccaagctgg tggaggagca cctcaaaagt gcccagtata agaaaccacc   1320
catcacagtg gactccgtct gcctcaagtg ggcaccccccc aagcacaagc aagtcaagct   1380
ctccaagaag tgagcagcct ggcccctgct gccggacctg agcctcctgg ctcccagcct   1440
gtaaatatgt atagacctgt tttgtcattt ttttaataaa gtcagttctg gtggccctgg   1500
actttggagg ggaagggg                                                 1518
```

<210> SEQ ID NO 48
<211> LENGTH: 2014
<212> TYPE: DNA
<213> ORGANISM: Homo Sapiens

<400> SEQUENCE: 48

```
aaaccctgaa gagcccaagc aatgtggttg taaaatttgc aaaataagat taaatcttaa     60
ctgcaatctg ttaacactgc tgtctccttt cactctttct cctatatcac actttcccac    120
atgttggatg gccttggagt ggtagccata agcatttttg gaattcaact aaaaactgaa    180
ggatccttga ggacggcagt acctggcata cctacacagt cagcgttcaa caagtgtttg    240
caaaggtaca ttggggcact gggggcacga gtgatctgtg acaatatccc tggtttggtg    300
agccggcagc ggcagctgtg ccagcgttac ccagacatca tgcgttcagt gggcgagggt    360
gcccgagaat ggatccgaga gtgtcagcac caattccgcc accaccgctg gaactgtacc    420
accctggacc gggaccacac cgtctttggc cgtgtcatgc tcagaagtag ccgagaggca    480
```

```
gcttttgtat atgccatctc atcagcaggg gtagtccacg ctattactcg cgcctgtagc    540
cagggtgaac tgagtgtgtg cagctgtgac ccctacaccc gtggccgaca ccatgaccag    600
cgtggggact ttgactgggg tggctgcagt gacaacatcc actacggtgt ccgttttgcc    660
aaggccttcg tggatgccaa ggagaagagg cttaaggatg cccgggccct catgaactta    720
cataataacc gctgtggtcg cacggctgtg cggcggtttc tgaagctgga gtgtaagtgc    780
catggcgtga gtggttcctg tactctgcgc acctgctggc gtgcactctc agatttccgc    840
cgcacaggtg attacctgcg gcgacgctat gatggggctg tgcaggtgat ggccacccaa    900
gatggtgcca acttcaccgc agcccgccaa ggctatcgcc gtgccacccg gactgatctt    960
gtctactttg acaactctcc agattactgt gtcttggaca aggctgcagg ttccctaggc   1020
actgcaggcc gtgtctgcag caagacatca aaaggaacag acggttgtga aatcatgtgc   1080
tgtggccgag ggtacgacac aactcgagtc acccgtgtta cccagtgtga gtgcaaattc   1140
cactggtgct gtgctgtacg gtgcaaggaa tgcagaaata ctgtggacgt ccatacttgc   1200
aaagccccca agaaggcaga gtggctggac cagacctgaa cacacagata cctcactcat   1260
ccctccaatt caagcctctc aactcaaaag cacaagatcc ttgcatgcac accttcctcc   1320
accctccacc ctgggctgct accgcttcta tttaaggatg tagagagtaa tccataggga   1380
ccatggtgtc ctggctggtt ccttagccct gggaaggagt tgtcagggga tataagaaac   1440
tgtgcaagct ccctgatttc ccgctctgga gatttgaagg gagagtagaa gagatagggg   1500
gtctttagag tgaaatgagt tgcactaaag tacgtagttg aggctccttt tttctttcct   1560
ttgcaccagc ttcccgacac ttcttggtgt gcaagaggaa gggtacctgt agagagcttc   1620
tttttgtttc tacctggcca aagttagatg ggacaaagat gaatggcatg tcccttctct   1680
gaagtccgtt tgagcagaac tacctggtac cccgaaagaa aaatcttagg ctaccacatt   1740
ctattattga gagcctgaga tgttagccat agtggacaag gttccattca catgctcata   1800
tgtttataaa ctgtgttttg tagaagaaaa agaatcataa caatacaaac acacattcat   1860
tctctctttt tctctctacc attctcaacc tgtattggac agcactgcct cttttgctta   1920
cttgctgcct gttcaaactg aggtggaatg cagtggttcc catgcttaac agatcattaa   1980
aacaccctag aacactccta ggatagatta atgt                               2014
```

<210> SEQ ID NO 49
<211> LENGTH: 3258
<212> TYPE: DNA
<213> ORGANISM: Homo Sapiens

<400> SEQUENCE: 49

```
aaggctgtgg accccagaga aggtggcagg tggcccccct aggagagctc tgggcacatt     60
cgaatcttcc caaactccaa taataaaaat tcgaagactt tggcagagag tgtgtgtgtg    120
tgtgtatggt tgttgggcgt aggacaggtt tcggggatgc gcggtacgcg gtaccacccc    180
tcggaggccc ccaccccag acgcccaggc cgcctcccca ctccccctca agcagcccca    240
gccggggact ttccgtcgcg gggaaggggc ggggaccctg agcgaaaggt gcggaggcgg    300
cctgccgggg tggttcggct tcccgttgcc gcctcgggcg ctgtacccag agctcgaaga    360
ggagcagcgc ggccgcgcgg acccggcaag gctgggccgg actcggggct cccgagggac    420
gccatgcggg gaggcagggg cgccccttc tggctgtggc cgctgcccaa gctggcgctg    480
ctgcctctgt tgtgggtgct tttccagcgg acgcgtcccc agggcagcgc cgggccactg    540
cagtgctacg gagttggacc cttgggcgac ttgaactgct cgtgggagcc tcttggggac    600
```

```
ctgggagccc cctccgagtt acacctccag agccaaaagt accgttccaa caaaacccag    660
actgtggcag tggcagccgg acggagctgg gtggccattc ctcgggaaca gctcaccatg    720
tctgacaaac tccttgtctg gggcactaag gcaggccagc ctctctggcc ccccgtcttc    780
gtgaacctag aaacccaaat gaagccaaac gcccccggc tgggccctga cgtggacttt    840
tccgaggatg acccctgga ggccactgtc cattgggccc cacctacatg gccatctcat    900
aaagttctga tctgccagtt ccactaccga agatgtcagg aggcggcctg gaccctgctg    960
gaaccggagc tgaagaccat acccctgacc cctgttgaga tccaagattt ggagctagcc   1020
actggctaca aagtgtatgg ccgctgccgg atggagaaag aagaggattt gtggggcgag   1080
tggagcccca ttttgtcctt ccagacaccg ccttctgctc caaaagatgt gtgggtatca   1140
gggaacctct gtgggacgcc tggaggagag gaacctttgc ttctatggaa ggccccaggg   1200
ccctgtgtgc aggtgagcta caaagtctgg ttctgggttg gaggtcgtga gctgagtcca   1260
gaaggaatta cctgctgctg ctccctaatt cccagtgggg cggagtgggc cagggtgtcc   1320
gctgtcaacg ccacaagctg ggagcctctc accaacctct ctttggtctg cttggattca   1380
gcctctgccc cccgtagcgt ggcagtcagc agcatcgctg ggagcacgga gctactggtg   1440
acctggcaac cggggcctgg ggaaccactg gagcatgtag tggactgggc tcgagatggg   1500
gacccccctgg agaaactcaa ctgggtccgg cttcccccctg ggaacctcag tgctctgtta   1560
ccagggaatt tcactgtcgg ggtcccctat cgaatcactg tgaccgcagt ctctgcttca   1620
ggcttggcct ctgcatcctc cgtctggggg ttcagggagg aattagcacc cctagtgggg   1680
ccaacgcttt ggcgactcca agatgcccct ccagggaccc ccgccatagc gtggggagag   1740
gtcccaaggc accagcttcg aggccacctc acccactaca ccttgtgtgc acagagtgga   1800
accagcccct ccgtctgcat gaatgtgagt ggcaacacac agagtgtcac cctgcctgac   1860
cttccttggg gtccctgtga gctgtgggtg acagcatcta ccatcgctgg acagggccct   1920
cctggtccca tcctccggct tcatctacca gataacaccc tgaggtggaa agttctgccg   1980
ggcatcctat tcttgtgggg cttgttcctg ttggggtgtg gcctgagcct ggccacctct   2040
ggaaggtgct accacctaag gcacaaagtg ctgccccgct gggtctggga gaaagttcct   2100
gatcctgcca acagcagttc aggccagccc cacatggagc aagtacctga ggcccagccc   2160
cttggggact tgcccatcct ggaagtggag gagatggagc cccgccggt tatggagtcc   2220
tcccagcccg cccaggccac cgccccgctt gactctgggt atgagaagca cttcctgccc   2280
acacctgagg agctgggcct tctggggccc cccaggccac aggttctggc ctgaaccaca   2340
cgtctggctg ggggctgcca gccaggctag agggatgctc atgcaggttg caccccagtc   2400
ctggattagc cctcttgatg gatgaagaca ctgaggactc agagaggctg agtcacttac   2460
ctgaggacac ccagccaggc agagctggga ttgaaggacc cctatagaga agggcttggc   2520
ccccatgggg aagacacgga tggaaggtgg agcaaaggaa aatacatgaa attgagagtg   2580
gcagctgcct gccaaaatct gttccgctgt aacagaactg aatttggacc ccagcacagt   2640
ggctcacgcc tgtaatccca gcactttggc aggccaaggt ggaaggatca cttagagcta   2700
ggagtttgag accagcctgg gcaatatagc aagacccctc actacaaaaa taaaacatca   2760
aaaacaaaaa caattagctg ggcatgatgg cacacacctg tagtccgagc cacttgggag   2820
gctgaggtgg gaggatcggt tgagcccagg agttcgaagc tgcagggacc tctgattgca   2880
ccactgcact ccaggctggg taacagaatg agaccttatc tcaaaaataa acaaactaat   2940
```

```
aaaaagcaaa aaaaaaaaaa aaagaaaaga aaaaacactg catttgggca ccatctcagc   3000

tcccttgcat ccaggtgcag catggactga gttcttgaca acagaatgtg gtcagaagtg   3060

acatatgcca acacggggtc tgggtggggg ctcccccaca tcctttcctt gcctatgagc   3120

tggaacataa cacatgccta tgatccagct ttggtcatac ccaaggggaa ggtggagcaa   3180

gaaatgaaaa ggaacctgaa tccctgaatg actgcatgga tagaaccact aagaaaaata   3240

aacttttata tttttata                                                 3258


<210> SEQ ID NO 50
<211> LENGTH: 4359
<212> TYPE: DNA
<213> ORGANISM: Homo Sapiens

<400> SEQUENCE: 50

gttgtaaact tcacctcccg ggggctcttc cccttctgta ccccttttgct gtttgtcccc    60

ctcctcccgg gtcctggagt ccgtcgtgtt ccaacagttt ttgctcttat tcccgtgggc   120

tgcctgggcc tcctttcacc cgtgagactt ggagcggccc ctggggtctt gggtgtgcag   180

cacggatcac gcgagacccc tgagacctca aatcatctaa cgtgaagcca cagacatctt   240

gggcaatttt aatcatcaag aaagaaatat gtcattaaga aatagcaggg tattttgaaa   300

gagttggaaa acatcatgaa tttgaatact tcaagtaata ctggtgatac ccaaaggttg   360

aagattgcct cattggatgt aaaacaaata cttaaaaatg aaacagagtt ggatattact   420

gataatctca ggaagaaact ccattgggct aaaaaagaaa agttagaaat aacaaccaaa   480

cacaatgcag agctggcaag ctatgagagc cagattgcca agctacggtc cgaggttgaa   540

aagggagaag cattgcgaca aagtctggaa tatgacctag ctgttgctag aaaggaagct   600

ggtcttggaa gacgggctgc tgaagaaaga ttagccgagg cacataggat ccaagaaaaa   660

ctctgtgcac agaattcaga acttcaagca aagacaaatg agactgagaa agcatttcag   720

acttctcagc aaaaatggaa agaagaatgc agaagatttg aacatgattt ggaggaaaga   780

gacaatatga tccaaaattg caatcgagaa tatgatttac ttatgaaaga aaaaagcaga   840

ctagagaaaa ctctacagga agcgttggaa aaacatcaac gggagaagaa tgagatggag   900

tctcatatca gggagacagc attggaggag tttagattac aagaagaaca atgggaagca   960

gaaagaagag aattacaatt tatagtacag gagcaagata ctgctgtgca aaatatgcat  1020

aagaaagtag aaaaattaga aacagaacat atggactgct ctgacctttt acggcgacaa  1080

acaagtgaac ttgaatttag cactcaacga gaggaacgcc ttagaaaaga atttgaggca  1140

actactctaa gagtgaggaa attagaagaa aacattgaag cagaaagagc agcgcatttg  1200

gaatcaaaat ttaattctga aattattcag ttacggattc gagaccttga aggagctttg  1260

caagtagaga aggccagtca agcagaagct gttgctgatt tggaaattat caagaatgaa  1320

ttcaaagaag ttgaaagtgc atatgagcga gaaaagcata atgcacaaga gagctttgca  1380

aaactaaatt tattagaaaa agagtatttc tccaaaaata agaaactaaa tgaagacatc  1440

gaggaacaga agaaagtaat tatagacctt tcaaagagac tccagtataa tgaaaaaagt  1500

tgcagtgaat tacaggaaga actagtaatg gctaagaagc accaggcctt cctagtagag  1560

acatgtgaaa ataacgtgaa agaattggaa tcgatcttgg acagctttac tgtgtcgggc  1620

cagtggacat caggcatcca caaggacaaa gataaacctc ccagcttctc tgttgtcctt  1680

gagagattga ggcgtacctt gacagattac cagaacaagc tggaagatgc atctaatgag  1740

gaaaaggcat gtaatgaact tgattctacg aaacagaaga tagactctca cactaaaaat  1800
```

```
ataaaggaac ttcaggataa actggctgat gttaataaag agttaagtca tttacacact   1860
aaatgtgcag accgagaggc tttaataagc actttaaaag tggaactaca aaatgtgctg   1920
cactgttggg agaaagaaaa ggctcaggca gcccagtctg aaagtgaact gcagaagctt   1980
tcccaggctt tccataagga tgcagaggag aagctaacct tccttcacac cttatatcag   2040
cacttggtag caggctgtgt gctcataaaa caaccagaag gcatgctgga taaattctct   2100
tggtctgagc tttgtgcagt cttacaggag aatgttgatg ccctgattgc agacctcaac   2160
agggctaatg agaagataag gcatctagag tatatctgta aaaacaagtc tgacacgatg   2220
agagagcttc agcagactca ggaagacacc tttaccaaag tggcagaaca gatcaaagcc   2280
caagagagct gctggcacag acaaaagaag gaactagagc tgcagtattc tgaactcttc   2340
ctggaggtgc agaagagggc acagaaattt caagaaattg ctgaaaaaaa catggaaaaa   2400
ttgaaccata ttgagaagtc acatgaacag ttggttcttg aaaattcgca cttcaaaaaa   2460
ctgttatcac agactcaaag ggaacagatg tccttgctgg cagcctgtgc attaatggct   2520
ggtgccttat atccccctcta tagccgatca tgcgccttgt ctacacagag agattttctc   2580
caggagcagg tcaacacctt tgagttgttc aaactggaaa ttagaactct agcccaggct   2640
ttgtcaactg tagaggaaaa gaagcaagag gaagccaaga tgaaaaagaa aacattcaaa   2700
ggattgatac gtatatttcg gaaaggtgtt attgctgttt tggcagcaaa cagactcaag   2760
atttgggcc aatcatgtgc ctctcttttt acctggatgg agagtttcaa agaaggcata   2820
ggcatgttag tgtgcacagg agagccccaa gacaagcata aatttccaaa acatcaaaag   2880
gagcagttgc gttgtttaca agcgctcagt tggctcacca gttctgacct tcttgctgca   2940
ataatcagtt ctatggctga attacaagac gtcattggta aagcagatcc aaattccaga   3000
atttgtggac atttactcat aggtgcagcc aagaattctt ttgcaaaact catggataaa   3060
attagtctgg taatggaatg tatacctctg cacagtagca ggagtattac atatgtagaa   3120
aaagattccc tggttcagag gctggcccat ggacttcata aagtaaacac actggccctg   3180
aaatatggtt tgcgtggcca tgtgcccatt acgaaaagca cagcatcgtt gcagaagcaa   3240
atacttggat ttacacaaag actgcatgct gcagaagtgg agcgccgctc actacgctta   3300
gaggtcacag aattcaaacg aagtgtgaat gaaatgaaaa aggagcttga caaagcccag   3360
ggtctgcaaa tgcaattaaa tgaatttaag cagtctaaat tgatcaccca tgagaagttt   3420
gaaagtgcat gtgaagaact aaataatgca ttacttcggg aagagcaggc acaaatgcta   3480
ttgaatgaac aggcacaaca actacaggaa ttgaattata aacttgaatt gcactccagt   3540
gaggaagctg acaaaaacca aactcttgga gaagctgtta agagtctctc cgaggcaaag   3600
atggagctga gaagaaaaga tcaatctctg cgtcagctca atagacatct tacccagctg   3660
gagcaggaca agcgtcgact ggaggagaac atccatgatg cagagagtgc cctccgcatg   3720
gcagccaaag acaaagaatg tgttgctaat cacatgagag cagtagaaaa tacgcttcac   3780
aaggtcagag atcagatctc gctgtcatgg tctgcggcaa gtaggaatga cttcacccta   3840
cagctaccca aactgcacct ggagaccttt gcaatggagg ggctcaaggg cgggccagag   3900
gtggtagcat gccaggctat gattaaaagt ttcatggatg tctaccagct tgcaagcact   3960
agaatcatga cattagagaa ggaaatgaca tctcatcgaa gtcacattgc agccttgaaa   4020
tcagaacttc acacagcttg tttacgtgaa aatgcaagtt tacaatcaat aggatcacga   4080
gaccattcaa atctctccat tccttcaaga gctcctcttc ctgctgacac aactggtatt   4140
```

-continued

```
ggggatttct taccattgaa agctgaactt gatactactt acactttctt aaaggagaca   4200

tttataaata ctgtgcccca tgctctgaca tcatctcact cctctccagt gactatgtct   4260

gctaatgcca acagaccaac tcagattgga ttatgacttc atgaaattaa aaaatggagg   4320

aagagttaac agtacaatta aaattgtttt gaatgggaa                         4359
```